US009701984B2

(12) United States Patent
Gao et al.

(10) Patent No.: US 9,701,984 B2
(45) Date of Patent: Jul. 11, 2017

(54) CNS TARGETING AAV VECTORS AND METHODS OF USE THEREOF

(71) Applicant: University of Massachusetts, Boston, MA (US)

(72) Inventors: Guangping Gao, Westborough, MA (US); Hongwei Zhang, Worcester, MA (US); Hongyan Wang, Worcester, MA (US); Zuoshang Xu, Wellesley, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/445,670

(22) Filed: Jul. 29, 2014

(65) Prior Publication Data

US 2014/0335054 A1    Nov. 13, 2014

Related U.S. Application Data

(63) Continuation of application No. 13/642,719, filed as application No. PCT/US2011/033616 on Apr. 22, 2011.

(60) Provisional application No. 61/327,627, filed on Apr. 23, 2010.

(51) Int. Cl.
| | |
|---|---|
| *A61K 31/713* | (2006.01) |
| *A61K 48/00* | (2006.01) |
| *C12N 15/113* | (2010.01) |
| *C12N 15/864* | (2006.01) |
| *C12N 15/86* | (2006.01) |
| *A61K 38/50* | (2006.01) |
| *C12N 9/80* | (2006.01) |
| *C12N 7/00* | (2006.01) |
| *C12N 15/63* | (2006.01) |

(52) U.S. Cl.
CPC ............ *C12N 15/86* (2013.01); *A61K 31/713* (2013.01); *A61K 38/50* (2013.01); *A61K 48/0075* (2013.01); *C12N 7/00* (2013.01); *C12N 9/80* (2013.01); *C12N 15/1137* (2013.01); *C12N 15/8645* (2013.01); *C12Y 305/01015* (2013.01); *A61K 48/00* (2013.01); *A61K 48/0058* (2013.01); *C12N 15/635* (2013.01); *C12N 2310/141* (2013.01); *C12N 2750/14133* (2013.01); *C12N 2750/14141* (2013.01); *C12N 2750/14143* (2013.01); *C12N 2750/14145* (2013.01); *C12N 2750/14162* (2013.01); *C12N 2810/10* (2013.01); *C12N 2840/007* (2013.01)

(58) Field of Classification Search
None
See application file for complete search history.

(56) References Cited

U.S. PATENT DOCUMENTS

| | | |
|---|---|---|
| 5,043,270 A | 8/1991 | Abrams et al. |
| 5,399,363 A | 3/1995 | Liversidge et al. |
| 5,478,745 A | 12/1995 | Samulski et al. |
| 5,543,158 A | 8/1996 | Gref et al. |
| 5,552,157 A | 9/1996 | Yagi |
| 5,565,213 A | 10/1996 | Nakamori et al. |
| 5,567,434 A | 10/1996 | Szoka |
| 5,641,515 A | 6/1997 | Ramtoola |
| 5,656,016 A | 8/1997 | Ogden |
| 5,697,899 A | 12/1997 | Hillman et al. |
| 5,738,868 A | 4/1998 | Shinkarenko |
| 5,741,516 A | 4/1998 | Webb et al. |
| 5,770,219 A | 6/1998 | Chiang et al. |
| 5,779,708 A | 7/1998 | Wu |
| 5,783,208 A | 7/1998 | Venkateshwaran et al. |
| 5,795,587 A | 8/1998 | Gao et al. |
| 5,797,898 A | 8/1998 | Santini et al. |
| 5,871,982 A | 2/1999 | Wilson et al. |
| 6,001,650 A | 12/1999 | Colosi |
| 6,083,716 A | 7/2000 | Wilson et al. |
| 6,156,303 A | 12/2000 | Russell et al. |
| 6,177,403 B1 | 1/2001 | Stedman |
| 6,251,677 B1 | 6/2001 | Wilson et al. |
| 6,365,394 B1 | 4/2002 | Gao et al. |
| 6,475,469 B1 | 11/2002 | Montgomery |
| 6,485,966 B2 | 11/2002 | Gao et al. |
| 6,498,244 B1 | 12/2002 | Patel et al. |
| 6,544,786 B1 | 4/2003 | Xiao et al. |

(Continued)

FOREIGN PATENT DOCUMENTS

| | | | |
|---|---|---|---|
| WO | WO 03/042397 | 5/2003 | |
| WO | WO 03/093460 | 11/2003 | |
| WO | WO 2005/033321 | 4/2005 | |
| WO | WO2006/031267 | * 3/2006 | ............ C12N 15/11 |
| WO | WO 2006/119432 A2 | 11/2006 | |
| WO | WO 2007/000668 A2 | 1/2007 | |
| WO | WO 2007/127264 A2 | 11/2007 | |
| WO | WO 2008/091703 | 7/2008 | |
| WO | WO 2008/147839 A1 | 12/2008 | |
| WO | WO 2008/150897 A2 | 12/2008 | |

(Continued)

OTHER PUBLICATIONS

Iwamoto et al., Global diffuse distribution in the brain and efficient gene delivery to the dorsal root ganglia by intrathecal injection of adeno-associated viral vector serotype 1, The Journal of Gene Medicine vol. 11, Issue 6, pp. 498-505, Jun. 2009. Article first published online: Mar. 31, 2009.*

(Continued)

*Primary Examiner* — Kevin Hill
*Assistant Examiner* — Arthur S Leonard
(74) *Attorney, Agent, or Firm* — Wolf, Greenfield & Sacks, P.C.

(57) ABSTRACT

The invention in some aspects relates to recombinant adeno-associated viruses useful for targeting transgenes to CNS tissue, and compositions comprising the same, and methods of use thereof. In some aspects, the invention provides methods and compositions for treating CNS-related disorders.

7 Claims, 47 Drawing Sheets

(56) References Cited

U.S. PATENT DOCUMENTS

| | | |
|---|---|---|
| 6,821,512 B1 | 11/2004 | Gao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,238,526 B2 | 7/2007 | Wilson et al. |
| 7,247,472 B2 | 7/2007 | Wilson et al. |
| 7,282,199 B2 | 10/2007 | Gao et al. |
| 7,344,872 B2 | 3/2008 | Gao et al. |
| 7,427,396 B2 | 9/2008 | Arbetman et al. |
| 7,456,015 B2 * | 11/2008 | Bohn et al. ............... 435/320.1 |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,284,357 B2 | 3/2016 | Gao et al. |
| 2001/0016355 A1 | 8/2001 | Samulski et al. |
| 2002/0019050 A1 | 2/2002 | Gao et al. |
| 2002/0164783 A1 | 11/2002 | Feldhaus |
| 2002/0173025 A1 | 11/2002 | Lazarus et al. |
| 2003/0040101 A1 | 2/2003 | Wilson et al. |
| 2003/0092161 A1 | 5/2003 | Gao et al. |
| 2003/0096399 A1 | 5/2003 | Barber et al. |
| 2003/0103939 A1 | 6/2003 | Engelhardt et al. |
| 2003/0110526 A1 | 6/2003 | Brown et al. |
| 2003/0119191 A1 | 6/2003 | Gao et al. |
| 2003/0138772 A1 | 7/2003 | Gao et al. |
| 2003/0207259 A1 | 11/2003 | Gao et al. |
| 2003/0228282 A1 | 12/2003 | Gao et al. |
| 2004/0101514 A1 | 5/2004 | Liu et al. |
| 2004/0136963 A1 | 7/2004 | Wilson et al. |
| 2004/0171807 A1 | 9/2004 | Gao et al. |
| 2005/0014262 A1 | 1/2005 | Gao et al. |
| 2005/0032219 A1 | 2/2005 | Aubourg et al. |
| 2005/0037988 A1 | 2/2005 | Zamore et al. |
| 2005/0069866 A1 | 3/2005 | Wilson et al. |
| 2005/0137153 A1 | 6/2005 | McSwiggen et al. |
| 2005/0287122 A1 | 12/2005 | Bartlett et al. |
| 2006/0018841 A1 | 1/2006 | Arbetman et al. |
| 2006/0063174 A1 | 3/2006 | Turner et al. |
| 2006/0093589 A1 | 5/2006 | Warrington et al. |
| 2006/0189564 A1 * | 8/2006 | Burright ............... A61K 31/70 514/44 A |
| 2006/0292117 A1 | 12/2006 | Loiler et al. |
| 2007/0004042 A1 | 1/2007 | Gao et al. |
| 2007/0036760 A1 | 2/2007 | Wilson et al. |
| 2007/0134203 A1 | 6/2007 | Gao et al. |
| 2007/0243526 A1 | 10/2007 | Kay et al. |
| 2007/0253936 A1 | 11/2007 | Kay et al. |
| 2007/0292410 A1 | 12/2007 | Cashman et al. |
| 2008/0075737 A1 | 3/2008 | Gao et al. |
| 2008/0075740 A1 | 3/2008 | Gao et al. |
| 2008/0090281 A1 | 4/2008 | Wilson et al. |
| 2008/0199509 A1 | 8/2008 | Nick et al. |
| 2008/0219954 A1 | 9/2008 | Gao et al. |
| 2008/0292595 A1 | 11/2008 | Arbetman et al. |
| 2009/0042828 A1 * | 2/2009 | Xu ............... C12N 9/0089 514/44 R |
| 2009/0111766 A1 | 4/2009 | Atkinson et al. |
| 2009/0131355 A1 | 5/2009 | Bot et al. |
| 2009/0149409 A1 | 6/2009 | Bohn et al. |
| 2009/0197338 A1 | 8/2009 | Vandenberghe et al. |
| 2010/0028998 A1 | 2/2010 | Roelvink et al. |
| 2010/0104561 A1 | 4/2010 | Zhong et al. |
| 2010/0186103 A1 | 7/2010 | Gao et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0258716 A1 | 10/2011 | Baltimore et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0101558 A1 | 4/2013 | Gao et al. |
| 2013/0109742 A1 | 5/2013 | Hewitt et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0296486 A1 | 10/2014 | Gao et al. |
| 2016/0135438 A1 | 5/2016 | Gao et al. |
| 2016/0186211 A1 | 6/2016 | Flotte et al. |

FOREIGN PATENT DOCUMENTS

| | | | |
|---|---|---|---|
| WO | WO 2009/130208 | 10/2009 | |
| WO | WO 2009/146178 * | 12/2009 | ............ C07K 14/00 |
| WO | WO 2010/034314 A1 | 4/2010 | |
| WO | WO 2010/071454 A1 | 6/2010 | |
| WO | WO 2010/129021 * | 11/2010 | ............ C12N 15/79 |
| WO | WO 2010/138263 A2 | 12/2010 | |
| WO | WO 2013/170078 A1 | 11/2013 | |
| WO | WO 2013/190059 A1 | 12/2013 | |
| WO | WO 2014/160092 A1 | 10/2014 | |

OTHER PUBLICATIONS

Jakobsson et al., Lentiviral Vectors for Use in the Central Nervous System. Molecular Therapy vol. 13, No. 3, Mar. 2006.*

Watson et al., Intrathecal administration of AAV vectors for the treatment of lysosomal storage in the brains of MPS I mice. Gene Therapy (2006)13, 917-925.*

Raoul et al., Lentiviral-mediated silencing of SOD1 through RNA interference retards disease onset and progression in a mouse model of ALS. Nature Medicine 11, 423-428 (2005).*

Storek et al. Intrathecal long-term gene expression by self-complementary adeno-associated virus type 1 suitable for chronic pain studies in rats. Mol Pain. Jan. 30, 2006;2:4. p. 1-11.*

Fraldi et al., Functional correction of CNS lesions in an MPS-IIIA mouse model by intracerebral AAV-mediated delivery of sulfamidase and SUMF1 genes. Hum. Mol. Genet. (2007) 16 (22): 2693-2702.*

Zincarelli et al., Analysis of AAV Serotypes 1-9 Mediated Gene Expression and Tropism in Mice After Systemic Injection. Molecular Therapy (2008) 16 6, 1073-1080.*

Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.*

Afione et al., In vivo model of adeno-associated virus vector persistence and rescue. J Virol. May 1996;70(5):3235-41.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Alisky et al., Gene therapy for amyotrophic lateral sclerosis and other motor neuron diseases. Hum Gene Ther. Nov. 20, 2000;11(17):2315-29.

Ameres et al., Target RNA-directed tailing and trimming purifies the sorting of endo-siRNAs between the two Drosophila argonaute proteins. RNA. Jan. 2011;17(1):54-63. doi: 10.1261/rna.2498411. Epub Nov. 24, 2010.

Ameres et al., Target RNA-directed trimming and tailing of small silencing RNAs. Science. Jun. 18, 2010;328(5985):1534-9. doi: 10.1126/science.1187058.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr Gene Ther. Apr. 2009;9(2):91-103.

Azzouz et al., VEGF delivery with retrogradely transported lentivector prolongs survival in a mouse ALS model. Nature. May 27, 2004;429(6990):413-7.

(56) References Cited

OTHER PUBLICATIONS

Bals et al., Transduction of well-differentiated airway epithelium by recombinant adeno-associated virus is limited by vector entry. J Virol. Jul. 1999;73(7):6085-8.

Barcia et al., Intraventricular and intracerebral delivery of anti-epileptic drugs in the kindling model. Neurotherapeutics. Apr. 2009;6(2):337-43.

Bernacki et al., Mucin gene expression during differentiation of human airway epithelia in vitro. Muc4 and muc5b are strongly induced. Am J Respir Cell Mol Biol. Apr. 1999;20(4):595-604.

Berns et al., Biology of adeno-associated virus. Curr Top Microbiol Immunol. 1996;218:1-23.

Berns et al., Detection of adeno-associated virus (AAV)-specific nucleotide sequences in DNA isolated from latently infected Detroit 6 cells. Virology. Dec. 1975;68(2):556-60.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Boillée et al., Onset and progression in inherited ALS determined by motor neurons and microglia. Science. Jun. 2, 2006;312(5778):1389-92.

Bolstad et al., A comparison of normalization methods for high density oligonucleotide array data based on variance and bias. Bioinformatics. Jan. 22, 2003;19(2):185-93.

Bourlais et al., Ophthalmic drug delivery systems—recent advances. Prog Retin Eye Res. Jan. 1998;17(1):33-58.

Brantly et al., Phase I trial of intramuscular injection of a recombinant adeno-associated virus serotype 2 alpha1-antitrypsin (AAT) vector in AAT-deficient adults. Hum Gene Ther. Dec. 2006;17(12):1177-86.

Brown et al., A microRNA-regulated lentiviral vector mediates stable correction of hemophilia B mice. Blood. Dec. 15, 2007;110(13):4144-52. Epub Aug. 28, 2007.

Brown et al., Endogenous microRNA can be broadly exploited to regulate transgene expression according to tissue, lineage and differentiation state. Nat Biotechnol. Dec. 2007;25(12):1457-67. Epub Nov. 16, 2007.

Brown et al., Endogenous microRNA regulation suppresses transgene expression in hematopoietic lineages and enables stable gene transfer. Nat Med. May 2006;12(5):585-91. Epub Apr. 23, 2006.

Bukh, A critical role for the chimpanzee model in the study of hepatitis C. Hepatology. Jun. 2004;39(6):1469-75.

Büssing et al., let-7 microRNAs in development, stem cells and cancer. Trends Mol Med. Sep. 2008;14(9):400-9. doi: 10.1016/j.molmed.2008.07.001. Epub Jul. 31, 2008.

Calcedo et al., Worldwide epidemiology of neutralizing antibodies to adeno-associated viruses. J Infect Dis. Feb. 1, 2009;199(3):381-90.

Carè et al., MicroRNA-133 controls cardiac hypertrophy. Nat Med. May 2007;13(5):613-8. Epub Apr. 29, 2007.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chang et al., miR-122, a mammalian liver-specific microRNA, is processed from her mRNA and may downregulate the high affinity cationic amino acid transporter CAT-1. RNA Biol. Jul. 2004;1(2):106-13. Epub Jul. 1, 2004.

Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.

Chen et al., Efficient transduction of vascular endothelial cells with recombinant adeno-associated virus serotype 1 and 5 vectors. Hum Gene Ther. Feb. 2005;16(2):235-47.

Chirmule et al., Humoral immunity to adeno-associated virus type 2 vectors following administration to murine and nonhuman primate muscle. J Virol. Mar. 2000;74(5):2420-5.

Choi et al., Effects of adeno-associated virus DNA hairpin structure on recombination. J Virol. Jun. 2005;79(11):6801-7.

Christensen et al., A let-7 microRNA-binding site polymorphism in the KRAS 3' UTR is associated with reduced survival in oral cancers. Carcinogenesis. Jun. 2009;30(6):1003-7. doi: 10.1093/carcin/bgp099. Epub Apr. 20, 2009.

Chu et al., SV40 DNA transfection of cells in suspension: analysis of efficiency of transcription and translation of T-antigen. Gene. Mar. 1981;13(2):197-202.

Cideciyan et al., Human RPE65 gene therapy for Leber congenital amaurosis: persistence of early visual improvements and safety at 1 year. Hum Gene Ther. Sep. 2009;20(9):999-1004.

Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.

Conrad et al., Safety of single-dose administration of an adeno-associated virus (AAV)-CFTR vector in the primate lung. Gene Ther. Aug. 1996;3(8):658-68.

Coulouarn et al., Loss of miR-122 expression in liver cancer correlates with suppression of the hepatic phenotype and gain of metastatic properties. Oncogene. Oct. 8, 2009;28(40):3526-36. doi: 10.1038/onc.2009.211. Epub Jul. 20, 2009.

Crowe et al., A comparison in chimpanzees of the immunogenicity and efficacy of live attenuated respiratory syncytial virus (RSV) temperature-sensitive mutant vaccines and vaccinia virus recombinants that express the surface glycoproteins of RSV. Vaccine. Nov. 1993;11(14):1395-404.

Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.

Curtin et al., Bidirectional promoter interference between two widely used internal heterologous promoters in a late-generation lentiviral construct. Gene Ther. Mar. 2008;15(5):384-90. doi: 10.1038/sj.gt.3303105. Epub Jan. 24, 2008.

Czech, MicroRNAs as therapeutic targets. N Engl J Med. Mar. 16, 2006;354(11):1194-5.

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.

Davidson et al., A model system for in vivo gene transfer into the central nervous system using an adenoviral vector. Nat Genet. Mar. 1993;3(3):219-23.

Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.

Daya et al., Gene therapy using adeno-associated virus vectors. Clin Microbiol Rev. Oct. 2008;21(4):583-93. doi: 10.1128/CMR.00008-08.

Di Giorgio et al., Non-cell autonomous effect of glia on motor neurons in an embryonic stem cell-based ALS model. Nat Neurosci. May 2007;10(5):608-14. Epub Apr. 15, 2007.

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

(56) References Cited

OTHER PUBLICATIONS

Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.

Ebert et al., MicroRNA sponges: competitive inhibitors of small RNAs in mammalian cells. Nat Methods. Sep. 2007;4(9):721-6. Epub Aug. 12, 2007.

Ehlert et al., Cellular toxicity following application of adeno-associated viral vector-mediated RNA interference in the nervous system. BMC Neurosci. Feb. 18, 2010;11:20.

Elmén et al., Antagonism of microRNA-122 in mice by systemically administered LNA-antimiR leads to up-regulation of a large set of predicted target mRNAs in the liver. Nucleic Acids Res. Mar. 2008;36(4):1153-62. Epub Dec. 23, 2007.

Elmen et al., LNA-mediated microRNA silencing in non-human primates. Nature. Apr. 17, 2008;452(7189):896-9. Epub Mar. 26, 2008.

Engelhardt et al., Adenovirus-mediated transfer of the CFTR gene to lung of nonhuman primates: biological efficacy study. Hum Gene Ther. Dec. 1993;4(6):759-69.

Esau et al., miR-122 regulation of lipid metabolism revealed by in vivo antisense targeting. Cell Metab. Feb. 2006;3(2):87-98.

Fabani et al., miR-122 targeting with LNA/2'-O-methyl oligonucleotide mixmers, peptide nucleic acids (PNA), and PNA-peptide conjugates. RNA. Feb. 2008;14(2):336-46. Epub Dec. 11, 2007.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fire et al., Potent and specific genetic interference by double-stranded RNA in Caenorhabditis elegans. Nature. Feb. 19, 1998;391(6669):806-11.

Fischer et al., Successful transgene expression with serial doses of aerosolized rAAV2 vectors in rhesus macaques. Mol Ther. Dec. 2003;8(6):918-26.

Fisher et al., Transduction with recombinant adeno-associated virus for gene therapy is limited by leading-strand synthesis. J Virol. Jan. 1996;70(1):520-32.

Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

Flotte, Recombinant adeno-associated virus (AAV) gene therapy vectors for, cystic fibrosis (CF), alpha-1 -antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.

Forman et al., A search for conserved sequences in coding regions reveals that the let-7 microRNA targets Dicer within its coding sequence. Proc Natl Acad Sci U S A. Sep. 30, 2008;105(39):14879-84. doi: 10.1073/pnas.0803230105. Epub Sep. 23, 2008.

Foust et al., Intravascular AAV9 preferentially targets neonatal-neurons and adult-astrocytes. Nature Biotechnology, 27; 59-65 2009.

Foust et al., Rescue of the spinal muscular atrophy phenotype in a mouse model by early postnatal delivery of SMN. Nat Biotechnol. Mar. 2010;28(3):271-4. doi: 10.1038/nbt.1610. Epub Feb. 28, 2010.

Fu et al., Evaluation of cellular immune responses in subjects chronically infected with HIV type 1. AIDS Res Hum Retroviruses. Jan. 2007;23(1):67-76.

Fu et al., Self-complementary adeno-associated virus serotype 2 vector: global distribution and broad dispersion of AAV-mediated transgene expression in mouse brain. Mol Ther. Dec. 2003;8(6):911-7.

Gao et al., Adeno-associated viruses undergo substantial evolution in primates during natural infections. Proc Natl Acad Sci U S A. May 13, 2003;100(10):6081-6. Epub Apr. 25, 2003.

Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.

Gao et al., Biology of AAV serotype vectors in liver-directed gene transfer to nonhuman primates. Mol Ther. Jan. 2006;13(1):77-87. Epub Oct. 10, 2005.

Gao et al., Clades of Adeno-associated viruses are widely disseminated in human tissues. J Virol. Jun. 2004;78(12):6381-8.

Gao et al., Erythropoietin gene therapy leads to autoimmune anemia in macaques. Blood. May 1, 2004;103(9):3300-2. Epub Dec. 24, 2003.

Gao et al., In situ synthesis of oligonucleotide microarrays. Biopolymers. Apr. 5, 2004;73(5):579-96.

Gao et al., Inadvertent gene transfer of co-packaged rep and cap sequences during the production of AAV vector and its potential impact on vector performance Molecular Therapy. May 2008;16(Suppl. 1):S105-S106. Abstract 279.

Gao et al., New recombinant serotypes of AAV vectors. Curr Gene Ther. Jun. 2005;5(3):285-97.

Gao et al., Novel adeno-associated viruses from rhesus monkeys as vectors for human gene therapy. Proc Natl Acad Sci USA. Sep. 3, 2002;99(18):11854-9. Epub Aug. 21, 2002.

Gao et al., Purification of recombinant adeno-associated virus vectors by column chromatography and its performance in vivo. Hum Gene Ther. Oct. 10, 2000;11(15):2079-91.

Gao et al., RAAV-mediated targeting in adult mice and its potential in generating animal models of tissue-specific somatic transgenics or knock down. Molecular Therapy. May 2008;16(1):S118-S119. Abstract 316.

GENBANK Submission; Accession No. ADZ26851; Wilson et al.; Jun. 30, 2005.

GENBANK Submission; NCBI, Accession No. AAB95450; Rutledge et al.; Jan. 12, 1998.

GENBANK Submission; NCBI, Accession No. AAS99264; Gao et al.; Jun. 24, 2004.

GENBANK Submission; NCBI, Accession No. ABA71701; Schmidt et al.; May 10, 2006.

GENBANK Submission; NCBI, Accession No. ACB55301; Vandenberghe et al.; Jul. 31, 2008.

GENBANK Submission; NCBI, Accession No. ACB55310; Vandenberghe et al.; Jul. 31, 2008.

GENBANK Submission; NCBI, Accession No. NP_049542; Xiao et al.; Mar. 11, 2010.

GENBANK Submission; NCBI, Accession No. YP_680426; Ruffing et al.; Nov. 19, 2010.

Gentner et al., Stable knockdown of microRNA in vivo by lentiviral vectors. Nat Methods. Jan. 2009;6(1):63-6. doi: 10.1038/nmeth.1277. Epub Nov. 30, 2008.

Girard et al., miR-122, a paradigm for the role of microRNAs in the liver. J Hepatol. Apr. 2008;48(4):648-56. doi: 10.1016/j.jhep.2008.01.019. Epub Feb. 12, 2008.

Graham et al., A new technique for the assay of infectivity of human adenovirus 5 DNA. Virology. Apr. 1973;52(2):456-67.

Gramantieri et al., Cyclin G1 is a target of miR-122a, a microRNA frequently down-regulated in human hepatocellular carcinoma. Cancer Res. Jul. 1, 2007;67(13):6092-9.

Griffiths-Jones et al., miRBase: microRNA sequences, targets and gene nomenclature. Nucleic Acids Res. Jan. 1, 2006;34(Database issue):D140-4.

Grimm et al., Fatality in mice due to oversaturation of cellular microRNA/short hairpin RNA pathways. Nature. May 25, 2006;441(7092):537-41.

Grimm et al., Therapeutic application of RNAi: is mRNA targeting finally ready for prime time? J Clin Invest. Dec. 2007;117(12):3633-41.

Gruenert et al., Culture and transformation of human airway epithelial cells. Am J Physiol. Mar. 1995;268(3 Pt 1):L347-60.

Haraguchi et al., Vectors expressing efficient RNA decoys achieve the long-term suppression of specific microRNA activity in mammalian cells. Nucleic Acids Res. Apr. 2009;37(6):e43. doi: 10.1093/nar/gkp040. Epub Feb. 17, 2009.

(56) References Cited

OTHER PUBLICATIONS

Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001;75(13):6199-203.
Horwich et al., Design and delivery of antisense oligonucleotides to block microRNA function in cultured *Drosophila* and human cells. Nat Protoc. 2008;3(10):1537-49. doi: 10.1038/nprot.2008.145.
Hutvágner et al., Sequence-specific inhibition of small RNA function. PLoS Biol. Apr. 2004;2(4):E98. Epub Feb. 24, 2004.
Jackman et al., Stabilization of the oxy form of tyrosinase by a single conservative amino acid substitution. Biochem J. Mar. 15, 1992;282 ( Pt 3):915-8.
Johnson et al., RAS is regulated by the let-7 microRNA family. Cell. Mar. 11, 2005;120(5):635-47.
Kaspar et al., Retrograde viral delivery of IGF-1 prolongs survival in a mouse ALS model. Science. Aug. 8, 2003;301(5634):839-42.
Kota et al., Therapeutic microRNA delivery suppresses tumorigenesis in a murine liver cancer model. Cell. Jun. 12, 2009;137(6):1005-17. doi: 10.1016/j.cell.2009.04.021.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Krützfeldt et al., Silencing of microRNAs in vivo with 'antagomirs'. Nature. Dec. 1, 2005;438(7068):685-9. Epub Oct. 30, 2005.
Kumar et al., Canavan disease: a white matter disorder. Ment Retard Dev Disabil Res Rev. 2006;12(2):157-65.
Kumar et al., Lack of aspartoacylase activity disrupts survival and differentiation of neural progenitors and oligodendrocytes in a mouse model of Canavan disease. J Neurosci Res. Nov. 15, 2009;87(15):3415-27. doi: 10.1002/jnr.22233.
Kutay et al., Downregulation of miR-122 in the rodent and human hepatocellular carcinomas. J Cell Biochem. Oct. 15, 2006;99(3):671-8.
Kwiatkowski et al., Clinical, genetic, and pharmacogenetic applications of the Invader assay. Mol Diagn. Dec. 1999;4(4):353-64.
Lanford et al., Therapeutic silencing of microRNA-122 in primates with chronic hepatitis C virus infection. Science. Jan. 8, 2010;327(5962):198-201. Epub Dec. 3, 2009.
Lebherz et al., Gene therapy with novel adeno-associated virus vectors substantially diminishes atherosclerosis in a murine model of familial hypercholesterolemia. J Gene Med. Jun. 2004;6(6):663-72.
Lewis et al., Conserved seed pairing, often flanked by adenosines, indicates that thousands of human genes are microRNA targets. Cell. Jan. 14, 2005;120(1):15-20.
Lewis et al., Prediction of mammalian microRNA targets. Cell. Dec. 26, 2003;115(7):787-98.
Li et al., Ex vivo transduction and transplantation of bone marrow cells for liver gene delivery of alpha1-antitrypsin. Mol Ther. Aug. 2010;18(8):1553-8. Epub Jun. 15, 2010.
Lin et al., Impact of preexisting vector immunity on the efficacy of adeno-associated virus-based HIV-1 Gag vaccines. Hum Gene Ther. Jul. 2008;19(7):663-9.
Liu et al., Biological Differences in rAAV Transduction of Airway Epithelia in Humans and in Old World Non-human Primates. Mol Ther. Dec. 2007;15(12):2114-23. Epub Jul. 31, 2007.
Liu et al., Comparative biology of rAAV transduction in ferret, pig and human airway epithelia. Gene Ther. Nov. 2007;14(21):1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Loiler et al., Targeting recombinant adeno-associated virus vectors to enhance gene transfer to pancreatic islets and liver. Gene Ther. Sep. 2003;10(18):1551-8.
Lomas et al., The mechanism of Z alpha 1-antitrypsin accumulation in the liver. Nature. Jun. 18, 1992;357(6379):605-7.
Lowenstein, Crossing the rubicon. Nat Biotechnol. Jan. 2009;27(1):42-4.
Loya et al., Transgenic microRNA inhibition with spatiotemporal specificity in intact organisms. Nat Methods. Dec. 2009;6(12):897-903. doi: 10.1038/nmeth.1402. Epub Nov. 15, 2009.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Mandel et al., Recombinant adeno-associated viral vectors as therapeutic agents to treat neurological disorders. Mol Ther. Mar. 2006;13(3):463-83. Epub Jan. 18, 2006.
Manfredsson et al., AAV9: a potential blood-brain barrier buster. Mol Ther. Mar. 2009;17(3):403-5.
Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].
Martin-Duque et al., Direct comparison of the insulating properties of two genetic elements in an adenoviral vector containing two different expression cassettes. Hum Gene Ther. Oct. 2004;15(10):995-1002.
Matalon et al., Adeno-associated virus-mediated aspartoacylase gene transfer to the brain of knockout mouse for canavan disease. Mol Ther. May 2003;7(5 Pt 1):580-7.
Mattan et al., Aspartoacylase deficiency affects early postnatal development of oligodendrocytes and myelination. Neurobiol Dis. Nov. 2010;40(2):432-43. doi: 10.1016/j.nbd.2010.07.003. Epub Jul. 14, 2010.
McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McGovern, Taking aim at HDL-C. Raising levels to reduce cardiovascular risk. Postgrad Med. Apr. 2005;117(4):29-30, 33-5, 39 passim.
McLean et al., Gene targeted therapeutics for liver disease in alpha-1 antitrypsin deficiency. Biologics. 2009;3:63-75. Epub Jul. 13, 2009.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Meister et al., Sequence-specific inhibition of microRNA- and siRNA-induced RNA silencing. RNA. Mar. 2004;10(3):544-50.
Mingozzi et al., CD8(+) T-cell responses to adeno-associated virus capsid in humans. Nat Med. Apr. 2007;13(4):419-22. Epub Mar. 18, 2007.
Moffett et al., N-Acetylaspartate in the CNS: from neurodiagnostics to neurobiology. Prog Neurobiol. Feb. 2007;81(2):89-131. Epub Jan. 5, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recom-

(56) References Cited

OTHER PUBLICATIONS binant AAV for Alpha-1 Antitrypsin Disease. Molecular Therapy May 2009;17(1):S391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr−/−-dependent allergy mouse model. Gene Ther. Feb. 2009;16(2):172-83. Epub Sep. 25, 2008.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
Nagai et al., Astrocytes expressing ALS-linked mutated SOD1 release factors selectively toxic to motor neurons. Nat Neurosci. May 2007;10(5):615-22.
Nakabayashi et al., Growth of human hepatoma cells lines with differentiated functions in chemically defined medium. Cancer Res. Sep. 1982;42(9):3858-63.
Naldini, Ex vivo gene transfer and correction for cell-based therapies. Nat Rev Genet. May 2011;12(5):301-15. doi: 10.1038/nrg2985. Epub Mar. 29, 2011.
O'Reilly et al., RNA interference-mediated suppression and replacement of human rhodopsin in vivo. Am J Hum Genet. Jul. 2007;81(1):127-35. Epub May 23, 2007.
Papaioannou et al., Efficacy of tribromoethanol anesthesia in mice. Lab Anim Sci. Apr. 1993;43(2):189-92.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Powell-Braxton et al., A mouse model of human familial hypercholesterolemia: markedly elevated low density lipoprotein cholesterol levels and severe atherosclerosis on a low-fat chow diet. Nat Med. Aug. 1998;4(8):934-8. Erratum in: Nat Med Oct. 1998;4(10):1200.
Propst et al., Prevalence of hepatocellular carcinoma in alpha-1-antitrypsin deficiency. J Hepatol. Dec. 1994;21(6):1006-11.
Ralph et al., Silencing mutant SOD1 using RNAi protects against neurodegeneration and extends survival in an ALS model. Nat Med. Apr. 2005;11(4):429-33. Epub Mar. 13, 2005.
Rayner et al., MiR-33 contributes to the regulation of cholesterol homeostasis. Science. Jun. 18, 2010;328(5985):1570-3. doi: 10.1126/science.1189862. Epub May. 13, 2010.
Remington's Pharmaceutical Sciences. 1975. Osol et al., Eds. 15th Edition. 1035-1038 and 1570-1580.
Roy et al., Characterization of a family of chimpanzee adenoviruses and development of molecular clones for gene transfer vectors. Hum Gene Ther. May 2004;15(5):519-30.
Sambrook et al, "Molecular Cloning. A Laboratory Manual", 2d ed., Cold Spring Harbor Laboratory, New York (1989).
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schnepp et al., Characterization of adeno-associated virus genomes isolated from human tissues. J Virol. Dec. 2005;79(23):14793-803.
Schwarz et al., Designing siRNA that distinguish between genes that differ by a single nucleotide. PLoS Genet. Sep. 8, 2006;2(9):e140, 1307-1318. Epub Jul. 24, 2006.
Seiler et al., Adeno-associated virus types 5 and 6 use distinct receptors for cell entry. Hum Gene Ther. Jan. 2006;17(1):10-9.
Sen et al., Micromanaging vascular biology: tiny microRNAs play big band. J Vasc Res. 2009;46(6):527-40. doi: 10.1159/000226221. Epub Jun. 30, 2009.
Sivasothy et al., Pathogenic alpha 1-antitrypsin polymers are formed by reactive loop-beta-sheet a linkage. J Biol Chem. Oct. 27, 2000;275(43):33663-8.
Smith, A regional survey of myelin development: some compositional and metabolic aspects. J Lipid Res. Sep. 1973;14(5):541-51.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh.10 rhesus macaque-derived adeno-associated virus vector. Mol Ther. Mar. 2007;15(3):481-91. Epub Dec. 19, 2006.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.
Soutar et al., Mechanisms of disease: genetic causes of familial hypercholesterolemia. Nat Clin Pract Cardiovasc Med. Apr. 2007;4(4):214-25.
Stein et al., Systemic and central nervous system correction of lysosomal storage in mucopolysaccharidosis type VII mice. J Virol. Apr. 1999;73(4):3424-9.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tannous, Gaussia luciferase reporter assay for monitoring biological processes in culture and in vivo. Nat Protoc. 2009;4(4):582-91. doi: 10.1038/nprot.2009.28.
Tenenbaum et al., Recombinant AAV-mediated gene delivery to the central nervous system. J Gene Med. Feb. 2004;6 Suppl 1:S212-22.
Tokumaru et al., let-7 regulates Dicer expression and constitutes a negative feedback loop. Carcinogenesis. Nov. 2008;29(11):2073-7. doi: 10.1093/carcin/bgn187. Epub Aug. 11, 2008.
Tomar et al., Use of adeno-associated viral vector for delivery of small interfering RNA. Oncogene. Aug. 28, 2003;22(36):5712-5.
Tsai et al., MicroRNA-122, a tumor suppressor microRNA that regulates intrahepatic metastasis of hepatocellular carcinoma. Hepatology. May 2009;49(5):1571-82. doi: 10.1002/hep.22806.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vaucheret et al., The action of ARGONAUTE1 in the miRNA pathway and its regulation by the miRNA pathway are crucial for plant development. Genes Dev. May 15, 2004;18(10):1187-97. Epub May 6, 2004.
Véniant et al., Lipoprotein clearance mechanisms in LDL receptor-deficient "Apo-B48-only" and "Apo-B100-only" mice. J Clin Invest. Oct. 15, 1998;102(8):1559-68.
Vermeulen et al., Double-stranded regions are essential design components of potent inhibitors of RISC function. RNA. May 2007;13(5):723-30. Epub Mar. 30, 2007.
Virella-Lowell et al., Enhancing rAAV vector expression in the lung. J Gene Med. Jul. 2005;7(7):842-50.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Waldman et al., Applications of microRNA in cancer: Exploring the advantages of miRNA. Clin Transl Sci. Jun. 2009;2(3):248-9. doi: 10.1111/j.1752-8062.2009.00110.x.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.

(56) References Cited

OTHER PUBLICATIONS

Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.

Wang et al., Vascular endothelial growth factor overexpression delays neurodegeneration and prolongs survival in amyotrophic lateral sclerosis mice. J Neurosci. Jan. 10, 2007;27(2):304-7.

Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.

Wu et al., Alpha2,3 and alpha2,6 N-linked sialic acids facilitate efficient binding and transduction by adeno-associated virus types 1 and 6. J Virol. Sep. 2006;80(18):9093-103.

Wu et al., Chronic lumbar catheterization of the spinal subarachnoid space in mice. J Neurosci Methods. Feb. 15, 2004;133(1-2):65-9.

Wu et al., Nerve injection of viral vectors efficiently transfers transgenes into motor neurons and delivers RNAi therapy against ALS. Antioxid Redox Signal. Jul. 2009;11(7):1523-34.

Xia et al., Allele-specific RNAi selectively silences mutant SOD1 and achieves significant therapeutic benefit in vivo. Neurobiol Dis. Sep. 2006;23(3):578-86. Epub Jul. 20, 2006.

Xia et al., Multiple shRNAs expressed by an inducible pol II promoter can knock down the expression of multiple target genes. Biotechniques. Jul. 2006;41(1):64-8.

Xie et al., Isolation of transcriptionally active novel AAV capsid sequences from chimpanzee tissues for vector development. Meeting Abstract: 12th Annual Meeting of the American Society of Gene Therapy. May 1, 2009. Abstract 91.

Xie et al., Characterization of positioning effect of pol III-shRNA transcription unit in scAAV vector genome on the packaging efficiency and functionality of shRNA silencing. Molecular Therapy. May 2010;18(1): S262. Abstract 671.

Xie et al., MicroRNA regulated tissue specific transduction by rAAV vector. Molecular Therapy. May 2009;17(1): S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.

Yamanaka et al., Astrocytes as determinants of disease progression in inherited amyotrophic lateral sclerosis. Nat Neurosci. Mar. 2008;11(3):251-3. doi: 10.1038/nn2047. Epub Feb. 3, 2008.

Yan et al., Unique biologic properties of recombinant AAV1 transduction in polarized human airway epithelia. J Biol Chem. Oct. 6, 2006;281(40):29684-92. Epub Aug. 9, 2006.

Yang et al., The muscle-specific microRNA miR-1 regulates cardiac arrhythmogenic potential by targeting GJA1 and KCNJ2. Nat Med. Apr. 2007;13(4):486-91. Epub Apr. 1, 2007. Erratum in: Nat Med. Dec. 2011;17(12):1693.

Yu et al., let-7 regulates self renewal and tumorigenicity of breast cancer cells. Cell. Dec. 14, 2007;131(6):1109-23.

Zabner et al., Adeno-associated virus type 5 (AAV5) but not AAV2 binds to the apical surfaces of airway epithelia and facilitates gene transfer. J Virol. Apr. 2000;74(8):3852-8.

Zern et al., A novel SV40-based vector successfully transduces and expresses an alpha 1-antitrypsin ribozyme in a human hepatoma-derived cell line. Gene Ther. Jan. 1999;6(1):114-20.

Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zolotukhin et al., Production and purification of serotype 1, 2, and 5 recombinant adeno-associated viral vectors. Methods. Oct. 2002;28(2):158-67.

Adachi et al., Drawing a high-resolution functional map of adeno-associated virus capsid by massively parallel sequencing. Nat Commun 2014;5:3075. doi: 10.1038/ncomms4075.

Asokan et al., The AAV vector toolkit: poised at the clinical crossroads. Mol Ther. Apr. 2012;20(4):699-708. doi: 10.1038/mt.2011.287. Epub Jan. 24, 2012.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Buning et al., Receptor targeting of adeno-associated virus vectors. Gene Ther. Jul. 2003;10(14):1142-51.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Lux et al., Green fluorescent protein-tagged adeno-associated virus particles allow the study of cytosolic and nuclear trafficking. J Virol. Sep. 2005;79(18):11776-87.

Maguire et al., Directed evolution of adeno-associated virus for glioma cell transduction. J Neurooncol. Feb. 2010;96(3):337-47. doi:10.1007/s11060-009-9972-7. Epub Jul. 19, 2009.

Pertin et al., Efficacy and specificity of recombinant adeno-associated virus serotype 6 mediated gene transfer to drg neurons through different routes of delivery. Poster sessions. Eur J. Pain. 2009;13:574. Abstract 229.

Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.

Weismann, Approaches and Considerations Towards a Safe and Effective Adeno-Associated Virus Mediated Therapeutic Intervention for GM 1-Gangliosidosis: A Dissertation. University Massachusetts Medical School. Aug. 5, 2014, pp. 94-182.

\* cited by examiner

SEQUENCE LISTING

```
<160> NUMBER OF SEQ ID NOS: 64

<210> SEQ ID NO 1
<211> LENGTH: 736
<212> TYPE: PRT
<213> ORGANISM: Adeno associated virus 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495
```

```
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
Asp Asp Glu Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys Asn Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: Adeno associated virus 2

<400> SEQUENCE: 2

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
```

-continued

```
Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
                180                 185                 190

Ala Ala Pro Ser Gly Leu Gly Thr Asn Thr Met Ala Thr Gly Ser Gly
                195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560
```

```
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
            580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 3
<211> LENGTH: 724
<212> TYPE: PRT
<213> ORGANISM: Adeno associated virus 5

<400> SEQUENCE: 3

Met Ser Phe Val Asp His Pro Pro Asp Trp Leu Glu Glu Val Gly Glu
1               5                   10                  15
Gly Leu Arg Glu Phe Leu Gly Leu Glu Ala Gly Pro Pro Lys Pro Lys
            20                  25                  30
Pro Asn Gln Gln His Gln Asp Gln Ala Arg Gly Leu Val Leu Pro Gly
        35                  40                  45
Tyr Asn Tyr Leu Gly Pro Gly Asn Gly Leu Asp Arg Gly Glu Pro Val
    50                  55                  60
Asn Arg Ala Asp Glu Val Ala Arg Glu His Asp Ile Ser Tyr Asn Glu
65                  70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
            100                 105                 110
Leu Gly Lys Ala Val Phe Gln Ala Lys Lys Arg Val Leu Glu Pro Phe
        115                 120                 125
Gly Leu Val Glu Glu Gly Ala Lys Thr Ala Pro Thr Gly Lys Arg Ile
    130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Gly Pro Leu Gly Asp Asn Asn Gln Gly Ala
        195                 200                 205
```

```
Asp Gly Val Gly Asn Ala Ser Gly Asp Trp His Cys Asp Ser Thr Trp
    210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
                260                 265                 270
Phe Asp Phe Asn Arg Phe His Ser His Trp Ser Pro Arg Asp Trp Gln
            275                 280                 285
Arg Leu Ile Asn Asn Tyr Trp Gly Phe Arg Pro Arg Ser Leu Arg Val
290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gly Tyr Gly Tyr
            355                 360                 365
Ala Thr Leu Asn Arg Asp Asn Thr Glu Asn Pro Thr Glu Arg Ser Ser
370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
            435                 440                 445
Phe Asn Lys Asn Leu Ala Gly Arg Tyr Ala Asn Thr Tyr Lys Asn Trp
450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
            500                 505                 510
Asn Asn Leu Gln Gly Ser Asn Thr Tyr Ala Leu Glu Asn Thr Met Ile
            515                 520                 525
Phe Asn Ser Gln Pro Ala Asn Pro Gly Thr Thr Ala Thr Tyr Leu Glu
530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
Thr Thr Ala Pro Ala Thr Gly Thr Tyr Asn Leu Gln Glu Ile Val Pro
            580                 585                 590
Gly Ser Val Trp Met Glu Arg Asp Val Tyr Leu Gln Gly Pro Ile Trp
            595                 600                 605
Ala Lys Ile Pro Glu Thr Gly Ala His Phe His Pro Ser Pro Ala Met
610                 615                 620
```

-continued

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 4
<211> LENGTH: 736
<212> TYPE: PRT
<213> ORGANISM: Adeno associated virus 6

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

```
Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
```

```
                    690                 695                 700
Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                    725                 730                 735
```

<210> SEQ ID NO 5
<211> LENGTH: 736
<212> TYPE: PRT
<213> ORGANISM: Adeno associated virus 6.2

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
                275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335
```

-continued

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 6
<211> LENGTH: 737
<212> TYPE: PRT

<213> ORGANISM: Adeno associated virus 7

<400> SEQUENCE: 6

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asn Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Ala Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Ser Val Gly Ser Gly Thr Val Ala Ala Gly Gly
        195                 200                 205
Gly Ala Pro Met Ala Asp Asn Asn Glu Gly Ala Asp Gly Val Gly Asn
    210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Glu Thr Ala Gly Ser Thr Asn Asp Asn
            260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Ile Gln Val Phe Ser Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Ile Pro Gln Tyr Gly Tyr Leu Thr Leu Asn Asn
    370                 375                 380
Gly Ser Gln Ser Val Gly Arg Ser Ser Phe Tyr Cys Leu Glu Tyr Phe
385                 390                 395                 400
```

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
            485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
            565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
            725                 730                 735

Leu

<210> SEQ ID NO 7
<211> LENGTH: 738
<212> TYPE: PRT
<213> ORGANISM: Adeno associated virus 8

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

```
Lys Ala Asn Gln Gln Lys Gln Asp Gly Arg Gly Leu Val Leu Pro
             35                  40                  45
Gly Tyr Lys Tyr Leu Gly Pro Phe Asn Gly Leu Asp Lys Gly Glu Pro
 50                      55                  60
Val Asn Ala Ala Asp Ala Ala Leu Glu His Asp Lys Ala Tyr Asp
 65                  70                  75                  80
Gln Gln Leu Gln Ala Gly Asp Asn Pro Tyr Leu Arg Tyr Asn His Ala
                 85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
    195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ala Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Thr Thr Gly Gly Thr Ala Asn Thr Gln Thr Leu Gly
```

```
                450             455             460
        Phe Ser Gln Gly Gly Pro Asn Thr Met Ala Asn Gln Ala Lys Asn Trp
        465                 470                 475                 480

Leu Pro Gly Pro Cys Tyr Arg Gln Gln Arg Val Ser Thr Thr Thr Gly
                        485                 490                 495

Gln Asn Asn Asn Ser Asn Phe Ala Trp Thr Ala Gly Thr Lys Tyr His
                            500                 505                 510

Leu Asn Gly Arg Asn Ser Leu Ala Asn Pro Gly Ile Ala Met Ala Thr
                        515                 520                 525

His Lys Asp Asp Glu Glu Arg Phe Phe Pro Ser Asn Gly Ile Leu Ile
                    530                 535                 540

Phe Gly Lys Gln Asn Ala Ala Arg Asp Asn Ala Asp Tyr Ser Asp Val
        545                 550                 555                 560

Met Leu Thr Ser Glu Glu Glu Ile Lys Thr Thr Asn Pro Val Ala Thr
                            565                 570                 575

Glu Glu Tyr Gly Ile Val Ala Asp Asn Leu Gln Gln Gln Asn Thr Ala
                        580                 585                 590

Pro Gln Ile Gly Thr Val Asn Ser Gln Gly Ala Leu Pro Gly Met Val
                    595                 600                 605

Trp Gln Asn Arg Asp Val Tyr Leu Gln Gly Pro Ile Trp Ala Lys Ile
                    610                 615                 620

Pro His Thr Asp Gly Asn Phe His Pro Ser Pro Leu Met Gly Gly Phe
        625                 630                 635                 640

Gly Leu Lys His Pro Pro Pro Gln Ile Leu Ile Lys Asn Thr Pro Val
                        645                 650                 655

Pro Ala Asp Pro Pro Thr Thr Phe Asn Gln Ser Lys Leu Asn Ser Phe
                    660                 665                 670

Ile Thr Gln Tyr Ser Thr Gly Gln Val Ser Val Glu Ile Glu Trp Glu
                    675                 680                 685

Leu Gln Lys Glu Asn Ser Lys Arg Trp Asn Pro Glu Ile Gln Tyr Thr
                    690                 695                 700

Ser Asn Tyr Tyr Lys Ser Thr Ser Val Asp Phe Ala Val Asn Thr Glu
        705                 710                 715                 720

Gly Val Tyr Ser Glu Pro Arg Pro Ile Gly Thr Arg Tyr Leu Thr Arg
                        725                 730                 735

Asn Leu

<210> SEQ ID NO 8
<211> LENGTH: 736
<212> TYPE: PRT
<213> ORGANISM: Adeno associated virus 9

<400> SEQUENCE: 8

Met Ala Ala Asp Gly Tyr Leu Pro Asp Trp Leu Glu Asp Asn Leu Ser
        1               5                   10                  15

Glu Gly Ile Arg Glu Trp Trp Ala Leu Lys Pro Gly Ala Pro Gln Pro
                        20                  25                  30

Lys Ala Asn Gln Gln His Gln Asp Asn Ala Arg Gly Leu Val Leu Pro
                    35                  40                  45

Gly Tyr Lys Tyr Leu Gly Pro Gly Asn Gly Leu Asp Lys Gly Glu Pro
                50                  55                  60

Val Asn Ala Ala Asp Ala Ala Ala Leu Glu His Asp Lys Ala Tyr Asp
        65                  70                  75                  80

Gln Gln Leu Lys Ala Gly Asp Asn Pro Tyr Leu Lys Tyr Asn His Ala
```

```
                        85                  90                  95
Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510
```

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 9
<211> LENGTH: 738
<212> TYPE: PRT
<213> ORGANISM: Adeno associated virus rh.10

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile

-continued

```
            145                 150                 155                 160
        Gly Lys Lys Gly Gln Gln Pro Ala Lys Lys Arg Leu Asn Phe Gly Gln
                        165                 170                 175

Thr Gly Asp Ser Glu Ser Val Pro Asp Pro Gln Pro Ile Gly Glu Pro
                        180                 185                 190

Pro Ala Gly Pro Ser Gly Leu Gly Ser Gly Thr Met Ala Ala Gly Gly
                        195                 200                 205

Gly Ala Pro Met Ala Asp Asn Asn Glu Gly Ala Asp Gly Val Gly Ser
                210                 215                 220

Ser Ser Gly Asn Trp His Cys Asp Ser Thr Trp Leu Gly Asp Arg Val
        225                 230                 235                 240

Ile Thr Thr Ser Thr Arg Thr Trp Ala Leu Pro Thr Tyr Asn Asn His
                        245                 250                 255

Leu Tyr Lys Gln Ile Ser Asn Gly Thr Ser Gly Gly Ser Thr Asn Asp
                        260                 265                 270

Asn Thr Tyr Phe Gly Tyr Ser Thr Pro Trp Gly Tyr Phe Asp Phe Asn
                        275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Asn Phe Lys Leu Phe Asn
        305                 310                 315                 320

Ile Gln Val Lys Glu Val Thr Gln Asn Glu Gly Thr Lys Thr Ile Ala
                        325                 330                 335

Asn Asn Leu Thr Ser Thr Ile Gln Val Phe Thr Asp Ser Glu Tyr Gln
                        340                 345                 350

Leu Pro Tyr Val Leu Gly Ser Ala His Gln Gly Cys Leu Pro Pro Phe
                        355                 360                 365

Pro Ala Asp Val Phe Met Ile Pro Gln Tyr Gly Tyr Leu Thr Leu Asn
                        370                 375                 380

Asn Gly Ser Gln Ala Val Gly Arg Ser Ser Phe Tyr Cys Leu Glu Tyr
        385                 390                 395                 400

Phe Pro Ser Gln Met Leu Arg Thr Gly Asn Asn Phe Glu Phe Ser Tyr
                        405                 410                 415

Gln Phe Glu Asp Val Pro Phe His Ser Ser Tyr Ala His Ser Gln Ser
                        420                 425                 430

Leu Asp Arg Leu Met Asn Pro Leu Ile Asp Gln Tyr Leu Tyr Tyr Leu
                        435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
        465                 470                 475                 480

Leu Pro Gly Pro Cys Tyr Arg Gln Gln Arg Val Ser Thr Thr Leu Ser
                        485                 490                 495

Gln Asn Asn Asn Ser Asn Phe Ala Trp Thr Gly Ala Thr Lys Tyr His
                        500                 505                 510

Leu Asn Gly Arg Asp Ser Leu Val Asn Pro Gly Val Ala Met Ala Thr
                        515                 520                 525

His Lys Asp Asp Glu Glu Arg Phe Phe Pro Ser Ser Gly Val Leu Met
                        530                 535                 540

Phe Gly Lys Gln Gly Ala Gly Lys Asp Asn Val Asp Tyr Ser Ser Val
        545                 550                 555                 560

Met Leu Thr Ser Glu Glu Glu Ile Lys Thr Thr Asn Pro Val Ala Thr
                        565                 570                 575
```

```
Glu Gln Tyr Gly Val Ala Asp Asn Leu Gln Gln Gln Asn Ala Ala
                580                 585                 590

Pro Ile Val Gly Ala Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 10
<211> LENGTH: 738
<212> TYPE: PRT
<213> ORGANISM: Adeno associated virus rh.39

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205
```

-continued

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

```
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 11
<211> LENGTH: 736
<212> TYPE: PRT
<213> ORGANISM: Adeno associated virus rh.43

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Glu Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Pro Asn Thr Met Ala Ala Gly Gly Gly
        195                 200                 205

Ala Pro Met Ala Asp Asn Asn Glu Gly Ala Asp Gly Val Gly Ser Ser
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

```
Tyr Lys Gln Ile Ser Asn Gly Thr Ser Gly Ala Thr Asn Asp Asn
                260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Thr Thr Gly Gly Thr Ala Asn Thr Gln Thr Leu Gly Phe
    450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Thr Thr Thr Gly Gln
                485                 490                 495

Asn Asn Asn Ser Asn Phe Ala Trp Thr Ala Gly Thr Lys Tyr His Leu
            500                 505                 510

Asn Gly Arg Asn Ser Leu Ala Asn Pro Gly Ile Ala Met Ala Thr His
        515                 520                 525

Lys Asp Asp Glu Glu Arg Phe Phe Pro Val Thr Gly Ser Cys Phe Trp
    530                 535                 540

Gln Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
```

```
            675                 680                 685
Lys Glu Asn Ser Lys Arg Trp Asn Pro Glu Ile Gln Tyr Thr Ser Asn
    690                 695                 700

Tyr Tyr Lys Ser Thr Ser Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 12
<211> LENGTH: 736
<212> TYPE: PRT
<213> ORGANISM: Adeno associated virus  CSp3

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Ile Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Arg Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320
```

-continued

```
Arg Val Lys Glu Val Thr Asp Asn Asn Gly Val Lys Thr Ile Thr Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Arg Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Val
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 13
<211> LENGTH: 313
<212> TYPE: PRT
<213> ORGANISM: Homo sapiens

<400> SEQUENCE: 13

Met Thr Ser Cys His Ile Ala Glu Glu His Ile Gln Lys Val Ala Ile
1               5                   10                  15

Phe Gly Gly Thr His Gly Asn Glu Leu Thr Gly Val Phe Leu Val Lys
            20                  25                  30

His Trp Leu Glu Asn Gly Ala Glu Ile Gln Arg Thr Gly Leu Glu Val
        35                  40                  45

Lys Pro Phe Ile Thr Asn Pro Arg Ala Val Lys Lys Cys Thr Arg Tyr
    50                  55                  60

Ile Asp Cys Asp Leu Asn Arg Ile Phe Asp Leu Glu Asn Leu Gly Lys
65                  70                  75                  80

Lys Met Ser Glu Asp Leu Pro Tyr Glu Val Arg Arg Ala Gln Glu Ile
                85                  90                  95

Asn His Leu Phe Gly Pro Lys Asp Ser Glu Asp Ser Tyr Asp Ile Ile
            100                 105                 110

Phe Asp Leu His Asn Thr Thr Ser Asn Met Gly Cys Thr Leu Ile Leu
        115                 120                 125

Glu Asp Ser Arg Asn Asn Phe Leu Ile Gln Met Phe His Tyr Ile Lys
130                 135                 140

Thr Ser Leu Ala Pro Leu Pro Cys Tyr Val Tyr Leu Ile Glu His Pro
145                 150                 155                 160

Ser Leu Lys Tyr Ala Thr Thr Arg Ser Ile Ala Lys Tyr Pro Val Gly
                165                 170                 175

Ile Glu Val Gly Pro Gln Pro Gln Gly Val Leu Arg Ala Asp Ile Leu
            180                 185                 190

Asp Gln Met Arg Lys Met Ile Lys His Ala Leu Asp Phe Ile His His
        195                 200                 205

Phe Asn Glu Gly Lys Glu Phe Pro Pro Cys Ala Ile Glu Val Tyr Lys
    210                 215                 220

Ile Ile Glu Lys Val Asp Tyr Pro Arg Asp Glu Asn Gly Glu Ile Ala
225                 230                 235                 240

Ala Ile Ile His Pro Asn Leu Gln Asp Gln Asp Trp Lys Pro Leu His
                245                 250                 255

Pro Gly Asp Pro Met Phe Leu Thr Leu Asp Gly Lys Thr Ile Pro Leu
            260                 265                 270

Gly Gly Asp Cys Thr Val Tyr Pro Val Phe Val Asn Glu Ala Ala Tyr
        275                 280                 285

Tyr Glu Lys Lys Glu Ala Phe Ala Lys Thr Thr Lys Leu Thr Leu Asn
    290                 295                 300

Ala Lys Ser Ile Arg Cys Cys Leu His
305                 310

<210> SEQ ID NO 14
<211> LENGTH: 942
<212> TYPE: DNA
<213> ORGANISM: Homo sapiens

<400> SEQUENCE: 14
atgacttctt gtcacattgc tgaagaacat atacaaaagg ttgctatctt tggaggaacc      60
catgggaatg agctaaccgg agtatttctg gttaagcatt ggctagagaa tggcgctgag     120

```
attcagagaa cagggctgga ggtaaaacca tttattacta accccagagc agtgaagaag    180
tgtaccagat atattgactg tgacctgaat cgcattttg accttgaaaa tcttggcaaa     240
aaaatgtcag aagatttgcc atatgaagtg agaagggctc agaaataaa tcatttattt     300 ggtccaaaag acagtgaaga ttcctatgac attattttg accttcacaa caccacctct     360
aacatggggt gcactcttat tcttgaggat tccaggaata acttttaat tcagatgttt     420 cattacatta agacttctct ggctccacta ccctgctacg tttatctgat tgagcatcct    480
tccctcaaat atgcgaccac tcgttccata gccaagtatc ctgtgggtat agaagttggt    540
cctcagcctc aaggggttct gagagctgat atcttggatc aaatgagaaa aatgattaaa    600
catgctcttg attttataca tcatttcaat gaaggaaaag aatttcctcc ctgcgccatt    660
gaggtctata aaattataga aaagttgat taccccgg atgaaaatgg agaaattgct       720
gctatcatcc atcctaatct gcaggatcaa gactggaaac cactgcatcc tggggatccc    780
atgtttttaa ctcttgatgg aagacgatc ccactgggcg gagactgtac cgtgtacccc     840
gtgtttgtga atgaggccgc atattacgaa aagaaagaag cttttgcaaa gacaactaaa    900
ctaacgctca atgcaaaaag tattcgctgc tgtttacatt ag                       942
```

```
<210> SEQ ID NO 15
<211> LENGTH: 312
<212> TYPE: PRT
<213> ORGANISM: Mus Musculus

<400> SEQUENCE: 15

Met Thr Ser Cys Val Ala Lys Glu Pro Ile Lys Lys Ile Ala Ile Phe
1               5                   10                  15

Gly Gly Thr His Gly Asn Glu Leu Thr Gly Val Phe Leu Val Thr His
            20                  25                  30

Trp Leu Arg Asn Gly Thr Glu Val His Arg Ala Gly Leu Asp Val Lys
        35                  40                  45

Pro Phe Ile Thr Asn Pro Arg Ala Val Glu Lys Cys Thr Arg Tyr Ile
    50                  55                  60

Asp Cys Asp Leu Asn Arg Val Phe Asp Leu Glu Asn Leu Ser Lys Glu
65                  70                  75                  80

Met Ser Glu Asp Leu Pro Tyr Glu Val Arg Arg Ala Gln Glu Ile Asn
                85                  90                  95

His Leu Phe Gly Pro Lys Asn Ser Asp Asp Ala Tyr Asp Leu Val Phe
            100                 105                 110

Asp Leu His Asn Thr Thr Ser Asn Met Gly Cys Thr Leu Ile Leu Glu
        115                 120                 125

Asp Ser Arg Asn Asp Phe Leu Ile Gln Met Phe His Tyr Ile Lys Thr
    130                 135                 140

Cys Met Ala Pro Leu Pro Cys Ser Val Tyr Leu Ile Glu His Pro Ser
145                 150                 155                 160

Leu Lys Tyr Ala Thr Thr Arg Ser Ile Ala Lys Tyr Pro Val Gly Ile
                165                 170                 175

Glu Val Gly Pro Gln Pro His Gly Val Leu Arg Ala Asp Ile Leu Asp
            180                 185                 190

Gln Met Arg Lys Met Ile Lys His Ala Leu Asp Phe Ile Gln His Phe
        195                 200                 205

Asn Glu Gly Lys Glu Phe Pro Pro Cys Ser Ile Asp Val Tyr Lys Ile
    210                 215                 220

Met Glu Lys Val Asp Tyr Pro Arg Asn Glu Ser Gly Asp Met Ala Ala
```

Val Ile His Pro Asn Leu Gln Asp Gln Asp Trp Lys Pro Leu His Pro
225                 230                 235                 240

Gly Asp Pro Val Phe Val Ser Leu Asp Gly Lys Val Ile Pro Leu Gly
            245                 250                 255

Gly Asp Cys Thr Val Tyr Pro Val Phe Val Asn Glu Ala Ala Tyr Tyr
        275                 280                 285

Glu Lys Lys Glu Ala Phe Ala Lys Thr Thr Lys Leu Thr Leu Ser Ala
    290                 295                 300

Lys Ser Ile Arg Ser Thr Leu His
305                 310

<210> SEQ ID NO 16
<211> LENGTH: 939
<212> TYPE: DNA
<213> ORGANISM: Mus Musculus

<400> SEQUENCE: 16

| | | | | | |
|---|---|---|---|---|---|
| atgacctctt | gtgttgctaa | agaacctatt | aagaagattg | ccatctttgg | agggactcat | 60 |
| ggaaatgaac | tgaccggagt | gtttctagtt | actcactggc | taaggaatgg | cactgaagtt | 120 |
| cacagagcag | ggctggacgt | gaagccattc | attaccaatc | caagggcggt | ggagaagtgc | 180 |
| accagataca | ttgactgtga | cctgaatcgt | gttttgacc | ttgaaaatct | tagcaaagag | 240 |
| atgtctgaag | acttgccata | tgaagtgaga | agggctcaag | aaataaatca | tttatttggt | 300 |
| ccaaaaaata | gtgatgatgc | ctatgacctt | gttttgacc | ttcacaacac | cacttctaac | 360 |
| atgggttgca | ctcttattct | tgaggattcc | aggaatgact | ttttaattca | gatgtttcac | 420 |
| tatattaaga | cttgcatggc | tccattaccc | tgctctgttt | atctcattga | gcatccttca | 480 |
| ctcaaatatg | caaccactcg | ttccattgcc | aagtatcctg | ttggtataga | agttggtcct | 540 |
| cagcctcacg | gtgtccttag | agctgatatt | ttagaccaaa | tgagaaaaat | gataaaacat | 600 |
| gctcttgatt | ttatacagca | tttcaatgaa | ggaaaagaat | tcctccctg | ttctattgac | 660 |
| gtctataaaa | taatggagaa | agttgattat | ccaaggaatg | aaagtggaga | catggctgct | 720 |
| gttattcatc | ctaatctgca | ggatcaagac | tggaaaccat | tgcaccctgg | agatcctgtg | 780 |
| tttgtgtctc | ttgatggaaa | agttattcca | ctgggtggag | actgtaccgt | gtacccagtg | 840 |
| tttgtgaatg | aagctgcata | ttatgaaaaa | aagaagcat | ttgcaaagac | aacaaaacta | 900 |
| acactcagcg | caaaaagcat | ccgctccact | ttgcactaa | | | 939 |

<210> SEQ ID NO 17
<211> LENGTH: 465
<212> TYPE: DNA
<213> ORGANISM: Homo sapiens

<400> SEQUENCE: 17

| | | | | | |
|---|---|---|---|---|---|
| atggcgacga | aggccgtgtg | cgtgctgaag | ggcgacggcc | cagtgcaggg | catcatcaat | 60 |
| ttcgagcaga | aggaaagtaa | tggaccagtg | aaggtgtggg | gaagcattaa | aggactgact | 120 |
| gaaggcctgc | atggattcca | tgttcatgag | tttggagata | atacagcagg | ctgtaccagt | 180 |
| gcaggtcctc | actttaatcc | tctatccaga | aaacacggtg | ggccaaagga | tgaagagagg | 240 |
| catgttggag | acttgggcaa | tgtgactgct | gacaaagatg | gtgtggccga | tgtgtctatt | 300 |
| gaagattctg | tgatctcact | ctcaggagac | cattgcatca | ttggccgcac | actggtggtc | 360 |
| catgaaaaag | cagatgactt | gggcaaaggt | ggaaatgaag | aaagtacaaa | gacaggaaac | 420 |

```
gctggaagtc gtttggcttg tggtgtaatt gggatcgccc aataa            465
```

<210> SEQ ID NO 18
<211> LENGTH: 154
<212> TYPE: PRT
<213> ORGANISM: Homo sapiens

<400> SEQUENCE: 18

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

<210> SEQ ID NO 19
<211> LENGTH: 465
<212> TYPE: DNA
<213> ORGANISM: Mus Musculus

<400> SEQUENCE: 19

```
atggcgatga aagcggtgtg cgtgctgaag ggcgacggtc cggtgcaggg aaccatccac   60
ttcgagcaga aggcaagcgg tgaaccagtt gtgttgtcag gacaaattac aggattaact  120
gaaggccagc atgggttcca cgtccatcag tatggggaca atacacaagg ctgtaccagt  180
gcaggacctc attttaatcc tcactctaag aaacatggtg gcccggcgga tgaagagagg  240
catgttggag acctgggcaa tgtgactgct ggaaaggacg gtgtggccaa tgtgtccatt  300
gaagatcgtg tgatctcact ctcaggagag cattccatca ttggccgtac aatggtggtc  360
catgagaaac aagatgactt gggcaaaggt ggaaatgaag aaagtacaaa gactggaaat  420
gctgggagcc gcttggcctg tggagtgatt gggattgcgc agtaa              465
```

<210> SEQ ID NO 20
<211> LENGTH: 154
<212> TYPE: PRT
<213> ORGANISM: Mus Musculus

<400> SEQUENCE: 20

```
Met Ala Met Lys Ala Val Cys Val Leu Lys Gly Asp Gly Pro Val Gln
1               5                   10                  15

Gly Thr Ile His Phe Glu Gln Lys Ala Ser Gly Glu Pro Val Val Leu
            20                  25                  30

Ser Gly Gln Ile Thr Gly Leu Thr Glu Gly Gln His Gly Phe His Val
```

|  |  |  | 35 |  |  |  | 40 |  |  |  | 45 |  |  |
|---|---|---|---|---|---|---|---|---|---|---|---|---|---|

His Gln Tyr Gly Asp Asn Thr Gln Gly Cys Thr Ser Ala Gly Pro His
 50                      55                      60

Phe Asn Pro His Ser Lys Lys His Gly Gly Pro Ala Asp Glu Glu Arg
 65                      70                      75                      80

His Val Gly Asp Leu Gly Asn Val Thr Ala Gly Lys Asp Gly Val Ala
                 85                      90                      95

Asn Val Ser Ile Glu Asp Arg Val Ile Ser Leu Ser Gly Glu His Ser
             100                     105                     110

Ile Ile Gly Arg Thr Met Val Val His Glu Lys Gln Asp Asp Leu Gly
         115                     120                     125

Lys Gly Gly Asn Glu Glu Ser Thr Lys Thr Gly Asn Ala Gly Ser Arg
     130                     135                     140

Leu Ala Cys Gly Val Ile Gly Ile Ala Gln
145                     150

<210> SEQ ID NO 21
<211> LENGTH: 5243
<212> TYPE: DNA
<213> ORGANISM: Artificial Sequence
<220> FEATURE:
<223> OTHER INFORMATION: Synthetic Oligonucleotide

<400> SEQUENCE: 21

```
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg     120
aagatcaatt caattcacgc gtcgacattg attattgact agttattaat agtaatcaat     180
tacggggtca ttagttcata gcccatatat ggagttccgc gttacataac ttacggtaaa     240
tggcccgcct ggctgaccgc ccaacgaccc ccgcccattg acgtcaataa tgacgtatgt     300
tcccatagta acgccaatag ggactttcca ttgacgtcaa tgggtggata tttacggtaa     360
actgcccact tggcagtaca tcaagtgtat catatgccaa gtacgccccc tattgacgtc     420
aatgacggta aatggcccgc ctggcattat gcccagtaca tgaccttatg gactttcct      480
acttggcagt acatctacgt attagtcatc gctattacca tgtcgaggcc acgttctgct     540
tcactctccc catctccccc ccctccccac cccaattttt gtatttattt attttttaat     600
tattttgtgc agcgatgggg gcggggggg ggggcgcgcg ccaggcgggg cggggcgggg     660
cgaggggcgg ggcggggcga ggcgagagg tgcggcggca gccaatcaga gcggcgcgct     720
ccgaaagttt cctttatgg cgaggcggcg gcggcggcgg ccctataaaa agcgaagcgc     780
gcggcgggcg ggagcaagct ctagcctcga gaattcacgc gtggtacctc tagagcagag     840
ctcgtttagt gaaccgtcag ttcgaaatcg ccaccatggt gagcaagggc gaggagctgt     900
tcaccggggt ggtgcccatc ctggtcgagc tggacggcga cgtaaacggc cacaagttca     960
gcgtgtccgg cgaggcgag gcgatgcca cctacggcaa gctgaccctg aagttcatct    1020
gcaccaccgg caagctgccc gtgccctggc ccaccctcgt gaccaccctg acctacggcg    1080
tgcagtgctt cagccgctac cccgaccaca tgaagcagca cgacttcttc aagtccgcca    1140
tgcccgaagg ctacgtccag gagcgcacca tcttcttcaa ggacgacggc aactacaaga    1200
cccgcgccga ggtgaagttc gagggcgaca ccctggtgaa ccgcatcgag ctgaagggca    1260
tcgacttcaa ggaggacggc aacatcctgg gcacaagct ggagtacaac tacaacagcc    1320
acaacgtcta tatcatggcc gacaagcaga agaacggcat caaggtgaac ttcaagatcc    1380
```

```
gccacaacat cgaggacggc agcgtgcagc tcgccgacca ctaccagcag aacaccccca    1440
tcggcgacgg ccccgtgctg ctgcccgaca accactacct gagcacccag tccgccctga    1500
gcaaagaccc caacgagaag cgcgatcaca tggtcctgct ggagttcgtg accgccgccg    1560
ggatcactct cggcatggac gagctgtaca agtaagtaac aggtaagtgc gatcgctaat    1620
gcgggaaagc tcttattcgg gtgagatggg ctggggcacc atctgggggac cctgacgtga   1680
agtttgtcac tgactggaga actcggtttg tcgtctgttg cggggcggc agttatggcg     1740
gtgccgttgg gcagtgcacc cgtacctttg ggagcgcgcg ccctcgtcgt gtcgtgacgt    1800
cacccgttct gttggtacct gctgttgaca gtgagcgacg caatgtgact tcgctgacaa    1860
agctgtgaag ccacagatgg gctttgtcag cagtcacatt gcgctgccta ctgcctcgga    1920
cttcaagggc tcgagaattc agggtggggc cacctgccgg taggtgtgcg gtaggctttt    1980
ctccgtcgca ggacgcaggg ttcgggccta gggtaggctc tcctgaatcg acaggcgccg    2040
gacctctggc ggccgcaaca acgcgttcct gaccattcat cctctttctt tttcctgcag    2100
gcttgtggaa gaaatgggat ccgatctttt tccctctgcc aaaaattatg gggacatcat    2160
gaagcccctt gagcatctga cttctggcta ataaaggaaa tttattttca ttgcaatagt    2220
gtgttggaat tttttgtgtc tctcactcgg cctaggtaga taagtagcat ggcgggttaa    2280
tcattaacta caaggaaccc ctagtgatgg agttggccac tccctctctg cgcgctcgct    2340
cgctcactga ggccgggcga ccaaaggtcg cccgacgccc gggctttgcc cggcggcct    2400
cagtgagcga gcgagcgcgc agccttaatt aacctaattc actggccgtc gttttacaac    2460
gtcgtgactg ggaaaaccct ggcgttaccc aacttaatcg ccttgcagca catccccctt    2520
tcgccagctg gcgtaatagc gaagaggccc gcaccgatcg cccttcccaa cagttgcgca    2580
gcctgaatgg cgaatgggac gcgccctgta gcggcgcatt aagcgcggcg ggtgtggtgg    2640
ttacgcgcag cgtgaccgct acacttgcca gcgccctagc gcccgctcct ttcgctttct    2700
tcccttcctt tctcgccacg ttcgccggct ttccccgtca gctctaaat cggggggctcc    2760
ctttagggtt ccgatttagt gctttacggc acctcgaccc caaaaaactt gattagggtg    2820
atggttcacg tagtgggcca tcgccctgat agacggtttt tcgccctttg acgttggagt    2880
ccacgttctt taatagtgga ctcttgttcc aaactggaac aacactcaac cctatctcgg    2940
tctattcttt tgatttataa gggattttgc cgatttcggc ctattggtta aaaaatgagc    3000
tgatttaaca aaaatttaac gcgaatttta acaaaatatt aacgcttaca atttaggtgg    3060
cacttttcgg ggaaatgtgc gcggaacccc tatttgttta ttttctaaaa tacattcaaa    3120
tatgtatccg ctcatgagac aataaccctg ataaatgctt caataatatt gaaaaaggaa    3180
gagtatgagt attcaacatt tccgtgtcgc ccttattccc ttttttgcgg cattttgcct    3240
tcctgttttt gctcacccag aaacgctggt gaaagtaaaa gatgctgaag atcagttggg    3300
tgcacgagtg ggttacatcg aactggatct caacagcggt aagatccttg agagttttcg    3360
ccccgaagaa cgttttccaa tgatgagcac ttttaaagtt ctgctatgtg gcgcggtatt    3420
atcccgtatt gacgccgggc aagagcaact cggtcgccgc atacactatt ctcagaatga    3480
cttggttgag tactcaccag tcacagaaaa gcatcttacg gatggcatga cagtaagaga    3540
attatgcagt gctgccataa ccatgagtga taacactgcg gccaacttac ttctgacaac    3600
gatcggagga ccgaaggagc taaccgcttt tttgcacaac atggggatc atgtaactcg    3660
ccttgatcgt tgggaaccgg agctgaatga agccatacca aacgacgagc gtgacaccac    3720
gatgcctgta gcaatggcaa caacgttgcg caaactatta actggcgaac tacttactct    3780
```

-continued

```
agcttcccgg caacaattaa tagactggat ggaggcggat aaagttgcag gaccacttct    3840
gcgctcggcc cttccggctg gctggtttat tgctgataaa tctggagccg gtgagcgtgg    3900
gtctcgcggt atcattgcag cactggggcc agatggtaag ccctcccgta tcgtagttat    3960
ctacacgacg gggagtcagg caactatgga tgaacgaaat agacagatcg ctgagatagg    4020
tgcctcactg attaagcatt ggtaactgtc agaccaagtt tactcatata tactttagat    4080
tgatttaaaa cttcattttt aatttaaaag gatctaggtg aagatccttt ttgataatct    4140
catgaccaaa atcccttaac gtgagttttc gttccactga gcgtcagacc ccgtagaaaa    4200
gatcaaagga tcttcttgag atcctttttt tctgcgcgta atctgctgct tgcaaacaaa    4260
aaaaccaccg ctaccagcgg tggtttgttt gccggatcaa gagctaccaa ctcttttccc    4320
gaaggtaact ggcttcagca gagcgcagat accaaatact gttcttctag tgtagccgta    4380
gttaggccac cacttcaaga actctgtagc accgcctaca tacctcgctc tgctaatcct    4440
gttaccagtg gctgctgcca gtggcgataa gtcgtgtctt accgggttgg actcaagacg    4500
atagttaccg gataaggcgc agcggtcggg ctgaacgggg ggttcgtgca cacagcccag    4560
cttggagcga acgacctaca ccgaactgag atacctacag cgtgagctat gagaaagcgc    4620
cacgcttccc gaagggagaa aggcggacag gtatccggta agcggcaggg tcggaacagg    4680
agagcgcacg agggagcttc caggggggaaa cgcctggtat ctttatagtc ctgtcgggtt    4740
tcgccacctc tgacttgagc gtcgattttt gtgatgctcg tcaggggggc ggagcctatg    4800
gaaaaacgcc agcaacgcgg cctttttacg gttcctggcc ttttgctggc cttttgctca    4860
catgttcttt cctgcgttat cccctgattc tgtggataac cgtattaccg cctttgagtg    4920
agctgatacc gctcgccgca gccgaacgac cgagcgcagc gagtcagtga gcgaggaagc    4980
ggaagagcgc ccaatacgca aaccgcctct ccccgcgcgt tggccgattc attaatgcag    5040
ctggcacgac aggtttcccg actggaaagc gggcagtgag cgcaacgcaa ttaatgtgag    5100
ttagctcact cattaggcac cccaggcttt acactttatg cttccggctc gtatgttgtg    5160
tggaattgtg agcggataac aatttcacac aggaaacagc tatgaccatg attacgccag    5220
atttaattaa ggccttaatt agg                                            5243
```

<210> SEQ ID NO 22
<211> LENGTH: 108
<212> TYPE: DNA
<213> ORGANISM: Artificial Sequence
<220> FEATURE:
<223> OTHER INFORMATION: Synthetic Oligonucleotide

<400> SEQUENCE: 22

```
tgctgttgac agtgagcgac atcatcaatt ttccgagcag aactgtgaag ccacagatgg      60
gttctgctcg aaattgatga tgctgcctac tgcctcggac ttcaaggg                 108
```

<210> SEQ ID NO 23
<211> LENGTH: 106
<212> TYPE: DNA
<213> ORGANISM: Artificial Sequence
<220> FEATURE:
<223> OTHER INFORMATION: Synthetic Oligonucleotide

<400> SEQUENCE: 23

```
tgctgttgac agtgagcgac gcattaaagg atcctgactg actgtgaagc cacagatggg      60
tcagtcagtc ctttaatgcg ctgcctactg cctcggactt caaggg                   106
```

<210> SEQ ID NO 24
<211> LENGTH: 108
<212> TYPE: DNA
<213> ORGANISM: Artificial Sequence
<220> FEATURE:
<223> OTHER INFORMATION: Synthetic Oligonucleotide

<400> SEQUENCE: 24
tgctgttgac agtgagcgac tgcatggatt ctccatgttc atctgtgaag ccacagatgg      60
gatgaacatg gaatccatgc agctgcctac tgcctcggac ttcaaggg                 108

<210> SEQ ID NO 25
<211> LENGTH: 106
<212> TYPE: DNA
<213> ORGANISM: Artificial Sequence
<220> FEATURE:
<223> OTHER INFORMATION: Synthetic Oligonucleotide

<400> SEQUENCE: 25
tgctgttgac agtgagcgac aaggatgaag atcgaggcat gctgtgaagc cacagatggg      60
catgcctctc ttcatccttg ctgcctactg cctcggactt caaggg                   106

<210> SEQ ID NO 26
<211> LENGTH: 110
<212> TYPE: DNA
<213> ORGANISM: Artificial Sequence
<220> FEATURE:
<223> OTHER INFORMATION: Synthetic Oligonucleotide

<400> SEQUENCE: 26
tgctgttgac agtgagcgac gcaatgtgac ttcgctgaca aagctgtgaa gccacagatg      60
ggctttgtca gcagtcacat tgcgctgcct actgcctcgg acttcaaggg               110

<210> SEQ ID NO 27
<211> LENGTH: 108
<212> TYPE: DNA
<213> ORGANISM: Artificial Sequence
<220> FEATURE:
<223> OTHER INFORMATION: Synthetic Oligonucleotide

<400> SEQUENCE: 27
tgctgttgac agtgagcgac cgatgtgtct atcttgaaga ttctgtgaag ccacagatgg      60
gaatcttcaa tagacacatc ggctgcctac tgcctcggac ttcaaggg                 108

<210> SEQ ID NO 28
<211> LENGTH: 106
<212> TYPE: DNA
<213> ORGANISM: Artificial Sequence
<220> FEATURE:
<223> OTHER INFORMATION: Synthetic Oligonucleotide

<400> SEQUENCE: 28
tgctgttgac agtgagcgac ggtggaaatg atcagaaagt actgtgaagc cacagatggg      60
tactttcttc atttccaccg ctgcctactg cctcggactt caaggg                   106

<210> SEQ ID NO 29
<211> LENGTH: 110
<212> TYPE: DNA
<213> ORGANISM: Artificial Sequence
<220> FEATURE:
<223> OTHER INFORMATION: Synthetic Oligonucleotide

<400> SEQUENCE: 29

```
tgctgttgac agtgagcgac gctgtagaaa ttcgtatcct gatctgtgaa gccacagatg      60
ggatcaggat acatttctac agcgctgcct actgcctcgg acttcaaggg               110
```

<210> SEQ ID NO 30
<211> LENGTH: 106
<212> TYPE: DNA
<213> ORGANISM: Artificial Sequence
<220> FEATURE:
<223> OTHER INFORMATION: Synthetic Oligonucleotide

<400> SEQUENCE: 30

```
tgctgttgac agtgagcgag gtattaaact tgtcagaatt tagtgaagcc acagatgtaa     60
attctgacaa gtttaatacc ctgcctactg cctcggactt caaggg                   106
```

<210> SEQ ID NO 31
<211> LENGTH: 106
<212> TYPE: DNA
<213> ORGANISM: Artificial Sequence
<220> FEATURE:
<223> OTHER INFORMATION: Synthetic Oligonucleotide

<400> SEQUENCE: 31

```
tgctgttgac agtgagcgac gatgctctaa tcggttctat caagtgaagc cacagatgtt     60
gatagaacct tagagcatcg ctgcctactg cctcggactt caaggg                   106
```

<210> SEQ ID NO 32
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 32

```
cgaaatacat acttctttac attccatt                                        28
```

<210> SEQ ID NO 33
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 33

```
cgaatggaat gtaaagaagt atgtattt                                        28
```

<210> SEQ ID NO 34
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 34

```
cgaaacaaac accattgtca cactccatt                                       29
```

<210> SEQ ID NO 35
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 35

```
cgaatggagt gtgacaatgg tgtttgttt                                       29
```

```
<210> SEQ ID NO 36
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 36
cgaaatacat acttctttac attccaatac atacttcttt acattccaat acatacttct    60
ttacattcca tt                                                        72

<210> SEQ ID NO 37
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 37
cgaatggaat gtaaagaagt atgtattgga atgtaaagaa gtatgtattg gaatgtaaag    60
aagtatgtat tt                                                        72

<210> SEQ ID NO 38
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 38
cgaaacaaac accattgtca cactccaaca aacaccattg tcacactcca acaaacacca    60
ttgtcacact ccatt                                                     75

<210> SEQ ID NO 39
<211> LENGTH: 75
<212> TYPE: DNA
<213> ORGANISM: Artificial Sequence
<220> FEATURE:
<223> OTHER INFORMATION: Synthetic Oligonucleotide

<400> SEQUENCE: 39
cgaatggagt gtgacaatgg tgtttgttgg agtgtgacaa tggtgtttgt tggagtgtga    60
caatggtgtt tgttt                                                     75

<210> SEQ ID NO 40
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 40
cgaaatacat acttctttac attccaacaa acaccattgt cacactccat t              51

<210> SEQ ID NO 41
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 41
cgaatggagt gtgacaatgg tgtttgttgg aatgtaaaga agtatgtatt t              51
```

```
<210> SEQ ID NO 42
<211> LENGTH: 173
<212> TYPE: DNA
<213> ORGANISM: Artificial Sequence
<220> FEATURE:
<223> OTHER INFORMATION: Synthetic Oligonucleotide

<400> SEQUENCE: 42
ttcgaactcg agatacatac ttctttacat tccaatacat acttctttac attccaatac      60
atacttcttt acattccacc atggactagt acaaacacca ttgtcacact ccaacaaaca     120
ccattgtcac actccaacaa acaccattgt cacactccag cggccgcttc gaa            173

<210> SEQ ID NO 43
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 43
atcgggcccg actgcagttt cagcgtttg                                        29

<210> SEQ ID NO 44
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 44
cgcgggcccg actttacatt acacacaat                                        29

<210> SEQ ID NO 45
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 45
cgcgggcccg actgatgtgt gagagagac                                        29

<210> SEQ ID NO 46
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 46
cgcgggcccg actttcggcc tcccgaggc                                        29

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
tgaagctgaa gcctgtgatg                                                  20
```

```
<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
gagcacctga cagcattgaa                                                  20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
ctcagcaaca gctcatggaa                                                  20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
ttacttctgg caccacacca                                                  20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
tggtgtggtg ccagaagtaa                                                  20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
caacagatgg ctggcaacta                                                  20

<210> SEQ ID NO 53
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 53
tgggagtggc accttcca                                                    18

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 54
cgaccactac cagcagaaca                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
cttgtacagc tcgtccatgc                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
aatggcctca gaatgactgc                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
agtcgctttc acagccaaat                                              20

<210> SEQ ID NO 58
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 58
atgccaacac agtgctgtct gg                                           22

<210> SEQ ID NO 59
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 59
tgcttgctga tccacatctg ct                                           22

<210> SEQ ID NO 60
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 60
tggagtgtga caatggtgtt tg                                           22
```

```
<210> SEQ ID NO 61
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 61
aactatacaa cctactacct ca                                           22

<210> SEQ ID NO 62
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 62
agcctatcct ggattacttg aa                                           22

<210> SEQ ID NO 63
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 63
acagttcttc aactggcagc tt                                           22

<210> SEQ ID NO 64
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 64
ctctgtatcg ttccaatttt agtata                                       26
```

CNS TARGETING AAV VECTORS AND METHODS OF USE THEREOF

RELATED APPLICATIONS

This application is a continuation under 35 U.S.C. §120 of U.S. application Ser. No. 13/642,719, entitled "CNS TARGETING AAV VECTORS AND METHODS OF USE THEREOF" filed on Oct. 24, 2012, which is a National Stage Application of PCT/US2011/033616, filed on Apr. 22, 2011, and entitled "CNS Targeting AAV Vectors and Methods of Use Thereof," which claims priority under 35 U.S.C. §119(e) of U.S. provisional application U.S. Ser. No. 61/327,627, filed Apr. 23, 2010, and entitled "CNS Targeting AAV Vectors and Methods of Use Thereof," the entire contents of each which are incorporated herein by reference.

FIELD OF THE INVENTION

The invention in some aspects relates to recombinant adeno-associated viruses useful for targeting transgenes to CNS tissue, and compositions comprising the same, and methods of use thereof.

BACKGROUND OF THE INVENTION

Gene therapy has been investigated for delivery of therapeutic genes to the CNS cells for treatment of various CNS disease, e.g., Canavan disease, ALS, Parkinson disease (PD), etc. In some limited cases, therapeutic benefits have been observed using certain viruses, e.g., recombinant adenovirus (rAd), lentivirus (LV) and adeno-associated virus (AAV) to express a variety of therapeutic genes. AAV2 has been used in clinical trials for treatment of PD and Leber congenital amaurosis (an eye disease) and preliminary findings suggest symptomatic improvements without noticeable toxicity [2-4].

However, AAV-based gene therapy to treat CNS disease has still faced major obstacle. Many CNS diseases including, for example, ALS affect both cortical and spinal motor neurons that are distributed in a very broad area in the CNS. It has frequently been the case that viral vectors injected into CNS tissue transduce cells only in the vicinity of the injection site, have a very limited spread and generally have not impacted the lifespan in CNS disease animal models [See, e.g., Ref. 5]. Still, a variety of other viral administration methods have been tested. One example, involves injecting the viral particles into skeletal muscle and allowing the nerve terminals to internalize the viral genome, which is then retrogradely transported back to the spinal motor neurons. This approach has shown some positive results in certain mouse models [68]. However, to apply this method in larger mammals, like adult humans, would be impractical. Overall, the transduction efficiency observed with muscle injection is relatively low. Some investigators have tried to improve this efficiency by modifying viral capsid proteins with the nerve binding domains of tetanus toxin or botulinum toxin. These efforts have not been fruitful due to various technical difficulties. Another problem with muscle injection in larger mammals, is a need for large doses, which is technically challenging, expensive, and carries a high risk for adverse effects, ranging from immune reaction to transduction of unintended cells (e.g., germ cells).

Another method that has been evaluated for delivering transgenes into motor neurons is to inject the virus into large nerves, which maximizes that exposure of the virus to motor axons, allowing the motor neurons to internalize the viral genome and retrogradely transport them back to the cell body. This method has been demonstrated to be more efficient in transducing motor neurons than muscle injection [9]. Still, to implement a method such as this in larger mammals would be challenging.

SUMMARY OF THE INVENTION

Aspects of the invention, are based on the discovery of recombinant AAVs that achieve wide-spread distribution throughout CNS tissue of a subject. In some embodiments, the rAAVs spread throughout CNS tissue following direct administration into the cerebrospinal fluid (CSF), e.g., via intrathecal and/or intracerebral injection. In other embodiments, the rAAVs cross the blood-brain-barrier and achieve wide-spread distribution throughout CNS tissue of a subject following intravenous administration. In some aspects the invention relates to rAAVs having distinct central nervous system tissue targeting capabilities (e.g., CNS tissue tropisms), which achieve stable and nontoxic gene transfer at high efficiencies. Methods involving co-administration via intrathecal and intracerebral (e.g., intraventricular) injection of rAAVs are provided in some aspects. For example, it has been discovered that rAAVs having a capsid protein comprising a sequence as set forth in SEQ ID NO: 9 achieves wide-spread distribution following intrathecal injection throughout the CNS, and thus, are particularly useful for treating CNS-associated disorders such as, for example, ALS. In still further aspects of the invention methods are provided for treating Canavan disease.

According to some aspects of the invention, methods for delivering a transgene to CNS tissue in a subject are provided. In some embodiments, the methods comprise administering an effective amount of a rAAV by intrathecal administration, wherein the rAAV comprises (i) a capsid protein comprising a sequence as set forth in SEQ ID NO: 9 and (ii) a nucleic acid comprising a promoter operably linked with a transgene. In some embodiments, the methods further comprise administering an effective amount of the rAAV by intracerebral administration. In some embodiments, the methods comprise administering an effective amount of a rAAV by intrathecal administration and by intracerebral administration, wherein the rAAV infects cells of CNS tissue in the subject and comprises a nucleic acid comprising a promoter operably linked with a transgene. In certain embodiments, the intracerebral administration is an intraventricular administration. In one embodiment, the intraventricular administration is an administration into a ventricular region of the forebrain of the subject. In certain embodiments, the intrathecal administration is in the lumbar region of the subject. In some embodiments, the dose of the rAAV for intrathecal administration is in a range of $10^{10}$ genome copies/subject to $10^{11}$ genome copies/subject. In some embodiments, the dose of the rAAV for intrathecal administration is in a range of $10^{11}$ genome copies/subject to $10^{12}$ genome copies/subject. In some embodiments, the dose of the rAAV for intrathecal administration is in a range of $10^{12}$ genome copies/subject to $10^{13}$ genome copies/subject. In some embodiments, the dose of the rAAV for intrathecal administration is in a range of $10^{13}$ genome copies/subject to $10^{14}$ genome copies/subject. In some embodiments, the dose of the rAAV for intracerebral administration is in a range of $10^{10}$ genome copies/subject to $10^{11}$ genome copies/subject. In some embodiments, the dose of the rAAV for intracerebral administration is in a range of $10^{11}$ genome copies/subject to $10^{12}$ genome copies/subject. In some embodiments, the dose of the rAAV for intracerebral administration is in a range of $10^{12}$ genome copies/subject to $10^{13}$ genome copies/subject. In some embodiments, the dose of the rAAV for intracerebral administration is in a range of $10^{13}$ genome copies/subject to $10^{14}$ genome copies/subject. In some embodiments, the dose of the rAAV for intracerebral or intrathecal administration is formulated for injection of a volume in a range of 1 µl to 10 µl. In some embodiments, the dose of the rAAV for intracerebral or intrathecal administration is formulated for injection of a volume in a range of 10 µl to 100 µl. In some embodiments, the rAAV for the intracerebral or intrathecal administration is formulated for injection of a volume in a range of 100 µl to 1 ml. In some embodiments, the rAAV for the intracerebral or intrathecal administration is formulated for injection of a volume of 1 ml or more. In some embodiments, the transgene encodes a reporter protein. In certain embodiments, the reporter protein is a fluorescent protein, an enzyme that catalyzes a reaction yielding a detectable product, or a cell surface antigen. In certain embodiments, the enzyme is a luciferase, a beta-glucuronidase, a chloramphenicol acetyltransferase, an aminoglycoside phosphotransferase, an aminocyclitol phosphotransferase, or a Puromycin N-acetyl-tranferase. In some embodiments, the transgene is a CNS-associated gene. In some embodiments, the CNS-associated gene is neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxlase (TH), GTP-cyclohydrolase (GTPCH), amino acid decorboxylase (AADC) or aspartoacylase (ASPA). In some embodiments, the transgene encodes an inhibitory RNA that binds specifically to SOD1 mRNA and inhibits expression of SOD1 in the subject. In some embodiments, the inhibitory RNA is an antisense RNA, a shRNA or a miRNA. In some embodiments, the inhibitory RNA has a sequence as set forth in SEQ ID NO: 26. Thus, according to some aspects of the invention a nucleic acid comprising a sequence as set forth in SEQ ID NO: 26 is provided. In some embodiments, a nucleic acid comprising a promoter operably linked with a region having a sequence as set forth in SEQ ID NO: 26 is provided.

In further aspects of the invention a recombinant AAV comprising a nucleic acid comprising a sequence as set forth in SEQ ID NO: 26 is provided. In some aspects of the invention a recombinant AAV comprising a nucleic acid comprising a promoter operably linked with a region having a sequence as set forth in SEQ ID NO: 26 is provided. In some embodiments the recombinant AAV further comprises a capsid protein comprising a sequence as set forth in SEQ ID NO: 9.

According to some aspects of the invention, methods for treating amyotrophic lateral sclerosis (ALS) in a subject in need thereof are provided. In some embodiments, the methods comprise administering an effective amount of a rAAV to CNS tissue of the subject, wherein the rAAV comprises (i) a capsid protein comprising a sequence as set forth in SEQ ID NO: 9 and (ii) a nucleic acid comprising a promoter operably linked with a region encoding an inhibitory RNA that binds specifically to SOD1 mRNA and inhibits expression of SOD1 in the subject. In some embodiments, the inhibitory RNA is an antisense RNA, a shRNA or a miRNA. In some embodiments, the inhibitory RNA has a sequence as set forth in SEQ ID NO: 26. In some embodiments, the methods comprise administering an effective amount of a rAAV to the subject, wherein the rAAV comprises a nucleic acid comprising a promoter operably linked with a region encoding a sequence as set forth in SEQ ID NO: 26 and wherein the rAAV infects cells of CNS tissue in the subject.

According to some aspects of the invention, methods for delivering a transgene to a CNS tissue in a subject are provided that comprise administering an effective amount of a rAAV by intravenous administration, wherein the rAAV infects cells of CNS tissue in the subject and comprises a nucleic acid comprising a promoter operably linked with a transgene. In some embodiments, the dose of the rAAV for intravenous administration is in a range of $10^{10}$ genome copies/subject to $10^{11}$ genome copies/subject. In some embodiments, the dose of the rAAV for intravenous administration is in a range of $10^{11}$ genome copies/subject to $10^{12}$ genome copies/subject. In some embodiments, the dose of the rAAV for intravenous administration is in a range of $10^{12}$ genome copies/subject to $10^{13}$ genome copies/subject. In some embodiments, the dose of the rAAV for intravenous administration is in a range of $10^{13}$ genome copies/subject to $10^{14}$ genome copies/subject. In some embodiments, the dose of the rAAV for intravenous administration is in a range of $10^{14}$ genome copies/subject to $10^{15}$ genome copies/subject. In some embodiments, the dose of the rAAV for intravenous administration is in a range of $10^{10}$ genome copies/kg to $10^{11}$ genome copies/kg. In some embodiments, the dose of the rAAV for intravenous administration is in a range of $10^{11}$ genome copies/kg to $10^{12}$ genome copies/kg. In some embodiments, the dose of the rAAV for intravenous administration is in a range of $10^{12}$ copies/kg to $10^{13}$ genome copies/kg. In some embodiments, the dose of the rAAV for intravenous administration is in a range of $10^{13}$ genome copies/kg to $10^{14}$ genome copies/kg.

According to some aspects of the invention, methods for delivering a transgene to a CNS tissue in a subject are provided that comprise administering to the subject an effective amount of a rAAV that comprises (i) a capsid protein having a sequence as set forth in any one of SEQ ID NO: 10 to 12 and (ii) a nucleic acid comprising a promoter operably linked with a transgene. In some embodiments, the methods comprise administering to the subject an effective amount of a rAAV comprising a transgene to a subject, wherein the rAAV comprises a capsid protein of a AAV serotype, or serotype variant, selected from the group consisting of: AAV1, AAV2, AAV5, AAV6, AV6.2, AAV7, AAV8, AAV9, rh.10, rh.39, rh.43 and CSp3, and wherein: (a) if the AAV serotype is AAV 1, the administration route is not intracerebral, intramuscular, intranerve, or intraventricular and/or the subject is not a mouse, rat or feline; (b) if the AAV serotype is AAV2, the administration route is not intracerebral or intraventricular administration and/or the subject is not a rat, mouse, feline, marmoset, or macaque; (c) if the AAV serotype is AAV5, the administration route is not intracerebral or intraventricular administration and/or the subject is not a rat, mouse, or marmoset; (d) if the AAV serotype is AAV6, the subject is not a mouse; (e) if the AAV serotype is AAV7, the administration route is not intracerebral administration and/or the subject is not a mouse or macaque; (f) if the AAV serotype is AAV8, the administration route is not intracerebral, intraperitoneal, or intravascular administration and/or the subject is not a mouse or macaque; (g) if the AAV serotype is AAV9, the administration route is not intracerebral or intravascular administration and/or the subject is not a rat or mouse; and (h) if the AAV serotype is AAVrh.10, the administration route is not intracerebral or intravascular administration and/or the subject is not a rat or mouse. In some embodiments, the AAV serotype, or serotype variant, is selected from AAV1, AAV6, AAV7, rh.39, rh.43, and CSp3, and the administration route is intravascular administration. In some embodiments, the AAV serotype is AAV7 and the administration route is intravascular administration. In some embodiments, the CNS tissue is selected from cortex, hippocampus, thalamus, hypothalamus, cerebellum, brain stem, cervical spinal cord, thoracic spinal cord, and lumbar spinal cord. In some embodiments, the transgene encodes a reporter protein. In certain embodiments, the reporter protein is a fluorescent protein, an enzyme that catalyzes a reaction yielding a detectable product, or a cell surface antigen. In certain embodiments, the enzyme is a luciferase, a beta-glucuronidase, a chloramphenicol acetyltransferase, an aminoglycoside phosphotransferase, an aminocyclitol phosphotransferase, or a Puromycin N-acetyl-tranferase. In some embodiments, the transgene is a CNS-associated gene. In certain embodiments, the CNS-associated gene is neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxlase (TM, GTP-cyclohydrolase (GTPCH), amino acid decorboxylase (AADC) or aspartoacylase (ASPA). In some embodiments, the rAAV is administered by intravenous injection.

According to some aspects of the invention a rAAV that comprises (i) a capsid protein having a sequence as set forth in any one of SEQ ID NO: 10 to 12 and (ii) a nucleic acid comprising a promoter operably linked with a CNS-associated gene is provided. In certain embodiments, the CNS-associated gene is neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TH), GTP-cyclohydrolase (GTPCH), amino acid decorboxylase (AADC) or aspartoacylase (ASPA). In some embodiments, mRNA expressed from the CNS-associated gene comprises a miRNA binding site of a miRNA that is preferentially expressed in non-CNS tissue. In certain embodiments, the miRNA binding site is a binding site for miR-122. In certain embodiments, the miRNA binding site is a binding site for miR-1. In some embodiments, mRNA expressed from the CNS-associated gene does not comprise a miRNA binding site of a miRNA that is preferentially expressed in CNS tissue. In some embodiments, the promoter is a CNS tissue specific promoter. In certain embodiments, the promoter is a promoter of a gene selected from: neuronal nuclei (NeuN), glial fibrillary acidic protein (GFAP), adenomatous polyposis coli (APC), and ionized calcium-binding adapter molecule 1 (Iba-1).

According to some aspects of the invention, a composition comprising a rAAV that comprises (i) a capsid protein having a sequence as set forth in SEQ ID NO: 10 to 12 and (ii) a nucleic acid comprising a promoter operably linked with a CNS-associated gene is provided. In certain embodiments the composition further comprises a pharmaceutically acceptable carrier. According to some aspects of the invention, a kit comprising a container housing the composition is provided. In some embodiments, the container is a sealed vial or ampule. In some embodiments, the container is a syringe.

According to some aspects of the invention, an isolated mammalian cell is provided that comprises a nucleic acid encoding a capsid protein having a sequence as set forth in any one of SEQ ID NO: 10 to 12 and a rAAV vector comprising a nucleic acid encoding a CNS-disease associated gene. In some embodiments, the isolated mammalian cell further comprises an AAV helper function vector. In some embodiments, isolated mammalian cell further comprises an accessory function vector. In certain embodiments, the CNS-associated gene is neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxlase (TH), GTP-cyclohydrolase (GTPCH), amino acid decorboxylase (AADC) or aspartoacylase (ASPA).

According to further aspects of the invention, a method for treating Canavan disease in a subject in need thereof is provided. In some embodiments, the methods comprise administering an effective amount of a rAAV to CNS tissue of the subject, wherein the rAAV comprises (i) a capsid protein other than a capsid protein of AAV serotype 2 and (ii) a nucleic acid comprising a promoter operably linked with a region encoding aspartoacylase (ASPA). Any of the rAAV serotypes disclosed herein may be used in the methods for treating Canavan disease. In some embodiments, the rAAV has a capsid protein having an amino acid sequence as set forth in SEQ ID NO: 8 or 9 or a variant thereof. In some embodiments, administering is performed intrathecally or intracerebrally. In some embodiments, administering is performed intravascularly.

In some embodiments, the methods comprise administering an effective amount of a rAAV to CNS tissue of the subject by a route other than intracerebral administration, wherein the rAAV comprises a nucleic acid comprising a promoter operably linked with a region encoding aspartoacylase (ASPA). In some embodiments, the methods comprise administering an effective amount of a rAAV to CNS tissue of the subject, wherein the rAAV comprises a nucleic acid comprising a promoter operably linked with a region encoding aspartoacylase (ASPA); and evaluating kidney function in the subject at least once after the administration. Any suitable method known in the art may be used to evaluate a subject's kidney function. The evaluation may involve, for example, an examination of blood or urine urea nitrogen levels, an examination of blood or urine creatinine levels, a creatinine clearance rate examination, a glomerular filtration rate examination, a filtration fraction examination, a renal plasma flow examination, an ultrasound examination, a microscopic examination of a kidney tissue biopsy or any other suitable kidney function test. It should be appreciated that in some embodiments an improvement in a subject's kidney function following treatment with an rAAV-mediated gene therapy is indicative of efficacy of the gene therapy for treating Canavan disease.

In some embodiments, the methods comprise administering an effective amount of a rAAV to CNS tissue of the subject, wherein the rAAV comprises a nucleic acid comprising a promoter operably linked with a region encoding aspartoacylase (ASPA); and evaluating vision of the subject at least once after the administration. Any suitable method known in the art may be used to evaluate a subject's vision. The evaluation may involve, for example, an external examination of the eye, a visual acuity examination, an examination of pupil function, a retinal examination, an ocular motility examination, an intraocular pressure test, or an ophthalmoscopic examination. The evaluation may involve a determination regarding a subject's ability to discriminate colors, objects or shapes or the ability of a subject to discern colors, objects or shapes from a particular distance. It should be appreciated that in some embodiments an improvement in a subject's vision following treatment with an rAAV-mediated gene therapy is indicative of efficacy of the gene therapy for treating Canavan disease.

In some embodiments, the nucleic acid expresses an aspartoacylase (ASPA) mRNA comprising one or more miRNA binds sites for one or more miRNAs that are more abundant in one or more non-CNS tissues in comparison to CNS tissue. Accordingly, in some embodiments, the mRNA is targeted for degradation by an miRNA in one or more non-CNS tissues. In some embodiments, the one or more non-CNS tissue is not kidney tissue or retinal tissue. In some embodiments, the one or more miRNAs that are more abundant in non-CNS tissues in comparison to CNS tissue are at least two-fold, at least three-fold, at least four-fold, at least five-fold, or at least ten-fold more abundant. MiRNAs that are more abundant in non-CNS tissue versus CNS tissue are known in the art. For example, one study discloses the expression levels of more than three-hundred different human miRNAs in 40 different tissues, including CNS tissue, kidney tissue. (See Liang Y, et al., *Characterization of microRNA expression profiles in normal human tissues*. BMC Genomics. 2007 Jun. 12; 8:166, the contents of which relating to miRNAs are incorporated herein by reference). Thus, in some embodiments, the skilled artisan could readily select (e.g., based on data such as are disclosed in Liang et al.) a suitable miRNA that is more abundant in non-CNS tissue and incorporate a binding site for that miRNA into the encoded mRNA.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

Forty μm thick cryosections were processed for double immunohistochemical staining for EGFP (green) and Neurons (NeuN, red). Bars represent 75 μm.

Figure 23:
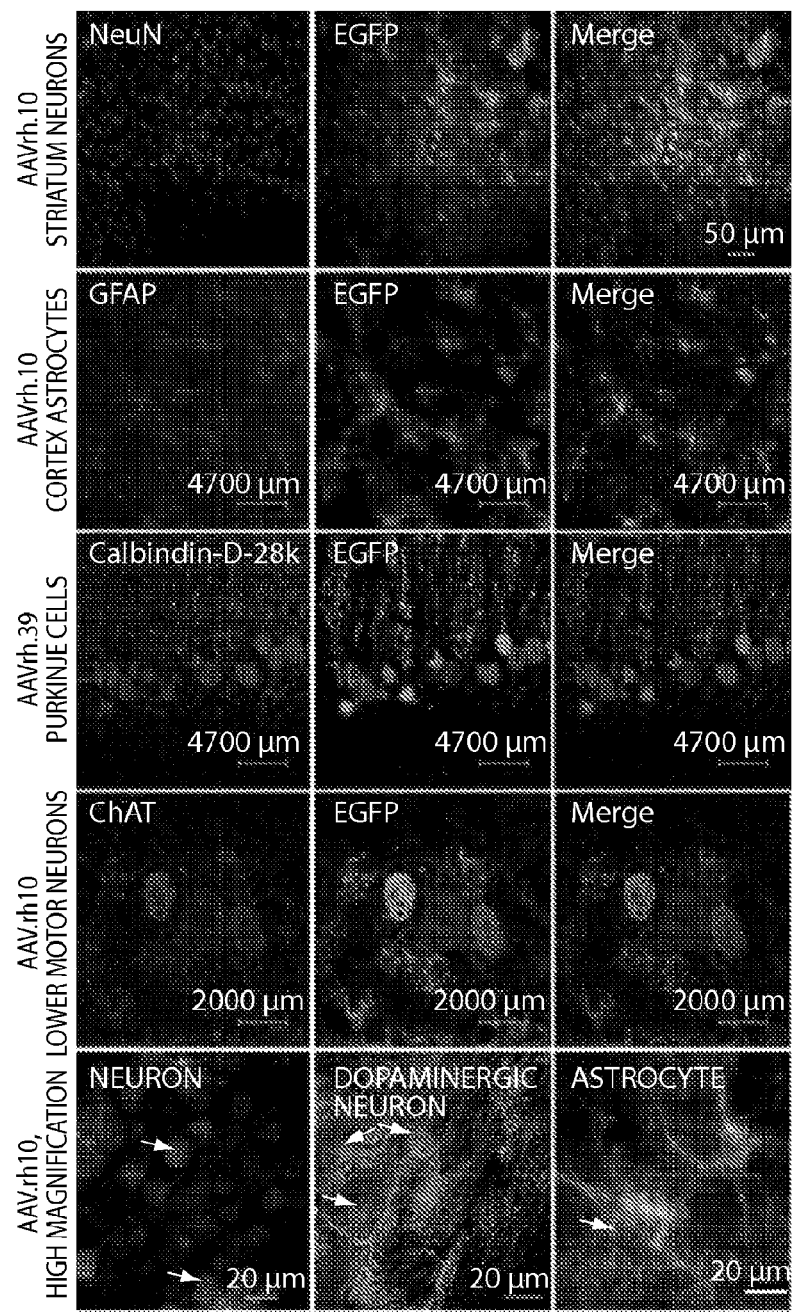

FIG. 23 depicts confocal microscopic analysis of the transduced cell types in mouse CNS after systemic delivery of rAAVs to P1 neonates. The 40 μm thick brain and spinal cord sections of the animals treated with different rAAVs were co-strained against anti-EGFP antibody and cell-type specific markers. Anti-NeuN was used to stain neuronal cells; anti-GFAP was used to stain astrocytes; anti-Calbindin was used to stain Purkinje cells; anti-ChAT was used to stain motor neurons; anti-DARPP was used to stain dopaminergic neurons in the substantia nigra. All rAAVs were examined, but for each cell type, only one representative picture was shown here.

Figure 24:
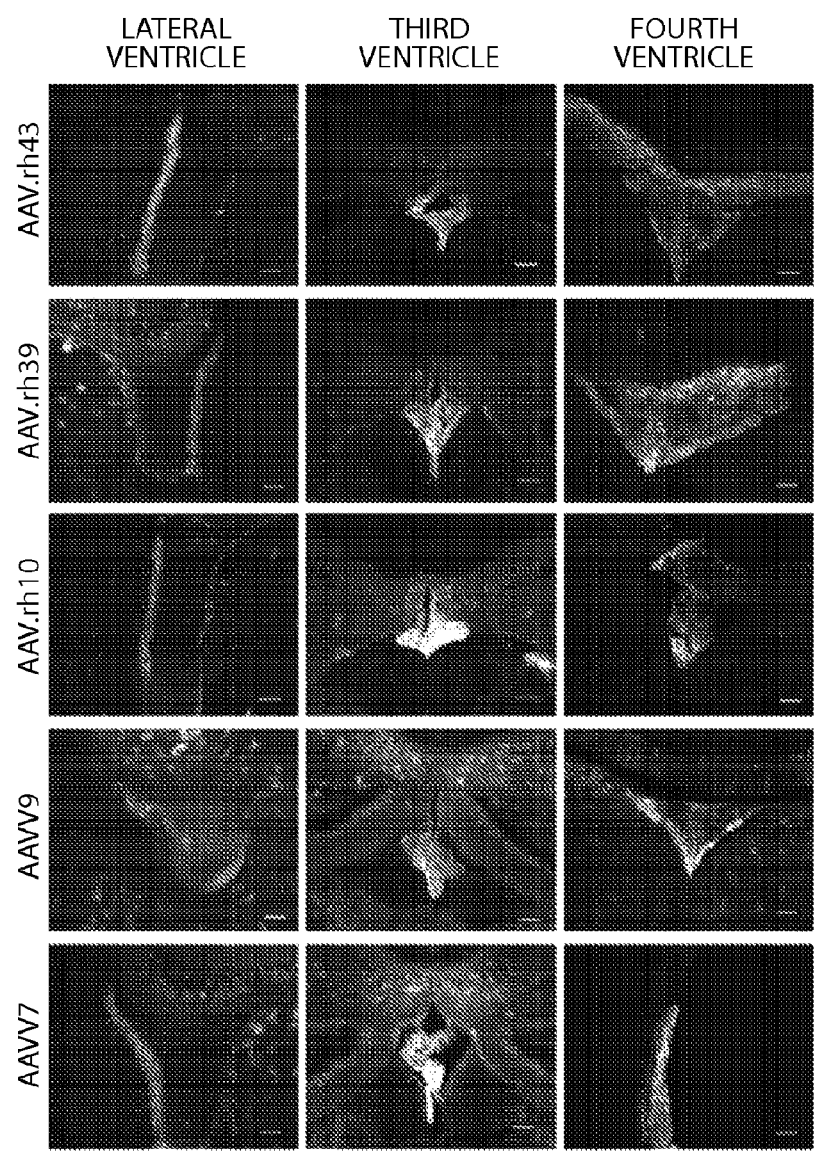

FIG. 24 depicts a transduction of the brain ventricular structures by intravascularly delivered rAAVs. Neonatal pups received $4 \times 10^{11}$ GCs of rAAVs at P1 and were necropsied 21 days after injection. The choroid plexuses in different ventricles were well preserved during tissue process. Forty μm thick cryosections were stained against anti-EGFP antibody. Bars represent 100 μm.

Figure 25A:
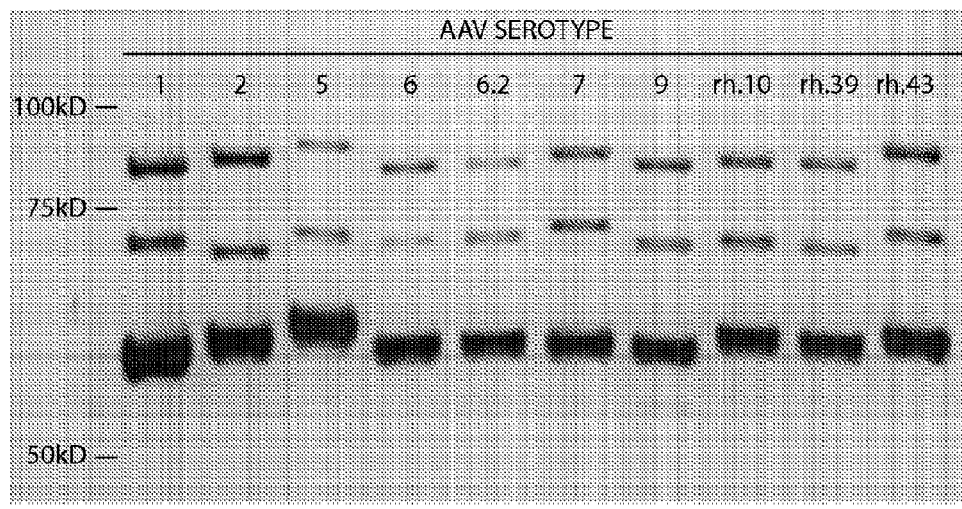
Figure 25B:
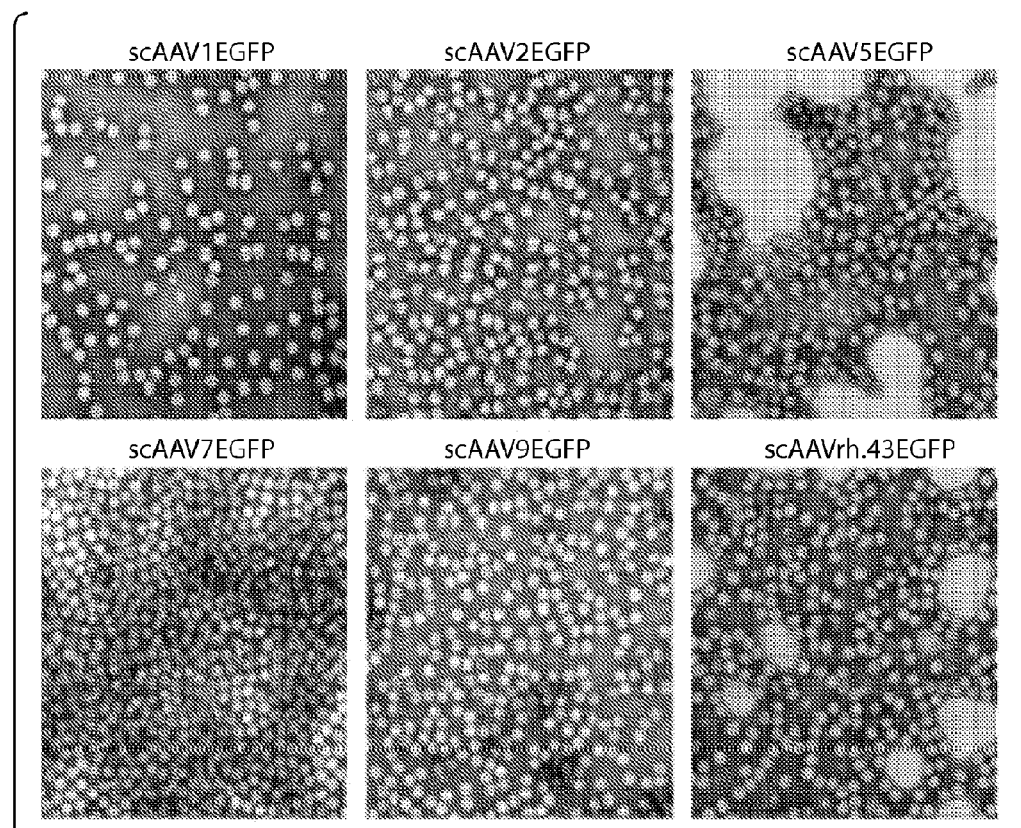

FIG. 25 depicts an analysis of purity and morphological integrity of rAAV vectors. A. Silver stained SDS-Page analysis of CsCl gradient purified rAAVCBEGFP vectors used in this study. Approximately 1.5×1010 virus particles each of rAAVs 1, 2, 5, 6, 6.2, 7, 9, rh10, rh39 and rh43 were loaded in the corresponding lane. B. Transmission electron microscopy of negative stained recombinant AAV virions. rAAV virions were spread on a freshly prepared carbon coated-Formvar support film and stained with 1% uranyl acetate for transmission microscopy. The images of virus particles from representative vector lots were taken at 92,000× and presented.

Figure 26:
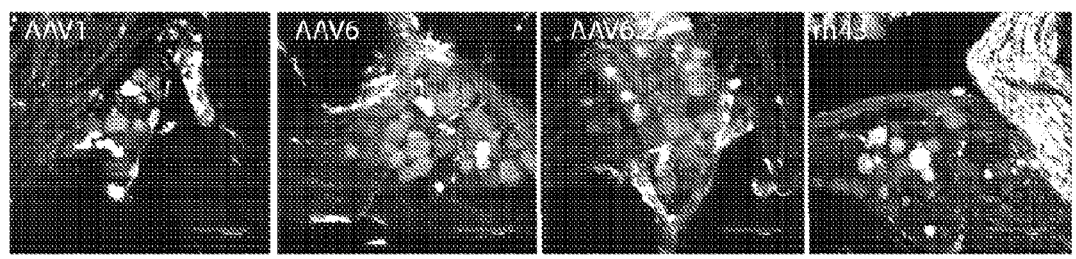

FIG. 26 depicts a transduction of neonatal mouse dorsal root ganglia by systemically delivered rAAVs 1, 6, 6.2 and rh43. Neonatal pups received $4 \times 10^{11}$ GCs of rAAVs at P1 were necropsied 21 days after injection. Forty μm thick cryosections were stained against anti-EGFP antibody. Bars represent 75 μm.

FIG. 27 depicts a transduction of the brain capillary vessels by intravascularly delivered rAAVs. Neonatal pups received $4 \times 10^{11}$ GCs of rAAVs at P1 were necropsied 21 days after injection. Forty μm thick cryosections of the brains were stained against: (a) anti-EGFP antibody (AAV1, AAV6, AAV6.2, AAV7, AAV9, AAVrh.10, AAVrh.39 and AAVrh.43); (b) anti-EGFP and anti-CD34 antibodies (rh.10 only). Bars represent 100 μm.

Figure 28:
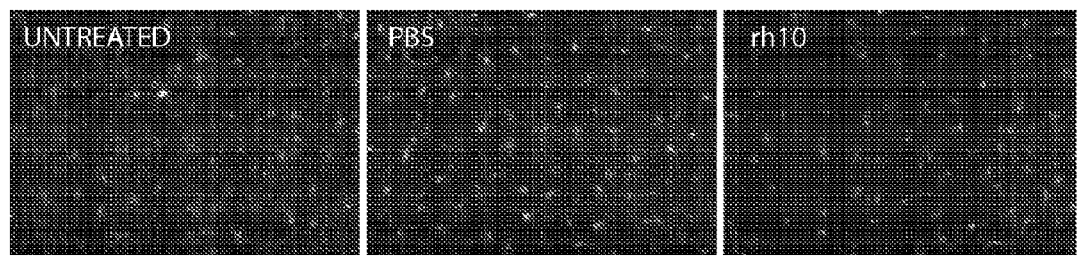

FIG. 28 depicts an evaluation of microgliosis in mice brain after systemic delivery of rAAVs to P1 neonates. The 40 μm thick brain sections of the animals treated with different rAAVs were co-strained against anti-EGFP antibody and anti-Ma-1. Only the staining result of rAAVrh.10 was shown.

Figure 29:
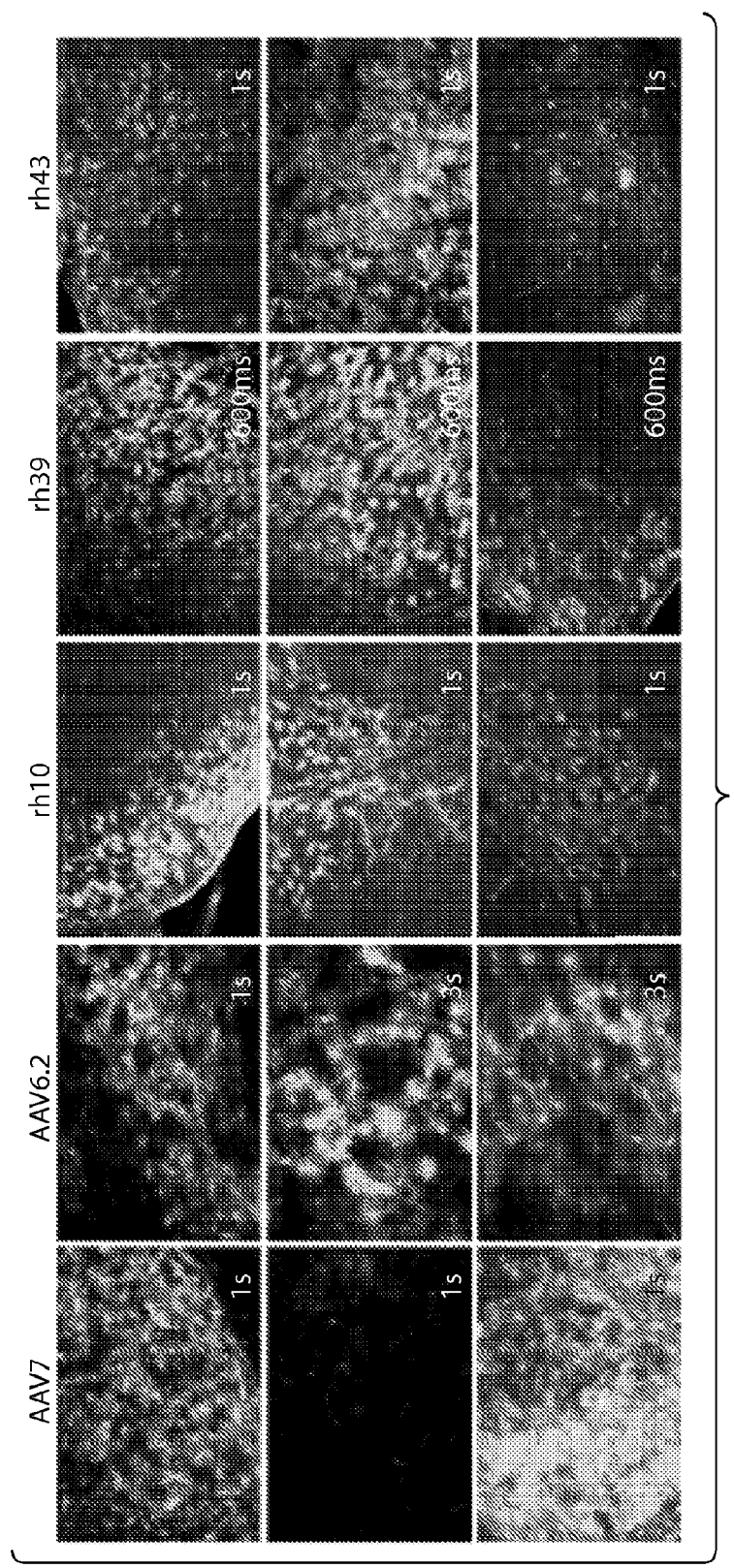

FIG. 29 depicts native EGFP expression in mice CNS after systemic delivery of rAAVs to P1 neonates. Neonatal pups received $4 \times 10^{11}$ GCs of rAAVs at P1 were necropsied 21 days after injection. Forty μm thick cryosections were mounted and observed under microscope without immunostaining. The exposure times for each image were indicated.

FIG. 30 depicts results showing the effects of rAAV based gene therapy in the treatment of Canavan disease. FIG. 30A shows that treatment corrected gait and motor function of the CD mice. FIG. 30B shows that treatment mitigated retinopathy and restored vision in CD mice. FIG. 30C shows that NAA levels in the treated CD mice approach those in the normal mice. FIG. 30D indicates that APSA activity is detected in the brains of CD mice. FIG. 30E indicates APSA expression is detected in the brains of CD mice.

Figure 31A:
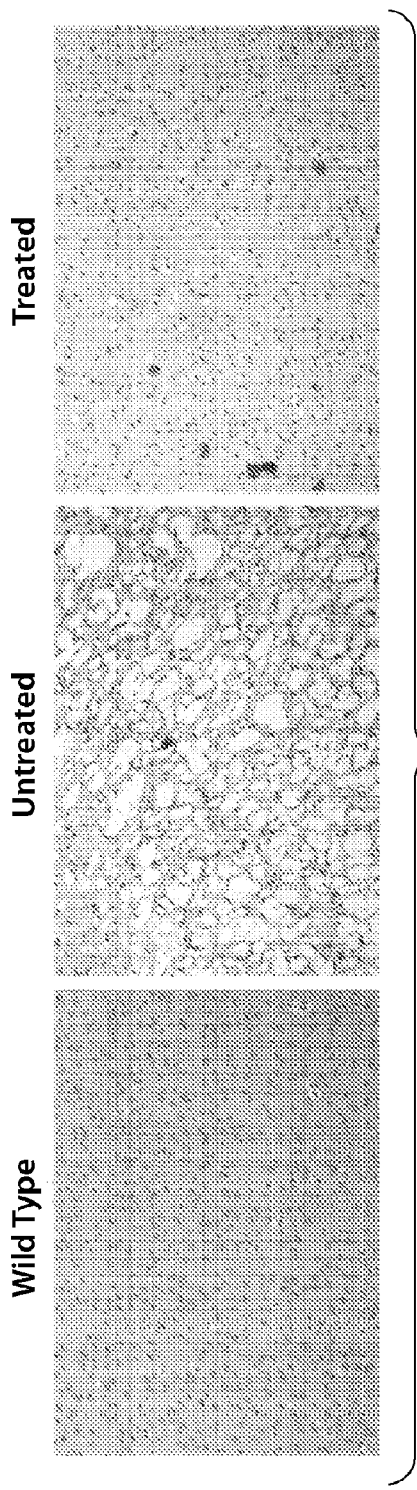
Figure 31B:
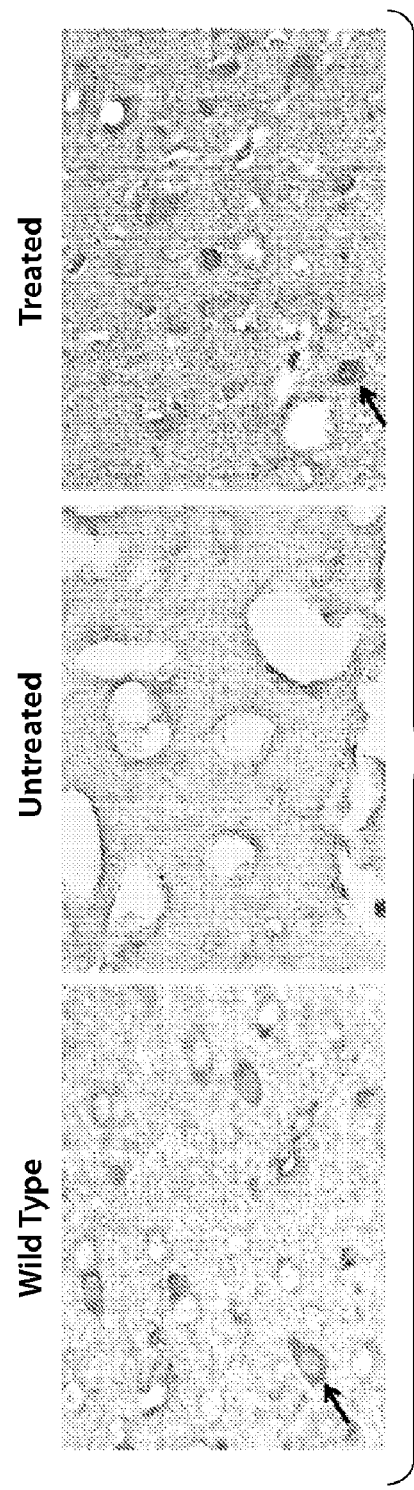

FIG. 31A depicts that vacuolation in both brain and spinal cord of the treated mice is more patchy and variable with generally smaller-sized vacuoles and that some areas of the cerebral cortex show almost no vacuolation. FIG. 31B shows ASPA expression in the cerebral cortex in situ.

Figure 32A:
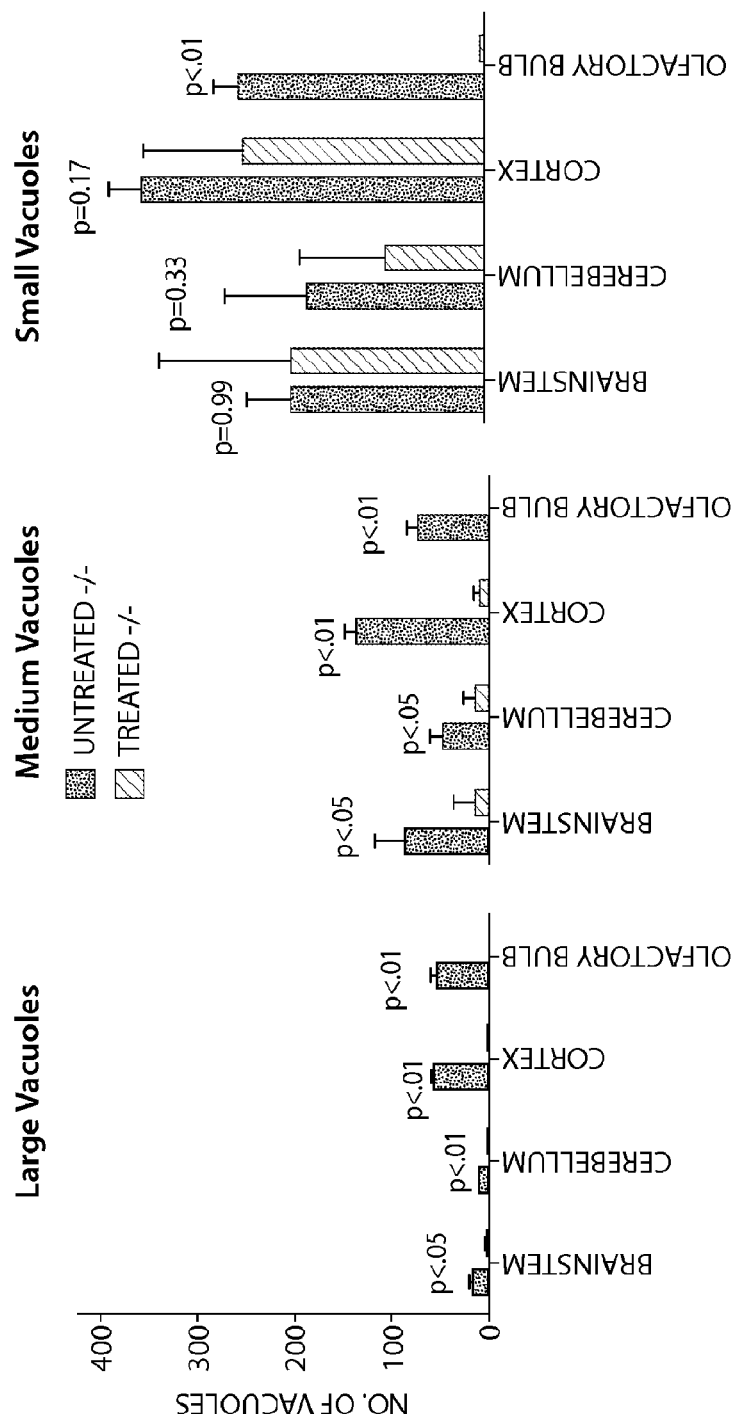
Figure 32B:
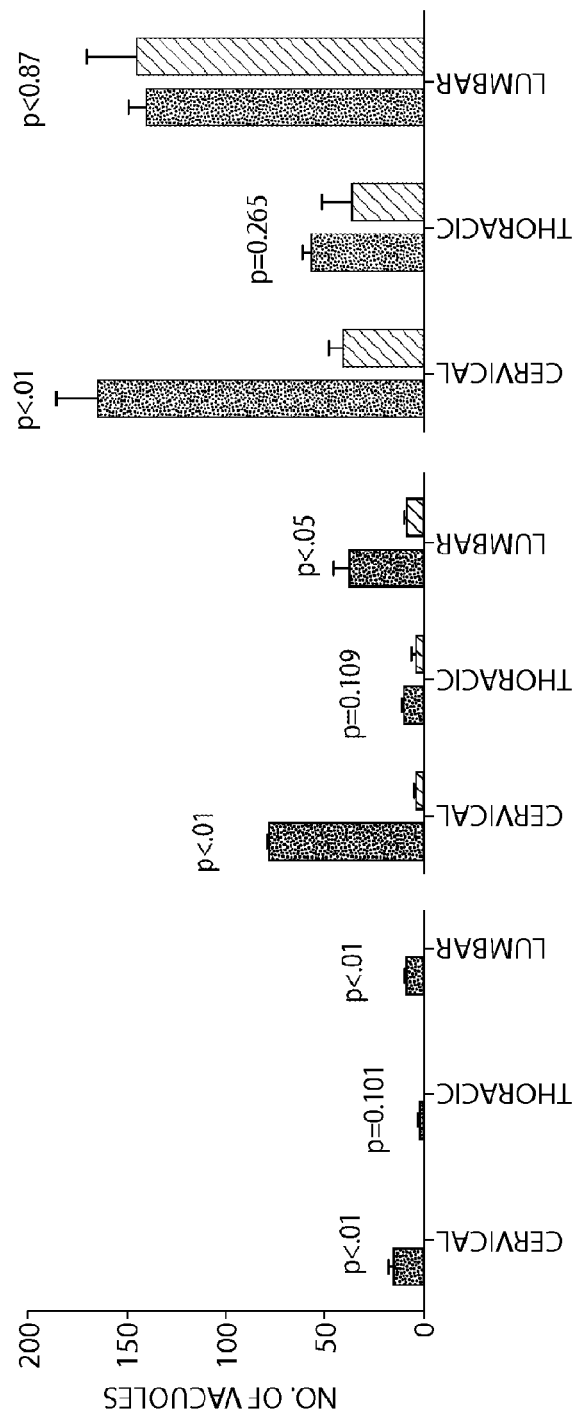

FIG. 32 depicts results of a quantitative analysis of vacuolation in various brain regions. FIG. 32A shows that olfactory bulb had a dramatic mitigation in the white matter degeneration after gene therapy and that the large vacuoles were essentially eliminated in other tissues. FIG. 32B shows results from a similar analysis on spinal cord sections.

FIG. 33 depicts results from a histopathological evaluation of kidneys in the CD mice. FIG. 33A shows that the renal tubular epithelium of the kidney was diffusely attenuated and exhibited enlargement of the tubular lumens in untreated CD mice. FIG. 33B shows that treated CD mouse had normal glomeruli. FIGS. 33C and 33D depict results of an analysis of two lead candidate vectors, rAAV9 and rh.10, respectively, for efficiency of kidney transduction after IV delivery.

DETAILED DESCRIPTION OF CERTAIN EMBODIMENTS OF THE INVENTION

Adeno-associated virus (AAV) is a small (26 nm) replication-defective, nonenveloped virus, that depends on the presence of a second virus, such as adenovirus or herpes virus, for its growth in cells. AAV is not known to cause disease and induces a very mild immune response. AAV can infect both dividing and non-dividing cells and may incorporate its genome into that of the host cell. Aspects of the invention provide methods for delivering a transgene to a CNS tissue in a subject using recombinant AAV-based gene transfer. Accordingly, methods and compositions for treating CNS-related disorders are provided herein. Further aspects of the invention, are based on the discovery of rAAVs that achieve wide-spread distribution throughout CNS tissue. In some embodiments, the rAAVs spread throughout CNS tissue following direct administration into the cerebrospinal fluid (CSF), e.g., via intrathecal and/or intracerebral injection. In other embodiments, the rAAVs cross the blood-brain-barrier and achieve wide-spread distribution throughout CNS tissue of a subject following intravenous administration. Such rAAVs are useful for the treatment of CNS-related disorders, including, for example, amyotrophic lateral sclerosis (ALS) and Canavan disease (CD).

Methods and Compositions for Targeting CNS Tissue

Methods for delivering a transgene to central nervous system (CNS) tissue in a subject are provided herein. The methods typically involve administering to a subject an effective amount of a rAAV comprising a nucleic acid vector for expressing a transgene in the subject. An "effective amount" of a rAAV is an amount sufficient to infect a sufficient number of cells of a target tissue in a subject. An effective amount of a rAAV may be an amount sufficient to have a therapeutic benefit in a subject, e.g., to extend the lifespan of a subject, to improve in the subject one or more symptoms of disease, e.g., a symptom of ALS, a symptom of Canavan disease, etc. In some cases, an effective amount of a rAAV may be an amount sufficient to produce a stable somatic transgenic animal model. The effective amount will depend on a variety of factors such as, for example, the species, age, weight, health of the subject, and the CNS tissue to be targeted, and may thus vary among subject and tissue. An effective amount may also depend on the mode of administration. For example, targeting a CNS tissue by intravascular injection may require different (e.g., higher) doses, in some cases, than targeting CNS tissue by intrathecal or intracerebral injection. In some cases, multiple doses of a rAAV are administered. An effective amount may also depend on the rAAV used. For example, dosages for targeting a CNS tissue may depend on the serotype (e.g., the capsid protein) of the rAAV. For example, the rAAV may have a capsid protein of a AAV serotype selected from the group consisting of: AAV1, AAV2, AAV5, AAV6, AAV6.2, AAV7, AAV8, AAV9, rh.10, rh.39, rh.43 and CSp3. In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

A method for delivering a transgene to CNS tissue in a subject may comprise administering a rAAV by a single route or by multiple routes. For example, delivering a transgene to CNS tissue in a subject may comprise administering to the subject, by intravenous administration, an effective amount of a rAAV that crosses the blood-brain-barrier. Delivering a transgene to CNS tissue in a subject may comprise administering to the subject an effective amount of a rAAV by intrathecal administration or intracerebral administration, e.g., by intraventricular injection. A method for delivering a transgene to CNS tissue in a subject may comprise co-administering of an effective amount of a rAAV by two different administration routes, e.g., by intrathecal administration and by intracerebral administration. Co-administration may be performed at approximately the same time, or different times.

The CNS tissue to be targeted may be selected from cortex, hippocampus, thalamus, hypothalamus, cerebellum, brain stem, cervical spinal cord, thoracic spinal cord, and lumbar spinal cord, for example. The administration route for targeting CNS tissue typically depends on the AAV serotype. For example, in certain instances where the AAV serotype is selected from AAV1, AAV6, AAV6.2, AAV7, AAV8, AAV9, rh.10, rh.39, rh.43 and CSp3, the administration route may be intravascular injection. In some instances, for example where the AAV serotype is selected from AAV1, AAV2, AAV5, AAV6, AAV6.2, AAV7, AAV8, AAV9, rh.10, rh.39, rh.43 and CSp3, the administration route may be intrathecal and/or intracerebral injection.

Intravascular Administration

As used herein the term "intravascular administration" refers to the administration of an agent, e.g., a composition comprising a rAAV, into the vasculature of a subject, including the venous and arterial circulatory systems of the subject. Typically, rAAVs that cross the blood-brain-barrier may be delivered by intravascular administration for targeting CNS tissue. In some cases, intravascular (e.g., intravenous) administration facilitates the use of larger volumes than other forms of administration (e.g., intrathecal, intracerebral). Thus, large doses of rAAVs (e.g., up to $10^{15}$ GC/subject) can be delivered at one time by intravascular (e.g., intravenous) administration. Methods for intravascular administration are well known in the art and include for example, use of a hypodermic needle, peripheral cannula, central venous line, etc.

Intrathecal and/or Intracerebral Administration

As used herein the term "intrathecal administration" refers to the administration of an agent, e.g., a composition comprising a rAAV, into the spinal canal. For example, intrathecal administration may comprise injection in the cervical region of the spinal canal, in the thoracic region of the spinal canal, or in the lumbar region of the spinal canal. Typically, intrathecal administration is performed by injecting an agent, e.g., a composition comprising a rAAV, into the subarachnoid cavity (subarachnoid space) of the spinal canal, which is the region between the arachnoid membrane and pia mater of the spinal canal. The subarachnoid space is occupied by spongy tissue consisting of trabecula (delicate connective tissue filaments that extend from the arachnoid mater and blend into the pia mater) and intercommunicating channels in which the cerebrospinal fluid is contained. In some embodiments, intrathecal administration is not administration into the spinal vasculature.

As used herein, the term "intracerebral administration" refers to administration of an agent into and/or around the brain. Intracerebral administration includes, but is not limited to, administration of an agent into the cerebrum, medulla, pons, cerebellum, intracranial cavity, and meninges surrounding the brain. Intracerebral administration may include administration into the dura mater, arachnoid mater, and pia mater of the brain. Intracerebral administration may include, in some embodiments, administration of an agent into the cerebrospinal fluid (CSF) of the subarachnoid space surrounding the brain. Intracerebral administration may include, in some embodiments, administration of an agent into ventricles of the brain, e.g., the right lateral ventricle, the left lateral ventricle, the third ventricle, the fourth ventricle. In some embodiments, intracerebral administration is not administration into the brain vasculature.

Intracerebral administration may involve direct injection into and/or around the brain. In some embodiments, intracerebral administration involves injection using stereotaxic procedures. Stereotaxic procedures are well know in the art and typically involve the use of a computer and a 3-dimensional scanning device that are used together to guide injection to a particular intracerebral region, e.g., a ventricular region. Micro-injection pumps (e.g., from World Precision Instruments) may also be used. In some embodiments, a microinjection pump is used to deliver a composition comprising a rAAV. In some embodiments, the infusion rate of the composition is in a range of 1 µl/minute to 100 µl/minute. As will be appreciated by the skilled artisan, infusion rates will depend on a variety of factors, including, for example, species of the subject, age of the subject, weight/size of the subject, serotype of the AAV, dosage required, intracerebral region targeted, etc. Thus, other infusion rates may be deemed by a skilled artisan to be appropriate in certain circumstances.

Methods and Compositions for Treating CNS-Related Disorders

Methods and compositions for treating CNS-related disorders are also provided herein. As used herein, a "CNS-related disorder" is a disease or condition of the central nervous system. A CNS-related disorder may affect the spinal cord (e.g., a myelopathy), brain (e.g., a encephalopathy) or tissues surrounding the brain and spinal cord. A CNS-related disorder may be of a genetic origin, either inherited or acquired through a somatic mutation. A CNS-related disorder may be a psychological condition or disorder, e.g., Attention Deficit Hyperactivity Disorder, Autism Spectrum Disorder, Mood Disorder, Schizophrenia, Depression, Rett Syndrome, etc. A CNS-related disorder may be an autoimmune disorder. A CNS-related disorder may also be a cancer of the CNS, e.g., brain cancer. A CNS-related disorder that is a cancer may be a primary cancer of the CNS, e.g., an astrocytoma, glioblastomas, etc., or may be a cancer that has metastasized to CNS tissue, e.g., a lung cancer that has metastasized to the brain. Further non-limiting examples of CNS-related disorders, include Parkinson's Disease, Lysosomal Storage Disease, Ischemia, Neuropathic Pain, Amyotrophic lateral sclerosis (ALS), Multiple Sclerosis (MS), and Canavan disease (CD).

Methods for treating amyotrophic lateral sclerosis (ALS) in a subject in need thereof are provided herein. A subject in need of a treatment for ALS is a subject having or suspected of having ALS. In some cases, ALS has been linked to a mutation in the gene coding for superoxide dismutase (SOD1). Elevated levels of SOD1 appear to be associated with ALS in some instances. It has been shown that transgenic expression of shRNA against SOD1 can knockdown mutant SOD1 expression, delay disease onset and extend survival (Xia et al. 2006, Neurobiol Dis 23: 578). Intrathecal infusion of siRNA against SOD1 at disease onset has also been found to knockdown mutant SOD1 expression and extend survival (Wang et al. 2008, JBC 283: 15845). Furthermore, nerve injection of adenovirus expressing shRNA against SOD1 at the disease onset can knockdown mutant SOD1 expression and extend survival (Wu et al. 2009, Antiox Redox Sig 11: 1523).

Aspects of the invention, are based on the discovery of AAV-based therapies that achieve, with low-toxicity, long-term inhibition of SOD1 expression that is wide-spread throughout CNS tissue of the subject. Methods for treating ALS that are provided herein, typically involve administering to CNS tissue of a subject an effective amount of a rAAV that harbors a nucleic acid comprising a promoter operably linked with a region encoding an inhibitory RNA that binds specifically to SOD1 mRNA (e.g., that hybridizes specifically to a nucleic acid having a sequence as set forth in SEQ ID NO 17 or 19) and inhibits expression of SOD1 in the subject. It has been discovered that rAAVs having a capsid protein comprising a sequence as set forth in SEQ ID NO: 9 achieve wide-spread distribution throughout the CNS following intrathecal injection and/or intracerebral injection, and thus, are particularly useful for treating ALS. This result is surprising in light of certain other rAAVs that infect cells only within the immediate vicinity of the injection site, or the achieve only a limited distribution, following intrathecal injection. Thus, rAAVs that achieve wide-spread distribution throughout the CNS are particularly useful as gene transfer vectors for treating ALS.

Figure 6A:
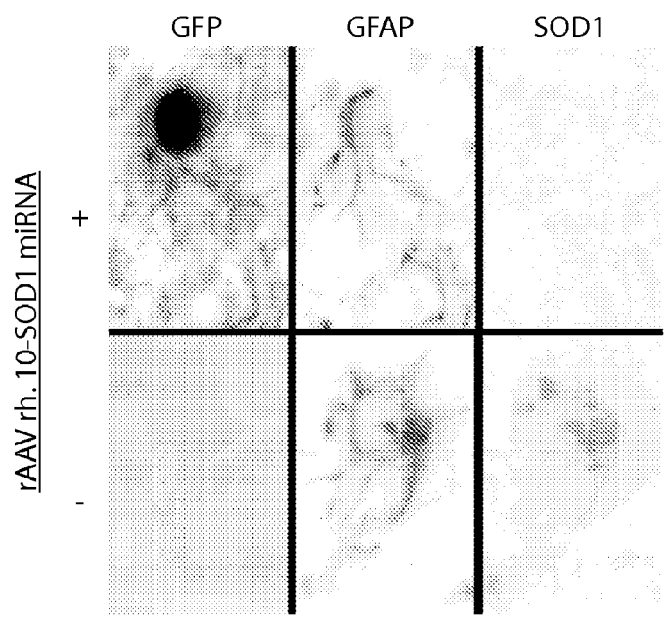
FIG. 6A depicts results of gene transfer studies in SOD1 (G93A) mutant mice showing that rAAV rh.10-SOD1 miRNA knockdowns levels of mutant SOD1 in astrocytes. Staining in motor neurons was also observed.

In some embodiments, it has been discovered that co-administration by intrathecal injection and intracerebral injection, e.g., intraventricular injection, of rAAVs having a capsid protein comprising a sequence as set forth in SEQ ID NO: 9 and a nucleic acid comprising a promoter operably linked with a region encoding an inhibitory RNA that binds specifically to SOD1 mRNA and inhibits expression of SOD1, achieves long-term inhibition of SOD1 and improves outcome (e.g., lifespan) in an animal model of ALS (See, e.g., FIG. 6A). In some embodiments, the inhibitory RNA is an antisense RNA, a shRNA or a miRNA. The inhibitory RNA may have a sequence as set forth in SEQ ID NO: 26. The inhibitory RNA may have a sequence as set forth in any one of SEQ ID NO: 22 to 30. Thus, in some embodiments, a nucleic acid comprising a promoter operably linked with a nucleic acid having a sequence as set forth in any one of SEQ ID NO: 22 to 30 is provided. In some embodiments, a recombinant AAV that harbors a nucleic acid comprising a sequence as set forth in any one of SEQ ID NO: 22 to 30 is provided. The recombinant AAV may have a capsid protein comprising a sequence as set forth in SEQ ID NO: 9. The recombinant AAV may have a capsid protein comprising a sequence as set forth in any one of SEQ ID NO: 1 to 12.

Methods for treating Canavan disease (CD) in a subject in need thereof are provided herein. A subject in need of a treatment for CD is a subject having or suspected of having CD. Canavan disease is caused by a defective ASPA gene which is responsible for the production of the enzyme aspartoacylase. This enzyme normally breaks down the concentrated brain molecule N-acetyl aspartate. Decreased aspartoacylase activity in subjects with CD prevents the normal breakdown of N-acetyl aspartate, and the lack of breakdown appears to interfere with growth of the myelin sheath of the nerve fibers in the brain. Symptoms of Canavan disease, which may appear in early infancy and progress rapidly, may include mental retardation, loss of previously acquired motor skills, feeding difficulties, abnormal muscle tone (i.e., floppiness or stiffness), poor head control, and megalocephaly (abnormally enlarged head). Paralysis, blindness, or seizures may also occur. Aspects of the invention improve one or more symptoms of CD in a subject by administering to the subject a recombinant AAV harboring a nucleic acid that expresses aspartoacylase (ASPA). For example, a method for treating Canavan disease in a subject in need thereof may comprise administering an effective amount of a rAAV to CNS tissue of the subject by intravascular administration, wherein the rAAV comprises a nucleic acid comprising a promoter operably linked with a region encoding ASPA (e.g., a region having a sequence as set forth in SEQ ID NO: 14 or 16). A method for treating Canavan disease in a subject in need thereof may comprise administering an effective amount of a rAAV to CNS tissue of the subject by intrathecal administration, wherein the rAAV comprises a nucleic acid comprising a promoter operably linked with a region encoding ASPA. In some cases, methods for treating CD involve administering, to CNS tissue of the subject, an effective amount of a rAAV that comprises a capsid protein other than a capsid protein of AAV serotype 2 (e.g., other than a protein having an amino acid sequence as set forth in SEQ ID NO: 2) and a nucleic acid comprising a promoter operably linked with a region encoding ASPA. In another example, a method for treating Canavan disease in a subject in need thereof comprises administering an effective amount of a rAAV to CNS tissue of the subject by a route other than intracerebral administration, wherein the rAAV comprises a nucleic acid comprising a promoter operably linked with a region encoding ASPA. In some embodiments, ASPA expressed in CNS tissue following administration of the rAAV results in a decrease in aspartoacylase activity and breakdown of N-acetyl aspartate in the CNS tissue. Thus, in some embodiments, a recombinant AAV vector is provided that comprises a nucleic acid encoding a sequence as set forth in SEQ ID NO: 14 or 16. In some embodiments, a recombinant AAV is provided that harbors a nucleic acid comprising a promoter operably linked with a region having a sequence as set forth in SEQ ID NO: 14 or 16. In some embodiments, a recombinant AAV is provided that harbors a nucleic acid comprising a promoter operably linked with a region encoding a protein having a sequence as set forth in SEQ ID NO: 13 or 15. The recombinant AAV may have a capsid protein comprising an amino acid sequence as set forth in any one of SEQ ID NO: 1 to 12. The recombinant AAV may have a capsid protein comprising a sequence as set forth in any one of SEQ ID NO: 1 and 3 to 12.

Recombinant AAVs

In some aspects, the invention provides isolated AAVs. As used herein with respect to AAVs, the term "isolated" refers to an AAV that has been isolated from its natural environment (e.g., from a host cell, tissue, or subject) or artificially produced. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, a rAAV having a capsid appropriate for the tissue being targeted can be selected. In some embodiments, the rAAV comprises a capsid protein having an amino acid sequence as set forth in any one of SEQ ID NOs 1 to 12, or a protein having substantial homology thereto.

Methods for obtaining recombinant AAVs having a desired capsid protein are well known in the art (See, for example, US 2003/0138772, the contents of which are incorporated herein by reference in their entirety). AAVs capsid protein that may be used in the rAAVs of the invention a include, for example, those disclosed in G. Gao, et al., J. Virol, 78(12):6381-6388 (June 2004); G. Gao, et al, Proc Natl Acad Sci USA, 100(10):6081-6086 (May 13, 2003); US 2003-0138772, US 2007/0036760, US 2009/0197338, and U.S. provisional application Ser. No. 61/182, 084, filed May 28, 2009, the contents of which relating to AAVs capsid proteins and associated nucleotide and amino acid sequences are incorporated herein by reference. Typically the methods involve culturing a host cell which contains a nucleic acid sequence encoding an AAV capsid protein (e.g., a nucleic acid encoding a protein having a sequence as set forth in any one of SEQ ID NOs 1-12) or fragment thereof; a functional rep gene; a recombinant AAV vector composed of, AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

The recombinant AAV vector, rep sequences, cap sequences, and helper functions required for producing the rAAV of the invention may be delivered to the packaging host cell using any appropriate genetic element (vector). The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring harbor Press, Cold Spring Harbor, N.Y. Similarly, methods of generating rAAV virions are well known and the selection of a suitable method is not a limitation on the present invention. See, e.g., K. Fisher et al, J. Virol., 70:520-532 (1993) and U.S. Pat. No. 5,478,745.

In some embodiments, recombinant AAVs may be produced using the triple transfection method (e.g., as described in detail in U.S. Pat. No. 6,001,650, the contents of which relating to the triple transfection method are incorporated herein by reference). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the invention provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

In some aspects, the invention provides isolated cells. As used herein with respect to cell, the term "isolated" refers to a cell that has been isolated from its natural environment (e.g., from a tissue or subject). As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

The foregoing methods for packaging recombinant vectors in desired AAV capsids to produce the rAAVs of the invention are not meant to be limiting and other suitable methods will be apparent to the skilled artisan.

Recombinant AAV Vectors

"Recombinant AAV (rAAV) vectors" of the invention are typically composed of, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types.

In addition to the major elements identified above for the recombinant AAV vector, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA).

For nucleic acids encoding proteins, a polyadenylation sequence generally is inserted following the transgene sequences and before the 3' AAV ITR sequence. A rAAV construct useful in the present invention may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931.; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the 13-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 268:1766-1769 (1995), see also Harvey et al, Curr. Opin. Chem. Biol., 2:512-518 (1998)), the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. IDSA, 88:5611-5 (1991)), and the neuron-specific vgf gene promoter (Piccioli et al., Neuron, 15:373-84 (1995)). In some embodiments, the tissue-specific promoter is a promoter of a gene selected from: neuronal nuclei (NeuN), glial fibrillary acidic protein (GFAP), adenomatous polyposis coli (APC), and ionized calcium-binding adapter molecule 1 (Iba-1). Other appropriate tissue specific promoters will be apparent to the skilled artisan. In some embodiments, the promoter is a chicken Beta-actin promoter.

In some embodiments, one or more bindings sites for one or more of miRNAs are incorporated in a transgene of a rAAV vector, to inhibit the expression of the transgene in one or more tissues of a subject harboring the transgenes, e.g., non-CNS tissues. The skilled artisan will appreciate that binding sites may be selected to control the expression of a transgene in a tissue specific manner. For example, expression of a transgene in the liver may be inhibited by incorporating a binding site for miR-122 such that mRNA expressed from the transgene binds to and is inhibited by miR-122 in the liver. Expression of a transgene in the heart may be inhibited by incorporating a binding site for miR-133a or miR-1, such that mRNA expressed from the transgene binds to and is inhibited by miR-133a or miR-1 in the heart. The miRNA target sites in the mRNA may be in the 5' UTR, the 3' UTR or in the coding region. Typically, the target site is in the 3' UTR of the mRNA. Furthermore, the transgene may be designed such that multiple miRNAs regulate the mRNA by recognizing the same or multiple sites. The presence of multiple miRNA binding sites may result in the cooperative action of multiple RISCs and provide highly efficient inhibition of expression. The target site sequence may comprise a total of 5-100, 10-60, or more nucleotides. The target site sequence may comprise at least 5 nucleotides of the sequence of a target gene binding site.

Transgene Coding Sequences: CNS-Related Genes

The composition of the transgene sequence of a rAAV vector will depend upon the use to which the resulting vector will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

In some aspects, the invention provides rAAV vectors for use in methods of preventing or treating one or more gene defects (e.g., heritable gene defects, somatic gene alterations) in a mammal, such as for example, a gene defect that results in a polypeptide deficiency or polypeptide excess in a subject, and particularly for treating or reducing the severity or extent of deficiency in a subject manifesting a CNS-associated disorder linked to a deficiency in such polypeptides in cells and tissues. In some embodiments, methods involve administration of a rAAV vector that encodes one or more therapeutic peptides, polypeptides, shRNAs, microRNAs, antisense nucleotides, etc. in a pharmaceutically-acceptable carrier to the subject in an amount and for a period of time sufficient to treat the CNS-associated disorder in the subject having or suspected of having such a disorder.

A rAAV vector may comprise as a transgene, a nucleic acid encoding a protein or functional RNA that modulates or treats a CNS-associated disorder. The following is a non-limiting list of genes associated with CNS-associated disorders: neuronal apoptosis inhibitory protein (NAIP), nerve growth factor (NGF), glial-derived growth factor (GDNF), brain-derived growth factor (BDNF), ciliary neurotrophic factor (CNTF), tyrosine hydroxylase (TII), GTP-cyclohydrolase (GTPCH), aspartoacylase (ASPA), superoxide dismutase (SOD1) and amino acid decorboxylase (AADC). For example, a useful transgene in the treatment of Parkinson's disease encodes TH, which is a rate limiting enzyme in the synthesis of dopamine. A transgene encoding GTPCII, which generates the TII cofactor tetrahydrobiopterin, may also be used in the treatment of Parkinson's disease. A transgene encoding GDNF or BDNF, or AADC, which facilitates conversion of L-Dopa to DA, may also be used for the treatment of Parkinson's disease. For the treatment of ALS, a useful transgene may encode: GDNF, BDNF or CNTF. Also for the treatment of ALS, a useful transgene may encode a functional RNA, e.g., shRNA, miRNA, that inhibits the expression of SOD1. For the treatment of ischemia a useful transgene may encode NAIP or NGF. A transgene encoding Beta-glucuronidase (GUS) may be useful for the treatment of certain lysosomal storage diseases (e.g., Mucopolysacharidosis type VII (MPS VII)). A transgene encoding a prodrug activation gene, e.g., HSV-Thymidine kinase which converts ganciclovir to a toxic nucleotide which disrupts DNA synthesis and leads to cell death, may be useful for treating certain cancers, e.g., when administered in combination with the prodrug. A transgene encoding an endogenous opioid, such a β-endorphin may be useful for treating pain. Other examples of transgenes that may be used in the rAAV vectors of the invention will be apparent to the skilled artisan (See, e.g., Costantini L C, et al., Gene Therapy (2000) 7, 93-109).

In some embodiments, the cloning capacity of the recombinant RNA vector may be limited and a desired coding sequence may involve the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

Recombinant AAV Administration rAAVS are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected tissue (e.g., intracerebral administration, intrathecal administration), intravenous, oral, inhalation (including intranasal and intratracheal delivery), intraocular, intravenous, intramuscular, subcutaneous, intradermal, intratumoral, and other parental routes of administration. Routes of administration may be combined, if desired.

Delivery of certain rAAVs to a subject may be, for example, by administration into the bloodstream of the subject. Administration into the bloodstream may be by injection into a vein, an artery, or any other vascular conduit. Moreover, in certain instances, it may be desirable to deliver the rAAVs to brain tissue, meninges, neuronal cells, glial cells, astrocytes, oligodendrocytes, cerebrospinal fluid (CSF), interstitial spaces and the like. In some embodiments, recombinant AAVs may be delivered directly to the spinal cord or brain by injection into the ventricular region, as well as to the striatum (e.g., the caudate nucleus or putamen of the striatum), and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000). In certain circumstances it will be desirable to deliver the rAAV-based therapeutic constructs in suitably formulated pharmaceutical compositions disclosed herein either subcutaneously, intrapancreatically, intranasally, parenterally, intravenously, intramuscularly, intracerebrally, intrathecally, intracerebrally, orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs.

Recombinant AAV Compositions

The rAAVs may be delivered to a subject in compositions according to any appropriate methods known in the art. The rAAV, preferably suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate (e.g., Macaque). The compositions of the invention may comprise a rAAV alone, or in combination with one or more other viruses (e.g., a second rAAV encoding having one or more different transgenes). In some embodiments, a compositions comprise 1, 2, 3, 4, 5, 6, 7, 8, 9, 10, or more different rAAVs each having one or more different transgenes.

Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of rAAV virions required to achieve a desired effect or "therapeutic effect," e.g., the units of dose in vector genomes/per kilogram of body weight (vg/kg), will vary based on several factors including, but not limited to: the route of rAAV administration, the level of gene or RNA expression required to achieve a therapeutic effect, the specific disease or disorder being treated, and the stability of the gene or RNA product. One of skill in the art can readily determine a rAAV virion dose range to treat a subject having a particular disease or disorder based on the aforementioned factors, as well as other factors that are well known in the art. An effective amount of the rAAV is generally in the range of from about 10 µl to about 100 ml of solution containing from about $10^9$ to $10^{16}$ genome copies per subject. Other volumes of solution may be used. The volume used will typically depend, among other things, on the size of the subject, the dose of the rAAV, and the route of administration. For example, for intrathecal or intracerebral administration a volume in range of 1 µl to 10 µl or 10 µl to 100 µl may be used. For intravenous administration a volume in range of 10 µl to 100 µl, 100 µl to 1 ml, 1 ml to 10 ml, or more may be used. In some cases, a dosage between about $10^{10}$ to $10^{12}$ rAAV genome copies per subject is appropriate. In certain embodiments, $10^{12}$ rAAV genome copies per subject is effective to target CNS tissues. In some embodiments the rAAV is administered at a dose of $10^{10}$, $10^{11}$, $10^{12}$, $10^{13}$, $10^{14}$, or $10^{15}$ genome copies per subject. In some embodiments the rAAV is administered at a dose of $10^{10}$, $10^{11}$, $10^{12}$, $10^{13}$, or $10^{14}$ genome copies per kg.

In some embodiments, rAAV compositions are formulated to reduce aggregation of AAV particles in the composition, particularly where high rAAV concentrations are present (e.g., ~$10^{13}$ GC/ml or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trails examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500.ANG., containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Kits and Related Compositions

The agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or IV needle tubing and bag.

EXAMPLES

Example 1

Characterization of 12 AAV Vectors for Intravascular Delivery to Target CNS and Detarget Non-CNS Tissues by miRNA Regulation The CNS gene transfer properties of 12 scAAVEGFP vectors of different serotypes, or natural variants were evaluated. RAAVs that cross the blood-brain-barrier (BBB) and target oligodendrocytes were discovered. Experiments were performed in neonatal mice (1 day old) and in adult mice (10 week old) (C57BL/6). The following AAV serotypes were tested: AAV1, AAV2, AAV5, AAV6, AAV6.2, AAV7, AAV8, AAV9, rh.10 (also referred to herein as AAVrh.10), rh.39, rh.43, CSp3.

The recombinant AAV vectors expressed an enhanced GFP reporter gene under the CMV-enhanced chicken β-actin hybrid promoter and were produced by transient transfection in 293 cells. The neonatal day 1 pups were anesthetized with isoflurane. Then 100 µL of rAAV vectors ($4 \times 10^{11}$ GC per mouse) was injected to the pups via superfacial temporal vein under a dissection microscope. In adult mice, rAAV was administered by tail vein injection (two different doses were evaluated $4 \times 10^{11}$ GC per mouse or $4 \times 10^{12}$ GC per mouse). Twenty-one days post injection, the treated animals were anesthetized and transcardially perfused with cold PBS and 4% (v/v) paraformaldehyde. Brains were extracted, immersed in 20% sucrose, and embedded in Tissue-Tek OCT. 40 µm thick sections were cut and stained in 12-well plate with primary antibodies, e.g., anti-NeuN, anti-EGFP and anti-GFAP, overnight at 4° C., then with secondary antibodies for 2 h at room temperature. Control mice received PBS injections.

In the neonatal study, the distribution of EGFP (+) cells throughout the brain at 3 wks post-infusion was observed. Large numbers of EGFP (+) cells with variable intensities were visible in different regions of the brains from the animals treated with 10 out of 12 vectors. In many instances the choroid plexus showed very strong EGFP expression, and transduced brain parenchyma cells appeared predominantly in periventricular regions. This indicates that a fraction of IV delivered vectors may enter the CNS via the choroid plexus-blood interface. In adults, substantial staining of brain vasculature was observed. Overall targeting efficiencies by AAVs to different regions of the brain was ranked as hypothalamus>medulla>cortex>hippocampus>cerebellum>thalamus. EGFP expression was not detected at high levels in neonatal mice that were administered rAAV2 or rAAV5 harboring the EGFP reporter gene by injection of $4 \times 10^{11}$ GC per mouse in the superfacial temporal vein. (See Table 1 and FIGS. 1 and 2 for summary data).

Figure 3:
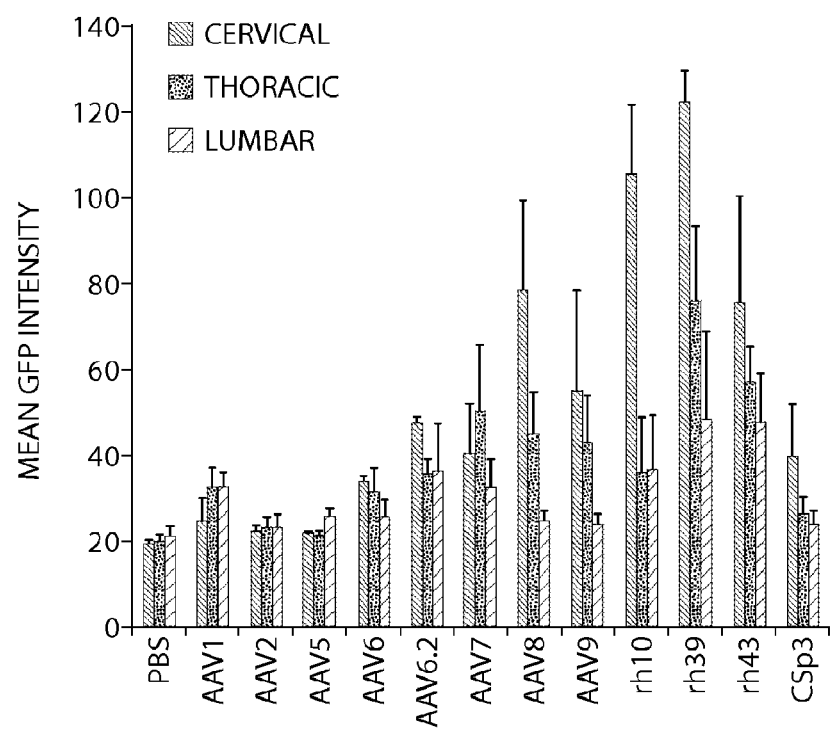
FIG. 3 depicts quantitation of EGFP expression in neonatal mice spinal cord (cervical, thoracic and lumber regions) 21 days post IV injection (5 mice per group). Neonatal mice were administered the rAAVs by intravenous administration (superfacial temporal vein injection).

Tissue sections were also immunofluorescently stained with anti-EGFP and -cell type specific marker antibodies to classify EGFP (+) cell types in the CNS. Detection sensitivity for EGFP (+) cells, particularly neurons and oligodendrocytes, was improved dramatically. Although different vectors transduced neurons at variable efficiencies, all 10 vectors (including AAV9) exhibited stronger tropisms to non-neuronal cells, especially astrocytes. One vector (AAV7) targeted oligodendrocytes more efficiently than the other 9 vectors. Several rAAVs transduced both neurons and/or astrocytes at higher efficiencies as compared to rAAV9 (AAVrh.10, rh.34, and rh.43). Extensive astrocyte transduction was observed in hypothalamus and medulla. Injection of certain vectors resulted in substantial neuron transduction in different regions of the brain, including neocortex, hippocampus, and hypothalamus. Some vectors appeared to transduce Purkinje cells in cerebella cortex (e.g., CSp3), while others effectively transduced blood vessel in neocortex, thalamus and hypothalamus. In addition, choroid plexuses in $3^{rd}$ ventricle, lateral ventricle and $4^{th}$ ventricle showed strong EGFP expression. EGFP expression was also evaluated in different spinal cord regions of neonatal and adult mice (results for neonatal studies are shown in FIG. 3).

Transduction of non-CNS tissues such as heart and skeletal muscle was observed (e.g., for AAV9, AAV8, and CSp3). In some cases, this may lead to some undesirable side effects. To address this issue, miRNA binding sites were incorporated into the 3' UTR of the transgene cassette and achieved highly specific and effective detargeting of AAV transduction from non-CNS tissues. To inhibit expression in liver, miRNA binding(s) for mR-122 were used. To inhibit expression in skeletal muscle and heart, miRNA binding(s) for mR-1 were used.

TABLE 1

AAV CNS TROPISMS

| | | AAV1 | AAV2 | AAV5 | AAV6 | AAV6.2 | AAV7 | AAV8 | AAV9 | rh.10 | rh.39 | rh.43 | CSp3 |
|---|---|---|---|---|---|---|---|---|---|---|---|---|---|
| Adult | Cortex | + | | | + | + | ++ | ++ | +++ | ++ | + | − | + |
| | Hippocampus | + | | | + | + | ++ | ++ | +++ | ++ | + | − | + |
| | Thalamus | + | | | + | + | ++ | ++ | ++++ | +++ | ++ | + | + |
| | Hypothalamus | + | | | ++ | + | +++ | ++ | ++ | +++ | +++ | + | ++ |
| | Cerebellum | + | | | ++ | + | ++ | +++ | +++ | ++++ | + | + | + |
| | Brain Stem | + | | | ++ | + | ++ | ++ | ++++ | +++ | ++ | − | + |
| | Cervical | +++ | | | + | + | +++ | +++ | ++++ | +++ | +++ | − | + |
| | Thoracic | +++ | | | + | + | +++ | +++ | ++++ | +++ | ++ | − | + |
| | Lumbar | +++ | | | + | + | +++ | +++ | ++++++ | +++ | ++ | − | + |
| Neo-Natal | Cortex | ++ | + | − | ++ | + | + | +++ | ++ | ++ | ++ | ++ | ++ |
| | Hippocampus | + | + | − | − | − | +++ | ++ | + | + | ++ | ++ | + |
| | Thalamus | + | + | − | − | + | ++ | + | + | + | ++ | + | + |
| | Hypothalamus | ++ | − | − | + | + | ++++++ | ++++++ | + | + | ++++++ | +++ | − |
| | Cerebellum | ++ | − | − | + | − | + | + | + | + | ++ | + | + |
| | Brain Stem | ++ | − | − | + | − | ++ | + | + | + | +++++ | +++ | +++ |
| | Cervical | − | − | − | + | ++ | ++ | +++ | ++ | +++++ | ++++ | +++ | ++ |
| | Thoracic | + | − | − | + | ++ | +++ | ++ | ++ | ++ | ++++ | +++ | + |
| | Lumbar | + | − | − | + | ++ | ++ | + | + | ++ | +++ | +++ | + |

Figure 1:
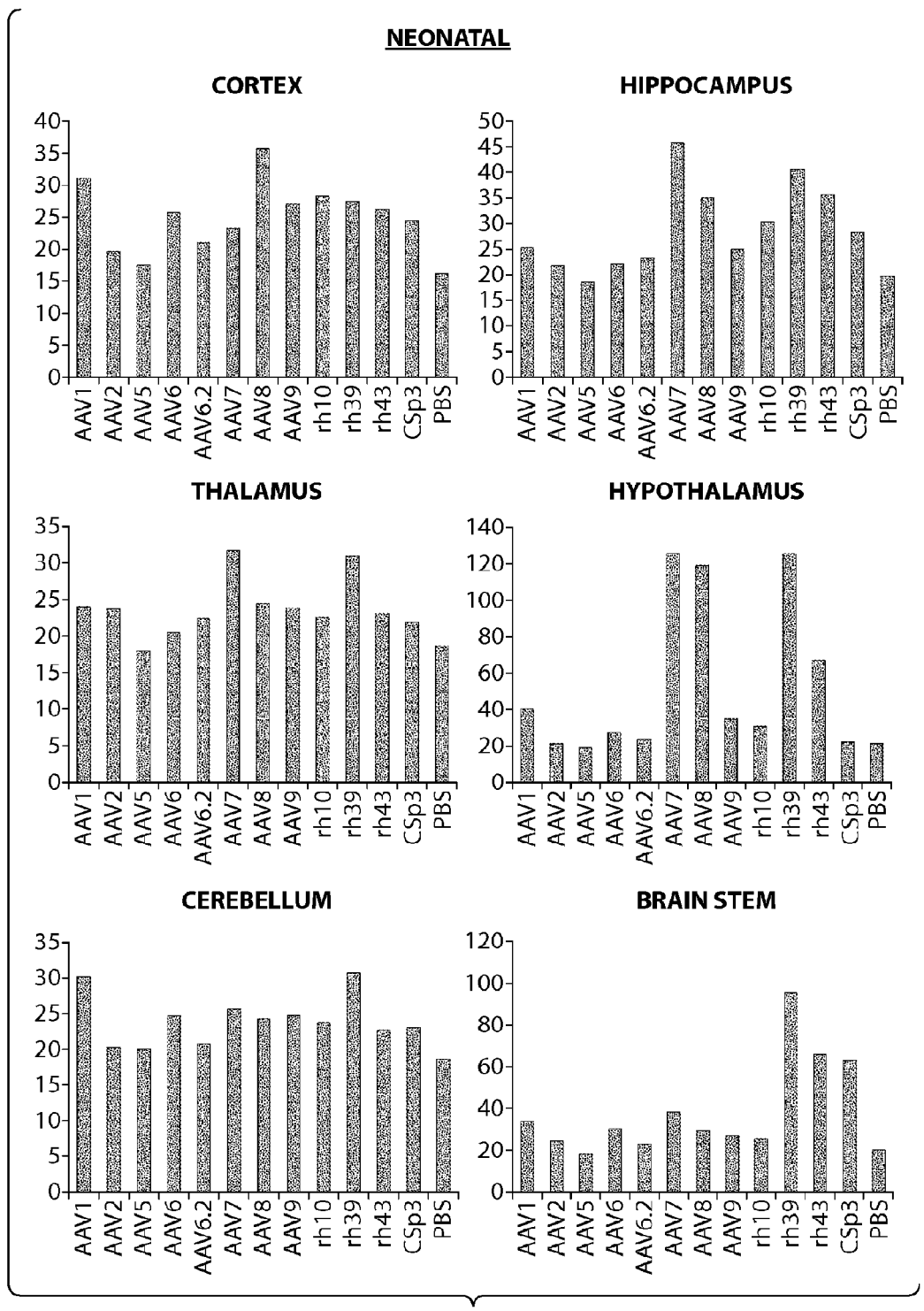
FIG. 1 depicts quantitative results of EGFP intensities from fluorescence microscopic images of a panel of CNS tissue sections from neonatal mice infected with various rAAVs harboring EGFP expression vectors. Neonatal mice were administered the rAAVs by intravenous administration (superfacial temporal vein injection).
Figures 1, 2:
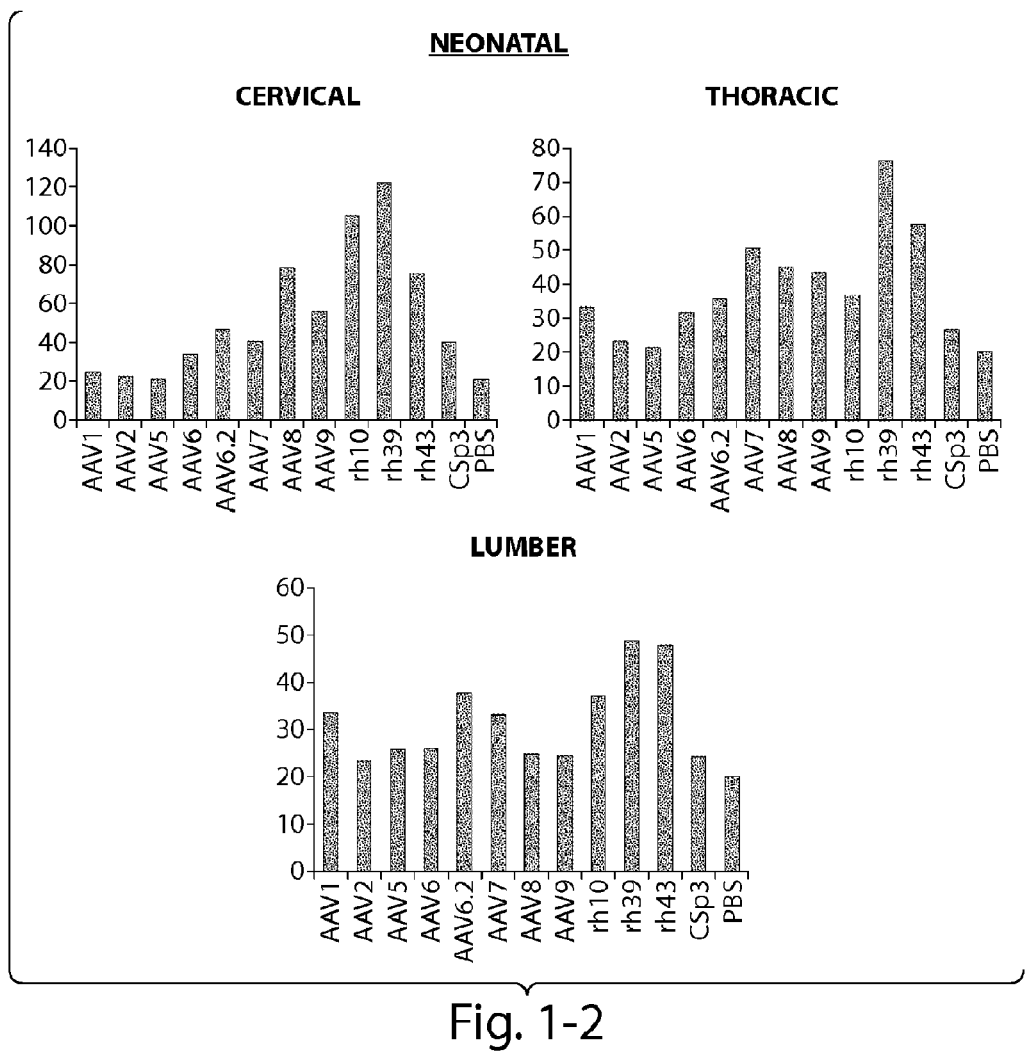
FIG. 2 depicts quantitative results of EGFP intensities from fluorescence microscopic images of a panel of CNS tissue sections from adult mice infected with various rAAVs harboring EGFP expression vectors. Adult mice were administered the rAAVs by intravenous administration (tail vein injection).
Figures 1, 2:
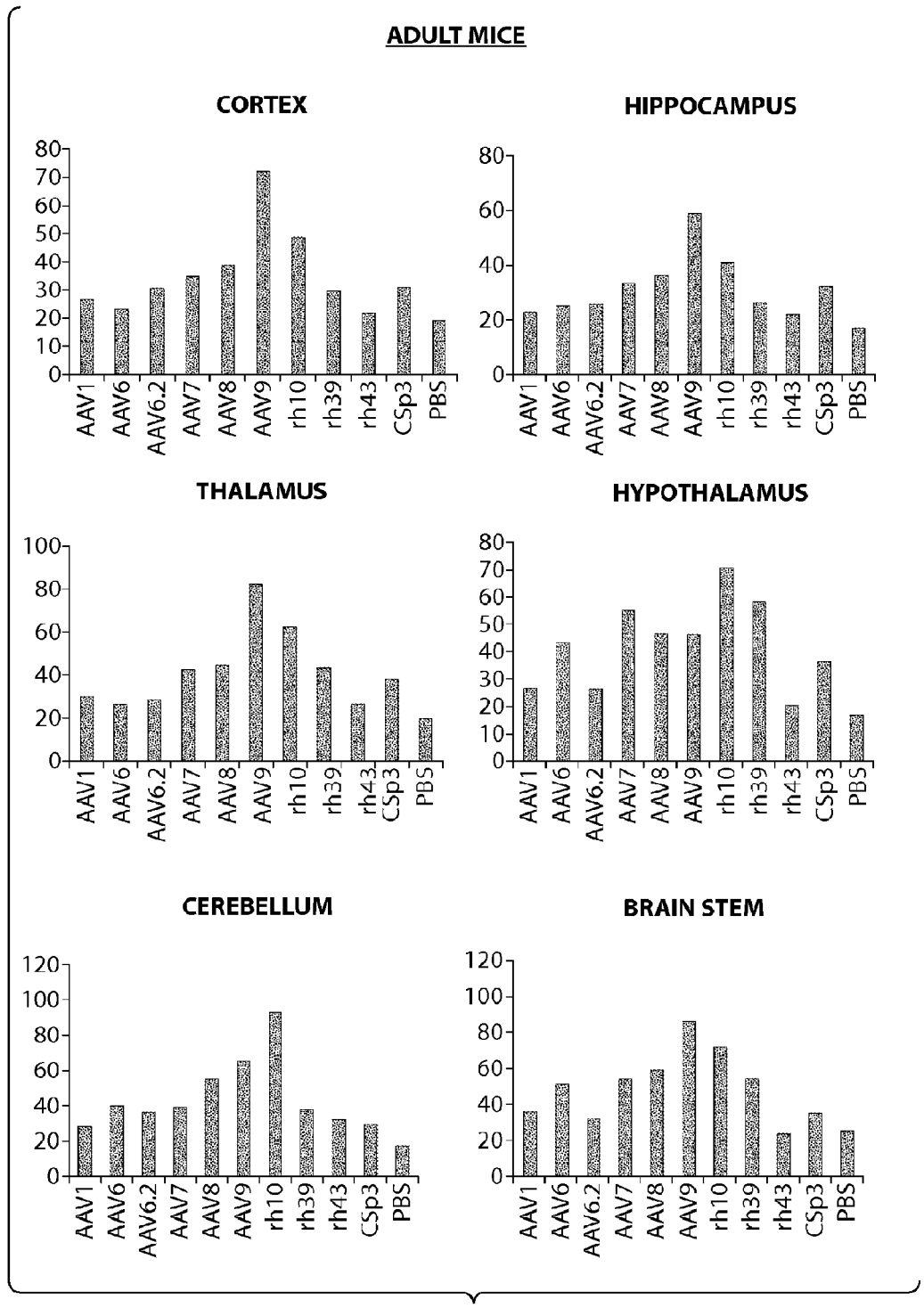
Figure 2:
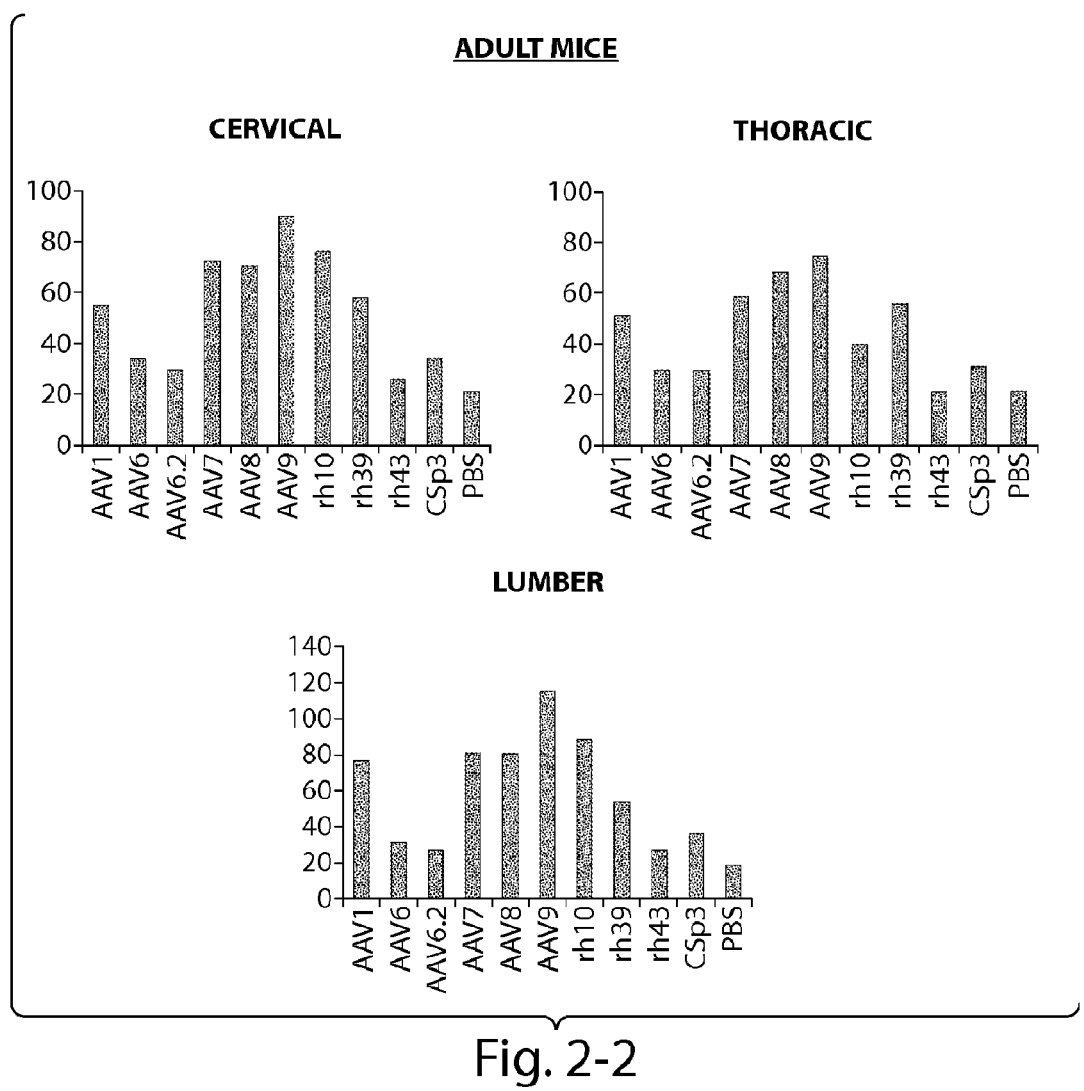

Extent of Tissue Tropsim (− no tropism; ++++++ high tropism) Based on Data in FIGS. 1 and 2.

Example 2

Construction and Evaluation of a Recombinant AAVrh.10 Vector to Treat CD

Canavan disease (CD) is an inherited neurodegenerative disorder caused by mutations in the aspartoacylase gene (ASPA), leading to accumulation of N-acetyl-aspartic acid (NAA) in oligodendrocytes with resultant spongy degeneration of white matter in the brain. An initial clinical study on rAAV2-based ASPA gene therapy for CD achieved very limited success. It is believed, without wishing to be bound by theory, that an effective CD gene therapy will transduce oligodendrocytes throughout the CNS.

A rAAV vector is constructed that comprises a promoter operably linked with a region encoding ASPA protein (SEQ ID NO: 13 or 15) as a gene therapy vector for CD. The construct employs CAG (chicken β-actin promoter with CMV enhancer) to drive the expression of ASPA having a coding sequence as set forth in SEQ ID NO: 14 or 16. The rAAV vector is package into rAAV particles using the triple transfection method. To evaluate its effectiveness, rAAV-ASPA is examined in an ASAP knock-out mouse model of CD for its ability to eliminate or attenuate the CD-like phenotypic of homozygous ASPA knock-out mice (Matalon R et al. The Journal of Gene Medicine, Volume 2 Issue 3, Pages 165-175). Homozygous ASPA knock-out mice exhibit neurological impairment, macrocephaly, generalized white matter disease, deficient ASPA activity and high levels of NAA in urine. Magnetic resonance imaging (MRI) and spectroscopy (MRS) of the brain of the homozygous mice show white matter changes characteristic of Canavan disease and elevated NAA levels. Heterozygous ASPA knock-out mice, which have no overt phenotype at birth, serve as controls.

Example 3

Therapeutic Efficacy and Safety Evaluation of an AAV Vector to Treat CD

The mouse model of CD is a C57BL/6 derived ASPA gene KO strain. The homozygous KO animals present biochemical and neurological defects similar to those observed in CD patients. CD mice provide an animal model for evaluating gene therapy and other therapeutics for the treatment of CD. CD mice are used to study the efficacy and safety of the novel gene therapy strategies for the treatment of CD.

Experiment Design

To examine therapeutic efficacy and safety, scAAV vectors (e.g., AAV7, AAV8, CSp3 and AAV9) carrying an optimized ASPA expression cassette are investigated in a preclinical gene therapy trial of CD. The vectors include miRNA binding site(s) to inhibit ASPA expression in non-CNS tissues. Both postnatal day-1 and 3-month-old adult animals are treated with each vector at two doses, 1 and $3 \times 10^{14}$ GC/kg by intravenous administration. For the neonatal CD mice, two litters of animals receive each vector at each dose via temporal vein injections for necropsy of one litter each at 1- and 3-month time points. For the 3-month-old adult CD mice, 12 male animals are treated with each vector at each dose via tail vein injections. Six each of the treated animals are necropsied 1 and 3 months later. In further experiments, both postnatal day-1 and 3-month-old adult animals are treated with vectors at a dose in a range of $10^{11}$ to $10^{12}$ GC/subject by direct intraventricular administration.

Functional and Neurological Measurements During the Live Phase of the Study

1). NAA metabolism. Urine samples are collected from the treated, untreated control, and wild type animals at days 14, 30, 45, 60, 75, and 90. The samples are analyzed by HPLC to determine the NAA levels.

2). NAA accumulation and NAA-induced water retention in brain. MRI/MRS-based neuroimaging studies are performed on the live animals in all study groups at 1, 2, and 3 months after the vector treatment to measure spectral peak integrals for creatine/phosphocreatine and NAA as well as abnormal hyperintense areas in the brain.

3). Liver function tests. Serum samples are collected from the animals in all study groups at days 14, 30, 60, and 90 to measure the levels of alanine transaminase (ALT) and aspartate aminotransferase (AST) as indicators of vector-related liver toxicity.

4). Neurological tests. Tremors, walking with splayed legs at a slow and shaky pace, and ataxia are among the prominent neurological features of the CD mice. At 1, 2, and 3 months after the gene therapy treatment, the animals in all study groups are subjected to a walking-pattern analysis by staining their feet with color ink and then recording their walking patterns as footprints on white paper. The animals also are tested and scored on a rotarod test for their ability to maintain balance.

Enzymatic and Histopathological Analyses at the Endpoints of the Study

1). ASPA activities in the brain and non-CNS tissues. On-target and off-target expression of ASPA are analyzed by collecting brain, liver, heart and pancreatic tissues at necropsy to measure ASAP activities in the respective tissue homogenates.

2). Brain white matter and liver pathologies. To examine potential improvement in brain white-matter pathology and vector-related liver toxicity resulting from the gene therapy, brain and liver tissues are harvested and fixed, paraffin-embedded and sectioned, and stained with hematoxylin and eosin. Histopathological examination is performed by a pathologist.

Example 4

Delivery of Therapeutic Genes to the CNS Cells by AAVrh.10

Figure 4A:
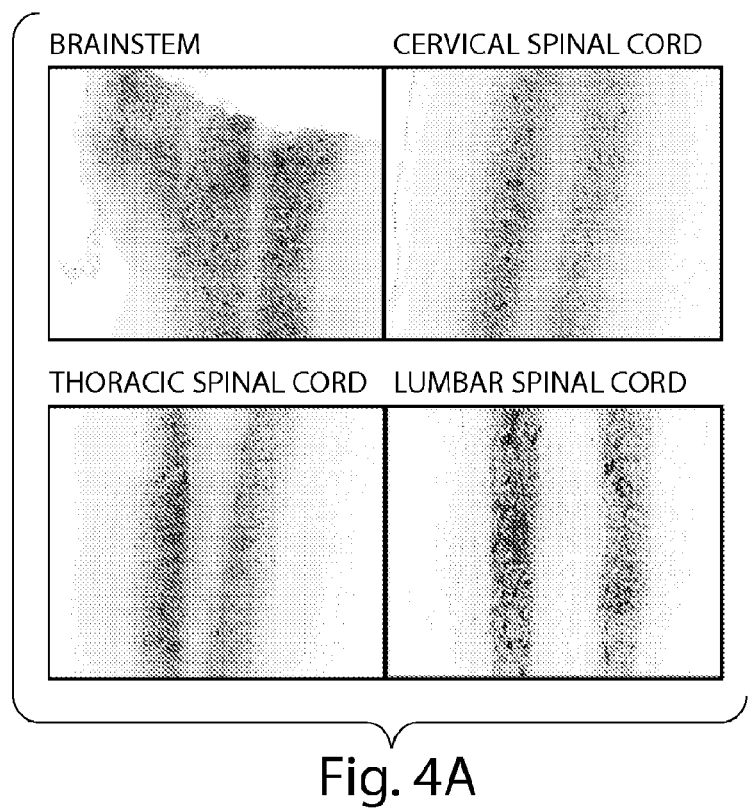
FIG. 4A depicts results showing that direct CSF injection of AAVrh.10 harboring a EGFP gene leads to EGFP expression in broad areas of the CNS. Tissue sections, prepared 60 days post virus injection, from brainstem, cervical spinal cord, thoracic spinal cord and lumbar spinal cord are shown. Gray/black pixels correspond with EGFP expression.
Figure 4B:
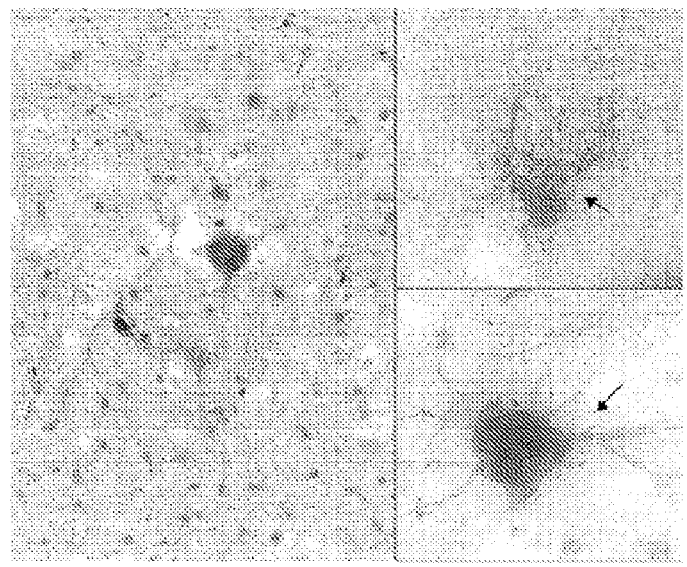
FIG. 4B depicts results showing that direct CSF injection of AAVrh.10 harboring a EGFP gene leads to EGFP expression in astrocytes. Gray/black pixels correspond with EGFP expression.

A screen of different AAV serotypes, was developed to identify candidates for a therapeutic gene transfer to the CNS. A recombinant AAV vector was constructed that expresses EGFP. The rAAV vector was packaged into four different AAVs: AAV1, 8, 9 and 10. Adult mice were injected with the AAVs into the CSF in the lumbar position. AAV1, 8 and 9 transduced cells only in the vicinity of the injection site at the lumber region of the spinal cord following administration of ~$4.8 \times 10^{10}$ particles. Surprisingly, AAVrh.10 transduced cells in the gray matter along the entire spinal cord and brainstem following the same injection protocol and dosage as AAV1, AAV8 and AAV9 (FIG. 4A). Recently, AAV9 has been shown to cross the blood brain barrier (BBB) and transduce spinal cord cells after intravenous injection. A weak signal was observed in the cerebellum and strong signals in the brainstem and spinal cord. A weak signal (similar to the cerebellum) in the forebrain was also observed. Without wishing to be bound by theory, it is believed that CSF flow and diffusion allows the virus spread along the entire spinal cord, but that the ability of a virus to flow and diffuse depends on the structure of the viral capsid. The transduced cell types include neurons and oligodendrocytes. But the majority appears to be astrocytes (FIG. 4B), as indicated by overlap of EGFP with GFAP-positive cells. Substantial overlap with the microglia marker, Iba-1 was not observed. A number of motor neurons were transduced as indicated by overlap of EGFP expression and NeuN staining. It was surprising that among the astrocytes, only those situated in the gray matter were transduced and those that were situated in the white matter and beneath the pia matter were not transduced. This was striking because the virus is likely to be exposed to astrocytes in these areas since it was administered in the subarachnoid space.

Example 5

Construction of a Recombinant AAVrh.10 Vector to Treat ALS

Figure 5A:
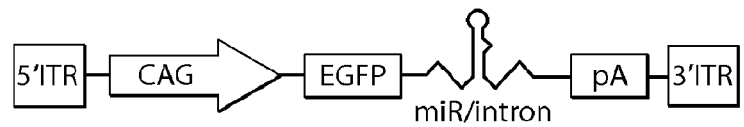
FIG. 5A depicts a rAAVrh.10 vector that expresses a microRNA targeting SOD1. The construct employs CAG (chicken β-actin promoter with a CMV enhancer) to drive the expression of EGFP and miR-SOD1 that is located in an intron in the 3'-UTR. pA stands for poly A signal. ITRs mark the inverted repeats of the AAV.

An recombinant AAV system was developed as a treatment for ALS. A rAAVrh.10 vector was constructed that expresses a microRNA targeting SOD1 (FIG. 5A). This microRNA was identified as miR-SOD1. The construct employed CAG (chicken β-actin promoter with CMV enhancer) to drive the expression of EGFP and miR-SOD1 that was located in an intron in the 3'-UTR.

Figure 5B:
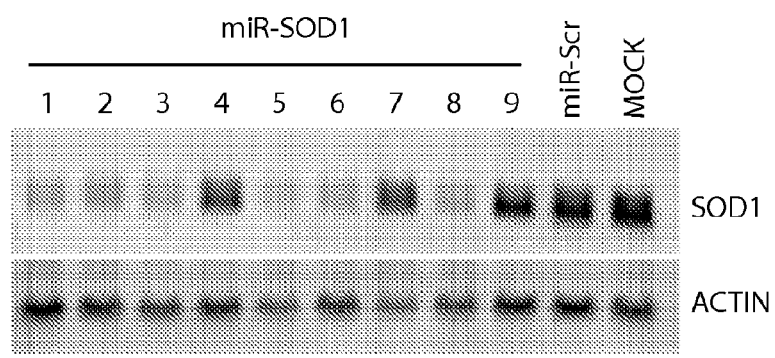
FIG. 5B depicts results of experiments that test the silencing potency of 9 different miRNA constructs, miR-SOD1#5 was found to silence SOD1 expression most potently.
Figure 5C:
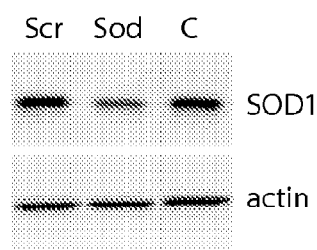
FIG. 5C depicts results of experiments in which miR-SOD1#5 was packaged into AAVrh.10 and used to infect IIEK293 cells. Total cellular protein was extracted 43 hours after the infection and blotted to detect SOD1. Scr stands for scrambled miRNA; Sod stands for miR-SOD1#5; and C stands for a control that expresses EGFP only.
Figure 5D:
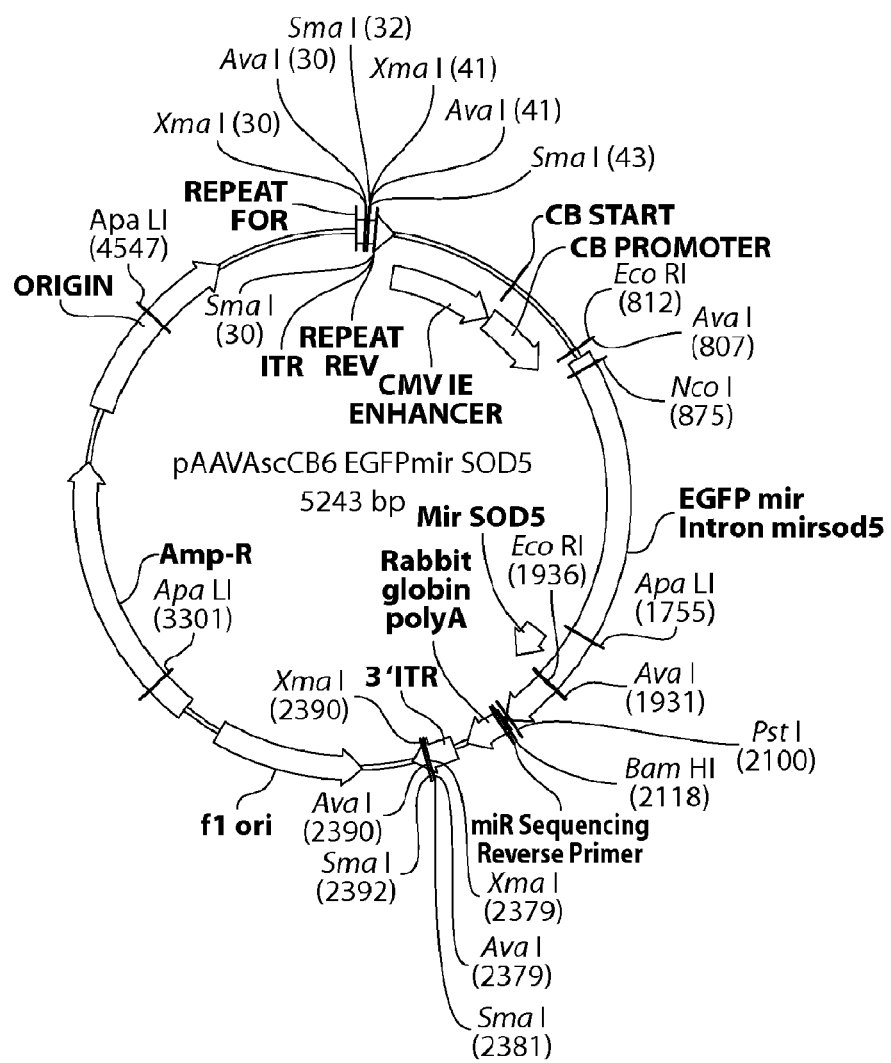
FIG. 5D depicts a plasmid map of pAAVscCB6 EGFPmir SOD5 (5243 bp) (SEQ ID NO: 21).

The silencing potency of 9 miRNA constructs was evaluated. The constructs were transfected into HEK293 cells. After 48 hours, RNA was isolated and Northern blot was carried out to detect SOD1 mRNA (FIG. 5B). MiR-SOD1#5 (SEQ ID NO: 26) silenced SOD1 expression most potently. Next, miR-SOD1#5 was packaged into AAVrh.10 (FIG. 5D), which was used to infect HEK293 cells. Total cellular protein was extracted 43 hours after the infection and blotted to detect SOD1 (FIG. 5C) Inhibition of expression of SOD1 at the protein level was observed.

Example 6

Delivery of Therapeutic Genes to the CNS Cells to Treat ALS

Large batches of AAVrh.10-miR-SOD1 and AAVrh.10-miR-Scr (scrambled miRNA) were produced using standard techniques. Self-complementary AAV (scAAV) was made because it mediates transduction with higher efficiency than conventional single stranded AAV [14]. A scAAVrh.10 was tested and found to express EGFP more rapidly (within 1 week) and stronger than a single stranded AAV.

AAVrh.10-miR-SOD1 was administered to one group of G93A mice (high SOD1 expressers) and AAVrh.10-miR-Scr to another group of G93A mice (n=15). The AAVrh.10 was injected intrathecally into the CSF in the lumbar area and injected intraventricularly into the forebrain in mice of 60 days of age (~4.8×10$^{10}$ particles in 8 ul).

Figure 6B:
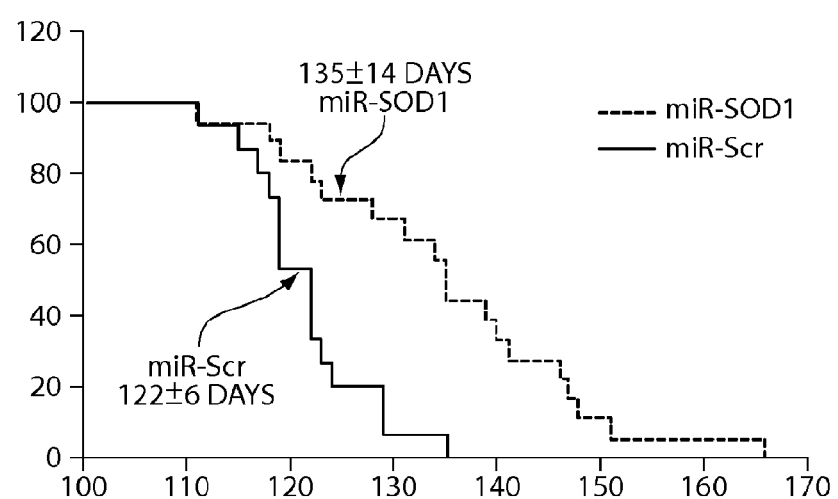
FIG. 6B depicts results of gene transfer studies in SOD1 (G93A) mutant mice showing that rAAV rh.10-SOD1 shRNA increases live span, compared with a rAAV rh.10-scrambled miRNA.
Figure 7A:
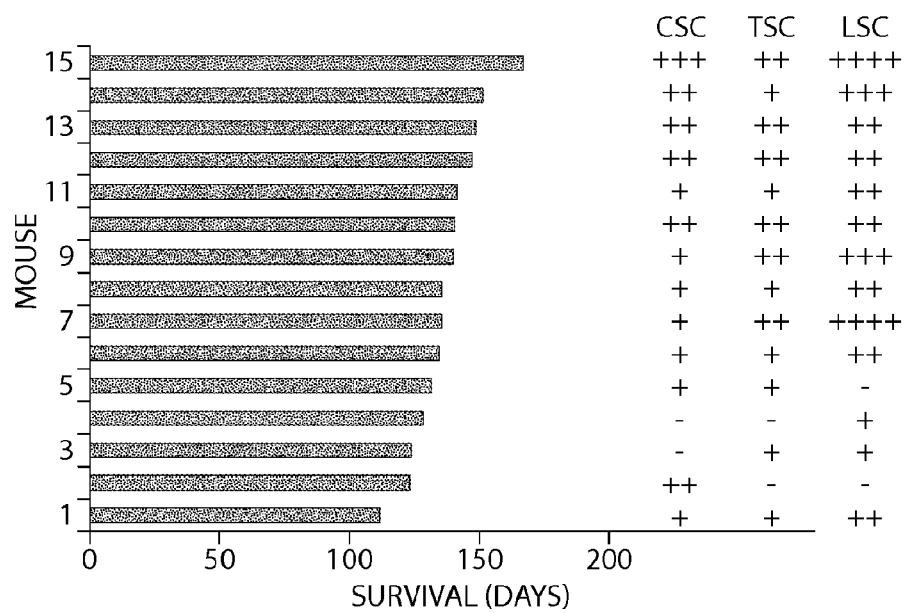
FIG. 7A depicts quantitation of EGFP expression in cervical, thoracic, and lumber spinal cord tissue compared with life spans individual mice infected with rAAV rh.10-SOD1 miRNA; rAAV rh.10-SOD1 was administered directly to the CSF.
Figure 7B:
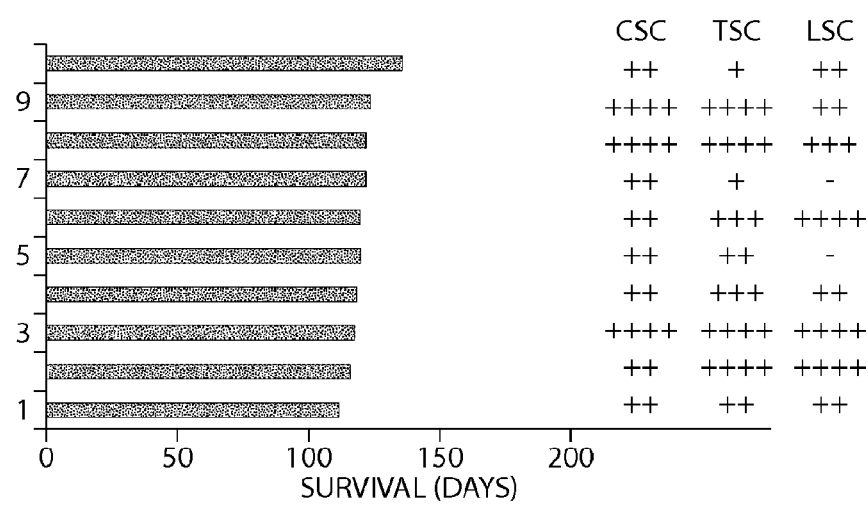
FIG. 7B depicts quantitation of EGFP expression in cervical, thoracic, and lumber spinal cord tissue compared with life spans of individual mice infected with rAAV rh.10-scrambled miRNA; rAAV rh.10-scrambled miRNA was administered directly to the CSF.
Figure 8:
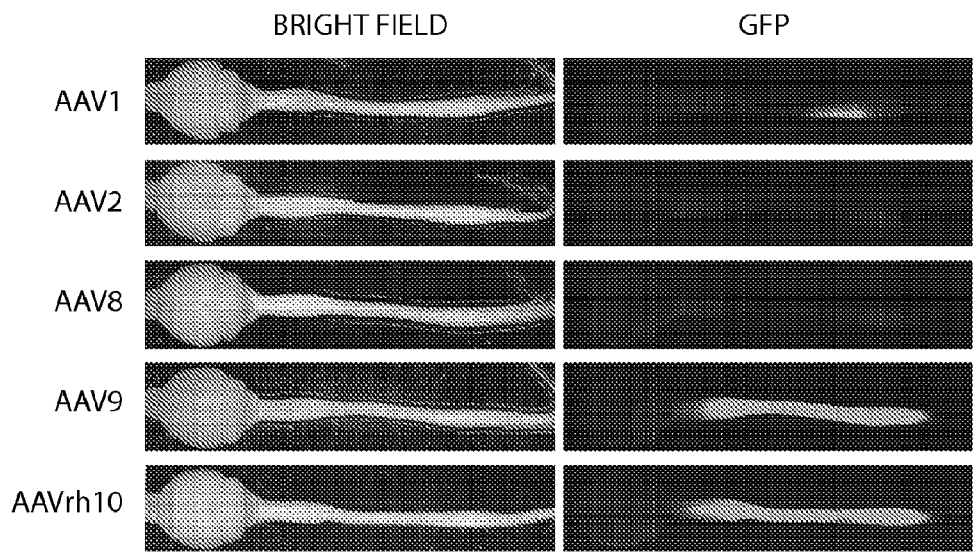
FIG. 8 depicts fluorescence microscopy analysis of mice that have been administered intrathecal injections of various AAVs. In this experiment, both AAV9 and AAVrh10 transduce cells along the full length of the spinal cord after a single injection into the CSF in lumbar subarachnoid space.

The animals were allowed to live their natural lifespan before succumbing to ALS. The lifespan was compared between the two groups. It was found that mice receiving the AAVrh.10-miR-SOD1 virus, which expresses a SOD1miR5 (SEQ ID NO: 26), lived on average 135 days (±14 days), whereas mice receiving the AAVrh.10-miR-Scr, which expresses a scrambled miRNA (SEQ ID NO: 31), lived on average 122 days (±6 days) (FIG. 6B). Moreover, by examining the extent of EGFP expression in cervical, thoracic, and lumber spinal cord tissue, a correlation in the levels of expression in these tissues, particularly with cervical tissue, and lifespan was observed in AAVrh.10-miR-SOD1 treated mice (FIG. 7A), but not AAVrh.10-miR-Scr treated mice (FIG. 7B). These results suggest that silencing mutant SOD1 expression in the cervical spinal cord is particularly beneficial in extending survival. A subset of the animals from each group were perfused with fixative, sectioned and stained for SOD1 in the spinal cord. SOD1 was detected using standard techniques [9]. SOD1 staining intensity in EGFP expressing cells was reduced compared with the non-EGFP cells that are transduced with AAVrh.10-miR-SOD1 (FIG. 6A, showing knockdown of SOD1 expression in astrocytes). Reduction of expression of SOD1 was not observed in cells transduced with AAVrh.10-miR-Scr.

Tissues from another subset of animals in both groups were dissected to estimate transduction levels. The levels of transduction were estimated by determining the viral genome content using PCR on DNA samples obtained from different CNS and non-CNS regions. Measurements in non-CNS tissues (e.g. liver) provided an indication of whether virus had leaked to the periphery. Northern and Western analysis was performed to measure the SOD1 levels in the spinal cord. The antibody used for SOD1 detection was polyclonal, sheep anti-human SOD1, by Biodesign International, catalog #K90077C.

Example 7

Combined Intrathecal/Intraventricular Administration Protocol

AAV viruses were injected into mouse CSF by lumbar intrathecal injection and/or brain third ventricle injection. Injection into mice lumbar subarachnoid space was carried out using a method modified from Wu et al. [22]. A thin catheter (about 5 cm) was made by stretching PE10 tube to the inner diameter 0.12 mm. The stretched section was cut to 1.7 to 1.9 mm, and two beads (1 mm apart) were made between the thin and the thick sections by heating and pressing the tube. To implant the catheter, the mouse was anesthetized by injection of Avertin (1.2% 2,2,2-tribromoethanol in 2% tert-amyl alcohol and PBS) intraperitoneally at 0.23 ml/10 g of body weight [23]. The catheter was then implanted between the L5 and L6 vertebra. The catheter was stitched to the surface muscle at the beaded area. Viruses of dose from 4.80E+10 Genome Copy (for virus screening, in 6 ul) to 2.40E+10 Genome copy (for therapy, in 8 ul) were injected via the catheter by a Hamilton syringe at a speed of 2 ul/minute. The catheter was sealed at the end by heat and left in place for one day. Wound was closed by clips. Injection into brain third ventricle was carried out using a Stoelting Stereotaxic Instrument and micro-injection pumps from World Precision Instruments following standard stereotaxic procedure. Same doses of virus were injected into the third ventricle at a rate of 1 ul/minutes.

Estimated doses for human and monkeys and comparison with IV injection are shown below. The two types of monkey are similar in size.

TABLE 2

Estimated Doses for Human and Monkeys

| Species | Avg CSF ml | Estimated CSF production rate ml/hour | Estimate dose(GC) | particles/g of body weight |
|---|---|---|---|---|
| mouse | 0.035 | 0.018 | 2.40E+10 | 1.2E+09 |
| human | 140 | 21 | 9.6E+13 | 1.3E+09 |

TABLE 2-continued

Estimated Doses for Human and Monkeys

| Species | Avg CSF ml | Estimated CSF production rate ml/hour | Estimate dose(GC) | particles/g of body weight |
|---|---|---|---|---|
| Macaca mulatta (rhesus monkeys) | 14 | 2.5 | 9.6E+12 | 1.7E+09 |
| Macaca fascicularis (cynomolgus macaque) | See, Foust K D, et al., Nature Biotechnology, Volume 28, Number 3, March 2010, 271-274 | | 1.00E+14 | 2.20E+11 |

REFERENCES FOR BACKGROUND AND EXAMPLES 1-7

1. Daya S, Berns K I: Gene Therapy Using Adeno-Associated Virus Vectors. Clin Microbiol Rev 2008, 21:583-593.
2. Eberling J L, Jagust W J, Christine C W, Starr P, Larson P, Bankiewicz K S, Aminoff M J: Results from a phase I safety trial of hAADC gene therapy for Parkinson disease. Neurology 2008, 70:1980-1983.
3. Feigin A, Kaplitt M G, Tang C, Lin T, Mattis P, Dhawan V, During M J, Eidelberg D: Modulation of metabolic brain networks after subthalamic gene therapy for Parkinson's disease. Proceedings of the National Academy of Sciences 2007, 104:19559-19564.
4. Cideciyan A V, Hauswirth W W, Aleman T S, Kaushal S, Schwartz S B, Boye S L, to Windsor E A M, Conlon T J, Sumaroka A, Pang J-j, et al: Human RPE65 Gene Therapy for Leber Congenital Amaurosis: Persistence of Early Visual Improvements and Safety at 1 Year. Hum Gen Ther, 0.
5. Raoul C, Abbas-Terki T, Bensadoun J-C, Guillot S, Haase G, Szulc J, Henderson C E, Aebischer P: Lentiviral-mediated silencing of SOD1 through RNA interference retards disease onset and progression in a mouse model of ALS. Nat Med 2005, 11:423-428.
6. Kaspar B K, Llado J, Sherkat N, Rothstein J D, Gage F H: Retrograde Viral Delivery of IGF-1 Prolongs Survival in a Mouse ALS Model. Science 2003, 301:839-842.
7. Azzouz M, Ralph G S, Storkebaum E, Walmsley L E, Mitrophanous K A, Kingsman S M, Carmeliet P, Mazarakis N D: VEGF delivery with retrogradely transported lentivector prolongs survival in a mouse ALS model. Nature 2004, 429:413-417.
8. Ralph G S, Radcliffe P A, Day D M, Carthy J M, Leroux M A, Lee D C P, Wong L-F, Bilsland L G, Greensmith L, Kingsman S M, et al: Silencing mutant SOD1 using RNAi protects against neurodegeneration and extends survival in an ALS model. Nat Med 2005, 11:429-433.
9. Wu R, Wang I I, Xia X, Zhou I I, Liu C, Castro M, Xu Z: Nerve Injection of Viral Vectors Efficiently Transfers Transgenes into Motor Neurons and Delivers RNAi Therapy Against ALS. Antioxidants & Redox Signaling 2009, 11:1523-1534.
10. Foust K D, Nurre E, Montgomery C L, Hernandez A, Chan C M, Kaspar B K: Intravascular AAV9 preferentially targets neonatal neurons and adult astrocytes. Nat Biotechnol 2009, 27:59-65.
11. Duque S, Joussemet B, Riviere C, Marais T, Dubreil L, Douar A M, Fyfe J, Moullier P, Colle M A, Barkats M: Intravenous administration of self-complementary AAV9 enables transgene delivery to adult motor neurons. Mol Ther 2009, 17:1187-1196.
12. Vandenberghe L H, Wilson J M, Gao G: Tailoring the AAV vector capsid for gene therapy. Gene Ther 2009, 16:311-319.
13. McBride J L, Boudreau R L, Harper S Q, Staber P D, Monteys A M, Martins I, Gilmore B L, Burstein H, Peluso R W, Poli sky B, et al: Artificial miRNAs mitigate shRNA-mediated toxicity in the brain: Implications for the therapeutic development of RNAi. Proceedings of the National Academy of Sciences 2008, 105:5868-5873.
14. McCarty D M: Self-complementary AAV Vectors; Advances and Applications. Mol Ther 2008, 16:1648-1656.
15. Boillee S, Yamanaka K, Lobsiger C S, Copeland N G, Jenkins N A, Kassiotis G, Kollias G, Cleveland D W: Onset and progression in inherited ALS determined by motor neurons and microglia. Science 2006, 312:1389-1392.
16. Xia X, Zhou H, Huang Y, Xu Z: Allele-specific RNAi selectively silences mutant SOD1 and achieves significant therapeutic benefit in vivo. Neurobiol Dis 2006, 23:578-586.
17. Yamanaka K, Chun S J, Boillee S, Fujimori-Tonou N, Yamashita H, Gutmann D H, Takahashi R, Misawa H, Cleveland D W: Astrocytes as determinants of disease progression in inherited amyotrophic lateral sclerosis. Nat Neurosci 2008, 11:251253.
18. Di Giorgio F P, Carrasco M A, Siao M C, Maniatis T, Eggan K: Non-cell autonomous effect of glia on motor neurons in an embryonic stem cell-based ALS model. Nat Neurosci 2007, 10:608-614.
19. Nagai M, Re D B, Nagata T, Chalazonitis A, Jessell T M, Wichterle H, Przedborski S: Astrocytes expressing ALS-linked mutated SOD1 release factors selectively toxic to motor neurons. Nat Neurosci 2007, 10:615-622.
20. Wang Y, Ou Mao X, Xie L, Banwait S, Marti H H, Greenberg D A, Jin K: Vascular Endothelial Growth Factor Overexpression Delays Neurodegeneration and Prolongs Survival in Amyotrophic Lateral Sclerosis Mice. J Neurosci 2007, 27:304-307.
21. Storkebaum E, Lambrechts D, Dewerchin M, Moreno-Murciano M-P, Appelmans S, Oh H, Van Damme P, Rutten B, Man W Y, De Mol M, et al: Treatment of motoneuron degeneration by intracerebroventricular delivery of VEGF in a rat model of ALS. Nat Neurosci 2005, 8:85-92.
22. Wu, W. P., Xu, X. J., and Hao, J. X. (2004) J. Neurosci. Methods 133, 65-69
23. Papaioannou, V. E., and Fox, J. G. (1993) Lab. Anim Sci. 43, 189-192

Example 8

MicroRNA-Regulated, Systemically Delivered rAAV9

Introduction to the Example

This example involves the use of tissue-specific, endogenous microRNAs (miRNAs) to repress rAAV expression outside the CNS, by engineering perfectly complementary miRNA-binding sites into the rAAV9 genome. The example describes recombinant adeno-associated viruses (rAAVs) that can cross the blood-brain-barrier and achieve efficient and stable transvascular gene transfer to the central nervous system (CNS), while de-targeting certain other tissues (e.g., liver, heart, skeletal muscle and other tissues) The approaches described in this example allowed simultaneous multi-tissue regulation and CNS-directed stable transgene expression without detectably perturbing the endogenous miRNA pathway. Regulation of rAAV expression by miRNA was primarily via site-specific cleavage of the transgene mRNA, generating specific 5' and 3' mRNA fragments.

Gene transfer mediated by recombinant adeno-associated virus (rAAV), as disclosed herein, is useful for treatment of a large number of neurological disorders. It has been found that rAAV vectors disclosed herein cross the blood-brain barrier and are specifically expressed in the CNS. Thus, the vectors may be used for intravascular delivery of rAAV for gene therapy of CNS diseases, including those that affect large areas of the brain and spinal cord.

This example describes the use of endogenous microRNAs (miRNAs) to suppress transgene expression outside the CNS miRNAs are small, noncoding RNAs that regulate gene expression by post-transcriptional silencing. In general, miRNAs may silence genes by two mechanisms. When partially complementary to mRNA sequences, they typically reduce target mRNA stability and protein expression (e.g., by two- to fourfold or less), a mode of regulation thought to tune mRNA expression. In contrast, when miRNAs are nearly perfectly complementary to their mRNA targets, they typically bring about cleavage of the mRNA, triggering its wholesale destruction.

In particular, this example describes the use of miRNAs to detarget rAAV9 expression both separately and concurrently in the liver, heart, and skeletal muscle, the three tissues that are most efficiently targeted by intravenously delivered rAAV9. Silencing of transgene expression in liver, heart, and muscle exploited the natural expression of the abundant (≥60,000 copies/cell) miRNAs, miR-122, which is expressed in hepatocytes, and miR-1, a miRNA found in the heart and skeletal muscle of virtually all animals. miR-122-binding sites have been successfully used to prevent hepatotoxicity of a transgene from an adenovirus vector. Perfectly complementary sites for miR-1, miR-122, or both were engineered into the 3' untranslated region (UTR) of a nuclear-targeted, β-galactosidase (nLacZ) reporter transgene whose expression was driven by a cytomegalovirus-enhancer, chicken β-actin (CB) promoter. This example presents multiple independent results indicating that the miRNAs repress nLacZ expression by cleaving the transgene mRNA at exactly the same site as by all Argonaute-bound small RNAs in eukaryotic cells. When delivered systemically in vivo, the miRNA-detargeted rAAV9 vector successfully expressed the reporter transgene in the CNS, but not the liver or heart or skeletal muscle.

Results miRNAs Efficiently Repress Reporter Gene Expression in Cultured Cells

Figure 12A:
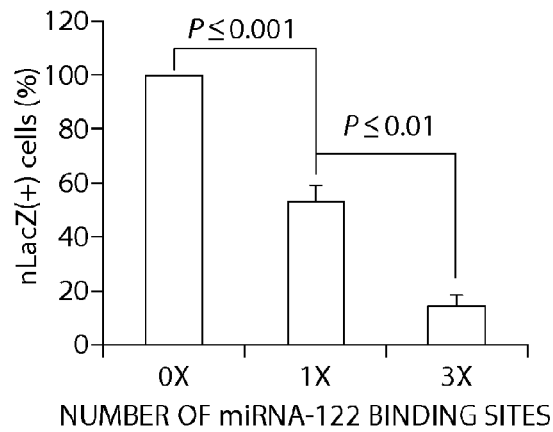
FIG. 12 depicts an in vitro validation of artificial miRNA-binding sites for reporter silencing. Plasmids harboring the rAAVCBnLacZ genome with or without miR-1 or miR-122-binding sites were transfected into human hepatoma (HuH7) cells (a) which express miR-122 or cotransfected into 293 cells, together with a plasmid expressing either pri-miR-122 (b) or pri-miR-1 (c) at molar ratios of 1:3 (low) or 1:10 (high). 0×: no miRNA-binding site; 1×: one miRNA-binding site; 3×: three miRNA-binding sites. The cells were fixed and stained histochemically with X-gal 48 hours after transfection and blue cells counted. The percentage of nLacZ-positive cells in each transfection were compared to transfection of the control plasmid (prAAVCBnLacZ). CB, chicken β-actin; miR, microRNA; nLacZ, β-galactosidase reporter transgene; rAAV, recombinant adeno-associated viruses.

To evaluate a strategy for rAAV-mediated transduction, one or three tandem copies of a perfectly complementary binding site for miR-1 or miR-122 were introduced into the 3' UTR of nLacZ in a rAAV plasmid vector. The constructs were transfected into HuH7 cells, a human hepatoma cell line expressing—16,000 copies of miR-122 per cell, and measured the number of nLacZ-positive cells. The number of nLacZ-expressing HuH7 cells for the one-site plasmid was about half that of the no site control; three sites reduced the number of nLacZ-expressing cells more than sevenfold (FIG. 12a).

Figure 12B:
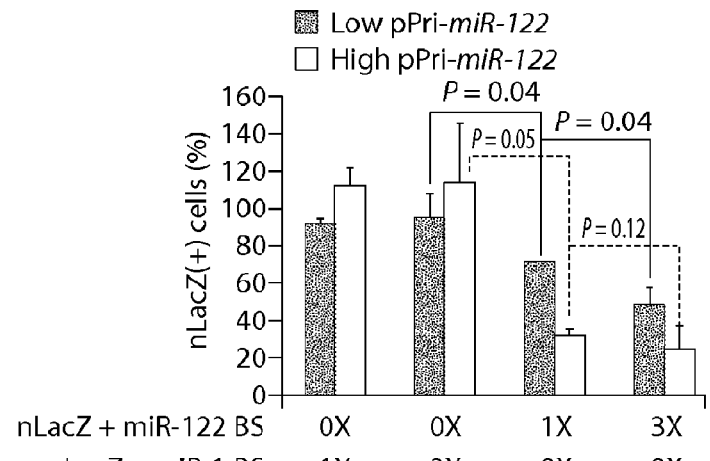
Figure 12C:
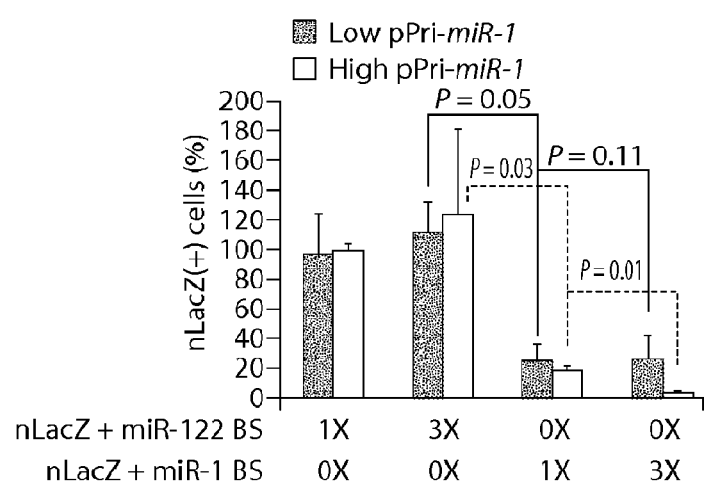

Next, expression of the nLacZ constructs was analyzed in human embryonic kidney 293 cells, which naturally express low levels of both miR-122 and miR-1, when miR-1 or miR122 was introduced as a pri-miRNA from a second plasmid. 293 cells were transfected with the nLacZ reporter plasmids carrying 0, 1, or 3 miR-122 or miR-1-binding sites, together with a plasmid expressing either pri-miR-122 (FIG. 12b) or pri-miR-1 (FIG. 12c). To vary the concentration of the miRNA, either a low (1:3) or a high (1:10) molar ratio of the nLacZ-binding site plasmid to the miRNA expression plasmid was used. When miR-122 or miR-1 was introduced into the cells, nLacZ expression was repressed only when the nLacZ reporter mRNA contained the corresponding miRNA-binding sites; there was no reduction of nLacZ-positive cells when miR-1 was coexpressed with nLacZ containing miR-122-binding sites or when miR-122 was coexpressed with nLacZ containing miR-1-binding sites (FIG. 12b,c).

Figure 13A:
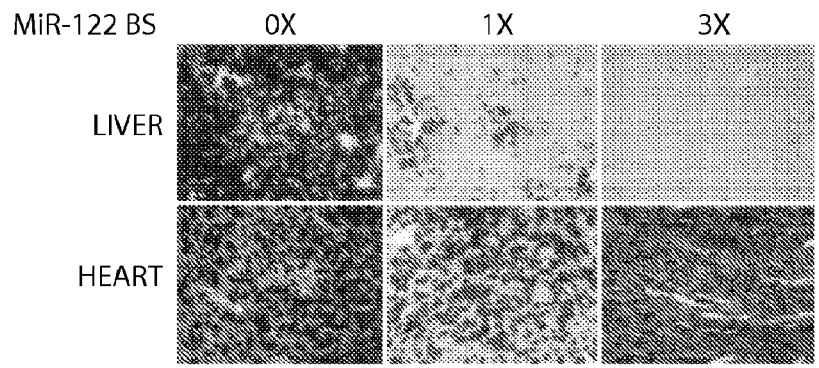
FIG. 13 depicts an in vivo evaluation of endogenous miRNA-mediated transgene silencing in an rAAV9 transduction. (a-c) Adult male C588L/6 mice were injected intravenously with $5 \times 10^{13}$ genome copies per kg (GC/kg) each of rAAV9CBnLacZ (no binding site) (a) rAAVCB9nLacZmiR-122BS (one miR-122-binding site) and rAAV9C8nlacZ-(miR-122BS)$_3$ (three miR-122-binding sites), (b) rAAV9CBnLacZ-miR-1 BS (one miR-1 binding site) and rAAV9CBnLacZ-(miR-1BS)$_3$ (three miR-1-binding sites), (c) rAAV9CBnLacZ-miR-1BS-miR-122BS (1× each binding site) and rAAV9CBnLacZ-(miR-1BS)$_3$-(miR-122BS)$_3$ (three miR-1 and three miR-122-binding sites). The animals were necropsied 4 weeks after vector administration, and appropriate tissues were harvested for cryosectioning and X-gal histochemical staining miR, microRNA; nLacZ, β-galactosidase reporter transgene; rAAV, recombinant adeno-associated viruses, and (d) quantification of β-galactosidase activities in liver tissue from animals that received rAAVnLacZ vectors with and without miRNA-binding sites.
Figure 13B:
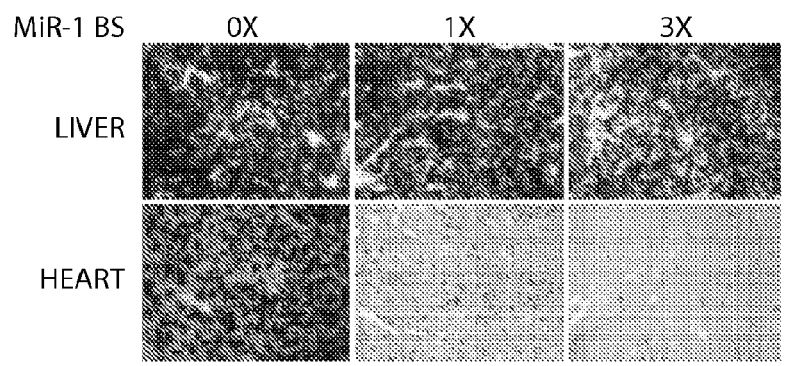

Tissue-Specific Endogenous miRNAs Regulate Expression of rAAV9 Delivered Systemically in Adult Mice To evaluate miRNA regulation of systemically delivered AAV9CBnLacZ vectors in vivo, AAV9CBnLacZ vectors carrying 0, 1, or 3 miRNA-binding sites perfectly complementary to either miR-122 or miR-1 were produced. The vectors were administered by tail vein injection to adult male C56BL/6 mice at a dose of $5 \times 10^{13}$ genome copies per kg (GC/kg) body weight. Four weeks later, the liver and heart of the transduced animals were examined. LacZ staining revealed that the nLacZ transgene was silenced by the endogenous miRNAs in the cell type and organ in which they are predominantly expressed: the transgene was specifically silenced by miR-122 in the liver and by miR-1 in the heart (FIG. 13a,b). While nLacZ positive cells were reduced in the livers of the animals treated with rAAV9CBnLacZ bearing one or three miR-122-binding sites, nLacZ expression levels in the hearts of the same animals were similar to those in the animals treated with AAV9CBnLacZ bearing no sites (FIG. 13a). Similarly, nLacZ expression was not detected in the hearts of the animals that received AAV9CBnLacZ containing one or three miR-1-binding sites, but nLacZ expression in the livers of the same animals was not affected as compared to that in the control animal (FIG. 13b). These data suggest that the greater the number of sites for a miRNA in rAAV, the lower the nLacZ expression in the tissue where the corresponding miRNA was expressed (FIG. 13a,b).

Figure 13C:
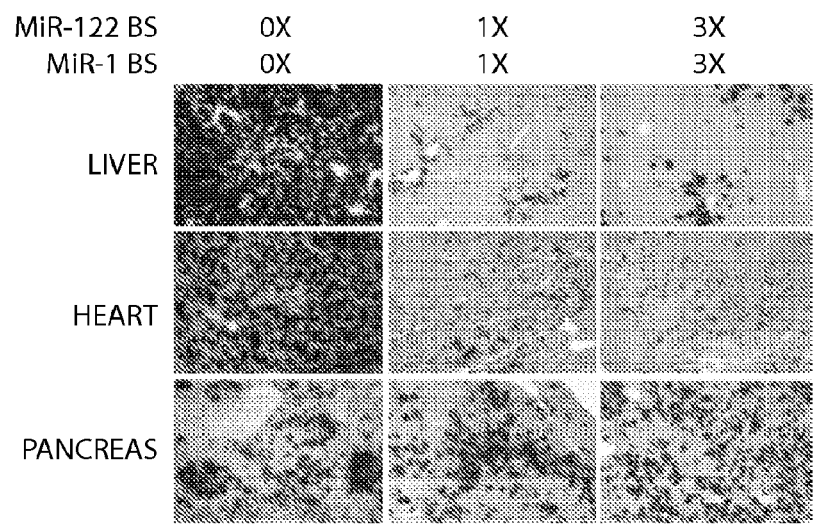
Figure 13D:
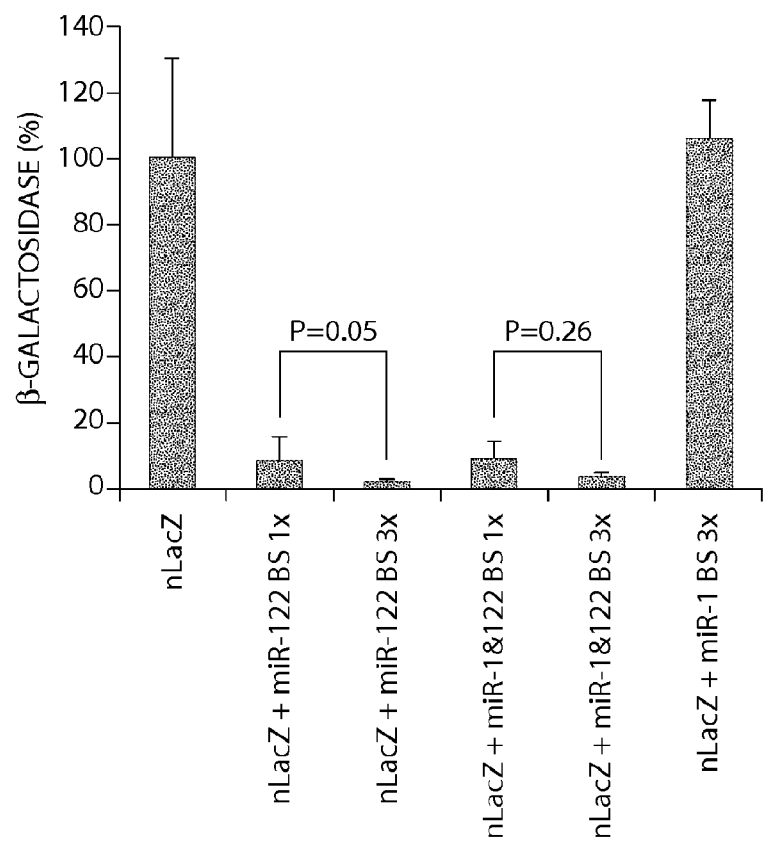

Next, to evaluate whether transgene silencing could be achieved simultaneously in multiple tissues, different numbers of both miR-122- and miR-1-binding sites were inserted in the 3' UTR of the rAAV9CBnLacZ genome and examined for their expression in rAAV9 transduced mice. Histochemical staining of tissue sections showed that nLacZ expression was suppressed in both heart and liver for rAAV9CBnLac containing one or three copies each of the miR-1- and miR-122-binding sites, but nLacZ was readily detectable in pancreas, where expression of both miR-122 and miR-1 was low (FIG. 13c). Quantitative, β-galactosidase assays of homogenized liver tissue similarly showed that nLacZ expression was significantly lower when the transgene contained the miRNA-binding sites (one miR-122-binding site: 7.8±7.4%, P value=0.005; three miR-122-binding sites: 1.6±1.0%, P value=0.005; one miR-1-plus one miR-122-binding site: 8.6±5.7%, P value=0.005; three miR-1-plus three miR-122-binding sites: 3.1±1.2%, P value=0.005; three miR-1-binding sites: 105.7±11.6%) (FIG. 13d).

miRNA Repression of rAAV Expression does not Perturb Endogenous miRNA Pathways

Figure 14A:
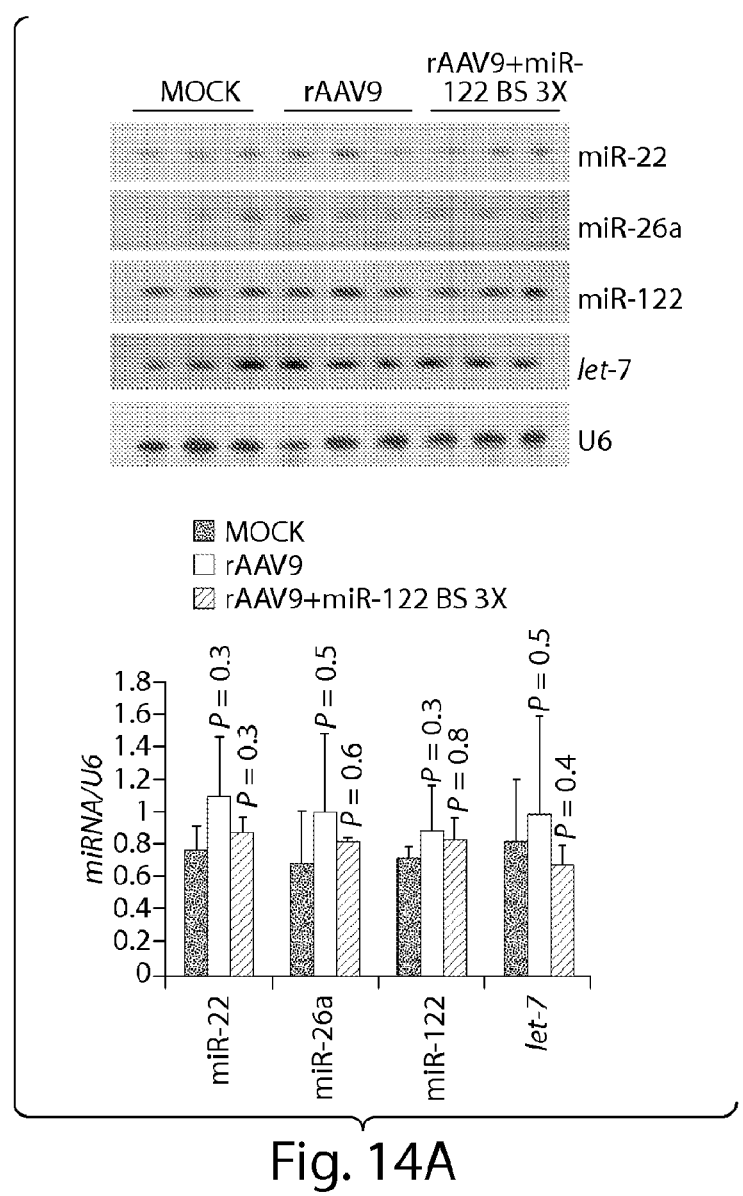
FIG. 14 depicts an analysis of expression levels of cognate miRNA, mRNA, and protein of endogenous miRNA target genes in mice transduced with rAAV9CBnLacZ with or without miRNA-binding sites. Total cellular RNA or protein was prepared from (a-c) liver or (d) heart. (a) Northern blot detection of miRNAs. U6 small nuclear RNA provided a loading control. (b) Quantitative reverse-transcription PCR measuring cyclin G1 mRNA. The data are presented as relative cyclin Gl mRNA levels normalized to β-actin. (c,d) Western blot analyses of protein levels of endogenous targets of miR-122 and miR-1. Total cellular protein prepared from (c) liver or (d) heart was analyzed for cyclin G1 and calmodulin. (e) Serum cholesterol levels. Serum samples from mice that received rAAV9 with or without miRNA-binding sites were collected after 4 weeks and measured for total cholesterol, high-density lipoprotein (HDL) and low-density lipoprotein (LDL). miR, microRNA; nLacZ, β-galactosidase reporter transgene; rAAV, recombinant adeno-associated viruses.

Highly expressed transgenes bearing miRNA-complementary sites have been reported to promote degradation of the corresponding miRNA. The levels of miR-122, miR-22, miR-26a, and let-7 were determined in rAAV transduced liver. No difference in abundance of the four miRNAs was detected among the three study groups (FIG. 14a). Moreover, data from high throughput sequencing analyses of small RNA from the livers of one animal each from the three study groups show no change in miRNA levels.

Figure 14B:
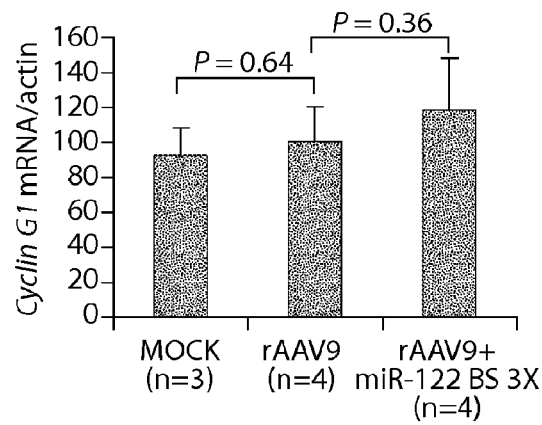
Figure 14C:
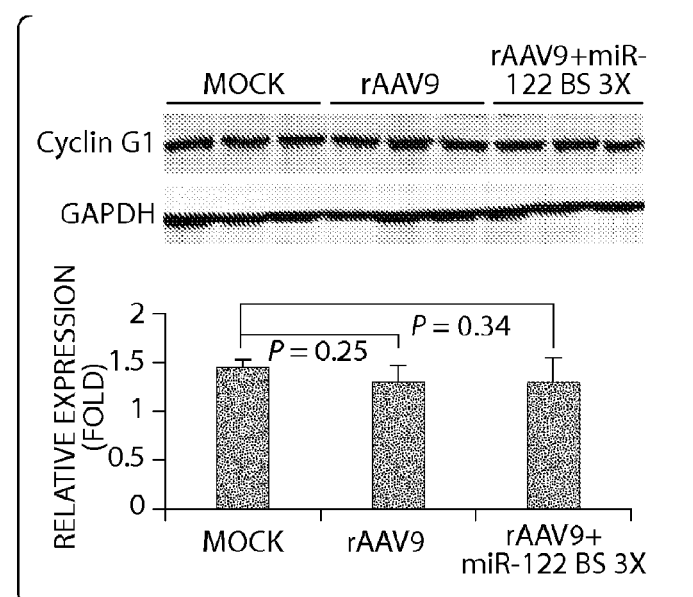
Figure 14D:
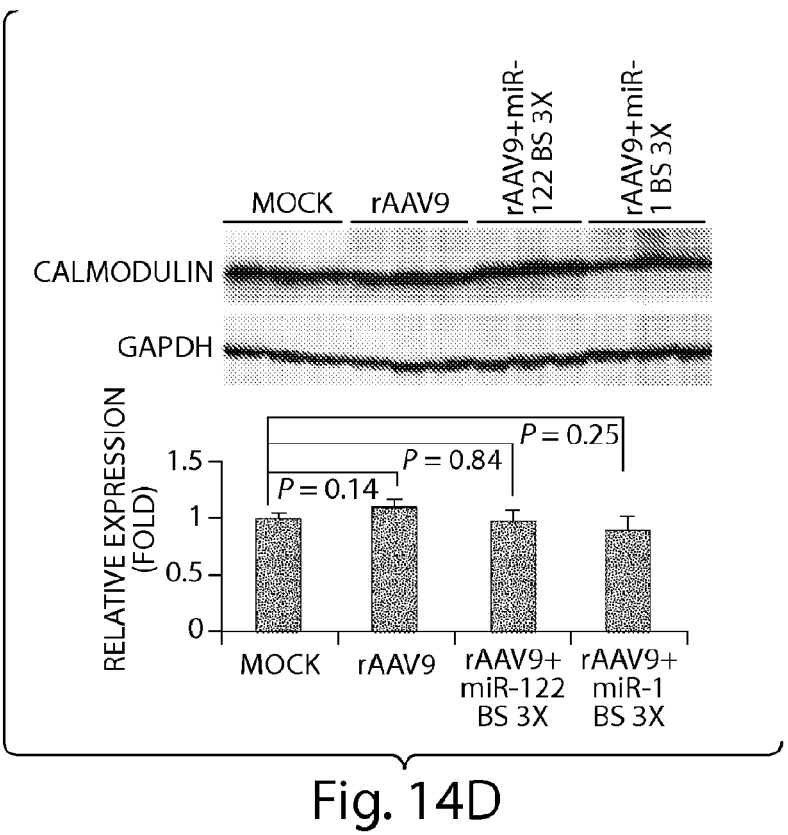
Figure 14E:
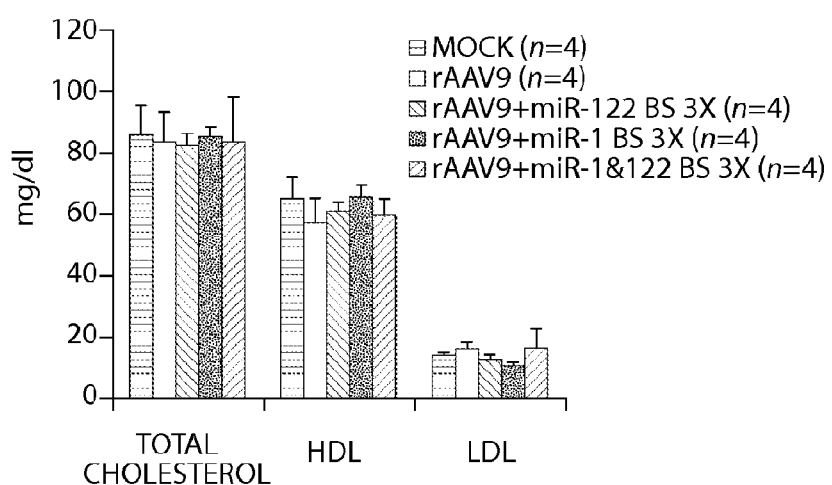

In order to determine whether the miRNA-binding sites in the transgene transcripts would deregulate the expression of the known endogenous target mRNAs of miR-122 or miR-1, the expression of cyclin G1, a miR-122 target in liver (FIG. 14b,c) and calmodulin, a miR-1 target in heart (FIG. 14d) were analyzed. No significant alteration in cyclin G1 or calmodulin expression was detected. miR-122 regulates cholesterol biosynthesis in the liver, and agents that block miR-122 function may produce readily detectable changes in serum cholesterol levels. No change in total cholesterol, high-density lipoprotein, or low-density lipoprotein levels was detected in mice 4 weeks after transduction with either control rAAV9 or rAAV9 expressing a transgene bearing miR-122-binding sites (FIG. 14e). It was concluded that in this example miRNA-mediated detargeting of rAAV expression had no detectable effect on endogenous miRNA expression or function.

Endogenous miRNAs Silence rAAV Transduction by Site-Specific Cleavage of Transgene mRNA To determine how miRNAs suppress expression of transgenes delivered by rAAV in vivo, the transgene mRNA in liver was characterized by conventional PCR (FIG. 15b), quantitative reverse transcription PCR (qRT-PCR) (FIG. 15c), Northern hybridization (FIG. 15d,e), and rapid amplification of 5' complimentary DNA (cDNA) ends (5' RACE; FIG. 15f). When primers were used that amplify the region between the 3' end of nLacZ ($A^+F$ primer) and the 5' end of the poly(A) signal ($A^+R$ primer), an amplicon that spans the miRNA-biding sites, a 145 basepair (bp) product was detected after 26 cycles of amplification for the samples that received control rAAV. An additional six cycles of amplification were required to detect a weak 220 bp band for the samples transduced by rAAV containing three miR-122-binding sites. These data are consistent with low levels of intact nLacZ mRNA (FIG. 15a,b).

Figure 15A:
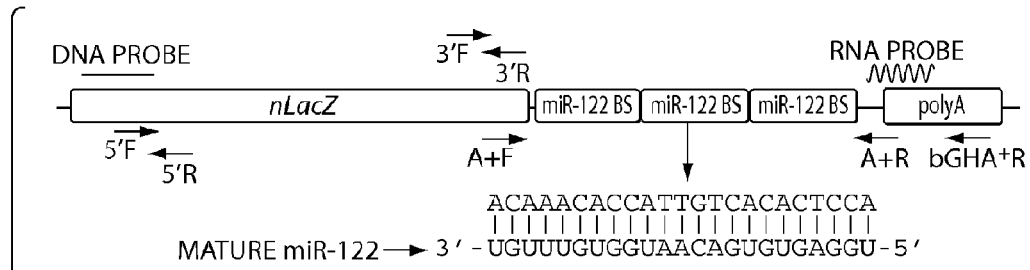
FIG. 15 depicts a molecular characterization of transgene mRNAs with or without miRNA binding sites. (a) Locations of the probes and primers, the sequences of mature miR-122 and its perfectly complementary binding site in the transgene mRNA are presented. (b) Total cellular RNA from liver was analyzed either by conventional reverse-transcription PCR (RT-PCR) by using primers that span a region between the 3' end of nLacZ and the 5' end of poly(A) signal (c) or by quantitative RT-PCR; data are presented as relative nLacZ mRNA levels normalized to β-actin. (d) For the northern blot analysis of nLacZ mRNA, 18S RNA served as a loading control, and the blots were hybridized with either a transgene DNA (e) or RNA probe. (f) In addition, poly(A) bearing mRNA from the liver of an animal received rAAV containing three miR-1- and three miR-122-binding sites was analyzed by 5' RACE; the PCR product was resolved on an ethidium bromide-stained agarose gel. miR, microRNA; nLacZ, β-galactosidase reporter transgene; rAAV, recombinant adeno-associated viruses.
Figure 15B:
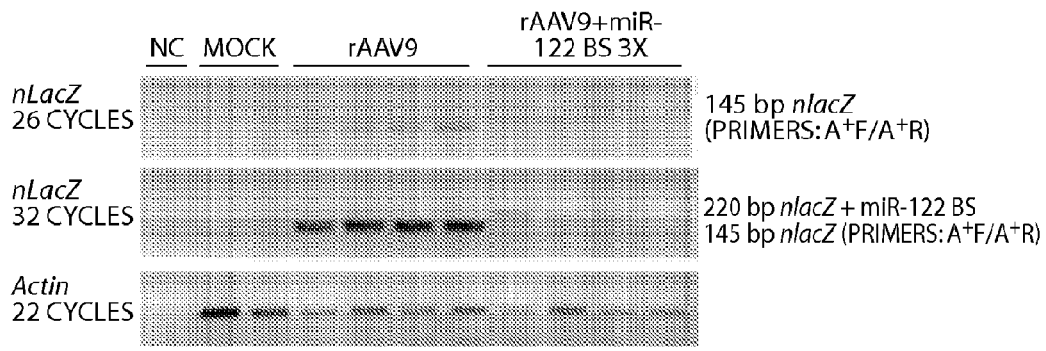
Figure 15C:
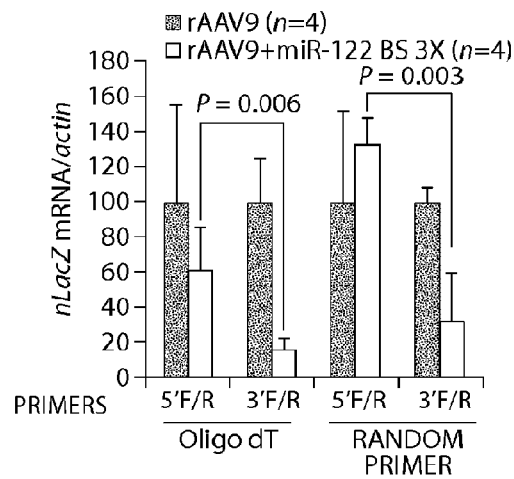

To quantitatively assess the extent of the miRNA-directed repression of the transgene transcripts, qRT-PCR was performed using either oligo(dT) or random hexamer primers for reverse-transcription and PCR primer pairs that span either a 5' (nLacZ5'F/5'R), or 3' (nLacZ3'F13'R) region of the nLacZ, coding sequence (FIG. 15a). The levels of nLacZ, mRNA were examined with intact 5' and 3' ends in total liver RNA extracted from four animals that received the control rAAV9CBnLacZ and four that received rAAV9CBnLacZ containing three miR-122-binding sites in the 3' UTR. Reductions ranging from 3±1 (random hexamer) to 7±1 (oligo[dT])-fold in nLacZ mRNA with an intact 3' end were observed in the animals that had received rAAV9 containing miR-122-binding sites, relative to the control. In contrast, little or no decrease in nLacZ mRNA with an intact 5' end were detected for the same samples using the 5'F/5'R primer pair (FIG. 15c). These results indicate that the primary mode of turnover of the mRNA that has been cleaved by a miRNA was 3'-to-5' exonucleolytic degradation.

To further characterize the fate of the transgene mRNA targeted by miR-1 or miR-122, Northern blot analyses was performed. A transgene probe binding to the 5' end of nLacZ mRNA detected a ~3.4 kb RNA in an animal injected with control rAAV9CbnLacZ, the expected size of the of the full-length nLacZ transcript; a slightly larger band was detected in the liver sample from a mouse treated with rAAV9CBnLacZ bearing three miR1-binding sites (FIG. 15a,d). In contrast to the single transcript detected for the rAAV9 expressing nLacZ bearing three miR-1-binding sites, two RNAs of different sizes were detected for the rAAV expressing nLacZ bearing three miR-122 sites (FIG. 15d).

Figure 15D:
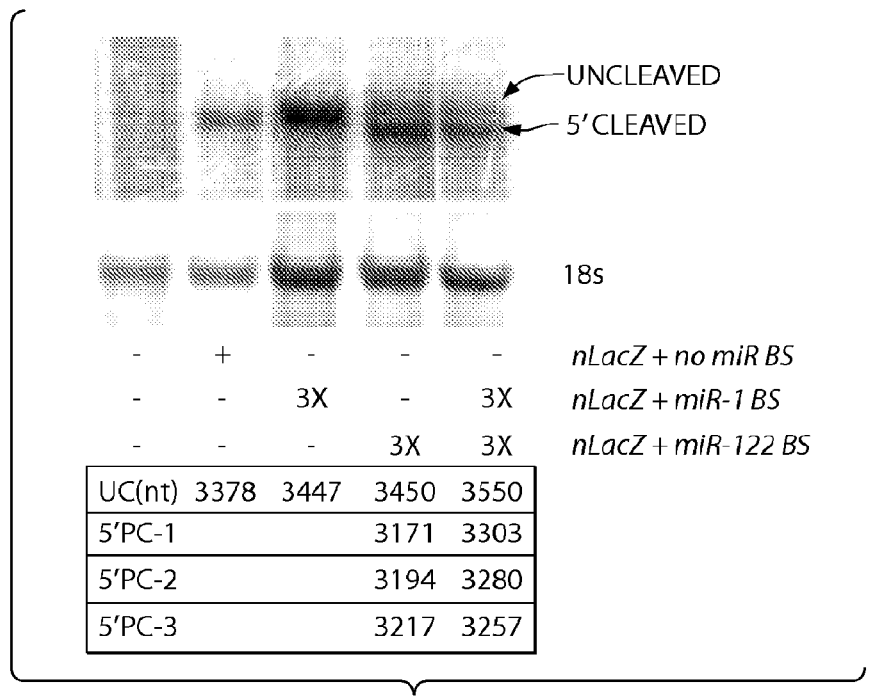

The lengths of these transcripts indicate that the longer transcript likely represents the full-length mRNA, whereas the shorter, more abundant transcript corresponds to 5' fragments of nLacZ RNA cleaved by miR-122 at the corresponding miR-122-binding sites in the 3' UTR (FIG. 15d).

Figure 15E:
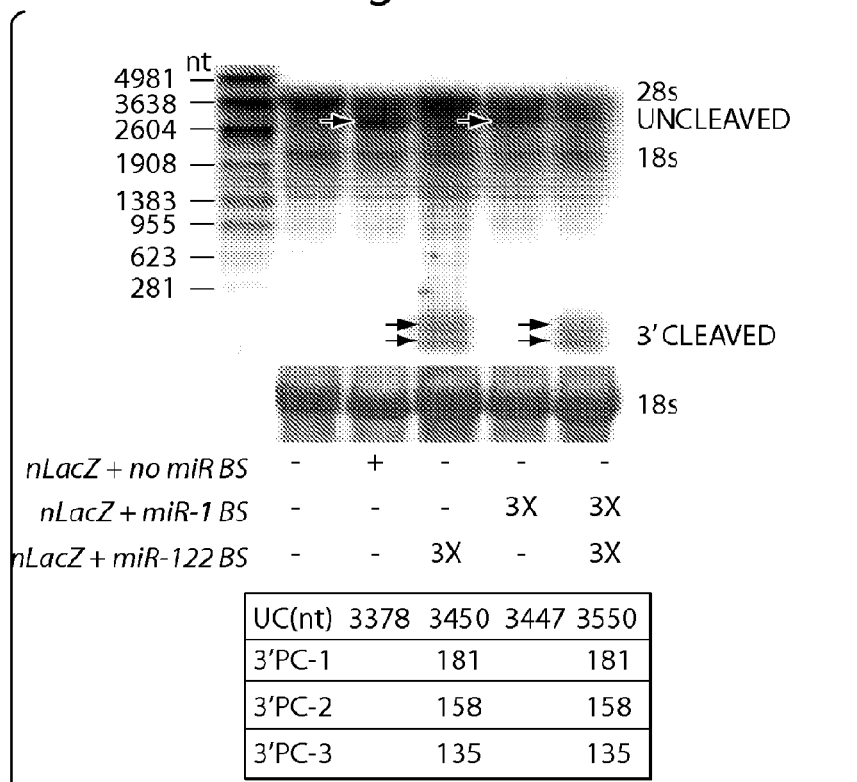
Figure 15F:
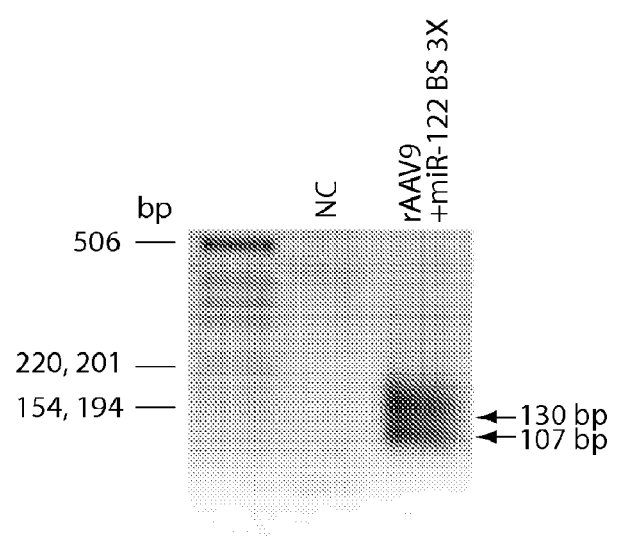

To confirm this observation, the Northern analysis was repeated using an RNA probe spanning a portion of 3' UTR of the transgene mRNA. In addition to detecting full-length nLacZ transcripts in the samples transduced by rAAV9 lacking miRNA-binding sites, two closely migrating species smaller than the 281 nucleotide RNA marker were detected. The size of these fragments was consistent with miRNA-directed 3' cleavage products of the nLacZ mRNA (FIG. 15e). These two 3' cleavage products were also detected by gel electrophoresis of the product from the 5' RACE experiment described below (FIG. 15f).

Figure 16A:
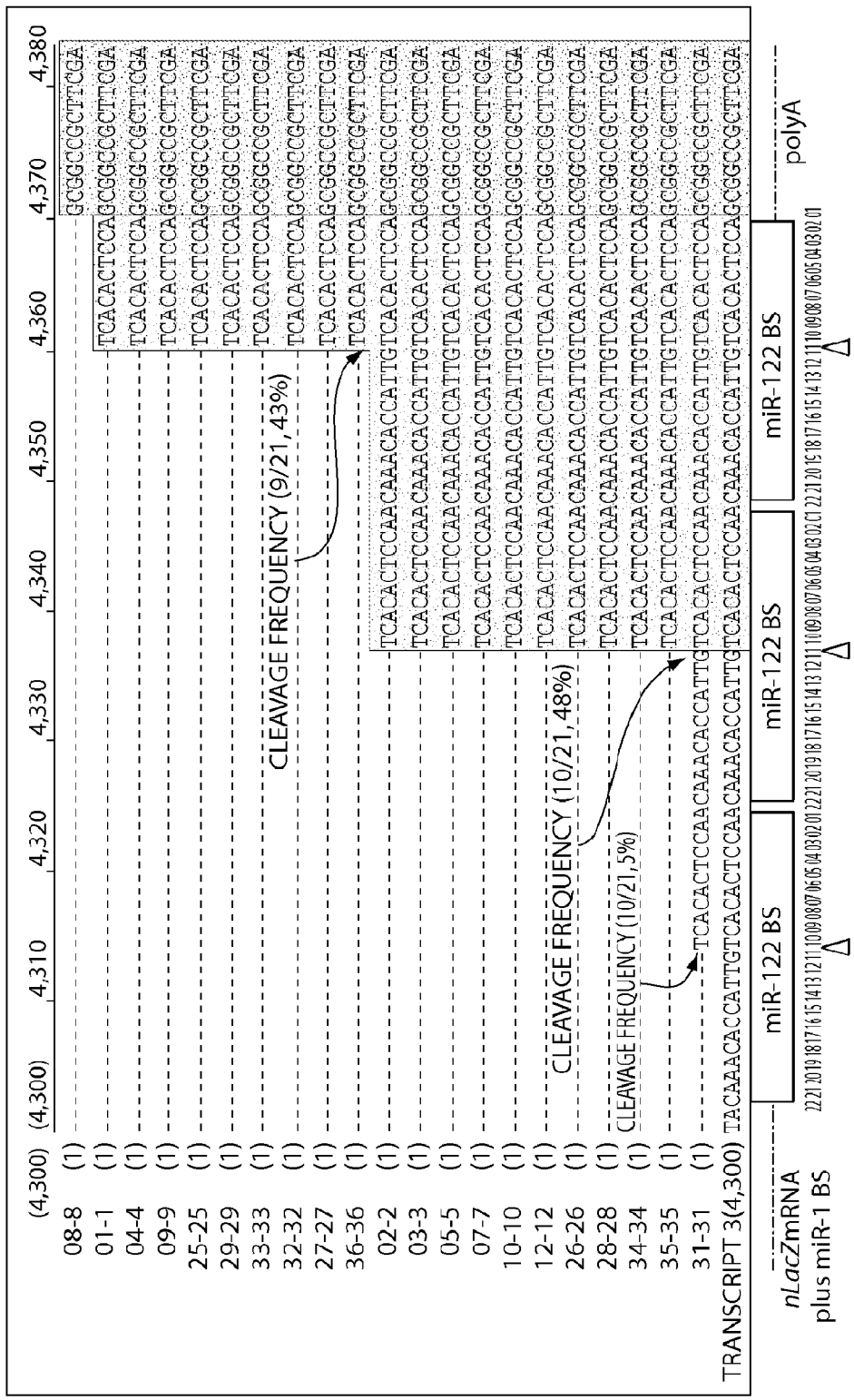
FIG. 16 depicts an alignment of sequences spanning the miRNA-binding sites and poly(A) signal regions recovered by 5 RACE. Poly(A)-containing mRNA was isolated from the (a) liver and (b) heart of an animal injected with rAAV9CBnLacZ-(miR-1BS)$_3$-(miR-122BS)$_3$. Twenty-one liver-derived and twenty-two heart-derived clones were sequenced. The putative cleavage sites in each clone are identified by arrows; the frequencies of miRNA-directed, site-specific cleavage for each miRNA-binding site are reported; triangles point to the positions of the expected miRNA-directed cleavage sites (a,b). miRNA, microRNA, nLacZ, β-galactosidase reporter transgene; rAAV, recombinant adeno-associated viruses.
Figure 16B:
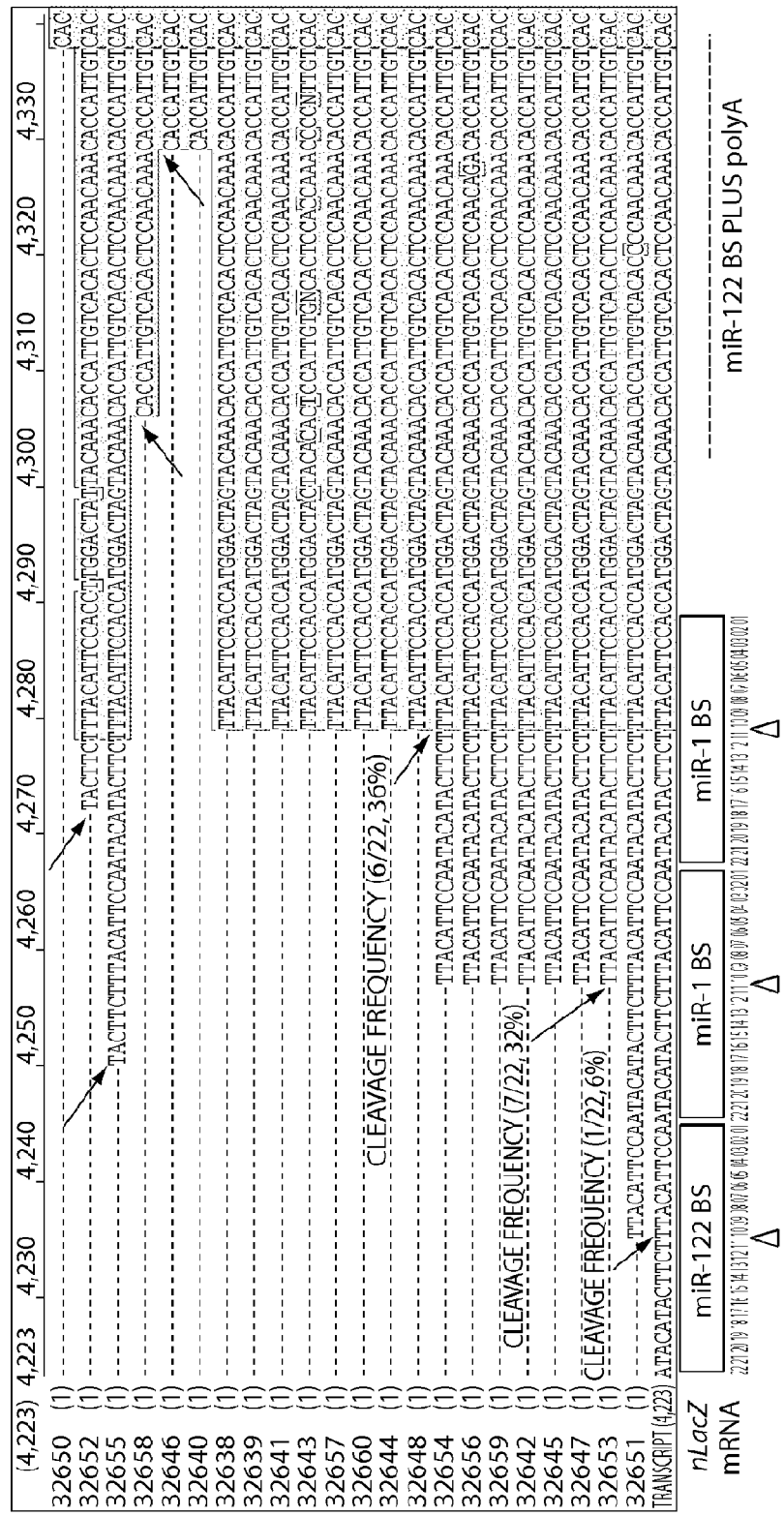
Figure 17A:
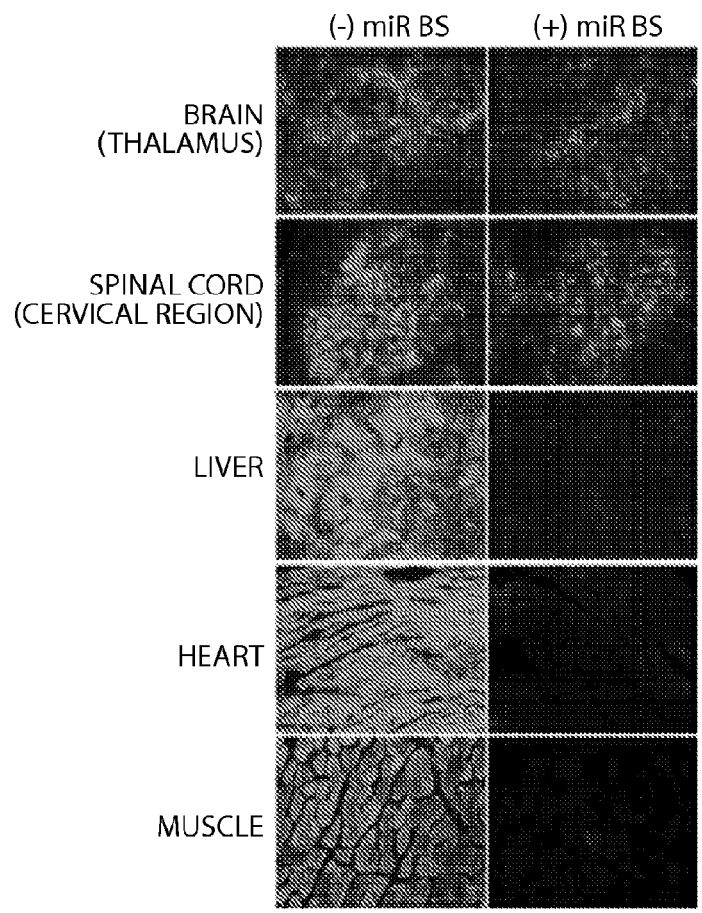
FIG. 17 depicts an endogenous miRNA-repressed, CNS-directed EGFP gene transfer by systemically delivered rAAV9. Ten-week-old male C57BL/6 mice were injected intravenously with scAAV9CBEGFP or scAAV9CBnLacZ (miR-1BS)$_3$-(miR-122BS)$_3$ at a dose of $2 \times 10^{14}$ genome copies per kg (GC/kg) body weight. The animals were necropsied 3 weeks later for whole body fixation by transcardiac perfusion. (a) Brain, spinal cord, liver, heart, and muscle were harvested for cryosectioning, immunofluorescent staining for EGFP (brain and cervical spinal cord), and fluorescence microscopy to detect EGFP. Total cellular DNA and RNA were extracted from brain, liver, heart and muscle to measure the amount of persistent vector genome by qPCR and EGFP mRNA by qRT-PCR. (b) For each tissue, the relative abundance of the EGFP mRNA containing miRNA-binding sites was compared to that of the EGFP mRNA lacking miRNA-binding sites. For each sample, mRNA abundance was normalized to the amount of vector genome detected in the tissue. EGFP, enhanced green fluorescent protein; miRNA, microRNA; nLacZ, β-galactosidase reporter transgene; qRT-PCR, quantitative reverse-transcription PCR; rAAV, recombinant adeno-associated viruses.
Figure 17B:
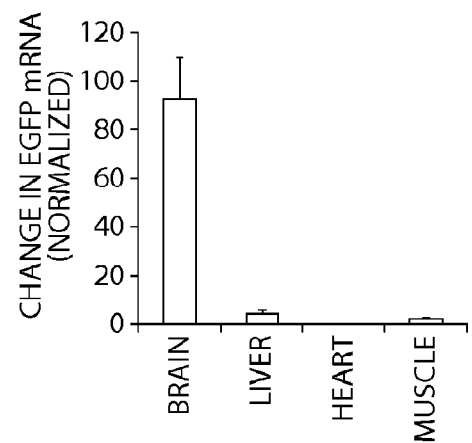

To determine whether such target cleavage occurs in vivo when the nLacZ transcript contained miR-1 or miR-122-binding sites, rapid amplification of 5' cDNA ends (5' RACE) was performed. FIG. 16 presents the sequences of 21 clones recovered using 5' RACE from liver RNA (FIG. 16a) and 22 clones isolated from heart RNA (FIG. 16b) from the animals injected with rAAV9 in which the nLacZ 3' UTR contained three miR-1 and three miR-122-binding sites. In liver, the sequence signatures for miR-122-directed cleavage of the transgene mRNA were detected at each miR-122-binding site: 5% for the first binding site, 48% for the second binding site, and 43% for the third binding site. All 5' ends mapped to the phosphate that lies between the target nucleotides that pair with positions 10 and 11 of the sequence perfectly complementary to miR-122, the precise site cleaved by small RNAs bound to Argonaute proteins in all eukaryotes (FIG. 17a). Similar results were obtained in the heart for the miR-1 sites (FIG. 17b).

Table 3 presents an expanded 5' RACE analysis for additional vector groups. It was noted that none of the 5' RACE products sequenced corresponded to miR-1-directed site-specific cleavage in liver or miR-122-directed site-specific cleavage in heart (Table 3). Although no cleavage was detected within miR-1-binding sites in the liver, some clones from heart were cleaved within the miR-122-binding sites, but not at the hallmark position for miRNA-directed cleavage.

Intravascularly Delivered rAAV9 can be Efficiently Controlled by Endogenous miRNAs MiRNA-1 and miRNA-122-binding sites were added into the scAAV9CB enhanced GFP (EGFP) vector genome and injected 10-week-old C57BL/6 male mice with $2\times10^{14}$ GC/kg. After 3 weeks, 40 µm sections of brain and spinal cord and 8 µm sections of liver, heart, and skeletal muscle were prepared and examined for EGFP protein expression. It was found that intravenously delivered scAAV9CBEGFP efficiently transduced the CNS; EGFP was readily detectable in the thalamus region of the brain and the cervical region of the spinal cord, but also in non-CNS tissues such as liver, heart, and muscle (FIG. 17a). In contrast, transgene expression in those non-CNS tissues was reduced when miR-1 and miR122-binding sites were included in the transgene; EGFP expression was unaltered in the CNS, where miR-1 and miR-122 were not present (FIG. 17a). Quantitative RT-PCR was used to measure the differential expression of the miRNA-repressed EGFP transgene in brain (41.2±7.7%), liver (3.0±0.5%), heart (0.4±0.1%), and muscle (1.3±0.4%), relative to the EGFP transgene lacking miRNA-binding sites (FIG. 17b). To eliminate changes associated with transduction efficiency between experiments, the data were normalized to the number of vector genomes detected in the experimental and control samples. Similar to the microscopic analyses of native EGFP expression, the qRT-PCR data show that the presence of miR-122- or miR-1-binding sites reduced transgene expression in liver (20-fold), heart (100-fold), and muscle (50-fold), but did not detectably alter transgene expression in brain.

Discussion of Results

This example shows that rAAV9 can be engineered so that endogenous miRNAs repress transgene expression outside the CNS. The results indicate that such engineered rAAV9s may be used in therapies for the degenerating neurons associated with Parkinson's disease, Alzheimer's disease and amyotrophic lateral sclerosis, by expressing neurotrophic growth factors such as insulin-like growth factor, brain-derived neurotrophic factor or glial-derived neurotrophic factor in the transduced astrocytes. This approaches eliminates or lessens non-CNS expression derived from the peripheral tissues transduced by systemically delivered rAAV9.

Figure 18:
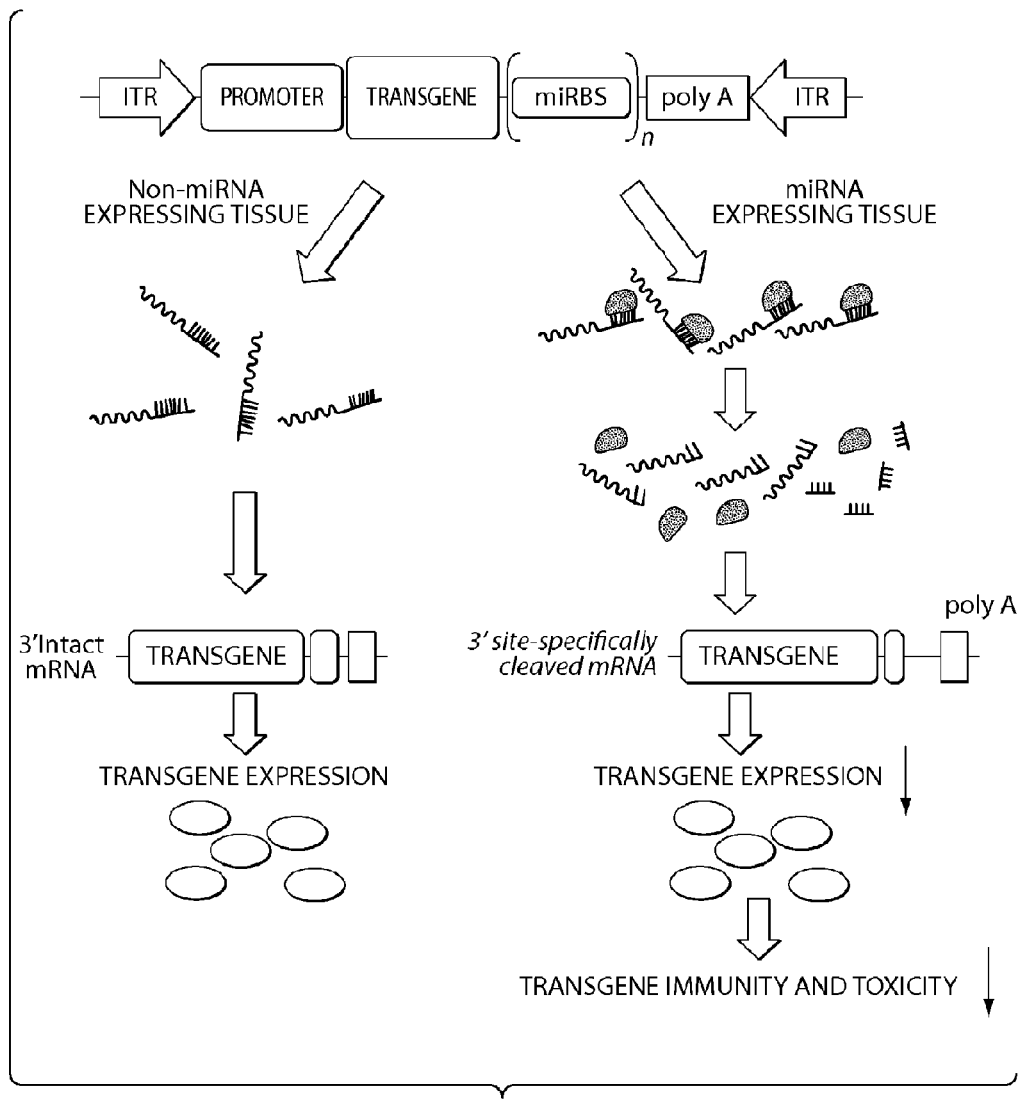
FIG. 18 depicts a molecular model for endogenous miRNA-regulated rAAV expression miRNA, microRNA; rAAV, recombinant adeno-associated viruses.

Achieving transgene expression in primarily only the target tissues is a consideration for the clinical development of safe CNS gene delivery. The results in this example indicate that endogenous miRNAs can be harnessed to restrict the tissue- and cell-type specificity of rAAV expression, as was initially shown for lentiviral vectors. The data demonstrate that endogenous miRNAs can effectively repress transgene expression from rAAV. In both heart and liver, the miRNAs repressed transgene expression by directing endonucleolytic cleavage of the transgene mRNA (FIG. 18). MiRNA regulation of rAAV expression did not perturb the expression or function of the corresponding endogenous miRNA, allowing transgene expression to be restricted to the CNS in mice. The example indicates that a strategy that combines multiple binding sites for miRNAs expressed in the periphery but not the CNS is useful for the development of safer, CNS-specific gene therapy vectors.

Materials And Methods

Vector Design, Construction, and Production.

Perfectly complementary miRNA-binding sites were designed based on the annotated miR-1 and miR-122 sequences in miRBase and inserted into the BstBI restriction site in the 3' UTR of the nLacZ expression cassette of the ubiquitously expressed pAAVCB nuclear-targeted β-galactosidase (nLacZ) plasmid using synthetic oligonucleotides (FIG. 15a and Table 3). This vector uses a hybrid cytomegalovirus enhancer/CB promoter cassette that is active in most cells and tissues. To express miR-122 and miR-1, pri-miR-122 and pri-miR-1 fragments were amplified by PCR from C57/B6 mouse genomic DNA (Table 4) and inserted into the XbaI restriction site 3' to a firefly luciferase cDNA in the pAAVCBELuc plasmid. The identity of each pri-miRNA was verified by sequencing. AAV9 vectors used in this study were generated, purified, and tittered.

Cell Culture and Transfection.

HEK-293 and HuH7 cells were cultured in Dulbecco's modified Eagle's medium supplemented with 10% fetal bovine serum and 100 mg/l of penicillin-streptomycin (Hyclone, South Logan, Utah). Cells were maintained in a humidified incubator at 37° C. and 5% $CO_2$. Plasmids were transiently transfected using Lipofectamine 2000 (Invitrogen, Carlsbad, Calif.) according to the manufacturer's instructions.

Mouse Studies.

Male C57BL/6 mice (Charles River Laboratories, Wilmington, Mass.) were obtained and maintained. To monitor lipid profiles of the study animals, serum samples were collected 4 weeks after rAAV9 injection and analyzed for total cholesterol, high-density lipoprotein and low-density lipoprotein on a COBAS C 111 analyzer (Roche Diagnostics, Lewes, UK). To evaluate endogenous miRNA-mediated, CNS-restricted EGFP gene transfer, 10-week-old male C57BL/6 mice were injected intravenously (tail vein) with AAV9CBnLacZ-[miR-122-binding site $(BS)_1$]. AAV9CBnLacZ-(miR-122BS)$_3$. AAV9CBnLacZ-(miR-1BS)$_1$. AAV9CBnLacZ-(miR-1BS)$_3$. AAV9CBnLacZ-(miR-1BS)$_1$-(miR-122BS)$_1$, and AAV9CBnLacZ-(miR-1BS)$_3$-(miR-122BS)$_3$, respectively, at $5 \times 10^{13}$ GC/kg body weight) or scAAV9CBEGFP at $2 \times 10^{14}$ GC/kg body weight). Animals receiving nLacZ vectors were necropsied 4 weeks later; 8 µm cryosections of liver, heart, and pancreas tissues were prepared for X-gal-histochemical staining. Animals that received EGFP vectors were necropsied 3 weeks later and fixed by transcardial perfusion with 4% (wt/vol) paraformaldehyde. Brain, spinal cord, liver, heart, and muscle were harvested for cryosectioning. Brain and cervical spinal cord tissue were stained as floating sections in a 12-well plate using rabbit anti-EGFP antibody (Invitrogen) diluted 1:500, followed by goat anti-rabbit secondary antibody (Invitrogen) diluted 1:400. Outside the CNS, EGFP expression was detected directly by fluorescence. EGFP and antibody fluorescence was recorded using a Nikon TE-2000S inverted microscope at ×10 magnification and an exposure time of 3 seconds for liver, heart, and muscle, and 5 seconds for thalamus (brain) and cervical spinal cord.

Vector Genome Quantification by qPCR.

Genome DNA was extracted from the selected tissues using QIAamp DNA Mini Kit (Qiagen, West Sussex, UK), according to the manufacturer's instructions. Quantitative PCR were carried out in triplicate using Ring DNA and 0.3 µmol/l EGFP-specific primers (EGFP-F and EGFP-R) using GoTaq qPCR master mix (Promega, Madison, Wis.) in a StepOne Plus real-time PCR instrument (Applied Biosystems, Foster City, Calif.).

qRT-PCR Analysis.

RNA was extracted using Trizol (Invitrogen), according to the manufacturer's instructions. Total RNA (0.5-1.0 µg) was primed with random hexamers or oligo(dT) and reverse-transcribed with MultiScribe Reverse Transcriptase (Applied Biosystems). Quantitative PCR were performed in triplicate with 0.3 mmol/l gene-specific primer pairs (nLacZ5'F/5'R, nLacZ 3'F/3'R, cyclinG1F/R and EGFP-F/EGFP-R) using the GoTaq qPCR master mix in a StepOne Plus Real-time PCR device. The specificity of qRT-PCR products derived from the 5' and 3' ends of nlacZ mRNA was confirmed by gel electrophoresis.

Northern Blot Analysis.

Total RNA was extracted from mouse liver and analyzed by Northern hybridization. To detect nLacZ mRNA, a 618 bp fragment of nLacZ cDNA was isolated by NcoI and PciI digestion of pAAVCBnLacZ and labeled with $\alpha$-$^{32}$P dCTP by random priming (Takara, Shiga, Japan). To detect 3' fragments of the cleaved nLacZ mRNA, an 111 bp fragment of the poly(A) sequence in the vector genome was cloned into pCR4-TOPO (Invitrogen) for preparation of antisense RNA probe labeled with $\alpha$-$^{32}$P CTP during in vitro transcription using the Riboprobe System T7 kit (Promega). To detect miR-122, miR-26a, miR-22, and let-7 or U6 in total liver RNA, small RNAs were resolved by denaturing 15% polyacrylamide gels, transferred to Hybond N+ membrane (Amersham BioSciences, Pittsburgh, Pa.), and crosslinked with 254 nm light (Stratagene, La Jolla, Calif.). Synthetic oligonucleotides, 5' end-labeled with $\gamma$-$^{32}$P ATP using T4 polynucleotide kinase (New England Biolabs, Beverly, Mass.), were used as DNA probes (Table 4) and hybridized in Church buffer (0.5 mol/l NaHPO$_4$, pH 7.2, 1 mmol/l EDTA, 7% (w/v) sodium dodecyl sulphate) at 37° C. Membranes were washed using 1×SSC (150 mM sodium chloride, 15 mM sodium citrate), 0.1% sodium dodecyl sulphate buffer, and then visualized using an FLA-5100 Imager (Fujifilm, Tokyo, Japan).

Western Blot Analysis.

Proteins were extracted with radioimmunoprecipitation assay buffer [25 mmol/l Tris-HCl, pH 7.6, 150 mmol/l NaCl, 1% (vol/vol) NP-40, 1% (wt/vol) sodium deoxycholate, 0.1% (w/v) sodium dodecyl sulphate] containing a protease inhibitor mixture (Boston BP, Boston, Mass.). Protein concentration was determined using the Bradford method (Bio-Rad, Melville, N.Y.). Protein samples, 50 ug each, were loaded onto 12% polyacrylamide gels, electrophoresed, and transferred to nitrocellulose membrane (Amersham BioSciences). Briefly, membranes were blocked with blocking buffer (LI-COR Biosciences, Lincoln, Nebr.) at room temperature for 2 hours, followed by incubation with either anti-GAPDH (Millipore, Billerica, Mass.), anti-cyclin GI (Santa Cruz Biotechnology, Santa Cruz, Calif.) or anti-calmodulin (Millipore) for 2 hours at room temperature. After three washes with PBS containing 0.1% (vol/vol) Tween-20, membranes were incubated with secondary antibodies conjugated to LI-COR IRDye for 1 hour at room temperature, and then antibodies detected using the Odyssey Imager (LI-COR).

$\beta$-Galactosidase Assay.

Proteins were extracted with radioimmunoprecipitation assay buffer and quantified as described above. Fifty micrograms of protein was used for each $\beta$-galactosidase assay using the Galacto-Star System (Applied Biosystems), according to the manufacturer's instructions.

5' RACE.

5' RACE was performed as described. The 5' RACE Outer Primer and the nLacZ gene-specific primer bGHpolyAR (Table 4) were used for the first round of nested PCR. The 5' RACE Inner Primer and the nLacZ gene-specific primer nLacZpolyR, which is located near the stop codon of nLacZ cDNA, were used for the second round of nested PCR (Table 4). PCR products were TOPO-cloned into pCR-4.0 (Invitrogen) and sequenced.

Statistical Analysis.

All results are reported as mean±SD and compared between groups using the two-tailed Student's t-test.

TABLE 3

Summary of microRNA-guided transgene mRNA cleavage in mouse liver and heart

| miR BS cleavage | Position | Cleavage site | | | | | | |
|---|---|---|---|---|---|---|---|---|
| | | Between 10 and 11 nt | | Between 17 and 18 nt | | Between 18 and 19 nt | | Random site |
| Liver 1 Copy of miR-122 BS (21 clones) | 1 | 17/21 | 81% | ND | | ND | | 19% |
| 3 Copies of miR-122 BS (11 clones) | 1 | ND | 100% | ND | | ND | | 0% |
| | 2 | 4/11 | | | | | | |
| | 3 | 7/11 | | | | | | |
| 3 Copies each of miR-1 and miR 122 miR 1 3x BS | 1 | ND | ND | ND | | ND | | 0% |
| BS in a single vector (21 clones) | 2 | ND | | | | | | |
| | 3 | ND | | | | | | |
| miR-122 3x BS | 1 | 1/21 | 95% | ND | | ND | | 5% |
| | 2 | 10/21 | | | | | | |
| | 3 | 9/21 | | | | | | |
| Heart 1 Copy of miR-1BS (12 clones) | 1 | 12/12 | 100% | ND | | ND | | 0% |
| 3 Copies of miR 1BS (21 clones) | 1 | ND | 80% | 4/21 | 20% | ND | | 0% |
| | 2 | 16/21 | | ND | | | | |
| | 3 | 1/21 | | ND | | | | |
| 3 Copies each of miR 1 and miR 122 miR-122 3x BS | 1 | ND | ND | ND | | 1/22 | 14% | 4% |
| BS in a single vector (22 clones) | 2 | ND | | | | 1/22 | | |
| | 3 | ND | | | | ND | | |
| miR 1 3x BS | 1 | 1/22 | 73% | ND | 9% | ND | | 0% |
| | 2 | 7/22 | | 1/22 | | | | |
| | 3 | 8/22 | | 1/22 | | | | |

TABLE 4

Oligonucleotide primers and probes used in Example 8.

| Oligo nucleotides | Sequence | SEQ ID NO |
|---|---|---|
| (miR-1)$_1$ sense | [PHOS]CGAAATACATACTTCTTTACATTCCATT | SEQ ID NO: 32 |
| (miR-1)$_1$ anti-sense | [PHOS]CGAATGGAATGTAAAGAAGTATGTATTT | SEQ ID NO: 33 |
| (miR-122)$_1$ sense | [PHOS]CGAAACAAACACCATTGTCACACTCCATT | SEQ ID NO: 34 |
| (miR-122)$_1$ anti-sense | [PHOS]CGAATGGAGTGTGACAATGGTGTTTGTTT | SEQ ID NO: 35 |
| (miR-1)$_3$ sense | [PHOS]CGAAATACATACTTCTTTACATTCCAATACATACTTCTTTACATTCCAATACATACTTCTTTACATTCCATT | SEQ ID NO: 36 |

TABLE 4-continued

Oligonucleotide primers and probes used in Example 8.

| Oligo nucleotides | Sequence | SEQ ID NO |
|---|---|---|
| (miR-1)$_3$ anti-sense | [PHOS]CGAATGGAATGTAAAGAAGTATGTATTGG AATGTAAAGAAGTATGTATTGGAATGTAAAGAAGT ATGTATTT | SEQ ID NO: 37 |
| (miR-122)$_3$ sense | [PHOS]CGAAACAAACACCATTGTCACACTCCAAC AAACACCATTGTCACACTCCAACAAACACCATTGT CACACTCCATT | SEQ ID NO: 38 |
| (miR-122)$_3$ anti-sense | [PHOS]CGAATGGAGTGTGACAATGGTGTTTGTTG GAGTGTGACAATGGTGTTTGTTGGAGTGTGACAAT GGTGTTTGTTT | SEQ ID NO: 39 |
| (miR-1)$_1$-(miR-122)$_1$ sense | [PHOS]CGAAATACATACTTCTTTACATTCCAACA AACACCATTGTCACACTCCATT | SEQ ID NO: 40 |
| (miR-1)$_1$-(miR-122)$_1$ anti-sense | [PHOS]CGAATGGAGTGTGACAATGGTGTTTGTTG GAATGTAAAGAAGTATGTATTT | SEQ ID NO: 41 |
| Synthesized (miR-1)$_3$-(miR-122)$_3$ fragment | TTCGAACTCGAGATACATACTTCTTTACATTCCAA TACATACTTCTTTACATTCCAATACATACTTCTTT ACATTCCACCATGGACTAGTACAAACACCATTGTC ACACTCCAACAAACACCATTGTCACACTCCAACAA ACACCATTGTCACACTCCAGCGGCCGCTTCGAA | SEQ ID NO: 42 |
| Pri-miR-122F | ATCGGGCCCGACTGCAGTTTCAGCGTTTG | SEQ ID NO: 43 |
| Pri-miR-122R | CGCGGGCCCGACTTTACATTACACACAAT | SEQ ID NO: 44 |
| Pri-miR-1F | CGCGGGCCCGACTGATGTGTGAGAGAGAC | SEQ ID NO: 45 |
| Pri-miR-1R | CGCGGGCCCGACTTTCGGCCTCCCGAGGC | SEQ ID NO: 46 |
| nLacZ5¢F(5¢F) | TGAAGCTGAAGCCTGTGATG | SEQ ID NO: 47 |
| nLacZ5¢R(5¢R) | GAGCACCTGACAGCATTGAA | SEQ ID NO: 48 |
| nLacZ3¢F(3¢F) | CTCAGCAACAGCTCATGGAA | SEQ ID NO: 49 |
| nLacZ3¢R(3¢R) | TTACTTCTGGCACCACACCA | SEQ ID NO: 50 |
| nLacZpolyF(A⁺F) | TGGTGTGGTGCCAGAAGTAA | SEQ ID NO: 51 |
| nLacZpolyR (A⁺R) | CAACAGATGGCTGGCAACTA | SEQ ID NO: 52 |
| bGHpolyAR(bGH⁺AR) | TGGGAGTGGCACCTTCCA | SEQ ID NO: 53 |
| EGFP-F | CGACCACTACCAGCAGAACA | SEQ ID NO: 54 |
| EGFP-R | CTTGTACAGCTCGTCCATGC | SEQ ID NO: 55 |
| CyclinG1F | AATGGCCTCAGAATGACTGC | SEQ ID NO: 56 |
| CyclinG1R | AGTCGCTTTCACAGCCAAAT | SEQ ID NO: 57 |
| MM-ActinF | ATGCCAACACAGTGCTGTCTGG | SEQ ID NO: 58 |
| MM-ActinR | TGCTTGCTGATCCACATCTGCT | SEQ ID NO: 59 |
| miR-122 probe | TGGAGTGTGACAATGGTGTTTG | SEQ ID NO: 60 |
| Let-7 probe | AACTATACAACCTACTACCTCA | SEQ ID NO: 61 |
| miR-26a probe | AGCCTATCCTGGATTACTTGAA | SEQ ID NO: 62 |
| miR-22 Probe | ACAGTTCTTCAACTG GCAGCTT | SEQ ID NO: 63 |
| U6 probe | CTCTGTATCGTTCCAATTTTAGTATA | SEQ ID NO: 64 |

Example 9

Intravenous Injection of rAAVs Mediated Widespread Transduction in Neonatal Mouse CNS Introduction to the Example This example describes an analysis of nine scAAV vectors for CNS gene transfer properties after systemic administration. This study involved identifying more effective vectors for the CNS gene transfer, In some aspects the study examined serotypes or natural variants of rAAVs for enhanced-permeation of the BBB. In some cases, the study sought to identify rAAV vectors with improved delivery of enhanced green fluorescent protein (EGFP) to the CNS following facial vein injection on postnatal day 1 (P1). AAV9 was included in the study. Except for rAAV2 and rAAV5, all other 7 vectors crossed the BBB with varied transduction efficiency, among which rAAVrh.10, rAAVrh.39, rAAVrh.43, rAAV9 and rhAAV7 rank in the top 5, mediating robust EGFP expression in both neuronal and glial cells throughout the CNS in this study. The performance of rAAVrh.10 was comparable to that of rAAV9 and in some case better. Several rAAVs efficiently transduce neurons, motor neurons, astrocytes and Purkinje cells; among them, rAAVrh.10 is at least as efficient as rAAV9 in many of the regions examined. Intravenously delivered rAAVs did not cause abnormal microgliosis in the CNS. The rAAVs that achieve stable widespread gene transfer in the CNS are useful as therapeutic vectors for neurological disorders affecting large regions of the CNS as well as convenient biological tools for neuroscience research.

Results

Figures 1, 19A:
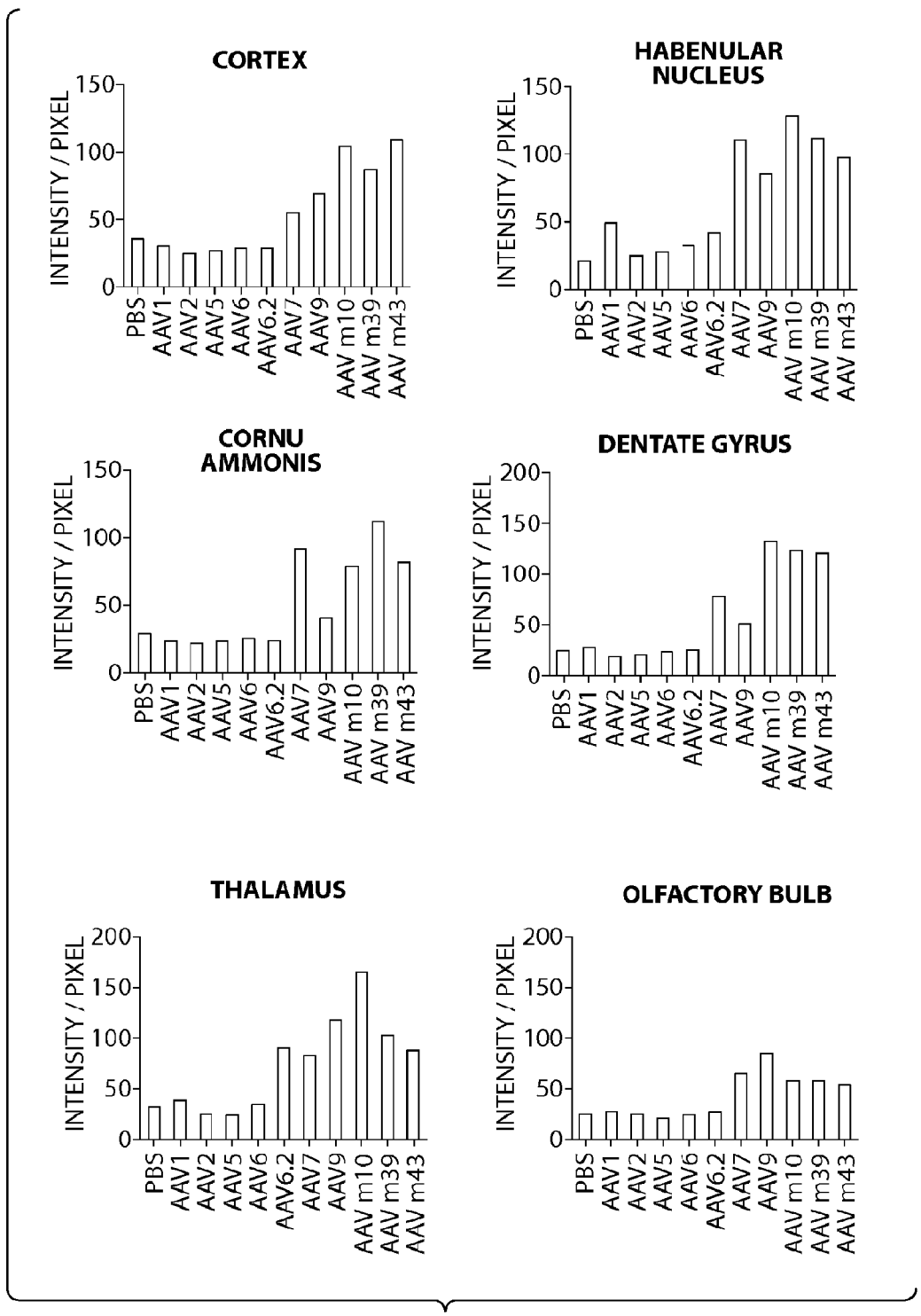
Figures 2, 19A:
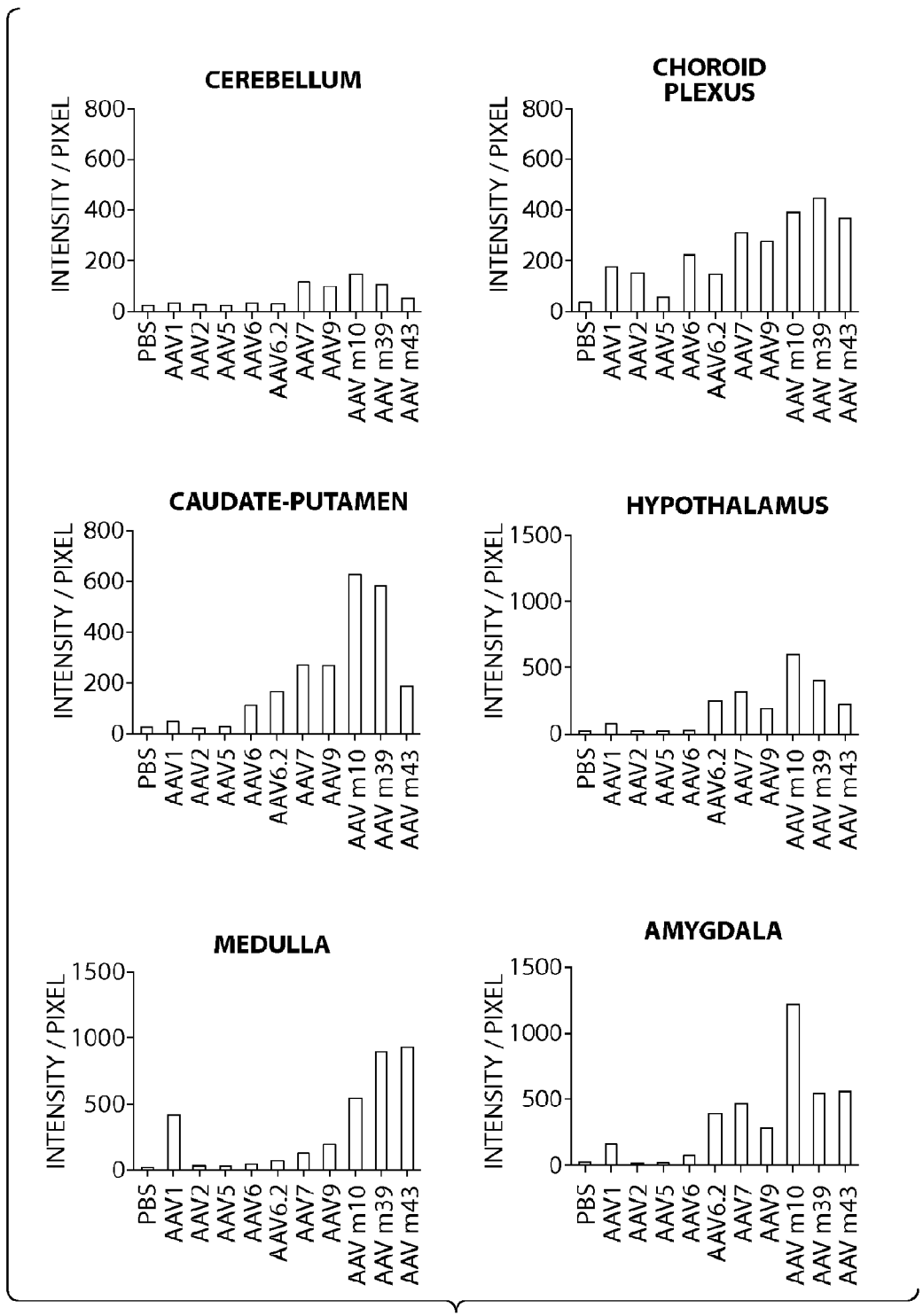
Figures 3, 19A:
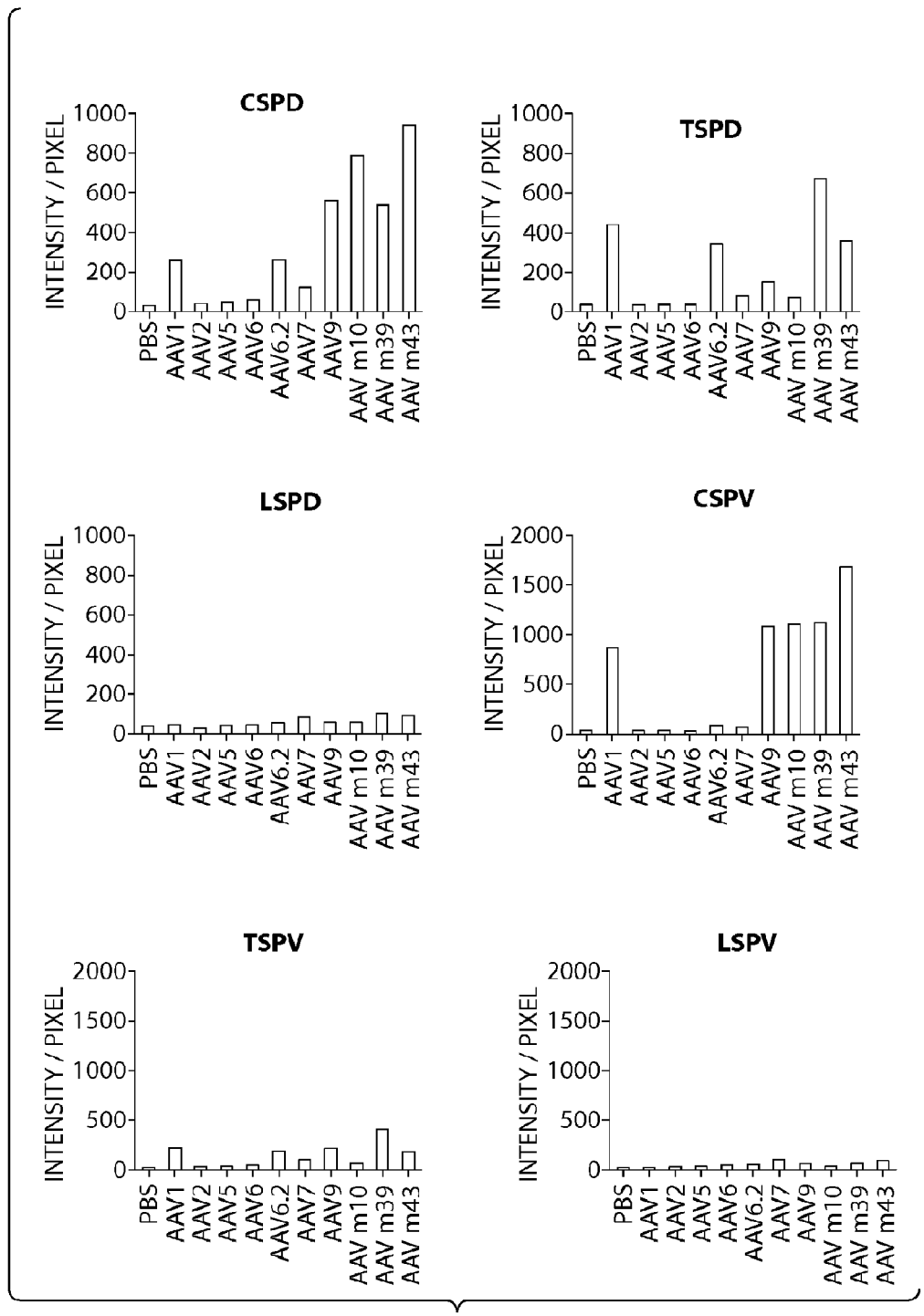
Figure 19B:
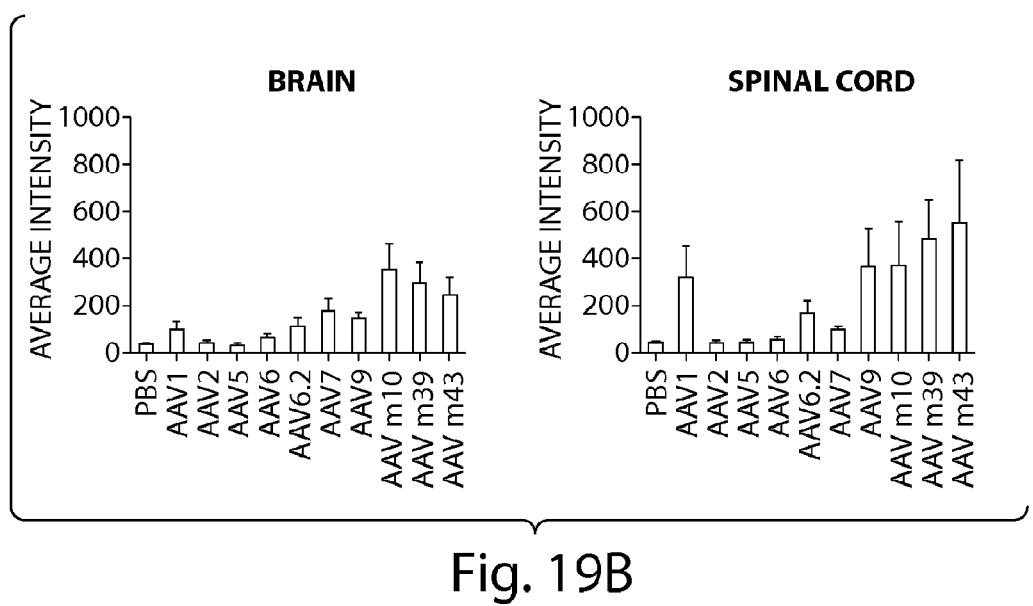
FIG. 19 depicts a quantification of GFP intensity levels in the brain and spinal cord of neonatal mice transduced with various AAV vectors. $4 \times 10^{11}$ genome copies (GCs) of ten different AAV vectors were injected into neonatal P1 pups through superfacial vein. The mice were sacrificed 21 days after injection. The brain tissues were extracted and 40 µm thick cryosections were prepared. The sections were stained against anti-EGFP antibody. The images were analyzed and the intensity/pixel values of all AAV serotypes in various regions in brain and spinal cord (A) were calculated by using Nikon NIS elements AR software version 3.2. Average intensities of the brain and spinal cord regions for different rAAVs were also presented (B). Region of interest (ROI) of each anatomical structure was fixed for all vectors to ensure the parallel comparison.

Twenty one days after vector administration in P1 mice, the CNS transduction profiles of the following recombinant AAV vectors encoding EGFP: rAAV1, rAAV2, rAAV5, rAAV6, rAAV6.2, rAAV7, rAAV9, rAAVrh.10, rAAVrh.39 and rhAAVrh.43 were compared. The vectors used in this study were comparable in purity and morphological integrity (FIG. 19). As assessed by the scoring system described in the methods, rAAV9 was among the top performers; most other rAAVs tested (rAAV1, rAAV6, rAAV6.2, rAAV7, rAAVrh.10, rAAVrh.39 and rAAVrh.43) also gave rise to EGFP expression throughout the CNS (Table 2). The number of apparent EGFP positive cells (Table 5) among sub-anatomical structures was influenced by the particular vector used. For these seven rAAVs, and rAAV9 (total of eight rAAVs), that permeated the BBB and accomplished CNS transduction after i.v. delivery, EGFP positive cells were found in hypothalamus followed by medulla, striatum, hippocampus, cortex and cerebellum. In contrast, the transduction efficiency in olfactory bulb and thalamus was relatively low (Table 5). A quantitative assessment of EGFP gene transfer efficiency was made of each rAAV. 12 sub-anatomically and functionally important regions in the brain were selected for quantitative analysis of the mean EGFP intensity/pixel in each region for each rAAV by using Nikon NIS elements AR software V. 32 (FIG. 19a) (see Methods). For the eight vectors that achieved CNS transduction after i.v. injection, the mean EGFP intensity/pixel was relatively low in cortex, habenular nucleus, cornu ammonis, dentate gyrus, thalamus, cerebellum and olfactory bulb, moderate in choroid plexus and caudate-putamen, but high in hypothalamus, medulla and amygdale (FIG. 19a). The average EGFP intensities of all 12 regions for different rAAVs were compared in FIG. 19b. AAVrh.10, AAVrh.39 and AAVrh.43 were noted for gene transduction efficiency in brain, followed by AAV7, AAV9, and AAV1 (FIGS. 19a and 19b). Those eight effective serotypes also mediated EGFP expression throughout the spinal cord, to different degrees. The same quantitative analysis was performed for each rAAV in the cervical, thoracic and lumbar sections of the spinal cord (FIG. 19a); the average EGFP intensities of the three sections for different rAAVs were also compared (FIG. 19b). AAV1, AAV9, AAVrh10, AAV.rh39 and AAV.rh43 displayed strong transduction in the spinal cord with the high EGFP intensity observed in the cervix, followed by thoracic and lumbar sections of the spinal cord (FIGS. 19a and 19b). For rAAV2 there were few EGFP-positive cells in hippocampus, cortex and hypothalamus. EGFP-positive cells were observed in the hypothalamus in AAV5-injected mice. A description of the observations made in different CNS structures is provided below. The subanatomic CNS structures may serve as a target for CNS gene therapy. In some cases, the subanatomic CNS structures are associated with pathological changes in one or more neurological disorders. In some cases, the subanatomic CNS structure have distinct transduction profiles for one or more rAAVs.

Striatum.

Figure 20:
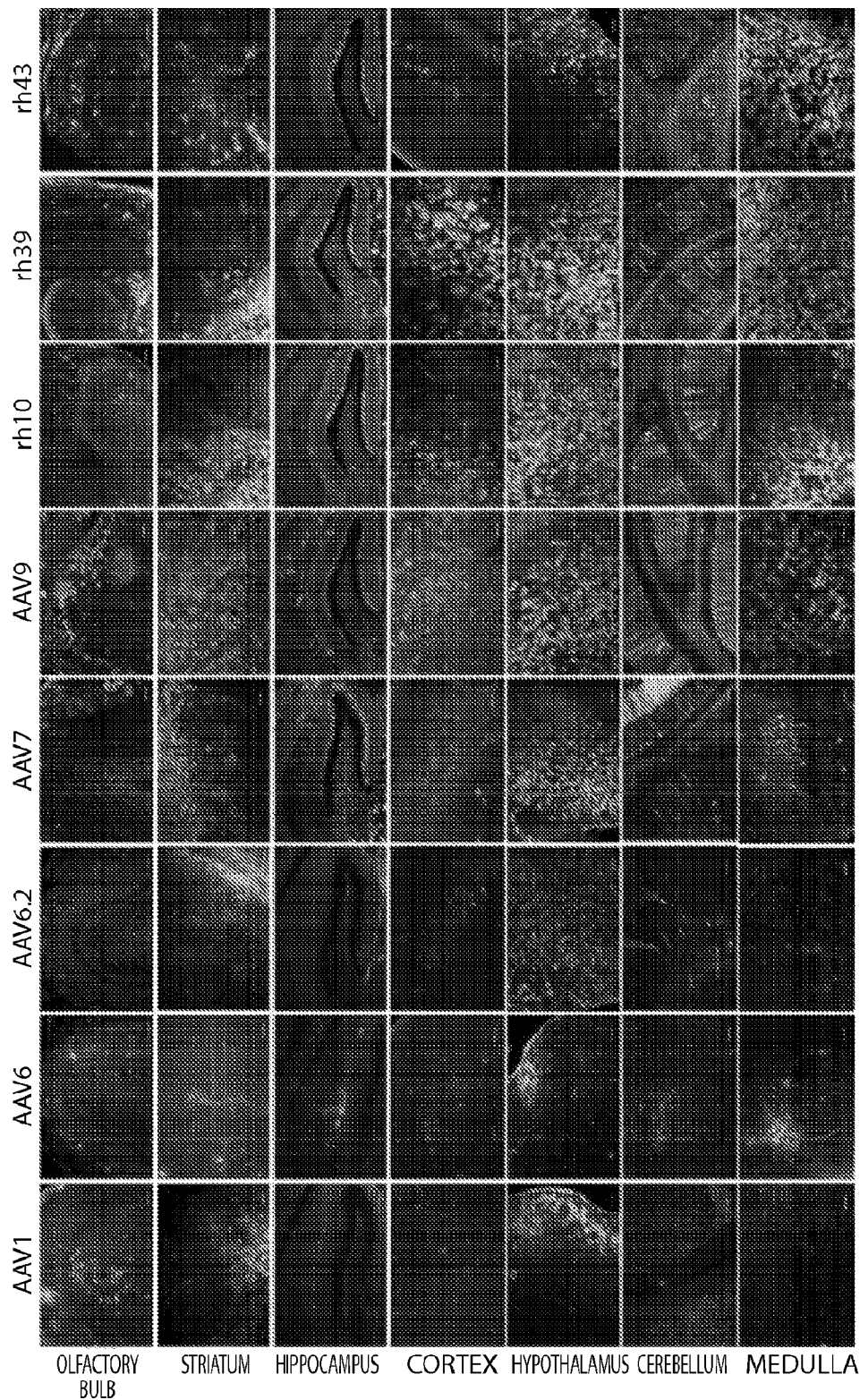
FIG. 20 depicts a strong and widespread EGFP expression in neonatal mouse brain after intravenous injection of rAAVs. $4 \times 10^{11}$ genome copies (GCs) of rAAVs 7, 9, rh.10, rh.39 and rh.43 were injected into neonatal P1 pups through superfacial vein. The mice were sacrificed 21 days after injection. The brain tissues were extracted and 40 µm thick cryosections were prepared. The sections were stained against anti-EGFP antibody. Bars represent 100 µm. The regions shown are: olfactory bulb, striatum, hippocampus, cortex, hypothalamus, cerebellum and medulla.

Pathology of the striatum is associated with Huntington's disease, choreas, choreoathetosis, and dyskinesias. Addiction may involve plasticity at striatal synapses. Systemic injection of rAAV9 in neonatal mice tranduces striatal tissue. In this study, a large number of cells with neuronal morphology in this region were also transduced by rAAVrh.10 (FIG. 20), which was confirmed by co-staining with a neuronal marker as described below. Other vectors, including rAAVrh.39 and rAAV7, also mediated moderate transduction in striatum (FIG. 20). In contrast, rAAV6, rAAV6.2, and rAAV1 resulted in relatively lower EGFP expression in this structure (FIG. 20).

Hippocampus.

The hippocampus is a region associated with long-term memory and spatial navigation, which is usually damaged by stress and pathogenesis of diseases such as epilepsy and Schizophrenia. Large numbers of EGFP-positive neurons were observed bilaterally in all regions of the hippocampus, namely dentate gyms, hilus, CA1, CA2 and CA3 for the mice received intravenous rAAVrh.10, rAAV9, rAAV7, rAAVrh.39, and rAAVrh.43 (ranked by transduction efficiency in this structure, Table 5 and FIGS. 19 and 20). In addition to the neuronal transduction pattern, EGFP-positive cells had morphologic appearance of astrocytes (FIG. 20). This was further confirmed by double staining with antibodies against EGFP and astrocytic marker as described below. For intravenously delivered rAAV1, rAAV6 and rAAV6.2 vectors there were small numbers of EGFP-positive cells in the hippocampus (FIG. 20).

Cortex.

Pathological changes in the cortex have been implicated in Alzheimer's and Parkinson's diseases. AA V7, AAV9, AAVrh.10, AAVrh.39 and AAVrh.43 vectors achieved moderate EGFP transduction in cortex (Table 5 and FIGS. 19 and 20). The morphology of transduced cells was consistent with both neurons and astrocytes as further confirmed by cellular marker staining and confocal microscopic analysis described below. Prominent EGFP-positive cells were typically observed in the ventrolateral regions of the cortex, including posterior agranular insular cortex, piriform cortex, lateral entorhinal cortex, posterolateral cortical amygdaloid nucleus and posteromedial cortical amygdaloid nucleus (FIG. 20). Strong EGFP signals spread from +1.5 to −3.3 mm in relation to the Bregma (0.0 mm). The cortical transduction efficiency of rAAVrh.10, rAAV9, rAAVrh.39 and rAAVrh.43 was comparable (Table 5 and FIGS. 19 and 20). AAV1, AAV6 and AAV6.2 vectors also transduced cells in the cortex (FIG. 20).

Hypothalamus.

A role for the hypothalamus is to secret neurohormones to control certain metabolic processes. The hypothalamus is also indicated in the etiology of diabetes. EGFP signal was observed in the hypothalamus for eight vectors. Intravenous administration of rAAVrh.10 resulted in the highest EGFP expression in the entire hypothalamus, followed by rAAVrh.39, rAAV7, rAAV6.2, rAAVrh.43, rAAV9, rAAV1 and rAAV6 (FIGS. 19 and 20 and Table 5). Interestingly most EGFP-positive cells in this structure have an astrocytic morphology which was ascertained by immunostaining for an astrocytic cell type specific marker as described below. The astrocytic EGFP signal tended to obscure direct examination of morphological details of other transduced cells. However, this was clarified by double immunofluorescent staining of tissue sections with antibodies for EGFP and neuronal cell markers as described below.

Cerebellum.

The pathological lesions in cerebellum are often found in diseases such as cerebellar-cognitive affective syndrome, developmental coordination disorder, posterior fossa syndrome, linguistic deficits, aging, attention deficit hyperreactivity disorder, autism, dementia and schizophrenia. EGFP-positive cells and fibers were detected in cerebellum for most rAAV vectors (Table 5 and FIGS. 19 and 20). A large number of EGFP-expressing cells were found in the Purkinje and granule cell layers for rAAV7, rAAV9, rAAVrh.10, rAAVrh.39 and rAAVrh.43 (FIG. 20). The transduction profile of rAAV1 vector indicated expression in cells in the granule cell layer, while rAAV6 and rAAV6.2 were localized in cells in the Purkinje cell layer (FIG. 20).

Medulla.

The medulla is a potential gene therapy target for treating chronic pain. Most rAAVs mediated moderate to robust EGFP expression in medulla with most green cells being present in the outer rim (FIG. 20). Transduction efficiencies of these rAAV in this region are ranked in the following order: rAAVrh.39=rAAVrh.43>rAAV.rh10>rAAV1>rAAV9>rAAV7>rAAV6.2>rAAV6 (Table 5 and FIG. 19a). The morphology of most EGFP-transduced cells was consistent with the cells being astrocytes.

Spinal Cord.

Figure 21:
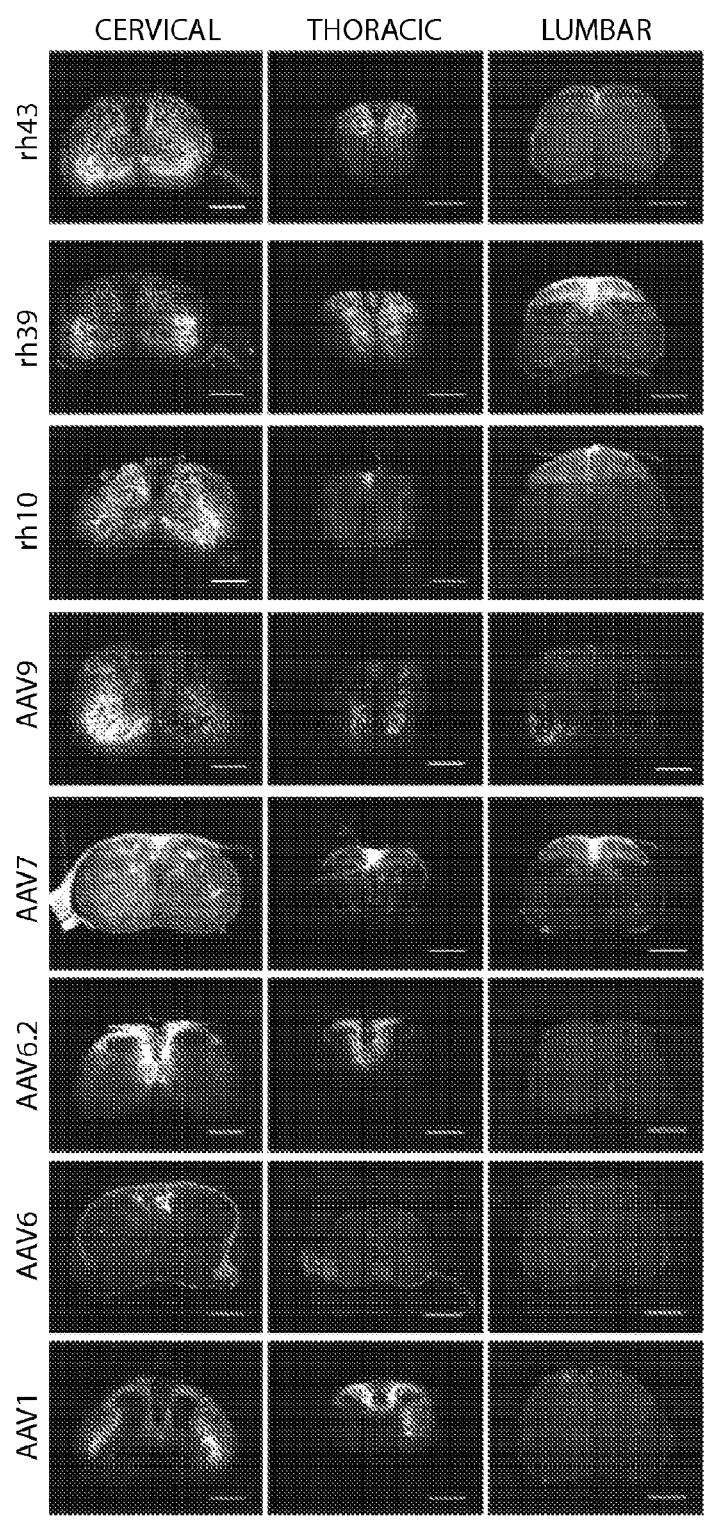
FIG. 21 depicts EGFP expression in neonatal mouse spinal cord after intravenous injection of rAAVs. $4 \times 10^{11}$ GCs of rAAVs 7, 9, rh.10, rh.39 and rh.43 were injected into neonatal P1 pups through superfacial vein. The mice were sacrificed 21 days after injection. The spinal cord tissues were extracted and 40 µm thick cryosections were prepared. The sections from cervical, thoracic and lumbar regions were stained against anti-EGFP antibody. Bars represent 100 µm.
Figure 22:
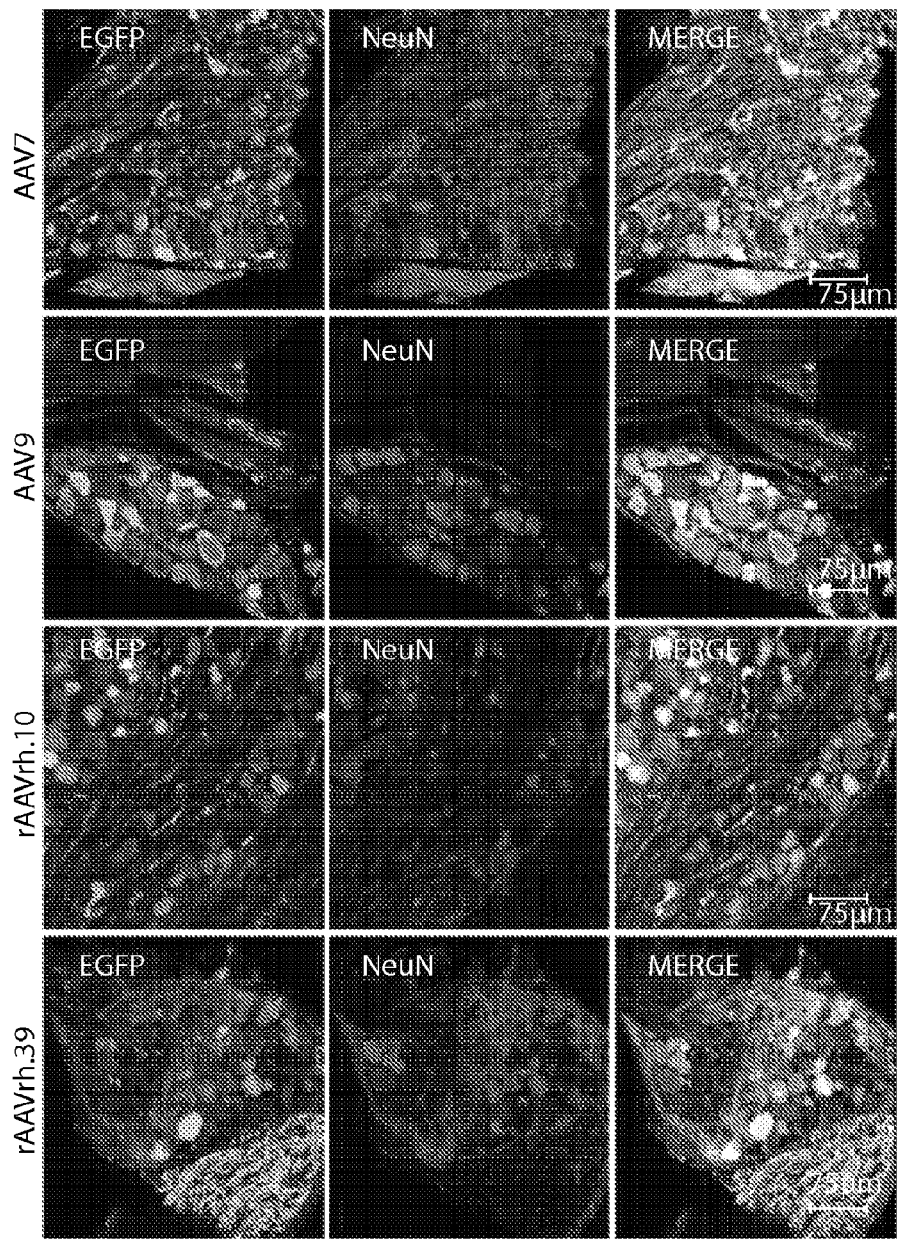
FIG. 22 depicts EGFP expression in dorsal root ganglia transduced by intravascularly delivered rAAVs1, 2, 6, 6.2, 7, 9, rh.10 and rh.39. Neonatal pups received $4 \times 10^{11}$ GCs of rAAVs at P1 and were necropsied 21 days after injection.

The spinal cord is involved with motor neurons diseases. rAAVrh.10, rAAV9, rAAVrh.39 and rAAVrh.43 gave rise to very robust EGFP expression in cervical gray and white matter, while rAAV1, rAAV6.2 and rAAV7 showed moderate EGFP intensity (Table 5 and FIGS. 19 and 21). For rAAV1 the EGFP signal was observed in white matter. The transduction ability of all effective rAAVs decreased from cervical to lumbar spinal cord. EGFP-positive cells were visible in the latter region. Large populations of EGFP-positive cells with astrocytic morphology were observed throughout the spinal cord (FIG. 21). In addition, rAAVrh.10, rAAV9, rAAVrh.39, rAAVrh.43 and rAAV7 also transduced cells with motor neuron morphology in the ventral regions of spinal cord (FIG. 21). Ascending dorsal column fibers showed clear EGFP signal. In addition, dorsal root ganglia (DRG) displayed remarkable transduction with strong EGFP expression in DRG neurons (FIG. 22 and FIG. 26). The identities of rAAV transduced cell types in the spinal cord were characterized by co-immunofluorescence staining with antibodies against EGFP and cell type specific markers as described below.

IV Administration of AAV Vectors Leads to Transduction of Different Cell Types in the CNS To confirm the identity of transduced cells in different regions of the CNS, double immunofluorescent staining was performed with antibodies for EGFP and NeuN (generic neuronal marker), glial fibrillary acid protein (GFAP; astrocyte marker), calbindin-D28K (Purkinje cell marker), and choline acetyl transferase (ChAT; motor neuron marker) (FIG. 23). The immunostaining results showed that a large number of NeuN positive cells expressed EGFP throughout the mouse brain, which indicated widespread neuronal transduction. The regions with high density of transduced neurons included striatum, hippocampus, cortex and hypothalamus. rAAVrh.10, rAAV9, rAAV7 and rAAVrh.39 vectors were efficient in mediating neuronal transduction, followed by AAV6.2, AAV1 and AAV6 (FIGS. 19 and 23). In addition, dopaminergic neurons in substantia nigra were transduced by AAV.rh10 (FIG. 23). Transduced cells in the CNS included GFAP-positive astrocytes with small cell bodies and highly ramified processes (FIG. 23). The calbindin-D28K immunostaining confirmed the identity of a number of transduced cells in the cerebellum as Purkinje cells, with EGFP expression in both cell body and their tree-like processes (FIG. 23). The rAAVs proficient in transducing Purkinje cells include: rAAVrh.10, rAAV9, rAAVrh.39, rAAV7, rAAV6.2 and rAAVrh.43. rAAV1 and rAAV6 transduced a portion of Purkinje cells with relatively low EGFP intensity (FIG. 19). Transduction of motor neurons was confirmed by the presence of large EGFP+/ChAT+ cells in the ventral spinal cord for several rAAV vectors (FIG. 23). rAAVrh.10, rAAV9, rAAV7, rAAVrh.39 showed comparable efficiency transduction of motor neurons (FIG. 21).

Figure 27A:
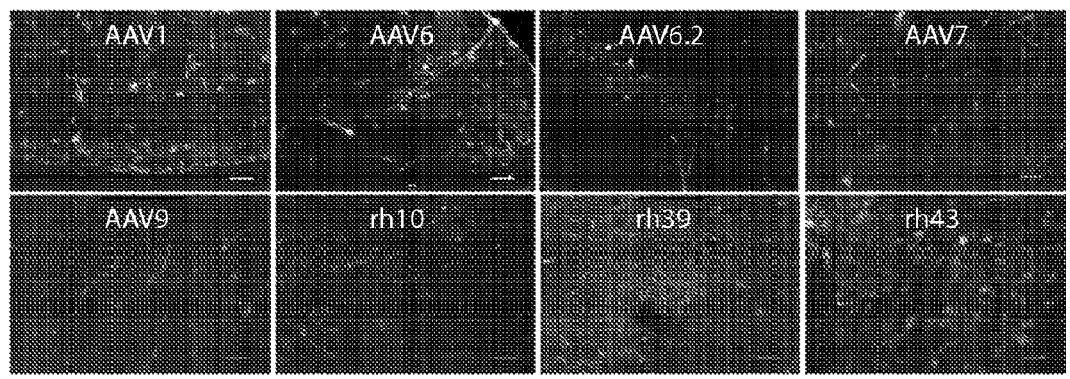
Figure 27B:
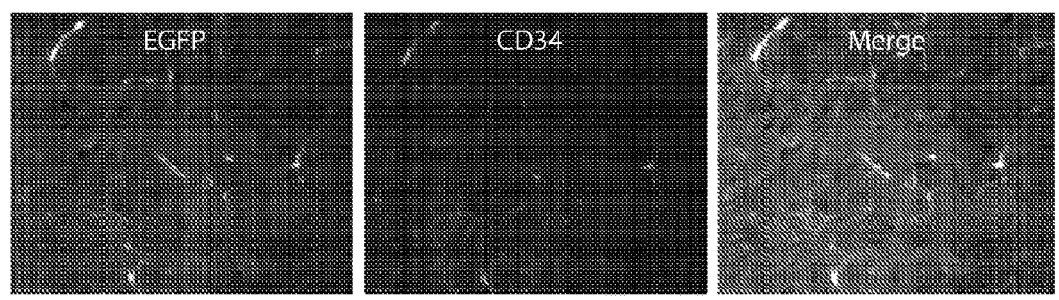

IV Administration of AAV Vectors Mediated Robust Transduction in Ventricles and Brain Blood Vessels EGFP expression was observed in the choroid plexus cells in lateral, $3^{rd}$ and $4^{th}$ ventricles of the animals infused with rAAVrh.39, rAAVrh.10, rAAVrh.43, rAAV7 and rAAV9 (ranked by transduction efficiency, Table 5 and FIGS. 19 and 24). EGFP expression in different ventricles of the same mouse brain was similar (FIG. 24). Ependymal cells lining the ventricles were also transduced. An observation regarding the distribution of EGFP-positive cells was the apparent gradient with the highest number of transduced cells in peri-ventricular regions and progressively lower numbers with increasing distance to the ventricles. This was apparent in areas around the $3^{rd}$ and $4^{th}$ ventricles than the lateral ventricles (FIG. 24). Extensive EGFP signal was also found with blood vessels throughout mouse brain and spinal cord. This was verified by dual immunofluorescent staining with antibodies directed to EGFP and a blood vessel endothelium specific marker, CD34 (FIGS. 27a and 27b). Unlike the rAAV transduction profiles in different regions of the brain parenchyma, the EGFP transduction of the blood vessels throughout the CNS was relatively uniform for any given vector. However, transduction of blood vessels was influenced by the particular rAAV used. A majority of rAAVs mediated moderate (e.g., rAAV6) to highly efficient (e.g. rAAVrh.10) blood vessel transduction in the CNS.

IV Injection of AAV Vectors Did not Cause Microgliosis

Brain sections were also stained with antibody against Iba-1 to label microgial cells. The Iba-1-positive cells in the sections from mice received rAAVrh.10 was no more than those in naïve or PBS-injected mice (FIG. 28). This result indicated that intravascularly delivered rAAVs do not cause sustained inflammation in the CNS of mice 3 weeks after the injection of P1 neonates.

Discussion of Results

In this study, the CNS transduction profile was evaluated for 10 different rAAV vectors delivered by intravascular infusion in neonatal mice. Most of the rAAVs can cross the BBB and mediate gene transfer to the neonatal mouse CNS with varying degrees of efficiency (FIGS. 19-21 and Table 5). After systemic administration, rAAVrh.10, rAAVrh.39, rAAVrh.43, and rAAV9 are the effective rAAVs with similar transduction capabilities and cellular tropism, as assessed by overall EGFP expression in the CNS. Specifically, a number of regions in the mouse CNS, including striatum, hippocampus, cortex, hypothalamus, cerebellum, medulla, and cervical spinal cord, revealed substantial EGFP expression. In addition, rAAV6.2 and rAAV7 were also effective. AAV1 and AAV6, achieved CNS transduction (Table 5). Native EGFP expression was detectable in brain and spinal cord sections for most of the rAAVs without immunostaining (FIG. 29).

This example has clinical significance for gene therapy of CNS-related disorders, including for young patients. For a variety of neurological diseases, early treatment during infancy may be necessary to prevent irreversible CNS injury. The capacity of rAAVs to transduce large numbers of neuronal cells in different regions is relevant for treating neurological diseases such as spinal muscular atrophies, neuronal ceroid lipofuscinoses, and spinocerebellar degenerations. The efficiency of some rAAV vectors in transducing Purkinje and granule layer cells indicates that the vectors may be used for treating spinocerebellar ataxias. Transduction of astrocytes by rAAVs expressing secreted neurotrophic factors may be also beneficial for a number of neurodegenerative diseases such as Canavan's disease and amyotrophic lateral sclerosis. The vascular transduction in the CNS may be relevant for treating brain ischemia and stroke. The clinical application of intravascular rAAV-mediated gene delivery may also extend to the peripheral nervous system (PNS). Efficient transduction of DRG provides new therapeutic strategies for patients suffering from chronic pain.

Systemic gene delivery to the CNS is also useful as a method to manipulate gene expression in research. Effective and stable transgene expression in the CNS by intravenous administration of rAAVs may be applied to establish somatic transgenic animal models, which is a potentially cheaper, faster and simpler method than conventional transgenesis. Somatic CNS gene knock-down animal models may also be created using the method described herein.

Figure 9:
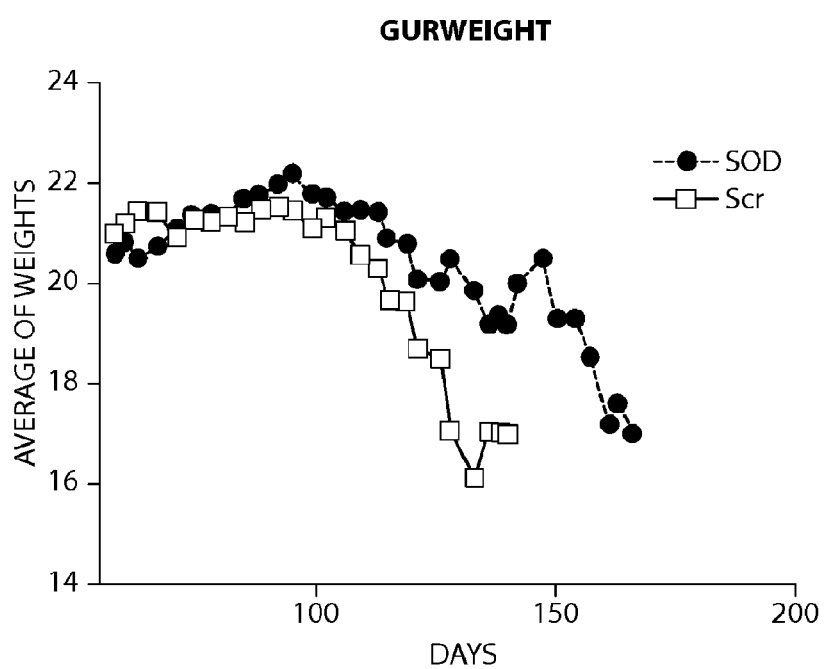
FIG. 9 depicts the effects of AAV10-miR-SOD1 treatment. AAV10-miR-SOD1 treatment slows disease progression as indicated by the slower loss of body weight in treated compared with the control G93A mice.
Figure 10:
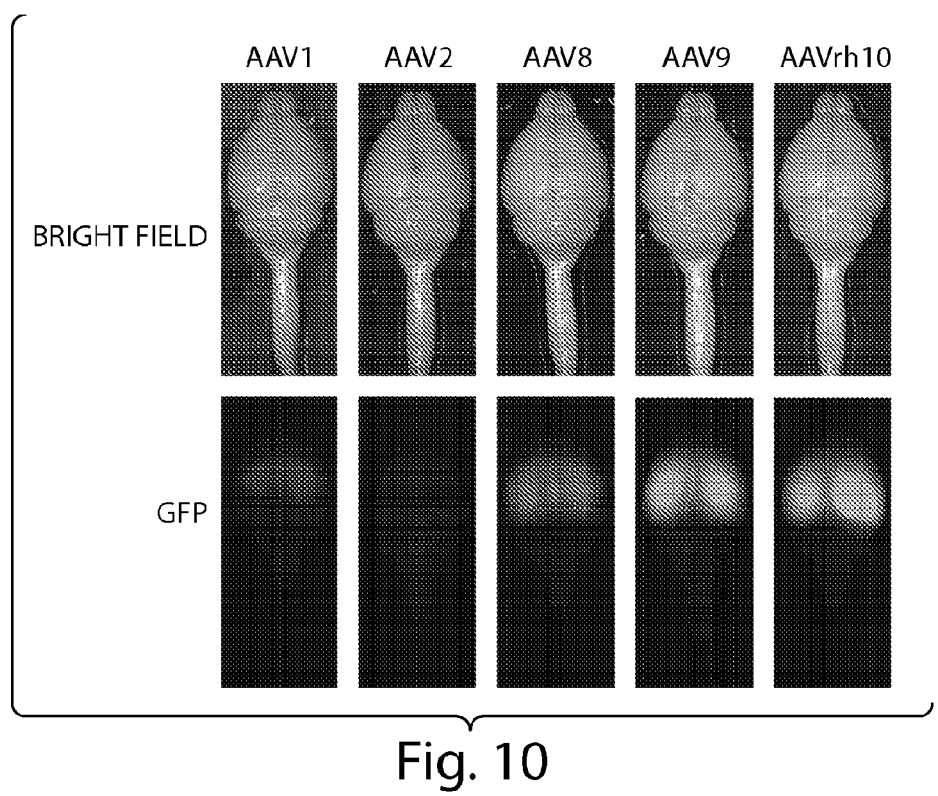
FIG. 10 depicts fluorescence microscopy analysis of mice that have been administered intrathecal injections of various AAVs. In this experiment, AAV9 and AAVrh10 can transduce cells in the broad forebrain areas after a single injection into the CSF in the third ventricle.
Figure 11:
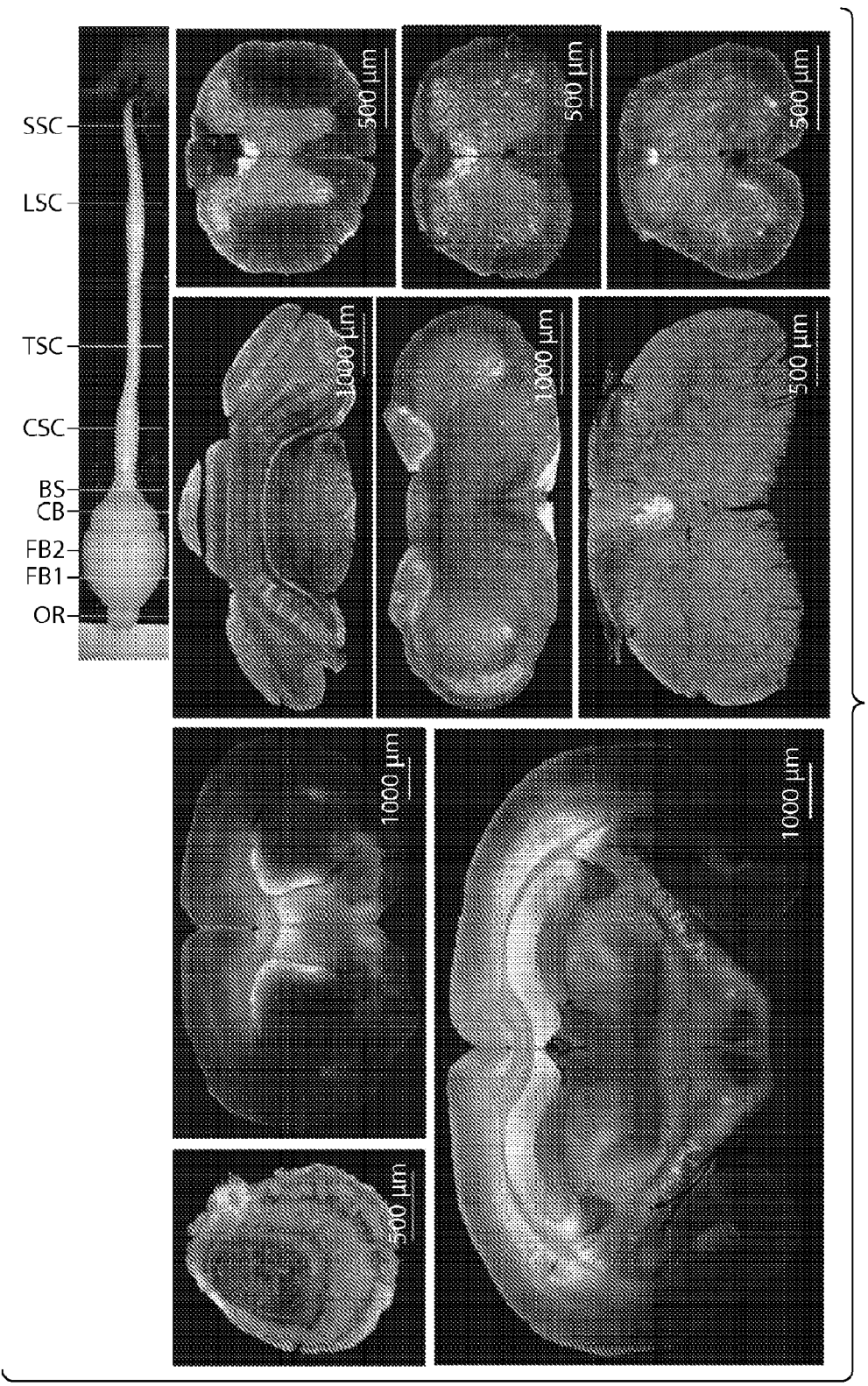
FIG. 11 depicts fluorescence microscopy analysis of tissue sections from AAV9-injected mice. A single injection of AAV9 and AAVrh10 into the third ventricle can transduce cells in the broad forebrain areas, including cortex, hippocampus, striatum, thalamus, cerebellum and some scattered cells in the spinal cord. The same general pattern is also observed in AAV10-injected mice.

Some rAAVs indeed demonstrated unique transduction profiles in the CNS. For instance, rAAV1 displayed transduced granule cells in the cerebellum, while rAAV6 and rAAV6.2 transduced Purkinje cells, and others transduced both types of cells (FIG. 9). This indicates that once across the BBB, the rAAVs have distinct tropisms, which can be attributed to the capsid because that the vector genome used in all vectors was the same.

AAV serotypes disclosed herein can efficiently transduce brain capillary endothelial cells, neurons and astrocytes. This indicates that these vectors may extravasate from the circulation and reach the CNS parenchyma, possibly by crossing the BBB. AAV may cross the endothelial barrier by a transcytosis pathway. In this study, choroid plexuses and their surrounding parenchymal tissue were efficiently transduced. In addition, there was an apparent gradient of EGFP intensity from peri-ventricular (higher) to deep parenchymal (lower) tissue. These observations indicate that AAV may enter the neonatal mouse CNS through the choroid plexus, followed by widespread distribution via CSF and/or interstitial fluid flow to transduce neuronal and glial cells.

Neuronal- or glial-specific promoters, such as synapsin-1, and GFAP promoters may be used to restrict gene expression to a specific cell type. A further method to achieve targeted CNS gene delivery is to utilize RNA interference to detarget the peripheral tissues by post-transcriptional regulatory mechanisms. By adding microRNA binding sites into the 3' end of the transgene cassettes, transgene expression after systemic administration of AAV vectors may be reduced or eliminated in tissues such as liver, heart and skeletal muscle, while maintaining CNS transduction.

Materials And Methods

AAV Production

ScAAV vectors were produced by trans-encapsidation of rAAV vector genome flanking by inverted terminal repeats (ITRs) from AAV2 with the capsids of different AAVs using the method transient transfection of 293 cells and CsCl gradient sedimentation as previously described. Vector preparations were titered by quantitative PCR. Purity of vectors was assessed by 4-12% SDS-acrylamide gel electrophoresis and silver staining (Invitrogen, Carlsbad, Calif.). Morphological integrity of each vector used in the study was examined by transmission electron microscopy of negative stained recombinant AAV virions. The expression of EGFP in the scAAV vector genome is directed by a hybrid CMV enhancer/chicken β-actin promoter.

Neonatal Mouse Injections

Wild-type C57BL/6 mice littermates were used. Mice breeding were conducted using programmatic timing method. Pregnant mice were monitored daily from embryonic day 17 to 21 to ensure the newborn pups could be dosed with vectors on P1. The mother (singly housed) of each litter to be injected was removed from the cage. Vectors were diluted to concentration of $4\times10^{12}$ GCs/mL in PBS and 100 μl of solution was subsequently drawn into 31 G insulin syringes (BD Ultra-Fine II U-100 Insulin Syringes). P1 pups of C57BL/6 mice were anesthetized using isoflurane and rested on ice. For intravenous injections, a dissection microscope was used to visualize the temporal vein (located just anterior to the ear). The needle was inserted into the vein and the plunger was manually depressed. Correct injection was verified by noting blanching of the vein. Each pup received $4\times10^{11}$ GCs of different scrAAVCBEGFP vectors (rAAV1, rAAV2, rAAV5, rAAV6, rAAV6.2, rAAV7, rAAV9, rAAVrh.10, rAAVrh.39, rAAVrh.43; n=6-8 mice per group) via the superficial temporal vein. After the injection pups were carefully cleaned, rubbed with their original bedding, and then returned to their original cage. The mother was then reintroduced to the cage after brief nose numbing using ethanol pads.

Histological Processing

The study animals were anesthetized 21 days post-injection, then transcardially perfused with 15 mL of cold PBS followed by 15 mL of fixation solution containing 4% paraformaldehyde (v/v) with 0.2% of glutaraldehyde (v/v) in PBS. Then the whole carcasses were post-fixed in fixation solution for 5 days. Spinal cords and brains were extracted under a bright-field dissecting microscope, rinsed in PBS, and then cryoprotected in 30% sucrose (w/v) in PBS at 4° C. Once the tissues sank to the bottom of the sucrose solution, they were embedded in Tissue-Tek OCT compound (Sakura Finetek, Torrance, Calif.) and frozen in a dry ice/ethanol bath. The tissue blocks were stored at −80° C. until sectioning. Serial 40 μm floating sections of the entire brain were cut in a Cryostat (Thermo Microm HM 550). For the spinal cord, 3 mm length sections were taken from cervical, thoracic and lumbar regions, and then serial 40 μm transverse sections prepared as above.

Immunostaining and Microscopy Imaging Analysis

Brain and spinal cord sections were stained as floating sections in 12-well plates. Sections were washed 3 times in PBS for 5 min each time, and then incubated in blocking solution containing 1% Triton-X100 (v/v) (Fisher, Pittsburgh, Pa.), 5% dry-milk (w/v) and 10% goat serum (v/v) (Invitrogen) for 2 h at room temperature. Then the sections were incubated with primary antibodies diluted in blocking solution at 4° C. overnight. The following day tissue sections were washed twice in 0.05% Tween-20 (v/v) in PBS (PBST) and once with PBS, with each washing step lasting 10 min. Afterwards sections were incubated with appropriate secondary antibodies in blocking solution at room temperature for 2 h. Sections were washed again as above before mounting on glass slides. Vectashield with DAPI (Vector Laboratories, Burlingame, Calif.) was used to coverslip all slides, and then they were analyzed using a fluorescent inverted microscope (Nikon Eclipse Ti) or a Leica TSC—SP2 AOBS confocal microscope equipped with a 63× oil lens and a DM-IRE2 inverted microscope. The primary antibodies used in this study were as follows: rabbit anti-GFP (Invitrogen), goat anti-ChAT and mouse anti-NeuN (both from Millipore, Billerica, Mass.), mouse anti-GFAP (Cell signaling, Danvers, Mass.), rat anti-CD34 (Abcam, Cambridge, Mass.), mouse anti-Calbindin D-28k (Sigma, St Louis, Mo.) and rabbit anti-DARPP (Abcam, Cambridge, Mass.). The secondary antibodies used in the study included: DyLight 488 AffiniPure Donkey Anti-rabbit IgG (Jackson ImmunoResearch, West Grove, Pa.); DyLight 549 AffiniPure Donkey Anti-Goat IgG (Jackson ImmunoResearch); DyLight 549 Affinipure Goat Anti-Rat IgG (Jackson ImmunoResearch); DyLight 594 AffiniPure Goat Anti-Mouse IgG (Jackson ImmunoResearch); goat anti-rabbit IgG-Alexa fluoro 488 (Invitrogen) and goat anti-mouse IgG-Alexa fluoro 568 (Invitrogen).

Semi-Quantitative and Quantitative Comparison of EGFP Transduction by Different Vectors To generate a quantifiable and comparable data format, a semi-quantitative scoring system was develop to estimate transduction efficiency of different rAAV vectors in different regions of the mouse CNS. Briefly, regions with no EGFP positive cells were marked as (−). Regions with very few EGFP positive cells were scored (+), regions with some EGFP positive cells were ranked as (++), regions with many EGFP positive cells were marked as (+++). Finally, regions filled with EGFP positive cells were marked as (++++).

Next, 12 sub-anatomically and functionally important regions in the brain as well as cervical, thoracic and lumbar sections of the spinal cord were selected for quantitative analysis of images that were taken on a Nikon Eclipse Ti inverted microscope equipped with a Retiga 2000-RV CCD cooled camera. Nikon NIS elements AR software v. 3.2 was used for intensity quantification. Prior to quantification, optimal light source intensity and exposure times were obtained by plotting an intensity/exposure time curve using fluorescence reference slides (Ted Pella, prod. 2273). It was found that the intensity and exposure times had linear correlation. In addition, overexposure and extreme underexposure distorts the linear correlation. The maximum intensity (ND1) and a 20 ms exposure were used for all sections to avoid overexposure. For quantification, fixed region of interest (ROI) was used to quantify the brightest area of any given brain region. A mean intensity (total intensity/size of ROI) was obtained for each region of all serotypes.

TABLE 5

Transduction characteristics of AAV serotypes following intravascular injections into neonatal mouse brain

| | Olfactory Bulb | | Striatum | | Hippocampus | | Cortex | | Thalamus | | Hypothalamus | | Cerebellum | |
|---|---|---|---|---|---|---|---|---|---|---|---|---|---|---|
| | score | n | score | n | score | n | score | n | score | n | score | n | score | n |
| AAV1 | + | 3 | ++ | 3 | ++ | 3 | ++ | 3 | + | 3 | +++ | 3 | +++ | 3 |
| AAV2 | − | 3 | − | 3 | + | 3 | + | 3 | + | 3 | + | 3 | + | 3 |
| AAV5 | − | 3 | − | 3 | − | 3 | + | 3 | − | 3 | + | 3 | − | 3 |
| AAV6 | + | 3 | + | 3 | ++ | 3 | ++ | 3 | + | 3 | +++ ++ | 2 1 | ++ | 3 |
| AAV6.2 | | 3 | +++ ++ | 2 1 | ++ | 3 | ++ | 3 | + | 3 | ++++ | 3 | ++ | 3 |
| AAV7 | +++ ++ | 1 2 | +++ | 3 | ++ | 2 1 | ++ | 3 | + | 3 | ++++ | 3 | +++ ++ | 1 2 |
| AAV9 | +++ ++ | 2 1 | +++ | 3 | ++ | 3 | +++ ++ | 1 2 | + | 3 | ++++ +++ | 1 2 | +++ ++ | 1 2 |
| rh10 | +++ ++ | 1 2 | ++++ ++ | 1 2 | +++ | 3 | +++ ++ | 2 1 | ++ + | 2 1 | ++++ | 3 | +++ ++ | 1 2 |
| rh39 | +++ ++ | 1 2 | ++++ +++ | 2 1 | +++ | 3 | +++ ++ | 1 2 | + | 3 | ++++ | 3 | +++ ++ | 1 2 |
| rh43 | ++ | 3 | +++ | 3 | +++ | 3 | +++ | 3 | + | 3 | ++++ +++ | 1 2 | ++ | 3 |

| | Medulla | | Cervical | | Thoracic | | Lumber | | Choroid Plexus | |
|---|---|---|---|---|---|---|---|---|---|---|
| | score | n | score | n | score | n | score | n | score | n |
| AAV1 | +++ | 3 | +++ | 3 | +++ | 3 | + | 3 | +++ | 3 |
| AAV2 | + | 3 | + | 3 | − | 3 | − | 3 | ++ | 3 |
| AAV5 | − | 3 | − | 3 | − | 3 | − | 3 | − | 3 |
| AAV6 | ++ | 3 | ++ | 3 | + | 3 | + | 3 | +++ | 3 |
| AAV6.2 | ++ | 3 | ++ | 3 | ++ | 3 | + | 3 | ++++ | 3 |
| AAV7 | ++ | 3 | ++ | 3 | + | 3 | + | 3 | ++++ | 3 |

TABLE 5-continued

Transduction characteristics of AAV serotypes following intravascular injections into neonatal mouse brain

| Serotype | Col 1 | Col 2 | Col 3 | Col 4 | Col 5 |
|---|---|---|---|---|---|
| AAV9 | ++ 3 | ++++ 1, +++ 2 | ++ 3 | + 3 | ++++ 3 |
| rh10 | +++ 3 | ++++ 1, +++ 2 | ++ 3 | + 3 | ++++ 3 |
| rh39 | ++++ 1, +++ 2 | ++++ 1, +++ 2 | +++ 3 | + 3 | ++++ 3 |
| rh43 | ++++ 1, +++ 2 | ++++ 2, +++ 1 | +++ 3 | + 3 | ++++ 3 |

Scoring:
(−) no transduction,
(+) very few positive cells,
(++) some positive cells,
(+++) many positive cells, and (++++) region is almost saturated with EGFP-positive cells. The number of animals (n) with the particular score is given to the right of the score.

Example 10

Evaluation of an rAAV Based Treatment in a Canavan Disease Model

Introduction to the Example

CD is a rare and fatal childhood leukodystrophy caused by autosomal recessive mutations in the aspartoacylase gene (ASPA) [as established by G.G.'s graduate work (12)]. ASPA deficiency in CD patients leads to elevated N-Acetyl-Aspartic Acid (NAA) in urine (a hallmark of CD) and spongy degeneration of white matter throughout the CNS, producing severe psychomotor retardation and early death. An ASPA$^{-/-}$ mouse model mimics the neuropathology and clinical manifestations seen in CD patients, i.e., spongy degeneration of white matter, motor deficits, developmental delays, and early death (within 3 weeks after birth).

In this study, i.v. deliverable rAAVs were used to target the CNS globally to treat diffused WM degeneration in CD mice. Single i.v. injections of ASPA vector to the neonatal CD mice corrected metabolic defect, psychomotor malfunction and other disease phenotypes, and prolonged survival. While untreated CD mice started showing growth retardation, psychomotor malfunction in the $2^{nd}$ wk after birth and uniformly died soon after weaning, the treated mice began to gain weight 2 wks after vector injection and nearly caught up with their heterozygous littermates within 7-8 weeks. Unlike CD mice, the mobility of the treated animals was similar to Wt littermates. Data from rotarod test on the treated mice showed no significant differences in the latency time among the treated CD mice and their age-matched Wt littermates, indicating that gene therapy corrected the ataxia, a typical neuromuscular symptom of CD. Biochemical characterization indicated reduction of NAA levels in the urine samples and restoration of ASPA activity in their brain and kidney tissues. Mitigation of the biochemical and clinical phenotypes was well correlated with globally ameliorated histopathology in not only the brain, spinal cord but also in the peripheral tissues such as kidney, indicating that CD is not just a CNS disorder.

Results

Figure 30A:
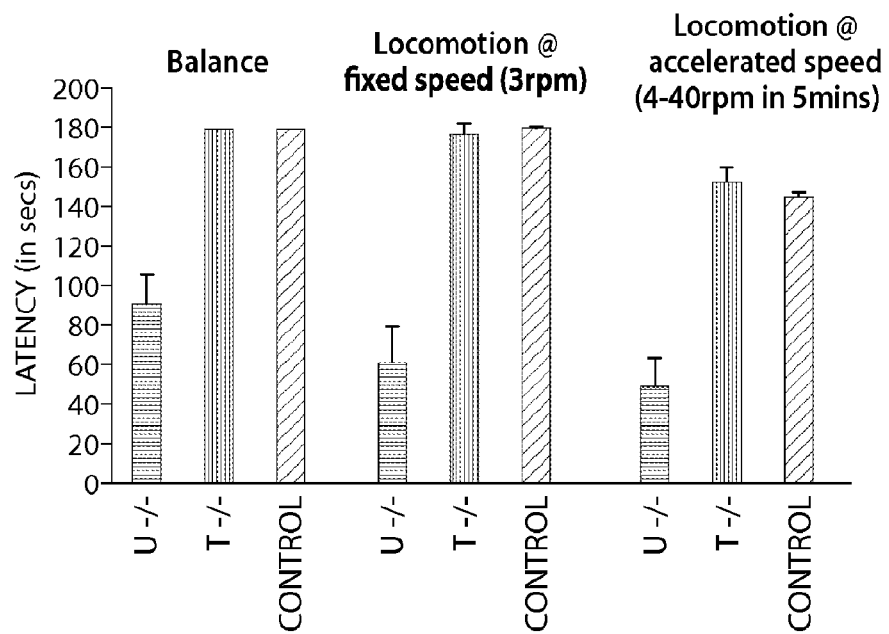
Figure 30B:
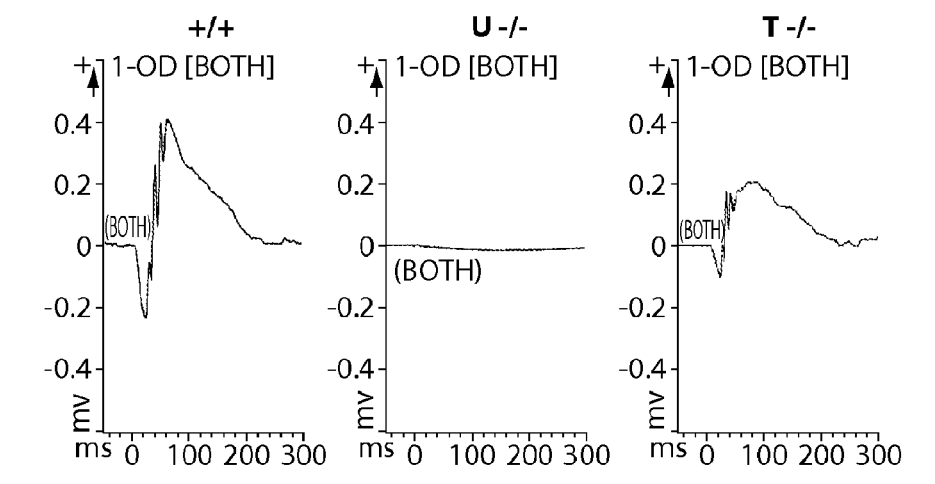
Figure 30C:
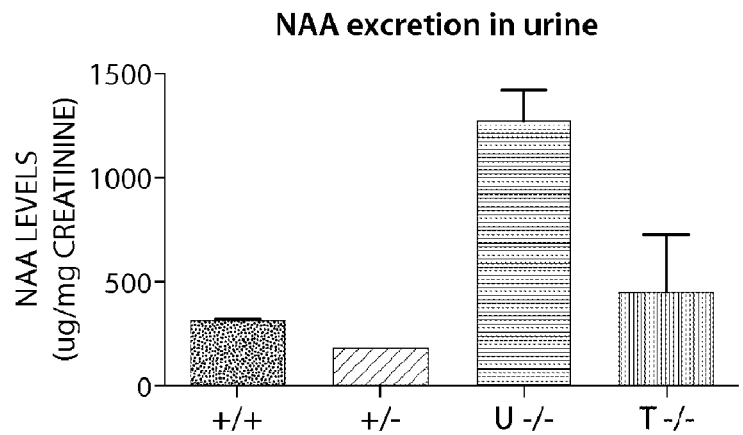
Figure 30D:
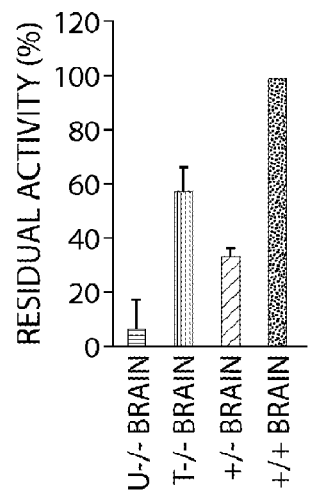
Figure 30E:
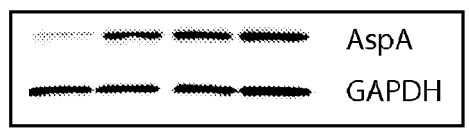

In CD mice were dosed at P1 (facial vein, 4×10$^{11}$ GCs) with AAV9ASPA. The mice were monitored for growth, gait, motor function on rotarod, NAA levels in urine and ASPA activities in brain. The results showed that i) Untreated CD mice started losing weight at the $2^{nd}$ week and died in the $3^{rd}$ week after birth; ii) The treated animals recovered their capacity to grow in the $5^{th}$ week and caught up with ASPA$^{+/-}$ animal by the $10^{th}$ week; iii). Gene therapy completely corrected gait of CD mice as well as motor function of the CD mice treated at P1 (FIG. 30A) as measured by rotarod test; iv). Gene therapy restored the vision of CD mice. The electroretinography (ERG) tests on the eyes of the CD mice showed non-recordable responses to light, while well-defined ERG responses were readily detectable in the treated CD mice (FIG. 30B). These data indicate a severer retinopathy and loss of vision in CD mice and gene therapy can mitigate the retinopathy and restore the vision of CD mice; v). Gene therapy clearly improved metabolic defects of NAA as the NAA levels in the treated CD mice approach those in the control mice (FIG. 30C); and vi) correction of NAA metabolism is well correlated with restoration of ASPA expression (FIG. 30E) and activities (FIG. 30D) in the brain of the treated CD mice.

To determine if the phenotypic corrections are correlated with alleviated neuropathology as well as in situ expression of ASPA in the brain sections of the treated CD mice, brain sections were analyzed at 3 months after gene therapy for neuropathology and ASPA immunohistochemistry. While the untreated mouse brain shows marked vacuolation that diffusely involves all regions of the brain and spinal cord, the vacuolation in both brain and spinal cord of the treated animal appears more patchy and variable with generally smaller-sized vacuoles. Some areas of the cerebral cortex show almost no vacuolation (FIG. 31A). In addition, avidin-biotin complex (ABC) system was used to stain brain sections to detect ASPA expression in the cerebral cortex in situ (FIG. 31B). To generate quantitative measurements on the improvement of neuropathology in the treated CD mice, the "vacuoles" in the brain and spinal cord sections caused by the white matter degeneration in the CD mice were quantified before and after gene therapy treatment. For this quantitative analysis, a Nikon Eclipse Ti inverted microscope and Nikon NIS elements AR software V.3.2 were used. Vacuoles that were >3,000 pixels, 1,000-3,000 pixels and 100-1,000 pixels were defined as large, medium and small vacuoles respectively. Among the 5 brain regions evaluated in this experiment, the olfactory bulb had the most dramatic mitigation in the white matter degeneration after gene therapy (FIG. 32A). For the other 3 regions, while the large vacuoles were completely eliminated and the numbers of medium vacuoles were remarkably reduced, the reduction in the numbers of small vacuoles (<100 um) was not as significant in this experiment (FIG. 32A). The same analysis on the spinal cord sections revealed a similar trend (FIG. 32B).

Figure 33A:
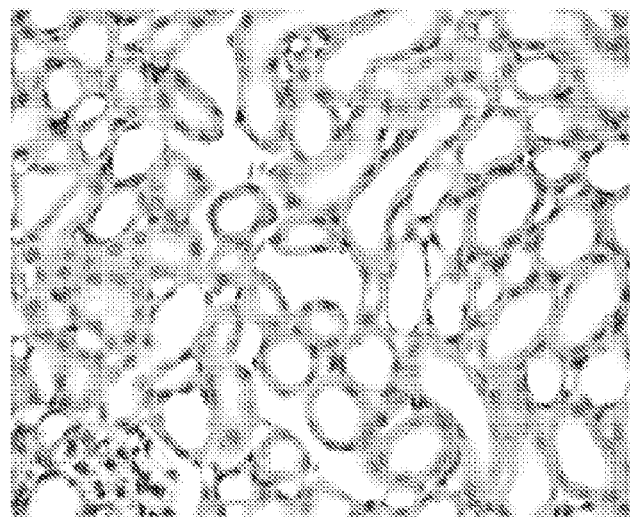
Figure 33B:
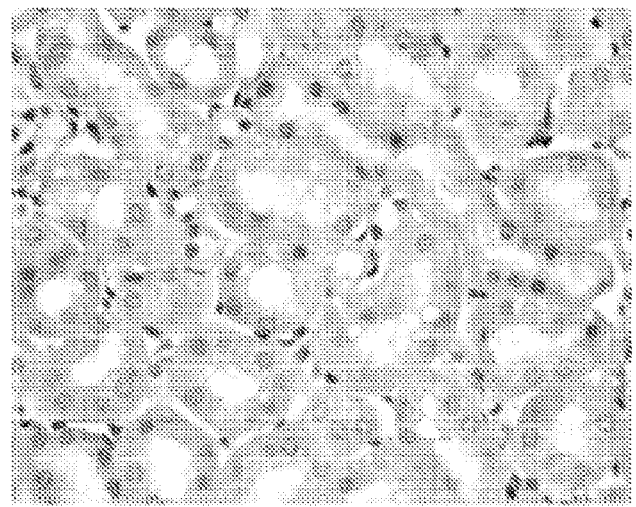
Figure 33C:
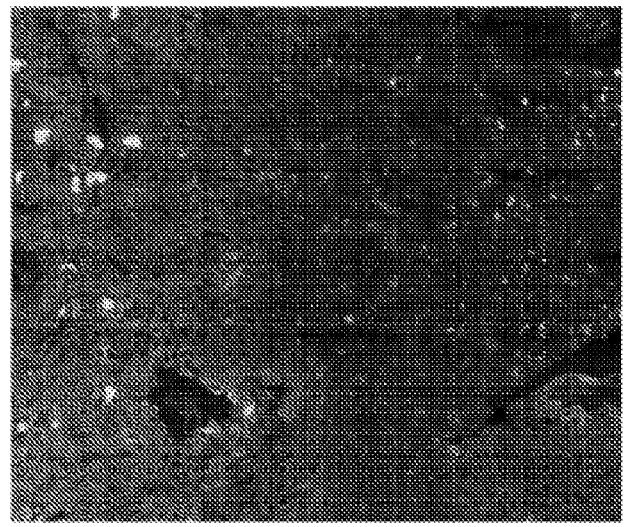
Figure 33D:
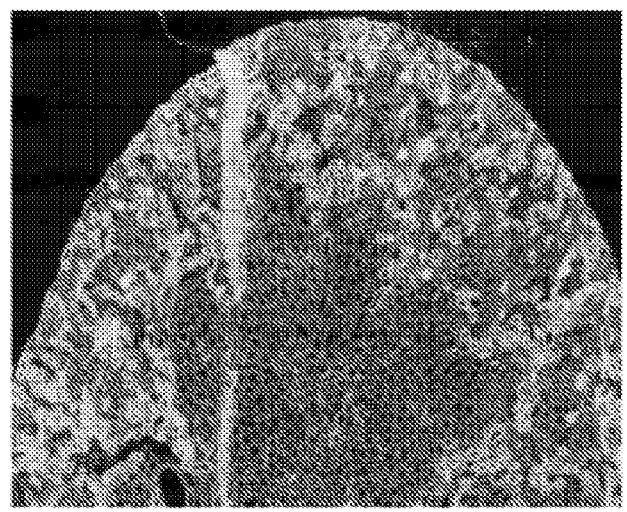

Histopathology of the kidneys in the CD mice were evaluated. The glomeruli showed normal structure but were associated with dilation of Bowman's spaces. The renal tubular epithelium was diffusely attenuated (or atrophic) in association with enlargement of the tubular lumens (FIG. 33A). In contrast, the treated CD mouse had normal glomeruli. Renal tubular epithelial cells were well-stained and normal in volume (FIG. 33B). These results indicate the involvement of kidney in the pathophysiology of CD and kidney as a peripheral target for CD gene therapy. This result also indicates renal tropism of AAV vectors as a consideration for selection of a vector for CD gene therapy. Two vectors, rAAV9 and rh.10 were evaluated for efficiency of kidney transduction after IV delivery to 10 week old C57BL/6 mice. The results indicate the use of rAAVrh.10 (FIG. 33D) as a useful vector for CD gene therapy because it transduces kidney efficiently in addition to its efficient CNS transduction (FIG. 33C).

NUCLEIC ACID AND AMINO ACID SEQUENCES

>gi|9632548|ref|NP_049542.1|capsid protein [Adeno-associated virus-1]

(SEQ ID NO: 1)

```
MAADGYLPDWLEDNLSEGIREWWDLKPGAPKPKANQQKQDDGRGLVLPGYKYLGPFNGLDKGEPVNAADAAALEHDKAYDQQLK
AGDNPYLRYNHADAEFQERLQEDTSFGGNLGRAVFQAKKRVLEPLGLVEEGAKTAPGKKRPVEQSPQEPDSSSGIGKTGQQPAK
KRLNFGQTGDSESVPDPQPLGEPPATPAAVGPTTMASGGGAPMADNNEGADGVGNASGNWHCDSTWLGDRVITTSTRTWALPTY
NNHLYKQISSASTGASNDNHYFGYSTPWGYFDFNRFHCHFSPRDWQRLINNNWGFRPKRLNFKLFNIQVKEVTTNDGVTTIANN
LTSTVQVFSDSEYQLPYVLGSAHQGCLPPFPADVFMIPQYGYLTLNNGSQAVGRSSFYCLEYFPSQMLRTGNNFTFSYTFEEVP
FHSSYAHSQSLDRLMNPLIDQYLYYLNRTQNQSGSAQNKDLLFSRGSPAGMSVQPKNWLPGPCYRQQRVSKTKTDNNNSNFTWT
GASKYNLNGRESIINPGTAMASHKDDEDKFFPMSGVMIFGKESAGASNTALDNVMITDEEEIKATNPVATERFGTVAVNFQSSS
TDPATGDVHAMGALPGMVWQDRDVYLQGPIWAKIPHTDGHFHPSPLMGGFGLKNPPPQILIKNTPVPANPPAEFSATKFASFIT
QYSTGQVSVEIEWELQKENSKRWNPEVQYTSNYAKSANVDFTVDNNGLYTEPRPIGTRYLTRPL
```

>gi|110645923|ref|YP_680426.1|major coat protein VP1 [Adeno-associated virus-2]

(SEQ ID NO: 2)

```
MAADGYLPDWLEDTLSEGIRQWWKLKPGPPPPKPAERHKDDSRGLVLPGYKYLGPFNGLDKGEPVNEADAAALEHDKAYDRQLD
SGDNPYLKYNHADAEFQERLKEDTSFGGNLGRAVFQAKKRVLEPLGLVEEPVKTAPGKKRPVEHSPVEPDSSSGTGKAGQQPAR
KRLNFGQTGDADSVPDPQPLGQPPAAPSGLGTNTMATGSGAPMADNNEGADGVGNSSGNWHCDSTWMGDRVITTSTRTWALPTY
NNHLYKQISSQSGASNDNHYFGYSTPWGYFDFNRFHCHFSPRDWQRLINNNWGFRPKRLNFKLFNIQVKEVTQNDGTTTIANNL
TSTVQVFTDSEYQLPYVLGSAHQGCLPPFPADVFMVPQYGYLTLNNGSQAVGRSSFYCLEYFPSQMLRTGNNFTFSYTFEDVPF
HSSYAHSQSLDRLMNPLIDQYLYYLSRTNTPSGTTTQSRLQFSQAGASDIRDQSRNWLPGPCYRQQRVSKTSADNNNSEYSWTG
ATKYHLNGRDSLVNPGPAMASHKDDEEKFFPQSGVLIFGKQGSEKTNVDIEKVMITDEEEIRTTNPVATEQYGSVSTNLQRGNR
QAATADVNTQGVLPGMVWQDRDVYLQGPIWAKIPHTDGHFHPSPLMGGFGLKHPPPQILIKNTPVPANPSTTFSAAKFASFITQ
YSTGQVSVEIEWELQKENSKRWNPEIQYTSNYNKSVNVDFTVDTNGVYSEPRPIGTRYLTRNL
```

>gi|51593838|ref|YP_068409.1|capsid protein [Adeno-associated virus-5]

(SEQ ID NO: 3)

```
MSFVDHPPDWLEEVGEGLREFLGLEAGPPKPKPNQQHQDQARGLVLPGYNYLGPGNGLDRGEPVNRADEVAREHDISYNEQLEA
GDNPYLKYNHADAEFQEKLADDTSFGGNLGKAVFQAKKRVLEPFGLVEEGAKTAPTGKRIDDHFPKRKKARTEEDSKPSTSSDA
EAGPSGSQQLQIPAQPASSLGADTMSAGGGGPLGDNNQGADGVGNASGDWHCDSTWMGDRVVTKSTRTWVLPSYNNHQYREIKS
GSVDGSNANAYFGYSTPWGYFDFNRFHSHWSPRDWQRLINNYWGFRPRSLRVKIFNIQVKEVTVQDSTTTIANNLTSTVQVFTD
DDYQLPYVVGNGTEGCLPAFPPQVFTLPQYGYATLNRDNTENPTERSSFFCLEYFPSKMLRTGNNFEFTYNFEEVPFHSSFAPS
QNLFKLANPLVDQYLYRFVSTNNTGGVQFNKNLAGRYANTYKNWFPGPMGRTQGWNLGSGVNRASVSAFATTNRMELEGASYQV
PPQPNGMTNNLQGSNTYALENTMIFNSQPANPGTTATYLEGNMLITSESETQPVNRVAYNVGGQMATNNQSSTTAPATGTYNLQ
EIVPGSVWMERDVYLQGPIWAKIPETGAHFHPSPAMGGFGLKHPPPMMLIKNTPVPGNITSFSDVPVSSFITQYSTGQVTVEME
WELKKENSKRWNPEIQYTNNYNDPQFVDFAPDSTGEYRTTRPIGTRYLTRPL
```

>gi|2766607|gb|AAB95450.1|capsid protein VP1 [Adeno-associated virus-6]

(SEQ ID NO: 4)

```
MAADGYLPDWLEDNLSEGIREWWDLKPGAPKPKANQQKQDDGRGLVLPGYKYLGPFNGLDKGEPVNAADAAALEHDKAYDQQLK
AGDNPYLRYNHADAEFQERLQEDTSFGGNLGRAVFQAKKRVLEPFGLVEEGAKTAPGKKRPVEQSPQEPDSSSGIGKTGQQPAK
KRLNFGQTGDSESVPDPQPLGEPPATPAAVGPTTMASGGGAPMADNNEGADGVGNASGNWHCDSTWLGDRVITTSTRTWALPTY
NNHLYKQISSASTGASNDNHYFGYSTPWGYFDFNRFHCHFSPRDWQRLINNNWGFRPKRLNFKLFNIQVKEVTTNDGVTTIANN
LTSTVQVFSDSEYQLPYVLGSAHQGCLPPFPADVFMIPQYGYLTLNNGSQAVGRSSFYCLEYFPSQMLRTGNNFTFSYTFEDVP
FHSSYAHSQSLDRLMNPLIDQYLYYLNRTQNQSGSAQNKDLLFSRGSPAGMSVQPKNWLPGPCYRQQRVSKTKTDNNNSNFTWT
GASKYNLNGRESIINPGTAMASHKDDKDKFFPMSGVMIFGKESAGASNTALDNVMITDEEEIKATNPVATERFGTVAVNLQSSS
TDPATGDVHVMGALPGMVWQDRDVYLQGPIWAKIPHTDGHFHPSPLMGGFGLKHPPPQILIKNTPVPANPPAEFSATKFASFIT
QYSTGQVSVEIEWELQKENSKRWNPEVQYTSNYAKSANVDFTVDNNGLYTEPRPIGTRYLTRPL
```

>gi|171850125|gb|ACB55302.1|capsid protein VP1 [Adeno-associated virus-6.2]

(SEQ ID NO: 5)

```
MAADGYLPDWLEDNLSEGIREWWDLKPGAPKPKANQQKQDDGRGLVLPGYKYLGPFNGLDKGEPVNAADAAALEIIDKAYDQQL
KAGDNPYLRYNIIADAEFQERLQEDTSFGGNLGRAVFQAKKRVLEPLGLVEEGAKTAPGKKRPVEQSPQEPDSSSGIGKTGQQP
AKKRLNFGQTGDSESVPDPQPLGEPPATPAAVGPTTMASGGGAPMADNNEGADGVGNASGNWHCDSTWLGDRVITTSTRTWALP
TYNNHLYKQISSASTGASNDNHYFGYSTPWGYFDFNRFHCHFSPRDWQRLINNNWGFRPKRLNFKLFNIQVKEVTTNDGVTTIA
NNLTSTVQVFSDSEYQLPYVLGSAHQGCLPPFPADVFMIPQYGYLTLNNGSQAVGRSSFYCLFYFPSQMLRTGNNFTFSYTFED
VPFHSSYAHSQSLDRLMNPLIDQYLYYLNRTQNQSGSAQNKDLLFSRGSPAGMSVQPKNWLPGPCYRQQRVSKTKTDNNNSNFT
WTGASKYNLNGRESIINPGTAMASHKDDKDKFFPMSGVMIFGKESAGASNTALDNVMITDEEEIKATNPVATERFGTVAVNLQS
SSTDPATGDVHVMGALPGMVWQDRDVYLQGPIWAKIPHTDGHFHPSPLMGGEGLKHPPPQILIKNTPVPANPPAEFSATKFASF
ITQYSTGQVSVEIEWELQKENSKRWNPEVQYTSNYAKSANVDFTVDNNGLYTEPRPIGTRYLTRPL
```

>gi|22652861|gb|AAN03855.1|AF513851_2 capsid protein [Adeno-associated virus-7]

(SEQ ID NO: 6)

```
MAADGYLPDWLEDNLSEGIREWWDLKPGAPKPKANQQKQDNGRGLVLPGYKYLGPFNGLDKGEPVNAADAAALEHDKAYDQQLK
AGDNPYLRYNHADAEFQERLQEDTSFGGNLGRAVFQAKKRVLEPLGLVEEGAKTAPAKKRPVEPSPQRSPDSSTGIGKKGQQPA
RKRLNFGQTGDSESVPDPQPLGEPPAAPSSVGSGTVAAGGGAPMADNNEGADGVGNASGNWHCDSTWLGDRVITTSTRTWALPT
YNNHLYKQISSETAGSTNDNTYFGYSTPWGYFDFNRFHCHFSPRDWQRLINNNWGFRPKKLRFKLFNIQVKEVTTNDGVTTIAN
NLTSTIQVFSDSEYQLPYVLGSAIIQGCLPPFPADVFMIPQYGYLTLNNGSQSVGRSSFYCLEYFPSQMLRTGNNFEFSYSFED
VPFHSSYAHSQSLDRLMNPLIDQYLYYLARTQSNPGGTAGNRELQFYQGGPSTMAEQAKNWLPGPCFRQQRVSKTLDQNNNSNF
```

| NUCLEIC ACID AND AMINO ACID SEQUENCES |
|---|

AWTGATKYHLNGRNSLVNPGVAMATHKDDEDRFFPSSGVLIFGKTGATNKTTLENVLMTNEEEIRPTNPVATEEYGIVSSNLQA
ANTAAQTQVVNNQGALPGMVWQNRDVYLQGPIVVAKIPHTDGNFHPSPLMGGFGLKHPPPQILIKNTPVPANPPEVFTPAKFAS
FITQYSTGQVSVEIEWELQKENSKRWNPEIQYTSNFEKQTGVDFAVDSQGVYSEPRPIGTRYLTRNL

>gi|22652864|gb|AAN03857.1|AF513852_2 capsid protein [Adeno-associated virus-8]

(SEQ ID NO: 7)

MAADGYLPDWLEDNLSEGIREWWALKPGAPKPKANQQKQDDGRGLVLPGYKYLGPFNGLDKGEPVNAADAAALEHDKAYDQQLQ
AGDNPYLRYNHADAEFQERLQEDTSFGGNLGRAVFQAKKRVLEPLGLVEEGAKTAPGKKRPVEPSPQRSPDSSTGIGKKGQQPA
RKRLNFGQTGDSESVPDPQPLGEPPAAPSGVGPNTMAAGGGAPMADNNEGADGVGSSSGNWHCDSTWLGDRVITTSTRTWALPT
YNNHLYKQISNGTSGGATNDNTYFGYSTPWGYFDFNRFHCHFSPRDWQRLINNNWGFRPKRLSFKLFNIQVKEVTQNEGTKTIA
NNLTSTIQVFTDSEYQLPYVLGSAHQGCLPPFPADVFMIPQYGYLTLNNGSQAVGRSSFYCLEYFPSQMLRTGNNFQFTYTFED
VPFHSSYAHSQSLDRLMNPLIDQYLYYLSRTQTTGGTANTQTLGFSQGGPNTMANQAKNWLPGPCYRQQRVSTTTGQNNNSNFA
WTAGTKYHLNGRNSLANPGIAMATHKDDEERFFPSNGILIFGKQNAARDNADYSDVMLTSEEEIKTTNPVATEEYGIVADNLQQ
QNTAPQIGTVNSQGALPGMVWQNRDVYLQGPIWAKIPHTDGNFHPSPLMGGFGLKHPPPQILIKNTPVPADPPTTFNQSKLNSF
ITQYSTGQVSVEIEWELQKENSKRWNPEIQYTSNYYKSTSVDFAVNTEGVYSEPRPIGTRYLTRNL

>gi|46487805|gb|AAS99264.1|capsid protein VP1 [Adeno-associated virus 9]

(SEQ ID NO: 8)

MAADGYLPDWLEDNLSEGIREWWALKPGAPQPKANQQHQDNARGLVLPGYKYLGPGNGLDKGEPVNAADAAALEHDKAYDQQLK
AGDNPYLKYNHADAEFQERLQEDTSFGGNLGRAVFQAKKRLLEPLGLVEEGVKTAPGKKRPVEQSPQEPDSSAGIGKSGAQPAK
KRLNFGQTGDTESVPDPQPIGEPPAAPSGVGSLTMASGGGAPVADNNEGADGVGSSSGNWHCDSQWLGDRVITTSTRTWALPTY
NNHLYKQISNSTSGGSSNDNAYFGYSTPWGYFDFNRFHCHFSPRDWQRLINNNWGFRPKRLNFKLFNIQVKEVTDNNGVKTIAN
NLTSTVQVFTDSDYQLPYVLGSAHEGCLPPFPADVFMIPQYGYLTLNDGSQAVGRSSFYCLEYFPSQMLRTGNNFQFSYEFENV
PFHSSYAHSQSLDRLMNPLIDQYLYYLSKTINGSGQNQQTLKFSVAGPSNMAVQGRNYIPGPSYRQQRVSTTVTQNNNSEFAWP
GASSWALNGRNSLMNPGPAMASHKEGEDRFFPLSGSLIFGKQGTGRDNVDADKVMITNEEEIKTTNPVATESYGQVATNHQSAQ
AQAQTGWVQNQGILPGMVWQDRDVYLQGPIWAKIPHTDGNFHPSPLMGGEGMKHPPPQIIKNTPVPADPPTAFNKDKLNSFIT
QYSTGQVSVEIEWELQKENSKRWNPEIQYTSNYYKSNNVEFAVNTEGVYSEPRPIGTRYLTRNL

>gi|29650526|gb|AAO88201.1|capsid protein [Non-human primate Adeno-associated virus] rh-10

(SEQ ID NO: 9)

MAADGYLPDWLEDNLSEGIREWWDLKPGAPKPKANQQKQDDGRGLVLPGYKYLGPFNGLDKGEPVNAADAAALEHDKAYDQQLK
AGDNPYLRYNHADAEFQERLQEDTSFGGNLGRAVFQAKKRVLEPLGLVEEGAKTAPGKKRPVEPSPQRSPDSSTGIGKKGQQPA
KKRLNFGQTGDSESVPDPQPIGEPPAGPSGLGSGTMAAGGGAPMADNNEGADGVGSSSGNWHCDSTWLGDRVITTSTRTWALPT
YNNHLYKQISNGTSGGSTNDNTYFGYSTPWGYFDFNRFHCHFSPRDWQRLINNNWGFRPKRLNFKLFNIQVKEVTQNEGTKTIA
NNLTSTIQVFTDSEYQLPYVLGSAHQGCLPPFPADVFMIPQYGYLTLNNGSQAVGRSSFYCLEYFPSQMLRTGNNFEFSYQFED
VPFHSSYAHSQSLDRLMNPLIDQYLYYLSRTQSTGGTAGTQQLLFSQAGPNNMSAQAKNWLPGPCYRQQRVSTTLSQNNNSNFA
WTGATKYHLNGRDSLVNPGVAMATHKDDEERFFPSSGVLMFGKQGAGKDNVDYSSVMLTSEEEIKTTNPVATEQYGVVADNLQQ
QNAAPIVGAVNSQGALPGMVWQNRDVYLQGPIWAKIPHTDGNFHPSPLMGGFGLKHPPPQILIKNTPVPADPPTTFSQAKLASF
ITQYSTGQVSVEIEWELQKENSKRWNPEIQYTSNYYKSTNVDFAVNTDGTYSEPRPIGTRYLTRNL

>gi|171850147|gb|ACB55313.1|capsid protein VP1 [Adeno-associated virus-rh.39]

(SEQ ID NO: 10)

MAADGYLPDWLEDNLSEGIREWWALKPGAPKPKANQQKQDDGRGLVLPGYKYLGPFNGLDKGEPVNAADAAALEHDKAYDQQLK
AGDNPYLRYNHADAEFQERLQEDTSFGGNLGRAVFQAKKRVLEPLGLVEEGAKTAPGKKRPVEPSPQRSPDSSTGIGKKGQQPA
KKRLNFGQTGDSESVPDPQPIGEPPAGPSGLGSGTMAAGGGAPMADNNEGADGVGSSSGNWHCDSTWLGDRVITTSTRTWALPT
YNNHLYKQISNGTSGGSTNDNTYFGYSTPWGYFDFNRFHCHFSPRDWQRLINNNWGFRPKRLSFKLFNIQVKEVTQNEGTKTIA
NNLTSTIQVFTDSEYQLPYVLGSAHQGCLPPFPADVFMIPQYGYLTLNNGSQAVGRSSFYCLEYFPSQMLRTGNNFEFSYTFED
VPFHSSYAHSQSLDRLMNPLIDQYLYLSRTQSTGGTQGTQQLLFSQAGPANMSAQAKNWLPGPCYRQQRVSTTLSQNNNSNFA
WTGATKYHLNGRDSLVNPGVAMATHKDDEERFFPSSGVLMFGKQGAGRDNVDYSSVMLTSEEEIKTTNPVATEQYGVVADNLQQ
TNTGPIVGNVNSQGALPGMVWQNRDVYLQGPIWAKIPHTDGNFHPSPLMGGFGLKHPPPQILIKNTPVPADPPTTFSQAKLASF
ITQYSTGQVSVEIEWELQKENSKRWNPEIQYTSNYYKSTNVDFAVNTEGTYSEPRPIGTRYLTRNL

>gi|46487767|gb|AAS99245.1|capsid protein VP1 [Adeno-associated virus rh.43]

(SEQ ID NO: 11)

MAADGYLPDWLEDNLSEGIREWWDLKPGAPKPKANQQKQDDGRGLVLPGYKYLGPFNGLDKGEPVNAADAAALEHDKAYDQQLE
AGDNPYLRYNHADAEFQERLQEDTSFGGNLGRAVFQAKKRVLEPLGLVEEGAKTAPGKKRPVEQSPQEPDSSSGIGKKGQQPAR
KRLNFGQTGDSESVPDPQPLGEPPAAPSGVGPNTMAAGGGAPMADNNEGADGVGSSSGNWHCDSTWLGDRVITTSTRTWALPTY
NNHLYKQISNGTSGGATNDNTYFGYSTPWGYFDFNRFHCHFSPRDWQRLINNNWGFRPKRLSFKLFNIQVKEVTQNEGTKTIAN
NLTSTIQVFTDSEYQLPYVLGSAHQGCLPPFPADVFMIPQYGYLTLNNGSQAVGRSSFYCLEYFPSQMLRTGNNFQFTYTFEDV
PFHSSYAHSQSLDRLMNPLIDQYLYYLSRTQTTGGTANTQTLGFSQGGPNTMANQAKNWLPGPCYRQQRVSTTTGQNNNSNFAW
TAGTKYHLNGRNSLANPGIAMATHKDDEERFFPVTGSCFWQQNAARDNADYSDVMLTSEEEIKTTNPVATEEYGIVADNLQQQN
TAPQIGTVNSQGALPGMVWQNRDVYLQGPIWAKIPHTDGNFHPSPLMGGFGLKHPPPQILIKNTPVPADPPTTFNQSKLNSFIT
QYSTGQVSVEIEWELQKENSKRWNPEIQYTSNYYKSTSVDFAVNTEGVYSEPRPIGTRYLTRNL

>capsid protein VP1 [Adeno-associated virus] CSp3

(SEQ ID NO: 12)

MAADGYLPDWLEDNLSEGIREWWALKPGAPQPKANQQIIQDNARGLVLPGYKYLGPGNGLDKGEPVNAADAAALEHDKAYDQQL
KAGDNPYLKYNHADAEFQERLKEDTSFGGNLGRAVFQAKKRLLEPLGLVEEAAKTAPGKKRPVEQSPQEPDSSAGIGKSGAQPA
KKRLNFGQTGDTESVPDPQPIGEPPAAPSGVGSLTIASGGGAPVADNNEGADGVGSSSGNWHCDSQWLGDRVITTSTRTWALPT
YNNHLYKRISNSTSGGSSNDNAYFGYSTPWGYFDFNRFHCHFSPRDWQRLINNNWGFRPKRLNFKLFNIRVKEVTDNNGVKTIT
NNLTSTVQVFTDSDYQLPYVLGSAHEGCLPPFPADVFMIPQYGYLTLNDGSQAVGRSSFYCLEYFPSQMLRTGNNFQFSYEFEN
VPFHSSYAHSQSLDRLMNPLIDQYLYYLSKTINGSGQNQQTLKFSVAGPSNMAVQGRNYIPGPSYRQQRVSTTVTRNNNSEFAW
PGASSWALNGRNSLMNPGPAMASHKEGEDRFFPLSGSLIFGKQGTGRDNVDADKVMITNEEEIKTTNPVATESYGQVATNHQSA
QAQAQTGWVQNQGILPGMVWQDRDVYLQGPIWAKIPIITDGNFIIPSPLMGGFGVKIIPPPQILIKNTPVPADPPTAFNKDKLN
SFITQYSTGQVSVEIEWELQKENSKRWNPEIQYTSNYYKSNNVEFAVNTEGVYSEPRPIGTRYLTRNL

NUCLEIC ACID AND AMINO ACID SEQUENCES

>gi|189339202|ref|NP_001121557.1|aspartoacylase [Homo sapiens]
(SEQ ID NO: 13)
MTSCHIAEEHIQKVAIFGGTHGNELTGVFLVKHWLENGAEIQRTGLEVKPFITNPRAVKKCTRYIDCDLNRIFDLENLGKKMSE
DLPYEVRRAQEINHLFGPKDSEDSYDIIFDLHNTTSNMGCTLILEDSRNNFLIQMFHYIKTSLAPLPCYVYLIEHPSLKYATTR
SIAKYPVGIEVGPQPQGVLRADILDQMRKMIKHALDFIHHFNEGKEFPPCAIEVYKIIEKVDYPRDENGEIAAIIHPNLQDQDW
KPLHPGDPMFLTLDGKTIPLGGDCTVYPVFVNEAAYYEKKEAFAKTTKLTLNAKSIRCCLH >gi1|89339201: 92-1033 Homo sapiens aspartoacylase (Canavan disease) (ASPA), transcript variant 2, mRNA
(SEQ ID NO: 14)
ATGACTTCTTGTCACATTGCTGAAGAACATATACAAAAGGTTGCTATCTTTGGAGGAACCCATGGGAATGAGCTAACCGGAGTA
TTTCTGGTTAAGCATTGGCTAGAGAATGGCGCTGAGATTCAGAGAACAGGGCTGGAGGTAAAACCATTTATTACTAACCCCAGA
GCAGTGAAGAAGTGTACCAGATATATTGACTGTGACCTGAATCGCATTTTTGACCTTGAAAATCTTGGCAAAAAATGTCAGAA
GATTTGCCATATGAAGTGAGAAGGGCTCAAGAAATAAATCATTTATTTGGTCCAAAAGACAGTGAAGATTCCTATGACATTATT
TTTGACCTTCACAACACCACCTCTAACATGGGGTGCACTCTTATTCTTGAGGATTCCAGGAATAACTTTTTAATTCAGATGTTT
CATTACATTAAGACTTCTCTGGCTCCACTACCCTGCTACGTTTATCTGATTGAGCATCCTTTCCCTCAAATATGCGACCACTCGT
TCCATAGCCAAGTATCCTGTGGGTATAGAAGTTGGTCCTCAGCCTCAAGGGGTTCTGAGAGCTGATATCTTGGATCAAATGAGA
AAAATGATTAAACATGCTCTTGATTTTATACATCATTTCAATGAAGGAAAAGAATTTCCTCCCTGCGCCATTGAGGTCTATAAA
ATTATAGAGAAAGTTGATTACCCCGGGATGAAAATGGAGAAATTGCTGCTATCATCCATCCTAATCTGCAGGATCAAGACTGG
AAACCACTGCATCCTGGGGATCCCATGTTTTTAACTCTTGATGGGAAGACGATCCCACTGGGCGGAGAAGCTTTTGCAAAGACA
ACTAAACGCTCAATGCAAAAAGTATTCGCTGCTGTAGCTTTTGCAAAGACAACTAAACTAACGCTCAATGCAAAAAGTAT
TCGCTGCTGTTTACATTAG >gi|31560279|ref|NP_075602.2|aspartoacylase [Mus Musculus]
(SEQ ID NO: 15)
MTSCVAKEPIKKIAIFGGTIIGNELTGVFLVTIIWLRNGTEVIIRAGLDVKPFITNPRAVEKCTRYIDCDLNRVFDLENLSKEM
SEDLPYEVRRAQEINHLFGPKNSDDAYDLVFDLHNTTSNMGCTLILEDSRNDFLIQMFHYIKTCMAPLPCSVYLIEHPSLKYAT
TRSIAKYPVGIEVGPQPHGVLRADILDQMRKMIKHALDFIQHFNEGKEFPPCSIDVYKIMEKVDYPRNESGDMAAVIHPNLQDQ
DWKPLHPGDPVFVSLDGKVIPLGGDCTVYPVFVNEAAYYEKKEAFAKTTKLTLSAKSIRSTLH >gi|142354273: 148-1086 Mus musculus aspartoacylase (Aspa), mRNA
(SEQ ID NO: 16)
ATGACCTCTTGTGTTGCTAAAGAACCTATTAAGAAGATTGCCATCTTTGGAGGGACTCATGGAAATGAACTGACCGGAGTGTTT
CTAGTTACTCACTGGCTAAGGAATGGCACTGAAGTTCACAGAGCAGGGCTGGACGTGAAGCCATTCATTACCAATCCAAGGGCG
GTGGAGAAGTGCACCAGATACATTGACTGTGACCTGAATCGTGTTTTTGACCTTGAAAATCTTAGCAAAGAGATGTCTGAAGAC
TTGCCATATGAAGTGAGAAGGGCTCAAGAAATAAATCATTTATTTGGTCCAAAAAATAGTGATGATGCCTATGACCTTGTTTTT
GACCTTCACAACACCACTTCTAACATGGGTTGCACTCTTATTCTTGAGGATTCCAGGAATGACTTTTTAATTCAGATGTTTCAC
TATATTAAGACTTGCATGGCTCCATTACCCTGCTCTGTTTATCTCATTGAGCATCCTTCACTCAAATATGCAACCACTCGTTCC
ATTGCCAAGTATCCTGTTGGTATAGAAGTTGGTCCTCAGCCTCACGGTGTCCTTAGAGCTGATATTTTAGACCAAATGAGAAAA
ATGATAAAACATGCTCTTGATTTTATACAGCATTTCAATGAAGGAAAAGAATTTCCTCCCTGTTCTATTGACGTCTATAAAATA
ATGGAGAAAGTTGATTATCCAAGGAATGAAAGTGGAGACATGGCTGCTGTTATTCATCCTAATCTGCAGGATCAAGACTGGAAA
CCATTGCACCCTGGAGATCCTGTGTTTGTGTCTCTTGATGGAAAAGTTATTCCACTGGGTGGAGACTGTACCGTGTACCCAGTG
TTTGTGAATGAAGCTGCATATTATGAAAAAAAAGAAGCATTTGCAAAGACAACAAAACTAACACTCAGCGCAAAAAGCATCCGC
TCCACTTTGCACTAA >gi|48762945: 149-613 Homo sapiens superoxide dismutase 1, soluble (SOD1), mRNA
(SEQ ID NO: 17)
ATGGCGACGAAGGCCGTGTGCGTGCTGAAGGGCGACGGCCCAGTGCAGGGCATCATCAATTTCGAGCAGAAGGAAAGTAATGGA
CCAGTGAAGGTGTGGGGAAGCATTAAAGGACTGACTGAAGGCCTGCATGGATTCCATGTTCATGAGTTTGGAGATAATACAGCA
GGCTGTACCAGTGCAGGTCCTCACTTTAATCCTCTATCCAGAAACACGGTGGGCCAAAGGATGAAGAGAGGCATGTTGGAGAC
TTGGGCAATGTGACTGCTGACAAAGATGGTGTGGCCGATGTGTCTATTGAAGATTCTGTGATCTCACTCTCAGGAGACCATTGC
ATCATTGGCCGCACACTGGTGGTCCATGAAAAGCAGATGACTTGGGCAAAGGTGGAAATGAAGAAGTACAAAGACAGGAAAC
GCTGGAAGTCGTTTGGCTTGTGGTGTAATTGGGATCGCCCAATAA >gi|4507149|ref|NP_000445.1|superoxide dismutase [Homo sapiens]
(SEQ ID NO: 18)
MATKAVCVLKGDGPVQGIINFEQKESNGPVKVWGSIKGLTEGLHGFHVHEFGDNTAGCTSAGPHFNPLSRKHGGPKDEERHVGD
LGNVTADKDGVADVSIEDSVISLSGDHCIIGRTLVVHEKADDLGKGGNEESTKTGNAGSRLACGVIGIAQ >gi|45597446: 117-581 Mus musculus superoxide dismutase 1, soluble (Sod1), mRNA
(SEQ ID NO: 19)
ATGGCGATGAAAGCGGTGTGCGTGCTGAAGGGCGACGGTCCGGTGCAGGGAACCATCCACTTCGAGCAGAAGGCAAGCGGTGAA
CCAGTTGTGTTGTCAGGACAAATTACAGGATTAACTGAAGGCCAGCATGGGTTCCACGTCCATCAGTATGGGGACAATACACAA
GGCTGTACCAGTGCAGGACCTCATTTTAATCCTCACTCTAAGAAACATGGTGGCCCGGCGGATGAAGAGAGGCATGTTGGAGAC
CTGGGCAATGTGACTGCTGGAAAGGACGGTGTGGCCAATGTGTCCATTGAAGATCGTGTGATCTCACTCTCAGGAGAGCATTCC
ATCATTGGCCGTACAATGGTGGTCCATGAGAAACAAGATGACTTGGGCAAAGGTGGAAATGAAGAAGTACAAAGACTGGAAAT
GCTGGGAGCCGCTTGGCCTGTGGAGTGATTGGGATTGCGCAGTAA >gi|45597447|ref|NP_035564.1|superoxide dismutase [Mus musculus]
(SEQ ID NO: 20)
MAMKAVCVLKGDGPVQGTIHFEQKASGEPVVLSGQITGLTEGQHGFHVHQYGDNTQGCTSAGPHFNPHSKKHGGPADEERHVGD
LGNVTAGKDGVANVSIEDRVISLSGEHSIIGRTMVVHEKQDDLGKGGNEESTKTGNAGSRLACGVIGIAQ >pAAVscCB6 EGFPmir SOD5 (direct) 5243 bp
(SEQ ID NO: 21)
CTGCGCGCTCGCTCGCTCACTGAGGCCGCCCGGGCAAAGCCCGGGCGTCGGGCGACCTTTGGTCGCCCGGCCTCAGTGAGCGAG
CGAGCGCGCAGAGAGGGAGTGTAGCCATGCTCTAGGAAGATCAATTCAATTCACGCGTCGACATTGATTATTGACTAGTTATTA

| NUCLEIC ACID AND AMINO ACID SEQUENCES |
|---|
| ATAGTAATCAATTACGGGGTCATTAGTTCATAGCCCATATATGGAGTTCCGCGTTACATAACTTACGGTAAATGGCCCGCCTGG
CTGACCGCCCAACGACCCCCGCCCATTGACGTCAATAATGACGTATGTTCCCATAGTAACGCCAATAGGGACTTTCCATTGACG
TCAATGGGTGGATATTTACGGTAAACTGCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTTCCTACTTGGCAGTACATCTACGTATTA
GTCATCGCTATTACCATGTCGAGGCCACGTTCTGCTTCACTCTCCCCATCTCCCCCCCCTCCCCACCCCCAATTTTGTATTTAT
TTATTTTTTAATTATTTTGTGCAGCGATGGGGGCGGGGGGGGGGGCGCGCGCCAGGCGGGGCGGGGCGGGGCGAGGGGCGGGG
CGGGGCGAGGCGGAGAGGTGCGGCGGCAGCCAATCAGAGCGGCGCGCTCCGAAAGTTTCCTTTTATGGCGAGGCGGCGGCGGCG
GCGGCCCTATAAAAAGCGAAGCGCGCGGCGGGCGGGAGCAAGCTCTAGCCTCGAGAATTCACGCGTGGTACCTCTAGAGCAGAG
CTCGTTTAGTGAACCGTCAGTTCGAAATCGCCACCATGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGCGATGCCACCTACGGCAAGCTGACCC
TGAAGTTCATCTGCACCACCGGCAAGCTGCCCGTGCCCTGGCCCACCCTCGTGACCACCCTGACCTACGGCGTGCAGTGCTTCA
GCCGCTACCCCGACCACATGAAGCAGCACGACTTCTTCAAGTCCGCCATGCCCGAAGGCTACGTCCAGGAGCGCACCATCTTCT
TCAAGGACGACGGCAACTACAAGACCCGCGCCGAGGTGAAGTTCGAGGGCGACACCCTGGTGAACCGCATCGAGCTGAAGGGCA
TCGACTTCAAGGAGGACGGCAACATCCTGGGGCACAAGCTGGAGTACAACTACAACAGCCACAACGTCTATATCATGGCCGACA
AGCAGAAGAACGGCATCAAGGTGAACTTCAAGATCCGCCACAACATCGAGGACGGCAGCGTGCAGCTCGCCGACCACTACCAGC
AGAACACCCCCATCGGCGACGGCCCCGTGCTGCTGCCCGACAACCACTACCTGAGCACCCAGTCCGCCCTGAGCAAAGACCCCA
ACGAGAAGCGCGATCACATGGTCCTGCTGGAGTTCGTGACCGCCGCCGGGATCACTCTCGGCATGGACGAGCTGTACAAGTAAG
TAACAGGTAAGTGCGATCGCTAATGCGGGAAAGCTCTTATTCGGGTGAGATGGGCTGGGGCACCATCTGGGGACCCTGACGTGA
AGTTTGTCACTGACTGGAGAACTCGGTTTGTCGTCTGTTGCGGGGGCGGCAGTTATGGCGGTGCCGTTGGGCAGTGCACCCGTA
CCTTTGGGAGCGCGCGCCTCGTCGTGTCGTGACGTCACCCGTTCTGTTGGTACCTGCTGTTGACAGTGAGCGACGCAATGTGA
CTTCGCTGACAAAGCTGTGAAGCCACAGATGGGCTTTGTCAGCAGTCACATTGCGCTGCCTACTGCCTCGGACTTCAAGGGCTC
GAGAATTCAGGGTGGGGCCACCTGCCGGTAGGTGTGCGGTAGGCTTTTCTCCGTCGCAGGACGCAGGGTTCGGGCCTAGGGTAG
GCTCTCCTGAATCGACAGGCGCCGGACCTCTGGCGGCCGCAACAACGCGTTCCTGACCATTCATCCTCTTTCTTTTTCCTGCAG
GCTTGTGGAAGAAATGGGATCCGATCTTTTTCCCTCTGCCAAAAATTATGGGGACATCATGGGGACCCCTTGAGCATCTGACTTC
TGGCTAATAAAGGAAATTTATTTTCATTGCAATAGTGTGTTGGAATTTTTTGTGTCTCTCACTCGGCCTAGGTAGATAAGTAGC
ATGGCGGGTTAATCATTAACTACAAGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGAGCGAGCGCGCAGCCTTAATTAACCTA
ATTCACTGGCCGTCGTTTTACAACGTCGTGACTGGGAAAACCCTGGCGTTACCCAACTTAATCGCCTTGCAGCACATCCCCCTT
TCGCCAGCTGGCGTAATAGCGAAGAGGCCCGCACCGATCGCCCTTCCCAACAGTTGCGCAGCCTGAATGGCGAATGGGACGCGC
CCTGTAGCGGCGCATTAAGCGCGGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAATCGGGGGCTCCCTTTAGGGTTCC
GATTTAGTGCTTTACGGCACCTCGACCCCAAAAAACTTGATTAGGGTGATGGTTCACGTAGTGGGCCATCGCCCTGATAGACGG
TTTTTCGCCCTTTGACGTTGGAGTCCACGTTCTTTAATAGTGGACTCTTGTTCCAAACTGGAACAACACTCAACCCTATCTCGG
TCTATTCTTTTGATTTATAAGGGATTTTGCCGATTTCGGCCTATTGGTTAAAAAATGAGCTGATTTAACAAAAATTTAACGCGA
ATTTTAACAAAATATTAACGCTTACAATTTAGGTGGCACTTTTCGGGGAAATGTGCGCGGAACCCCTATTTGTTTATTTTTCTA
AATACATTCAAATATGTATCCGCTCATGAGACAATAACCCTGATAAATGCTTCAATAATATTGAAAAAGGAAGAGTATGAGTAT
TCAACATTTCCGTGTCGCCCTTATTCCCTTTTTTGCGGCATTTTGCCTTCCTGTTTTTGCTCACCCAGAAACGCTGGTGAAAGT
AAAAGATGCTGAAGATCAGTTGGGTGCACGAGTGGGTTACATCGAACTGGATCTCAACAGCGGTAAGATCCTTGAGAGTTTTCG
CCCCGAAGAACGTTTTCCAATGATGAGCACTTTTAAAGTTCTGCTATGTGGCGCGGTATTATCCCGTATTGACGCCGGGCAAGA
GCAACTCGGTCGCCGCATACACTATTCTCAGAATGACTTGGTTGAGTACTCACCAGTCACAGAAAAGCATCTTACGGATGGCAT
GACAGTAAGAGAATTATGCAGTGCTGCCATAACCATGAGTGATAACACTGCGGCCAACTTACTTCTGACAACGATCGGAGGACC
GAAGGAGCTAACCGCTTTTTTGCACAACATGGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCGCAAACTATTAACTGGCGAACTACTTACTCT
TAGCTTCCCGGCAACAATTAATAGACTGGATGGAGGCGGATAAAGTTGCAGGACCACTTCTGCGCTCGGCCCTTCCGGCTGGCT
GGTTTATTGCTGATAAATCTGGAGCCGGTGAGCGTGGGTCTCGCGGTATCATTGCAGCACTGGGGCCAGATGGTAAGCCCTCCC
GTATCGTAGTTATCTACACGACGGGGAGTCAGGCAACTATGGATGAACGAAATAGACAGATCGCTGAGATAGGTGCCTCACTGA
TTAAGCATTGGTAACTGTCAGACCAAGTTTACTCATATATACTTTAGATTGATTTAAAACTTCATTTTTAATTTAAAAGGATCT
AGGTGAAGATCCTTTTTGATAATCTCATGACCAAAATCCCTTAACGTGAGTTTTCGTTCCACTGAGCGTCAGACCCCGTAGAAA
AGATCAAAGGATCTTCTTGAGATCCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGCGCAGATACCAAATACTGTTCTTC
TAGTGTAGCCGTAGTTAGGCCACCACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGGATAAGGCGCAGCGGTCGGGCTGAA
CGGGGGGTTCGTGCACACAGCCCAGCTTGGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGTCGATTTTTGTGATGCTCGTCAGGGG
GGCGGAGCCTATGGAAAAACGCCAGCAACGCGGCCTTTTTACGGTTCCTGGCCTTTTGCTGGCCTTTTGCTCACATGTTCTTTC
CTGCGTTATCCCCTGATTCTGTGGATAACCGTATTACCGCCTTTGAGTGAGCTGATACCGCTCGCCGCAGCCGAACGACCGAGC
GCAGCGAGTCAGTGAGCGAGGAAGCGGAAGAGCGCCCAATACGCAAACCGCCTCTCCCCGCGCGTTGGCCGATTCATTAATGCA
GCTGGCACGACAGGTTTCCCGACTGGAAAGCGGGCAGTGAGCGCAACGCAATTAATGTGAGTTAGCTCACTCATTAGGCACCCC
AGGCTTTACACTTTATGCTTCCGGCTCGTATGTTGTGTGGAATTGTGAGCGGATAACAATTTCACACAGGAAACAGCTATGACC
ATGATTACGCCAGATTTAATTAAGGCCTTAATTAGG |

>sod1mir1 (direct) 108 bp (SEQ ID NO: 22)
TGCTGTTGACAGTGAGCGACATCATCAATTTTCCGAGCAGAACTGTGAAGCCACAGATGGGTTCTGCTCGAAATTGATGATGCT
GCCTACTGCCTCGGACTTCAAGGG >sod1mir2 (direct) 106 bp (SEQ ID NO: 23)
TGCTGTTGACAGTGAGCGACGCATTAAAGGATCCTGACTGACTGTGAAGCCACAGATGGGTCAGTCAGTCCTTTAATGCGCTGC
CTACTGCCTCGGACTTCAAGGG >sod1mir3 (direct) 108 bp (SEQ ID NO: 24)
TGCTGTTGACAGTGAGCGACTGCATGGATTCTCCATGTTCATCTGTGAAGCCACAGATGGGATGAACATGGAATCCATGCAGCT
GCCTACTGCCTCGGACTTCAAGGG

NUCLEIC ACID AND AMINO ACID SEQUENCES

```
>sod1mir4 (direct) 106 bp
                                                               (SEQ ID NO: 25)
TGCTGTTGACAGTGAGCGACAAGGATGAAGATCGAGGCATGCTGTGAAGCCACAGATGGGCATGCCTCTCTTCATCCTTGCTGC
CTACTGCCTCGGACTTCAAGGG >sod1mir5 (direct) 110 bp
                                                               (SEQ ID NO: 26)
TGCTGTTGACAGTGAGCGACGCAATGTGACTTCGCTGACAAAGCTGTGAAGCCACAGATGGGCTTTGTCAGCAGTCACATTGCG
CTGCCTACTGCCTCGGACTTCAAGGG >sod1mir6 (direct) 108 bp
                                                               (SEQ ID NO: 27)
TGCTGTTGACAGTGAGCGACCGATGTGTCTATCTTGAAGATTCTGTGAAGCCACAGATGGGAATCTTCAATAGACACATCGGCT
GCCTACTGCCTCGGACTTCAAGGG >sod1mir7 (direct) 106 bp
                                                               (SEQ ID NO: 28)
TGCTGTTGACAGTGAGCGACGGTGGAAATGATCAGAAAGTACTGTGAAGCCACAGATGGGTACTTTCTTCATTTCCACCGCTGC
CTACTGCCTCGGACTTCAAGGG >sod1mir8 (direct) 110 bp
                                                               (SEQ ID NO: 29)
TGCTGTTGACAGTGAGCGACGCTGTAGAAATTCGTATCCTGATCTGTGAAGCCACAGATGGGATCAGGATACATTTCTACAGCG
CTGCCTACTGCCTCGGACTTCAAGGG >sod1mir9 (direct) 106 bp
                                                               (SEQ ID NO: 30)
TGCTGTTGACAGTGAGCGAGGTATTAAACTTGTCAGAATTTAGTGAAGCCACAGATGTAAATTCTGACAAGTTTAATACCCTGC
CTACTGCCTCGGACTTCAAGGG >pAAVscCB6 EGFPmir scr (1820 bp-1925 bp, direct) 106 bp
                                                               (SEQ ID NO: 31)
TGCTGTTGACAGTGAGCGACGATGCTCTAATCGGTTCTATCAAGTGAAGCCACAGATGTTGATAGAACCTTAGAGCATCGCTGC
CTACTGCCTCGGACTTCAAGGG
```

This invention is not limited in its application to the details of construction and the arrangement of components set forth in this description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for delivering a transgene to CNS tissue in a subject, the method comprising: administering an effective amount of a rAAV comprising a promoter operably linked with a transgene to central nervous system (CNS) tissue by intrathecal administration, wherein the rAAV infects cells of the CNS of the subject, wherein the transgene encodes an inhibitory RNA that has the sequence of SEQ ID NO: 26, wherein the inhibitory RNA is complementary with and specifically binds to a target site sequence of the SOD1 mRNA and inhibits expression of SOD1 protein in the subject, wherein the target site sequence of the SOD1 mRNA comprises at least 5 nucleotides that are complementary with a sequence as set forth in SEQ ID NO: 26.

2. The method of claim 1, wherein the intrathecal administration is in the lumbar region of the subject.

3. The method of claim 1, wherein the dose of the rAAV for intrathecal administration is in a range of $10^{10}$ genome copies to $10^{14}$ genome copies.

4. The method of claim 1, wherein the intrathecal administration is in the cervical region of the subject.

5. The method of claim 1, wherein the intrathecal administration is in the thoracic region of the subject.

6. The method of claim 1, wherein the cells of CNS tissue are oligodendrocytes, astrocytes, neurons, brain parenchyma cells, and/or Purkinje cells.

7. The method of claim 1, wherein the inhibitory RNA is an antisense RNA, a shRNA or a miRNA.

* * * * *